US008158616B2

(12) United States Patent
Rodgers et al.

(10) Patent No.: US 8,158,616 B2
(45) Date of Patent: Apr. 17, 2012

(54) AZETIDINE AND CYCLOBUTANE DERIVATIVES AS JAK INHIBITORS

(75) Inventors: James D. Rodgers, Landenberg, PA (US); Stacey Shepard, Voorhees, NJ (US)

(73) Assignee: Incyte Corporation, Wilmington, DE (US)

( * ) Notice: Subject to any disclaimer, the term of this patent is extended or adjusted under 35 U.S.C. 154(b) by 455 days.

(21) Appl. No.: 12/401,348

(22) Filed: Mar. 10, 2009

(65) Prior Publication Data

US 2009/0233903 A1 Sep. 17, 2009

Related U.S. Application Data

(60) Provisional application No. 61/035,662, filed on Mar. 11, 2008, provisional application No. 61/144,982, filed on Jan. 15, 2009.

(51) Int. Cl.
  *C07D 487/04* (2006.01)
  *A61K 31/397* (2006.01)
  *A61P 19/02* (2006.01)
(52) U.S. Cl. .................................. 514/210.21; 544/280
(58) Field of Classification Search .................. 544/280; 514/210.21
  See application file for complete search history.

(56) References Cited

U.S. PATENT DOCUMENTS

| 4,548,990 | A | 10/1985 | Mueller et al. |
|---|---|---|---|
| 5,521,184 | A | 5/1996 | Zimmermann |
| 6,335,342 | B1 | 1/2002 | Longo et al. |
| 6,486,322 | B1 | 11/2002 | Longo et al. |
| 6,579,882 | B2 | 6/2003 | Stewart et al. |
| 7,005,436 | B2 | 2/2006 | Lloyd et al. |
| 2003/0165576 | A1 | 9/2003 | Fujii et al. |
| 2004/0009222 | A1 | 1/2004 | Chou et al. |
| 2004/0009983 | A1 | 1/2004 | Cox et al. |
| 2004/0198737 | A1 | 10/2004 | Cox et al. |
| 2005/0153989 | A1 | 7/2005 | Grotzfeld et al. |
| 2006/0004010 | A1 | 1/2006 | Habashita et al. |
| 2006/0106020 | A1 | 5/2006 | Rodgers et al. |
| 2006/0183761 | A1 | 8/2006 | Ledeboer et al. |
| 2006/0183906 | A1 | 8/2006 | Rodgers et al. |
| 2007/0135461 | A1 | 6/2007 | Rodgers et al. |
| 2007/0149506 | A1 | 6/2007 | Arvanitis et al. |
| 2008/0188500 | A1 | 8/2008 | Arvanitis et al. |
| 2008/0207584 | A1 | 8/2008 | Habashita et al. |
| 2008/0312258 | A1 | 12/2008 | Rodgers et al. |
| 2008/0312259 | A1 | 12/2008 | Rodgers et al. |
| 2009/0181959 | A1 | 7/2009 | Rodgers et al. |
| 2010/0022522 | A1 | 1/2010 | Rodgers et al. |
| 2011/0223210 | A1 | 9/2011 | Rodgers et al. |
| 2011/0224157 | A1 | 9/2011 | Rodgers et al. |

FOREIGN PATENT DOCUMENTS

| DE | 30 36 390 | 5/1982 |
|---|---|---|
| WO | WO 97/02262 | 1/1997 |
| WO | WO 97/02266 | 1/1997 |
| WO | WO 99/62908 | 12/1999 |
| WO | WO 99/65908 | 12/1999 |
| WO | WO 99/65909 | 12/1999 |
| WO | WO 00/09495 | 2/2000 |
| WO | WO 00/53595 | 9/2000 |
| WO | WO 00/63168 | 10/2000 |
| WO | WO 01/14402 | 3/2001 |
| WO | WO 01/42246 | 6/2001 |
| WO | WO 01/64655 | 9/2001 |
| WO | WO 02/00196 | 1/2002 |
| WO | WO 02/00661 | 1/2002 |
| WO | WO 02/055084 | 7/2002 |
| WO | WO 02/060492 | 8/2002 |
| WO | WO 02/096909 | 12/2002 |
| WO | WO 03/011285 | 2/2003 |
| WO | WO 03/024967 | 3/2003 |
| WO | WO 03/037347 | 5/2003 |
| WO | WO 03/048162 | 6/2003 |
| WO | WO 03/099771 | 12/2003 |
| WO | WO 2004/005281 | 1/2004 |
| WO | WO 2004/041814 | 5/2004 |
| WO | WO 2004/046120 | 6/2004 |
| WO | WO 2004/047843 | 6/2004 |
| WO | WO 2004/056786 | 7/2004 |
| WO | WO 2004/072063 | 8/2004 |
| WO | WO 2004/080980 | 9/2004 |
| WO | WO 2004/099204 | 11/2004 |
| WO | WO 2004/099205 | 11/2004 |
| WO | WO 2005/013986 | 2/2005 |
| WO | WO 2005/028444 | 3/2005 |
| WO | WO 2005/051393 | 6/2005 |
| WO | WO 2005/060972 | 7/2005 |
| WO | WO 2005/095400 | 10/2005 |
| WO | WO 2005/105146 | 11/2005 |
| WO | WO 2005/105814 | 11/2005 |
| WO | WO 2005/105988 | 11/2005 |
| WO | WO 2005/110410 | 11/2005 |
| WO | WO/2005/117909 | 12/2005 |
| WO | WO 2005/121130 | 12/2005 |
| WO | WO 2006/013114 | 2/2006 |
| WO | WO 2006/046023 | 5/2006 |

(Continued)

OTHER PUBLICATIONS

Amendment and Response in Reply to Action of Apr. 20, 2007 filed Jul. 17, 2007 for U.S. Appl. No. 11/313,394.
International Search Report and Written Opinion for International Appln. No. PCT/US2005/046207 dated May 15, 2007.
International Search Report and Written Opinion for International Appln. No. PCT/US2006/047369 dated Apr. 24, 2007.
International Search Report and Written Opinion for International Appln. No. PCT/US2009/036635 dated Jun. 3, 2009.
Final Office Action dated Feb. 7, 2008 in connection with U.S. Appl. No. 11/115,702.
Non-final Office Action dated Apr. 20, 2007 in connection with U.S. Appl. No. 11/313,394.
Non-final Office Action dated Aug. 22, 2007 in connection with U.S. Appl. No. 11/115,702.
Non-final Office Action dated Dec. 3, 2007 in connection with U.S. Appl. No. 11/524,641.

(Continued)

*Primary Examiner* — Susanna Moore
(74) *Attorney, Agent, or Firm* — James J. Sales

(57) ABSTRACT

The present invention relates to azetidine and cyclobutane derivatives, as well as their compositions, methods of use, and processes for preparation, which are JAK inhibitors useful in the treatment of JAK-associated diseases including, for example, inflammatory and autoimmune disorders, as well as cancer.

3 Claims, No Drawings

FOREIGN PATENT DOCUMENTS

| WO | WO 2006/046024 | 5/2006 |
|---|---|---|
| WO | WO 2006/056399 | 6/2006 |
| WO | WO 2006/096270 | 9/2006 |
| WO | WO 2006/127587 | 11/2006 |
| WO | WO 2006/129199 | 12/2006 |
| WO | WO 2006/136823 | 12/2006 |
| WO | WO 2007/025090 | 3/2007 |
| WO | WO 2007/041130 | 4/2007 |
| WO | WO 2007/070514 | 6/2007 |
| WO | WO 2007/076423 | 7/2007 |
| WO | WO 2007/084557 | 7/2007 |
| WO | WO 2007/117494 | 10/2007 |

OTHER PUBLICATIONS

Notice of Allowance and Fee(s) Due dated Sep. 21, 2007 in connection with U.S. Appl. No. 11/313,394.
Response to Action of Aug. 22, 2007 dated Nov. 19, 2007 in connection with U.S. Appl. No. 11/115,702.
Response to Restriction Requirement dated May 29, 2007 in connection with U.S. Appl. No. 11/115,702.
Restriction Requirement dated Mar. 6, 2007 in connection with U.S. Appl. No. 11/115,702.
Li et al., entitled "4-Pyrazolyl-N-Arylpyrimidin-2-Amines and 4-Pyrazolyl-N-Heteroarylpyrimidin-2-Amines As Janus Kinase Inhibitors," U.S. Appl. No. 12/270,135, filed Nov. 13, 2008.
Ren et al., "Compounds and Compositions as Protein Kinase Inhibitors," U.S. Appl. No. 60/578,491, filed Jun. 10, 2004.
"INCB18424 Discussion" presentation at the American Society of Hematology, 49th Annual Meeting and Exposition, Atlanta, GA. Abstract #558, Dec. 10, 2007.
26$^{th}$ Annual JPMorgan Healthcare Conference presentation dated Jan. 8, 2008.
Abelson et al., "Alternate reference values for tear film break-up time in normal and dry eye populations", Lacrimal Gland, Tear Film, and Dry Eye Syndromes 3 Part B, Adv Exp Med Biol 2002; 506:1121-1125.
Abelson et al., "Dry eye syndrome: diagnosis, clinical trials, and pharmaceutical treatment—'improving clinical trials'. Lacrimal Gland, Tear Film, and Dry Eye Syndromes 3 Part B", Adv Exp Med Biol 2002; 506:1079-86).
Adv Pharmacol. 2000;47:113-74.
Agents Actions. Jan. 1993;38(1-2):116-21.
Albach et al., "Diagnosis of keratoconjunctivitis sicca in rheumatoid arthritis. The value of various tests", Ophthalmologe Apr. 1994;91(2):229-34—in German (with English abstract/summary).
Barabino et al., Experimental Eye Research 2004, 79, 613-621.
Barr et al., "Corneal scarring in the Collaborative Longitudinal Evaluation of Keratoconus (CLEK) Study: baseline prevalence and repeatability of detection", Cornea 1999;18(1):34-46.
Baudouin et al., "Flow cytometry in impression cytology specimens. A new method for evaluation of conjunctival Inflammation", Invest Ophthalmol Vis Sci 1997a;38:1458-1464.
Begley, et al., "Use of the dry eye questionnaire to measure symptoms of ocular irritation in patients with aqueous tear deficient dry eye", Cornea, 2002:21:664-70).
Bell, Malcolm, and Zalay, Andrew, "Synthesis of Substituted 3-Amino[6, 5-b] triazinoindoles." Journal of Heterocyclic Chemistry, 12(5):1001-1004, Oct. 1975.
Bioreversible Carriers in Drug Design, ed. Edward B. Roche, American Pharmaceutical Association and Pergamon Press, 1987*.
Blume-Jensen P et al, Nature 2001, 411(6835):355-365.
Bolen JB. Nonreceptor tyrosine protein kinases. Oncogene. 1993, 8(8):2025-31.
Bollrath et al., "gp130-Mediated Stat3 Activation in Enterocytes Regulates Cell Survival and Cell-Cycle Progression during Colitis-Associated Tumorigenesis," Cancer Cell, 15:91-102 (2009).
Borie, D.C. et al., Transplantation. Dec. 27, 2005;80(12):1756-64.
Boudny, V., and Kovarik, J., Neoplasm. 49:349-355, 2002.
Bourcier et al., "Expression of CD40 and CD40 ligand in the human conjunctival epithelium", Invest Ophthalmol Vis Sci 2000;41:120-126.
Bowman, T., et al. Oncogene 19:2474-2488, 2000.
Brignole et al., "Expression of Fas antigen (CD95) in the human conjunctival epithelium. Positive correlation with class II HLA DR expression in inflammatory conditions", Exp Eye Res 1998;67:687-697.
Brignole et al., "Flow cytometric analysis of inflammatory markers in conjunctival epithelial cells of patients with dry eyes" Invest Ophthalmol Vis Sci 2000; 41:1356-1363.
Brignole et al., "Flow cytometric analysis of inflammatory markers in KCS: 6-month treatment with topical cyclosporin A", Invest Ophthalmol Vis Sci 2001; 42:90-95.
Brignole et al., "Flow cytometry in conjunctival impression cytology: a new tool for exploring ocular surface pathologies", Exp Eye Res 2004;78:473-481.
Bromberg et al., "Inflammation and Cancer: IL-6 and STAT3 Complete the Link," Cancer Cell, 15:79-80 (2009).
Bron, et al., "Grading of corneal and conjunctival staining in the context of other dry eye tests", Cornea 2003;22(7):640-50.
Bron, et al., "Methodologies to Diagnose and Monitor Dry Eye Disease: Report of the Diagnostic Methodology Subcommittee of the International Dry Eye Workshop (2007)", The Ocular Surface, 5(2), 108-152 (Apr. 2007).
Burger, R., et al. Hematol J. 2:42-53, 2001.
Candotti, F., L. Notarangelo, et al. (2002). "Molecular aspects of primary immunodeficiencies: lessons from cytokine and other signaling pathways." J Clin Invest 109(10): 1261-9.
Candotti, F., S. A. Oakes, et al. (1997). "Structural and functional basis for JAK3-deficient severe combined immunodeficiency." Blood 90(10): 3996-4003.
Carey and Sundberg, Advanced Organic Chemistry, Part B: Reactions and Synthesis, 4th ed., Kluwer Academic/Plenum Publishers:New York, pp. 111-119 (2001).
Carey and Sundberg, Advanced Organic Chemistry, Part B: Reactions and Synthesis, 4th ed., Kluwer Academic/Plenum Publishers:New York, pp. 747-757, 2001.
Cermak et al, "Is complete androgen insensitivity syndrome associated with alterations in the meibomium gland and ocular surface", Cornea 2003;22:516-521.
Cetkovic-Cvrlje, M., A. L. Dragt, et al. (2003). "Targeting JAK3 with JANEX-1 for prevention of autoimmune type 1 diabetes in NOD mice." Clin Irnmunol 106(3): 213-25, 2005.
Chalandon, Yves, and Schwaller, Jürg, "Targeting mutated protein tyrosine kinases and their signaling pathways in hematologic malignancies." Hematologica, 90:949-968.
Changelian, P.S. et al. Science, 2003, 302, 875-878.
Chen, C.L. et al., "Stat3 Activation in Human Endometrial and Cervical Cancer", British journal of Cancer, 96,, 591-599, 2007.
Chew et al., "An instrument for quantifying meibomian lipid on the lid margin: the Meibometer", Curr Eye Res 1993a;12:247-254.
Chew et al., "The casual level of meibomian lipids in humans", Current Eye Research 1993b;12:255 -259.
Cho et al, "Review of the tear break-up time and a closer look at the tear break-up time of Hong Kong Chinese", Optom Vis Sci 1993;70(1):30-8.
Conklyn, M. et al., Journal of Leukocyte Biology, 2004, 76, 1248-1255.
Craig et al. Tear lipid layer structure and stability following expression of the meibomian glands. Ophthalmic Physiol Opt 1995, 15(6):569-74.
Current Protocols in Immunology, vol. 3., Coligan, J.E. et al, Wiley Press*, 2003.
Daniels et al., "Imatinib mesylate inhibits the profibrogenic activity of TGF-β and prevents bleomycinmediated lung fibrosis." J. Clin. Invest., 114(9):1308-1316, Nov. 2004.
Danjo et al., "Observation of precorneal tear film in patients with Sjogren's syndrome", Acta Ophthalmol Scand 1995;73:501-5.
De Vos, J., M. Jourdan, et al. (2000). "JAK2 tyrosine kinase inhibitor tyrphostin AG490 downregulates the mitogen-activated protein kinase (MAPK) and signal transducer and activator of transcription (STAT) pathways and induces apoptosis in myeloma cells." Br J Haematol 109(4): 823-8.
Deuse, T. et al., Transplantation, 2008, 85(6) 885-892.
Doane, "An instrument for in vivo tear film interferometry", Optom Vis Sci 1989; 66: 383-8.

Doleschall G., and Lempert, K. "Thermal and Acid Catalysed Degradations of 3-Alkylthio-6,7-Dihydro-[I.2.4]Triazino[1.6-c]Quinazolin-5-Ium-I-Olates," Tetrahedron, 30:3997-4012, 1974.
Dudley, A.C. et al. Biochem. J. 2005, 390(Pt 2):427-36.
Einmahl, *Adv. Drug. Deliv. Rev.* 53:45-73 (2001), which is incorporated herein by reference in its entirety), or a tamarind seed polysaccharide (e.g., as described in Ghelardi, et al., Antimicrob. Agents Chemother. 48:3396-3401 (2004).
Eliason, et al., "Staining of the conjunctiva and conjunctival tear film", Br J Ophthalmol 1990;74:519-22.
Farrell et al., "A classification for dry eyes following comparison of tear thinning time with Schirmer tear test", Acta Ophthalmol (Copenh) 1992; 70(3):357-60.
Farrell et al., "A clinical procedure to predict the value of temporary occlusion therapy in keratoconjunctivitis sicca" Ophthal Physiol Opt 2003;23:1-8.
Farris, "Tear osmolarity—a new gold standard?" Adv Exp Med Biol 350:495-503, 1994.
Fridman, J. et al. "Selective JAK Inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13$^{th}$ Congress, Jun. 12-15, Copenhagen, Denmark.
Fridman, Jordan et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Abstract #3538, poster #757, Dec. 10, 2007.
Fridman, Jordan et al. "Efficacy and Tolerability of Novel JAK Inhibitors in Animal Models of Rheumatoid Arthritis" poster presented at the ACR/ARHP (American College of Rheumatology/Association of Rheumatology Health Professionals) Scientific Meeting 2007, Boston, MA. Nov. 10, 2007. Abstract 1771, poster 285.
Fridman, Jordan, et al. "Discovery and Preclinical Development of Selective JAK Inhibitors for the Treatment of Myeloproliferative Disorders" poster presented at the 4th International Congress on Myeloproliferative Diseases and Myelodysplastic Syndromes, New York, NY. Nov. 8-10, 2007. Poster 0009.
Fridman, Jordan, et al. "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007.
Fujihara et al., "Evaluation of human conjunctival epithelium by a combination of brush cytology and flow cytometry: an approach to the quantitative technique", Diagn Cytopathol 1997;17:456-60.
Fukagawa et al., "Histological evaluation of brush cytology of rabbit conjunctiva", Nippon Garika Gakkai Zasshi 1993;97:1173-8.
Gaertner, "Cyclization ofl-Alkylamino-3-halo-2-alkanolst o 1-Alkyl-3-azetidinols," *J. Org. Chem.*, 1967, 32, 2972.
Glasson et al., "Differences in clinical parameters and tear film of tolerant and intolerant contact lens wearers", Invest Ophthalmol Vis Sci 2003;44:5116-5124.
Gobbels et al., Tear secretion in dry eyes as assessed by objective fluorophotometry. Ger J Ophthalmol 1992; 1:350-353.
Golding et al., "X-ray and scanning electron microscopic analysis of the structural composition of tear ferns", Cornea Jan. 1994;13(1):58-66.
Gooseman et al., "The intramolecular *b*-fluorine . . . ammonium interaction in 4- and 8- membered rings," Chemical Communications v. 30, pp. 3190-3192, 2006.
Gorre, M.E. et al., "Clinical Resistance to STI-571 Cancer Therapy Caused by BCR-ABL Gene Mutation or Amplification." Science, 293:876, 2001.
Gotlieb, Alice, Presentation at the 2008 American Academy of Dermatology, 66th Annual Meeting, San Antonio, TX. Feb. 1, 2008, symposium-303.
Goto et al., Color mapping of tear lipid layer thickness distribution from the image analysis in DR-1 tear lipid layer interference images (ARVO abstract). ARVO 2004.
Goto et al., "Computer-synthesis of an interference color chart of human tear lipid layer by a colorimetric approach",Invest Ophthalmol Vis Sci 2003;44:4693-7.
Goto et al., "Differentiation of lipid tear deficiency dry eye by kinetic analysis of tear interference images", Arch Ophthalmol 2003;121:173-80.
Goto et al., "Evaluation of the tear film stability after laser in situ keratomileusis using the tear film stability analysis system", Am J Ophthalmol 2004b Jan;137(1):116-20.
Goto et al., "Tear Film Stability Analysis System: Introducing a new application for videokeratography", Cornea 2004a; Nov;23(8):S65-S70.
Goto, et al., Kinetic analysis of tear interference images in aqueous tear deficiency dry eye before and after punctal occlusion. Invest Ophthalmol Vis Sci 2003;44:1897-905.
Gottlieb, A.B., et al, Nat Rev Drug Disc., 2008, 4:19-34.
Green, T.W., and P.G.M. Wuts, Protective Groups in Organic Synthesis, 3rd. Ed., Wiley & Sons, Inc., New York (1999)*.
Grivennikov, et al., "IL-6 and STAT3 are required for survival of intestinal epithelial cells and the development of colitis-associated cancer", *Cancer Cell*, 15:103-111 (2009).
Groneberg et al., "Animal models of allergic and inflammatory conjunctivitis," Allergy 2003, 58, 1101-1113.
Guillon, "Tear film photography and contact lens wear", J Br Contact Lens Assoc 1982;5:84-7.
Hamzé, "Synthesis of Various 3-Substituted 1,2,4-Oxadiazole-Containing Chiral $\beta^3$-and r-Amino Acids from Fmoc-Protected Aspartic Acid," J. Org. Chem., 2003, 68(19), pp. 7316-7321.
Helal et al., "Stereoselective Synthesis of *cis*-1,3-Disubstituted Cyclobutyl Kinase Inhibitors," Organic Letters (2004), 6(11), pp. 1853-1856.
Higuchi, T. and V. Stella, "Pro-drugs as Novel Delivery Systems," vol. 14 of the A.C.S. Symposium Series*, 1975.
Holly et al., "Lacrimation kinetics in Humans as determined by a novel technique", in Holly FJ (ed). The preocular tear film. Lubbock TX, Lubbock Dry Eye Institute, 1986, pp. 76-88).
Immunol Today. Jan. 1998;19(1):37-44.
Ishizaki, T. et al. Molecular Pharmacology, 2000, 57, 976-983.
Itagaki, Noriaki; Kimura, Mari; Sugahara, Tsutomu; Iwabuchi, Yoshiharu. (Organic Letters 2005; 7(19); 4181-4183.
James, C., et al. Nature 434:1144-1148, 2005.
Jester et al., "In vivo biomcroscopy and photography of meibomian glands in a rabbit model of meibomian gland dysfunction", Invest Ophthalmol Vis Sci 1982;22:660-7.
Johnson et al., "The effect of instilled fluorescein solution volume on the values and repeatability of TBUT measurements", Cornea 2005;24:811-7.
Journal of Pharmaceutical Science, 66, 1 (1977).
Kaercher, "Ocular symptoms and signs in patients with ectodermal dysplasia symdromes", Grafes Arch Clin Exp Ophthalmol 2004;495-500.
Kawamura, M., D. W. McVicar, et al. (1994). "Molecular cloning of L-JAK, a Janus family protein-tyrosine kinase expressed in natural killer cells and activated leukocytes." Proc Natl Acad Sci U S A 91(14): 6374-8).
Kharas, Michael, and Fruman, David, "ABL Oncogenes and Phosphoinositide 3-Kinase: Mechanism of Activation and Downstream Effectors." Cancer Res., 65(6):2047-2053, Mar. 15, 2005.
King-Smith et al., "Three interferometric methods for measuring the thickness of layers of the tear film", Optom Vis Sci 1999;76:19-32.
Kojima et al., "A new noninvasive tear stability analysis system for the assessment of dry eyes" Invest Ophthalmol Vis Sci 2004;May;45(5):1369-74).
Komuro et al., "Assessment of meibomian gland function by a newly developed laser meibometer", Adv Exp Med Biol 2002;506:517-520.
Korb et al., "The effect of two novel lubricant eye drops on tear film lipid layer thickness in subjects with dry eye symptoms", Optom Vis Sci 2005; 82: 594-601.
Korb, et al., "Increase in tear film lipid layer thickness following treatment of meibomian gland dysfunction", Adv Exp Med Biol 1994;350:293-8.
Kortylewski, et al., "Regulation of the IL-23 and IL-12 balance by Stat3 signaling in the tumor microenvironment", *Cancer Cell*, 15:114-123 (2009).

Kruh et al., "The complete coding sequence of arg defines the Abelson subfamily of cytoplasmic tyrosine kinases." Proc. Natl. Acad. Sci., 87:5802-5806, Aug. 1990.

Kubinyi, H. "QSAR: Hansch Analysis and Related Approaches," Methods and Principles in Medicinal Chemistry, Manhold, R. ed. Weinhein, NY, 1993.

Kudelacz, E. et al. European Journal of Pharmacology 582 (2008) 154-161.

Kuppens et al., "Basal tear turnover and topical timolol in glaucoma patients and healthy controls by Fluorophotometry", Invest Ophthalmol Vis Sci 1992; 33:3442-3448.

Lemp "Report of National Eye Institute/Industry Workshop on clinical trials in dry eyes", CLAO J 1995;21:221-232.

Lemp et al., "Corneal desiccation despite normal tear volume", Ann Ophthalmol 1970;284:258-261.

Lemp, "The Definition and Classification of Dry Eye Disease: Report of the Definition and Classification Subcommittee of the International Dry Eye WorkShop", The Ocular Surface, 5(2), 75-92 Apr. 2007.

Levine, et al., Cancer Cell, vol. 7, 2005: 387-397.

Levy, R. et al. "INCB018424 A Selective Janus Kinase 1/2 Inhibitor" Presentation at the $50^{th}$ American Society of Hematology Annual Meeting (ASH), Dec. 8, 2008.

Lin, Q. et al., "Enantioselective synthesis of Janus kinase inhibitor INCB018424 via an organocatalytic aza-Michael reaction," Organic Letters (2009), 11(9), 1999-2002.

Madden et al. Comparative study of two non-invasive tear film stability techniques. Curr Eye Res 1994; 13(4):263-9.

Madhusudan S, Ganesan TS. Tyrosine kinase inhibitors in cancer therapy. Clin Biochem. 2004, 37(7):618-35.

Mainstone et al., "Tear meniscus measurement in the diagnosis of dry eye", Curr Eye Res 1996; 15:653-661.

Manning, G. et al., Science. 2002, 298(5600):1912-1934.

March, Advanced Organic Chemistry: Reactions, Mechanisms, and Structure, 3rd ed., John Wiley & Sons:NewYork, pp. 845-855 (1985).

Marquardt et al., "Modification of tear film break-up time test for increased reliability" in Holly ed. The Preocular Tear Film inHealth, Disease and Contact Lens Wear. Lubbock, Texas: Dry Eye Institute, 1986:57-63.

Maruyama et al., "Effect of environmental conditions on tear dynamics in soft contact lens wearers", Invest Ophthalmol Vis Sci 2004;45(8):2563-8.

Mathers et al., "Assessment of the tear film with tandem scanning confocal microscopy", Cornea 1997;16:162-8.

Mathers et al., "Tear film changes associated with normal aging", Cornea 1996; 15:229-334.

Mathers et al., "Tear flow and evaporation in patients with and without dry eye", Ophthalmology 1996; 103:664-669.

Mathers et al., "Video imaging of the meibomian gland", Arch Ophthalmol 1994;112:448-9.

Mathers, "Evaporation from the ocular surface", Exp Eye Res 2004; 78:389-394.

McNamara et al., "Fluorometry in contact lens research: The next step", Optom Vis Sci 1998; 75:316-322.

Mengher et al., "Non-invasive tear film break-up time: sensitivity and specificity", Acta Ophthalmol (Copenh) 1986; 64(4):441-4.

Mesa, R.A., et al. "INCB018424, A Selective JAK 1/2 Inhibitor, Significantly Improves the Compromised Nutritional Status and Frank Cachexia in Patients with Myelofibrosis (MF)" Poster #1760 at the American Society of Hematology Annual Meeting (ASH), Dec. 6, 2008.

Methods in Molecular Biology: vol. 225, Inflammation Protocols., Winyard, P.G. and Willoughby, D.A., Humana Press, 2003*.

Milici, A.J., et al., Arthritis Research & Therapy 2008, 10:R14 (http://arthritis-research.com/content/10/1/R14).

Mishima S, "Determination of tear volume and tear flow", Invest Ophthalmol 1966; 5:264-275.

Mishima, "Some physiological aspects of the precorneal tear film", Arch Ophthalmol 1965;73:233-241.

Miyaura and Suzuki, "Palladium-Catalyzed Cross-Coupling Reactions of Organoboron Compounds," Chem. Rev. 1995, 95, 2457-2483.

Miyoshi et al., "Interleukin-8 concentrations in conjunctival epithelium brush cytology samples correlate with neutrophil, eosinophil infiltration, and corneal damage", Cornea 2001;20:743-7.

Moreland, L. et al. "A Randomized Placebo-Controlled Study of INCB018424, a Selective Janus Kinase 1&2 (JAK 1&2) Inhibitor in Rheumatoid Arthritis (RA)" Presentation at the American College of Rheumatology meeting, Oct. 26, 2008.

Nakagawara, Akira, "Trk receptor tyrosine kinases: A bridge between cancer and neural development." Cancer Letters, 169:107-114, 2001.

Nally et al., "Ocular discomfort and tear film break-up time in dry eye patients: A correlation", Invest Ophthalmol Vis Sci 2000;41:4:1436.

Nelson et al., "Tear film osmolality determination: an evaluation of potential errors in measurement" Curr Eye Res Sep.;5(9):677-81, 1986.

Neubauer, H., A. Cumano, et al. (1998). Cell 93(3): 397-409.

Nichols et al., "The lack of association between signs and symptoms in patients with dry eye disease", Cornea 2004; 23:762-770.

Nichols et al., "The repeatability of clinical measurements of dry eye" Cornea 2004;23:272-85.

Nicholoff, B. J. et al., "Recent insights into the immunopathogenesis of psoriasis provide new therapeutic opportunities", *The Journal of Clinical Investigation*, vol. 113, No. 12, Jun. 2004, pp. 1664-1674.

Nishio, M. et al. FEBS Letters, 1999, 445, 87-91.

Norn, "Quantitative tear ferning. Clinical investigations", Acta Ophthalmol (Copenh) Jun. 1994;72(3):369-72.

Oguz et al., "The height and radius of the tear meniscus and methods for examining these parameters", Cornea 2000;19:497-500.

Ortmann, R. A., T. Cheng, et al. (2000). "Janus kinases and signal transducers and activators of transcription: their roles in cytokine signaling, development and immunoregulation." Arthritis Res 2(1): 16-32.

Ousler et al., "Factors that influence the inter-blink interval (IBI) as measured by the ocular protection index (OPI)", (Poster presentation) ARVO 2002.

Palmer, Amparo, and Klein, Rudiger, "Multiple roles of ephrins in morphogenesis, neuronal networking, and brain function." *Genes & Dev.*, 17:1429-1450, 2003.

Parganas, E., D. Wang, et al (1998). Cell 93(3): 385-95.

Park et al., Analytical Biochemistry 1999, 269, 94-104.

Patani, G.A. et al. Chem. Rev. 1996, 96, 3147-3176.

Pearce et al., "Spatial location studies on the chemical composition of human tear ferns", Ophthalmic Physiol Opt 2000;JuI;20(4):306-13.

Pearce, "An improved fluorophotometric method for tear turnover assessment", Optom Vis Sci 2001; 78:30-36).

Pensyl et al., "The repeatability of tear mucus ferning grading", Optom Vis Sci Aug. 1998;75(8):600-4.

Pernis, A. B. and P. B. Rothman (2002). "JAK-STAT signaling in asthma." J Clin Invest 109(10): 1279-83.

Pflugfelder, et al., "Evaluation of subjective assessments and objective diagnostic tests for dianosing tear-film disorders known to cause ocular irritation", Cornea 1998;17(1):38-56.

Pirard, B. et al. J. Chem. Inf. Comput. Sci. 2000, 40, 1431-1440.

Pisella et al., Flow cytometric analysis of conjunctival epithelium in ocular rosacea and keratoconjunctivitis sicca. Ophthalmology 2000;107:1841-1849.

Pisella, et al., Conjunctival proinflammatory and proapoptotic effects of latanoprost, preserved timolol and unpreserved timolol: an ex vivo and in vitro study. Invest Ophthalmol Vis Sci 2004;45:1360-1368).

Poster/presentation by Punwani et al. "Initial Efficacy and Safety of Topical INCYB018424 Cream, a Selective Janus Kinase 1&2 (JAK 1&2) Inhibitor in Psoriasis" $17^{th}$ Congress of the European Academy of Dermatology and Venereology, Paris, France, Sep. 17, 2008.

Press Release dated Sep. 18, 2008: "Incyte's Topical JAK Inhibitor Demonstrates Positive Proof-of-Concept Results in Patients with Mild to Moderate Psoriasis".

Quesada et al, Tetrahedron, 62 (2006) 6673-6680.

Remington's Pharmaceutical Sciences, 17th ed., Mack Publishing Company, Easton, Pa., 1985, p. 1418.

Robin et al., In vivo transillumination biomicroscopy and photography of meibomian gland dysfunction. Ophthalmology 1985;92:1423-6.

Rodig, S. J., M. A. Meraz, et al. (1998). "Disruption of the Jak1 gene demonstrates obligatory and nonredundant roles of the Jaks in cytokine-induced biologic responses." Cell 93(3): 373-83.

Rolando et al., "Tear mucus crystallization in children with cystic fibrosis", Ophthalmologica 1988;197(4):202-6).

Rolando et al., "Tear mucus ferning test in keratoconjunctivitis sicca",in: Holly FJ, Lamberts DW, MacKeen DL (eds.): The preocular tear film in health, disease, and contact lens wear,. 1st Intern Tear Film Symposium. Lubbok (Texas, USA), Dry Eye Institute, 1986, 203-210.

Rolando et al., "The effect of hyperosmolarity on tear mucus ferning", Fortschr Ophthalmol 1986;83:644-646.

Rolando, Tear mucus ferning test in normal and keratoconjunctivitis sicca eyes. Chibret Int J Ophthalmol 1984;2(4):32-41.

Rousvoal, G. et al. Transpl Int. Dec. 2006;19(12):1014-21.

Saemann, M. D., C. Diakos, et al. (2003). "Prevention of CD40-triggered dendritic cell maturation and induction of T-cell hyporeactivity by targeting of Janus kinase 3." Am J Transplant 3(11): 1341-9.

Saettone et al. "Ocular inserts for topical delivery," *Advanced Drug Delivery Reviews* 16: 95-106, 1998.

Schrader et al., "Animal Models of Dry Eye," Developmental Opthalmology, Karger 2008, 41, 298-312.

Scott, M. J., C. J. Godshall, et al. (2002). "Jaks, STATs, Cytokines, and Sepsis." Clin Diagn Lab Immunol 9(6): 1153-9.

Seto, Y., H. Nakajima, et al. (2003). "Enhanced Th2 cell-mediated allergic inflammation in Tyk2-deficient mice." J Immunol 170(2): 1077-83.

Shah et al., "Multiple BCR-ABL kinase domain mutations confer polyclonal resistance to the tyrosine kinase inhibitor imatinib (STI571) in chronic phase and blast crisis chronic myeloid leukemia." Cancer Cell, 2:117-125, Aug. 2002.

Shimazaki et al., "Meibomian gland dysfunction in patients with Sjogren syndrome", Ophthalmology 1998;105(8):1485-8.

Smith et al, "Basic pathogenic mechanisms operating in experimental model acute anterior uveitis," Immunology and Cell Biology 1998, 76, 497-512.

Sriram, K. et al. J. Biol. Chem. 2004, 279(19):19936-47, Epub Mar. 2, 2004.

Staerk, J., et al. JBC 280:41893-41899, 2005.

Sullivan et al., 4th International Conference on the Lacrimal Gland, Tear Film & Ocular Surface and Dry Eye Syndromes, Nov. 2004.

Takano et al., "Inflammatory cells in brush cytology samples correlate with the severity of corneal lesions in atopic keratoconjunctivitis", Br J Ophthalmol 2004;88:1504-5.

Takemoto, S., J. C. Mulloy, et al. (1997). "Proliferation of adult T cell leukemia/lymphoma cells is associated with the constitutive activation of JAK/STAT proteins." Proc Natl Acad Sci U S A 94(25): 13897-902.

Tefferi, A. et al. "The Clinical Phenotype of Myelofibrosis Encompasses a Chronic Inflammatory State that is Favorably Altered by INCB018424, A Selective Inhibitor of JAK1/2" Poster #2804 at the American Society of Hematology Annual Meeting (ASH), Dec. 7, 2008.

Thompson, J.E., et al. Bioorganic & Medicinal Chemistry Letters 12 (2002) 1219-1223.

Tiffany et al., Meniscometry using the Tearscope-plus (ARVO abstract). Invest Ophthalmol Vis Sci 2001;42, s37.

Tiffany, "Refractive index of meibomian and other lipids", Cuff Eye Res 1986;5:887-9.

Tsubota et al., "Brush cytology for the evaluation of dry-eye", Nippon Ganka Gakkai Zasshi 1990a ;94:224-30; in Japanese with English abstract.

Tsubota et al., "Conjunctival brush cytology", Acta Cytol 1990 b;34:233-5.

Tsubota et al., "Detection by brush cytology of mast cells and eosinophils in allergic and vernal conjunctivitis"; Cornea 1991;10:525-31).

Van Best et al., "Measurement of basal tear turnover using a standardized protocol", Graefe's Arch Clin Exp Ophthalmol 1995; 233:1-7.

van Bijsterveld, "Diagnostic tests in the sicca syndrome" Arch Ophthalmol 1969;82:10-14.

Verstovsek, S. et al. "Characterization of JAK2 V617F Allele Burden in Advanced Myelofibrosis (MF) Patients: No Change in V617F:WT JAK2 Ratio in Patients with High Allele Burdens Despite Profound Clinical Improvement Following Treatment with the JAK Inhibitor INCB018424" Poster #2802 at the American Society of Hematology Annual Meeting (ASH), Dec. 7, 2008.

Verstovsek, S. et al. "The JAK Inhibitor INCB018424 Demonstrates Durable and Marked Clinical Responses in Primary Myelofibrosis (PMF) and Post-Polycythemia/Essential Thrombocythemia Myelofibrosis (Post-PV/ET-MF)" Poster #1762 at the American Society of Hematology Annual Meeting (ASH), Dec. 6, 2008.

Verstovsek, S. et al. "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #0444, presented Saturday Jun. 14, 2008 at the European Hematology Association, 13$^{th}$ Congress, Jun. 12-15, Copenhagen, Denmark.

Verstovsek, S. et al. INCB18424, an Oral, Selective JAK2 Inhibitor, Shows Significant Clinical Activity in a Phase I/II Study in Patient with Primary Myelofibrosis (PMF) and Post Polycythemia Vera/ Essential Thrombocythemia Myelofibrosis (Post-PV/ET MF), presentation at the American Society of Hematology 49th Annual Meeting and Exposition, Dec. 10, 2007.

Vitali et al. "The European Community Study Group on diagnostic criteria for Sjogren's syndrome. Sensitivity and specificity of tests for ocular and oral involvement in Sjogren's syndrome." 1992; *Ann Rheum Dis*, 53(10): 637-47.

W. Williams, et al. "Initial Efficacy of INCB018424, a selective Janus Kinase1& 2 (JAK1&2) Inhibitor in Rheumatoid Arthritis (RA)." W. Williams, European League Against Rheumatism (EULAR) meeting presentation and abstract (Jun. 11-14, 2008, Paris, France). *Annals Rheum Dis* 67SII:62, 2008.

Wagh, et al., "Polymers used in ocular dosage form and drug delivery systems", *Asian J. Pharm.*, pp. 12-17 (Jan. 2008).

Welch et al., "An approach to a more standardized method of evaluating tear film break-up time" Invest Ophthalmol Vis Sci 2003; 2485/B324.

White et al., "Human basic tear fluid osmolality. I. Importance of sample collection strategy", Acta Ophthalmol (Copenh) Aug.;71(4):524-9, 1993.

Wu T.Y.H., et al. Organic Letters, 2003, 5(20), 3587-3590.

Yokoi et al., "A newly developed video-meibography system featuring a newly designed probe", Jpn J Ophthalmol 2007; 51: 53-6).

Yokoi et al., "Assessment of meibomian gland function in dry eye using meibometry", Arch Ophthalmol 1999;117:723-9).

Yokoi et al., "Correlation of tear lipid layer interference patterns with the diagnosis and severity of dry eye", Am J Ophthalmol 1996;122:818-24.

Yokoi et al., "Non-invasive methods of assessing the tear film", Exp Eye Res 2004;78:399-407).

Zou, Xiaoming, and Calame, Kathryn, "Signaling Pathways Activated by Oncogenic Forms of Abl Tyrosine Kinase." Journal of Biological Chemistry, 274(26):18141-18144, 1999.

AZETIDINE AND CYCLOBUTANE DERIVATIVES AS JAK INHIBITORS

CROSS-REFERENCE TO RELATED APPLICATIONS

This application claims the benefit of U.S. Ser. No. 61/035,662, filed Mar. 11, 2008, and U.S. Ser. No. 61/144,982, filed Jan. 15, 2009, the disclosures of each of which are incorporated herein by reference in their entireties.

FIELD OF THE INVENTION

The present invention relates to azetidine and cyclobutane derivatives, as well as their compositions and methods of use and preparation, which are JAK inhibitors useful in the treatment of JAK-associated diseases including, for example, inflammatory and autoimmune disorders, as well as cancer.

BACKGROUND OF THE INVENTION

Protein kinases (PKs) are a group of enzymes that regulate diverse, important biological processes including cell growth, survival and differentiation, organ formation and morphogenesis, neovascularization, tissue repair and regeneration, among others. Protein kinases exert their physiological functions through catalyzing the phosphorylation of proteins (or substrates) and thereby modulating the cellular activities of the substrates in various biological contexts. In addition to the functions in normal tissues/organs, many protein kinases also play more specialized roles in a host of human diseases including cancer. A subset of protein kinases (also referred to as oncogenic protein kinases), when dysregulated, can cause tumor formation and growth, and further contribute to tumor maintenance and progression. Thus far, oncogenic protein kinases represent one of the largest and most attractive groups of protein targets for cancer intervention and drug development.

The Janus Kinase (JAK) family plays a role in the cytokine-dependent regulation of proliferation and function of cells involved in immune response. Currently, there are four known mammalian JAK family members: JAK1 (also known as Janus kinase-1), JAK2 (also known as Janus kinase-2), JAK3 (also known as Janus kinase, leukocyte; JAKL; L-JAK and Janus kinase-3) and TYK2 (also known as protein-tyrosine kinase 2). The JAK proteins range in size from 120 to 140 kDa and comprise seven conserved JAK homology (JH) domains; one of these is a functional catalytic kinase domain, and another is a pseudokinase domain potentially serving a regulatory function and/or serving as a docking site for STATs.

Blocking signal transduction at the level of the JAK kinases holds promise for developing treatments for inflammatory diseases, autoimmune diseases, myeloproliferative diseases, and human cancers, to name a few. Inhibition of the JAK kinases is also envisioned to have therapeutic benefits in patients suffering from skin immune disorders such as psoriasis, and skin sensitization. Accordingly, inhibitors of Janus kinases or related kinases are widely sought and several publications report effective classes of compounds. For example, certain JAK inhibitors, including pyrrolopyridine and pyrrolopyrimidines, are reported in U.S. Ser. No. 11/637,545, filed Dec. 12, 2006.

Thus, new or improved agents which inhibit kinases such as Janus kinases are continually needed for developing new and more effective pharmaceuticals to treat cancer and other diseases. The compounds and processes described herein are directed toward these needs and other ends.

SUMMARY OF THE INVENTION

The present invention provides, inter alia, JAK inhibitors of Formulas I, II, III, and IV:

I

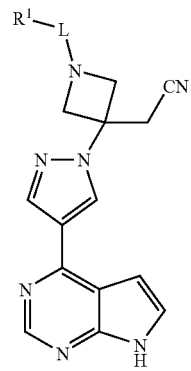

II

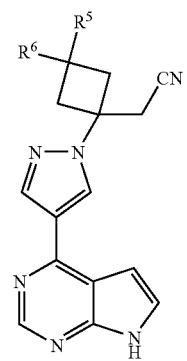

III

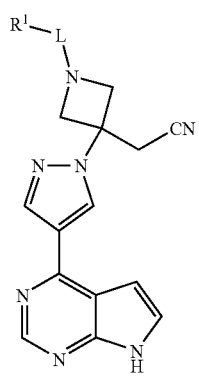

IV

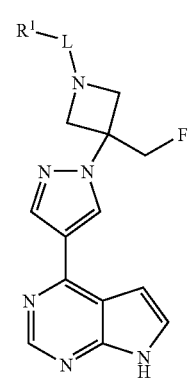

or pharmaceutically acceptable salts thereof, wherein constituent members are defined below.

The present invention further provides pharmaceutical compositions comprising a compound of Formula I, II, III, or IV, or a pharmaceutically acceptable salt thereof, and at least one pharmaceutically acceptable carrier.

The present invention further provides methods of treating any of the various JAK-associated diseases and disorders named herein by administering to a patient a therapeutically effective amount of a compound of Formula I, II, III, or IV, or a pharmaceutically acceptable salt of the same.

The present invention further provides methods for the preparation of the compounds of Formulas I, II, III, and IV.

DETAILED DESCRIPTION

The present invention provides, inter alia, JAK inhibitors of Formula I:

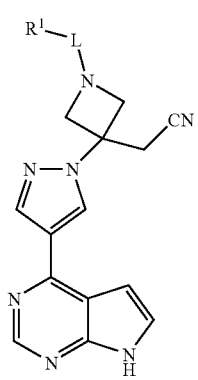

I or pharmaceutically acceptable salts thereof, wherein:

L is $SO_2$ or CO;

$R^1$ is $C_{1-6}$ alkyl, $C_{3-7}$ cycloalkyl, phenyl, 5- or 6-membered heteroaryl, indolyl, $NR^2R^3$, or $OR^4$, wherein said alkyl, cycloalkyl, phenyl, or heteroaryl is optionally substituted with 1, 2, or 3 substituents independently selected from F, CN, and $C_{1-4}$ alkyl;

$R^2$ and $R^3$ are independently selected from H, $C_{1-4}$ alkyl, and phenyl; and $R^4$ is $C_{1-6}$ alkyl, phenyl, or benzyl.

In some embodiments, when L is $SO_2$, then $R^1$ is other than $OR^4$.

In some embodiments, when L is $SO_2$, then $R^1$ is $C_{1-6}$ alkyl, $C_{3-7}$ cycloalkyl, phenyl, 5- or 6-membered heteroaryl, or $NR^2R^3$, wherein said alkyl, cycloalkyl, phenyl, or heteroaryl is optionally substituted with 1, 2, or 3 substituents independently selected from F and $C_{1-4}$ alkyl.

In some embodiments, when L is CO, then $R^1$ is $C_{3-7}$ cycloalkyl, phenyl, 5- or 6-membered heteroaryl, indolyl, $NR^2R^3$, or $OR^4$, wherein said cycloalkyl, phenyl, or heteroaryl is optionally substituted with 1, 2, or 3 substituents independently selected from CN and $C_{1-4}$ alkyl.

In some embodiments, L is $SO_2$.

In some embodiments, L is CO.

In some embodiments, $R^1$ is methyl, ethyl, n-propyl, isopropyl, n-butyl, t-butyl, 2-methylprop-1-yl, 1-methylprop-1-yl, each optionally substituted with 1, 2, or 3 F.

In some embodiments, $R^1$ is $C_{1-4}$ alkyl.

In some embodiments, $R^1$ is ethyl.

In some embodiments, $R^1$ is $C_{3-7}$ cycloalkyl optionally substituted by $C_{1-4}$ alkyl.

In some embodiments, $R^1$ is phenyl optionally substituted with F, methyl, or CN.

In some embodiments, $R^1$ is 5-membered heteroaryl selected from thienyl, pyrazolyl, pyrrolyl, 1,2,4-oxadiazolyl, and isoxazolyl, each optionally substituted with $C_{1-4}$ alkyl.

In some embodiments, $R^1$ is pyridinyl.

In some embodiments, $R^1$ is $NR^2R^3$ or $OR^4$.

In some embodiments, L is $SO_2$ and $R^1$ is $C_{1-6}$ alkyl.

The present invention further provides compounds of Formula II:

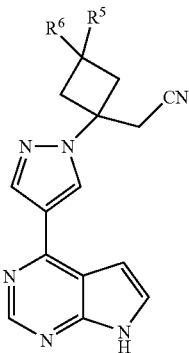

II or pharmaceutically acceptable salts thereof, wherein:

$R^5$ and $R^6$ are independently selected from H, F, CN, OH, $C_{1-4}$ alkyl, benzyloxy, $C_{2-8}$ dialkylaminosulfonyl, and 5-membered heteroaryl, wherein said alkyl is optionally substituted by 1, 2, or 3 substituents selected from F, OH, CN, and $C_{1-4}$ alkoxy, and wherein said 5-membered heteroaryl is optionally substituted with $C_{1-4}$ alkyl.

In some embodiments, when one of $R^5$ and $R^6$ is OH, then the other of $R^5$ and $R^6$ is other than CN or F.

In some embodiments, one of $R^5$ and $R^6$ is H and the other is selected from H, F, CN, OH, $C_{1-4}$ alkyl, benzyloxy, $C_{2-8}$ dialkylaminosulfonyl, and 5-membered heteroaryl, wherein said alkyl is optionally substituted by 1, 2, or 3 substituents selected from F, OH, CN, and $C_{1-4}$ alkoxy, and wherein said 5-membered heteroaryl is optionally substituted with $C_{1-4}$ alkyl.

In some embodiments, $R^5$ and $R^6$ are independently selected from H, F, CN, OH, and methyl.

In some embodiments, $R^5$ and $R^6$ are independently selected from H and CN.

The present invention further provides a compound of Formula III or IV:

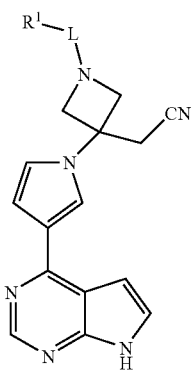

III

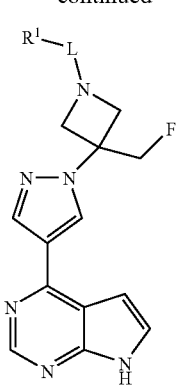

IV or a pharmaceutically acceptable salt thereof, wherein:
L is SO$_2$ or CO;
R$^1$ is C$_{1-6}$ alkyl, C$_{3-7}$ cycloalkyl, phenyl, 5- or 6-membered heteroaryl, indolyl, NR$^2$R$^3$, or OR$^4$, wherein said alkyl, cycloalkyl, phenyl, or heteroaryl is optionally substituted with 1, 2, or 3 substituents independently selected from F, CN, and C$_{1-4}$ alkyl;
R$^2$ and R$^3$ are independently selected from H, C$_{1-4}$ alkyl, and phenyl; and
R$^4$ is C$_{1-6}$ alkyl, phenyl, or benzyl;
wherein when L is SO$_2$, R$^1$ is other than OR$^4$.
In some embodiments, L is SO$_2$.
In some embodiments, L is CO.
In some embodiments, R$^1$ is methyl, ethyl, n-propyl, isopropyl, n-butyl, t-butyl, 2-methylprop-1-yl, 1-methylprop-1-yl, each optionally substituted with 1, 2, or 3 F.
In some embodiments, R$^1$ is C$_{1-4}$ alkyl.
In some embodiments, R$^1$ is ethyl.
In some embodiments, R$^1$ is C$_{3-7}$ cycloalkyl optionally substituted by C$_{1-4}$ alkyl.
In some embodiments, R$^1$ is phenyl optionally substituted with F, methyl, or CN.
In some embodiments, R$^1$ is 5-membered heteroaryl selected from thienyl, pyrazolyl, pyrrolyl, 1,2,4-oxadiazolyl, and isoxazolyl, each optionally substituted with C$_{1-4}$ alkyl.
In some embodiments, R$^1$ is pyridinyl.
In some embodiments, R$^1$ is NR2R or OR$^4$.
In some embodiments, L is SO$_2$ and R$^1$ is C$_{1-6}$ alkyl.

At various places in the present specification, substituents of compounds of the invention are disclosed in groups or in ranges. It is specifically intended that the invention include each and every individual subcombination of the members of such groups and ranges. For example, the term "C$_{1-6}$ alkyl" is specifically intended to individually disclose methyl, ethyl, C$_3$ alkyl, C$_4$ alkyl, C$_5$ alkyl, and C$_6$ alkyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, sec-butyl, t-butyl), pentyl (e.g., n-pentyl, isopentyl, sec-pentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. A linking alkyl group is referred to herein as "alkylene."

As used herein, "cycloalkyl" refers to non-aromatic cyclic hydrocarbons including cyclized alkyl, alkenyl, and alkynyl groups. Cycloalkyl groups can include mono- or polycyclic (e.g., having 2, 3 or 4 fused rings) groups and spirocycles. Ring-forming carbon atoms of a cycloalkyl group can be optionally substituted by oxo or sulfido. Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcamyl, adamantyl, and the like. In some embodiments, the cycloalkyl group is cyclopropyl. Also included in the definition of cycloalkyl are moieties that have one or more aromatic rings fused (i.e., having a bond in common with) to the cycloalkyl ring, for example, benzo or thienyl derivatives of cyclopentane, cyclopentene, cyclohexane, and the like. A cycloalkyl group containing a fused aromatic ring can be attached through any ring-forming atom including a ring-forming atom of the fused aromatic ring.

As used herein, "heteroaryl" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl is pyridinyl. In some embodiments, the heteroaryl is thienyl, pyrazolyl, pyrrolyl, 1,2,4-oxadiazolyl, or isoxazolyl. In some embodiments, the heteroaryl is indolyl. In some embodiments, any ring-forming N in a heteroaryl moiety can be substituted by oxo. In some embodiments, the heteroaryl group has from 1 to about 20 carbon atoms, and in further embodiments from about 3 to about 20 carbon atoms. In some embodiments, the heteroaryl group contains 3 to about 14, 4 to about 14, 3 to about 7, or 5 to 6 ring-forming atoms. In some embodiments, the heteroaryl group has 1 to about 4, 1 to about 3, or 1 to 2 heteroatoms.

As used herein, "benzyloxy" refers to —O-benzyl.
As used herein, "dialkylaminosulfonyl" refers to —SO$_2$—N(alkyl)$_2$.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, amide—imidic acid pairs, enamine—imine pairs, and annular forms where a proton can occupy two or more positions of a heterocyclic system, for example, 1H- and 3H-imidazole, 1H-, 2H- and 4H-1, 2,4-triazole, 1H- and 2H-isoindole, and 1H- and 2H-pyrazole. Tautomeric forms can be in equilibrium or sterically locked into one form by appropriate substitution.

Compounds of the invention further include hydrates and solvates, as well as anhydrous and non-solvated forms.

The term, "compound," as used herein is meant to include all stereoisomers, geometric iosomers, tautomers, and isotopes of the structures depicted.

All compounds, and pharmaceuticaly acceptable salts thereof, can be found together with other substances such as water and solvents (e.g. hydrates and solvates) or can be isolated.

Compounds of the invention can also include all isotopes of atoms occurring in the intermediates or final compounds. Isotopes include those atoms having the same atomic number but different mass numbers. For example, isotopes of hydrogen include tritium and deuterium.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

The present invention provides a method of forming a compound of Formula I as shown below in Schemes 1, 2, and 3. Accordingly, in step (i) of Scheme 1, the compound of Formula I is prepared by a method comprising treating a compound of Formula Ia:

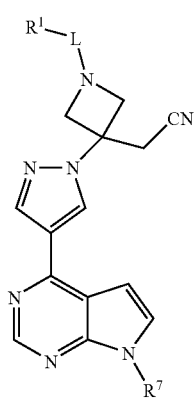

to remove the R$^7$ moiety; wherein:

L is SO$_2$ or CO;

R$^1$ is C$_{1-6}$ alkyl, C$_{3-7}$ cycloalkyl, phenyl, 5- or 6-membered heteroaryl, indolyl, NR$^2$R$^3$, or OR$^4$, wherein the alkyl, cycloalkyl, phenyl, or heteroaryl is optionally substituted with 1, 2, or 3 substituents independently selected from F, CN, and C$_{1-4}$ alkyl;

R$^2$ and R$^3$ are independently selected from H, C$_{1-4}$ alkyl, and phenyl;

R$^4$ is C$_{1-6}$ alkyl, phenyl, or benzyl; and

R$^7$ is a protecting group;

wherein when L is SO$_2$, R$^1$ is other than OR$^4$.

Appropriate R$^7$ protecting groups include, but are not limited to the protecting groups for amines delineated in Wuts and Greene, Protective Groups in Organic Synthesis, 4th ed., John Wiley & Sons: New Jersey, pages 696-887 (and, in particular, pages 872-887) (2007), which is incorporated herein by reference in its entirety. In some embodiments, the protecting group for the R$^7$ group is one which is stable to conditions for removing the R$^{10}$ protecting group in step (vi) of Scheme 2. In some embodiments, the protecting group for the R$^7$ group is one which is stable to conditions for removing the R$^9$ protecting group in step (iv) of Scheme 1. In some embodiments, R$^7$ is a group which is resistant to room temperature acidic conditions. In some embodiments, the R$^7$ is a group which is not removed in 1 to 5 N hydrochloric acid at room temperature, at a temperature from about 10° C. to about 40° C., at a temperature from about 15° C. to about 40° C., or at a temperature from about 15° C. to about 30° C. In some embodiments, R$^7$ is benzyloxycarbonyl (Cbz), 2,2,2-trichloroethoxycarbonyl (Troc), 2-(trimethylsilyl)ethoxycarbonyl (Teoc), 2-(4-trifluoromethylphenylsulfonyl)ethoxycarbonyl (Tsc), t-butoxycarbonyl (BOC), 1-adamantyloxycarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBOC), vinyl, 2-chloroethyl, 2-phenylsulfonylethyl, allyl, benzyl, 2-nitrobenzyl, 4-nitrobenzyl, diphenyl-4-pyridylmethyl, N',N'-dimethylhydrazinyl, methoxymethyl, t-butoxymethyl (Bum), benzyloxymethyl (BOM), or 2-tetrahydropyranyl (THP). In some embodiments, R$^7$ is 2-(trimethylsilyl)ethoxymethyl (SEM). In some embodiments, R$^7$ is N-pivaloyloxymethyl (POM).

Treatment of the compound of Formula Ia to remove the R$^7$ group can be accomplished by methods known in the art for the removal of particular protecting groups for amines, such as those in Wuts and Greene, Protective Groups in Organic Synthesis, 4th ed., John Wiley & Sons: New Jersey, pages 696-887 (and, in particular, pages 872-887) (2007), which is incorporated herein by reference in its entirety. For example, in some embodiments, the R$^7$ group is removed by treating with fluoride ion (e.g., treating with tetrabutylammonium fluoride), hydrochloric acid, pyridinium p-toluenesulfonic acid (PPTS), or a Lewis acid (e.g., lithium tetrafluoroborate)). In some embodiments, the treating comprises treating with lithium tetrafluoroborate, followed by treating with ammonium hydroxide (e.g., when R$^7$ is 2-(trimethylsilyl)ethoxymethyl). In some embodiments, the treating comprises treating with base (e.g., R$^7$ is N-pivaloyloxymethyl). In some embodiments, the base is an alkali metal hydroxide. In some embodiments, the base is sodium hydroxide. In some embodiments, the treating comprises treating with sodium hydroxide or ammonia in a solvent such as methanol or water.

In some embodiments, to deprotect the SEM-protection group, a mild, two stage protocol is employed. The SEM-protected substrate of Formula Ia is treated with lithium tetrafluoroborate (LiBF$_4$) or trifluoroborate etherate in aqueous acetonitrile at ambient or elevated temperature (in some embodiments, at about 80° C.) for ten to twenty hours. The resulting corresponding hydroxymethyl intermediate is then subsequently treated with aqueous ammonium hydroxide (NH$_4$OH) at room temperature to provide the compound of Formula I.

In some embodiments, for the POM-deprotection, an aqueous sodium hydroxide (NaOH) or lithium hydroxide (LiOH) solution is used. Thus, a suspension of the POM-protected compound of Formula Ia, is treated with a 1 N aqueous sodium hydroxide solution at room temperature for two to three hours. The desired product of Formula I can be obtained after the typical acid-base work-up.

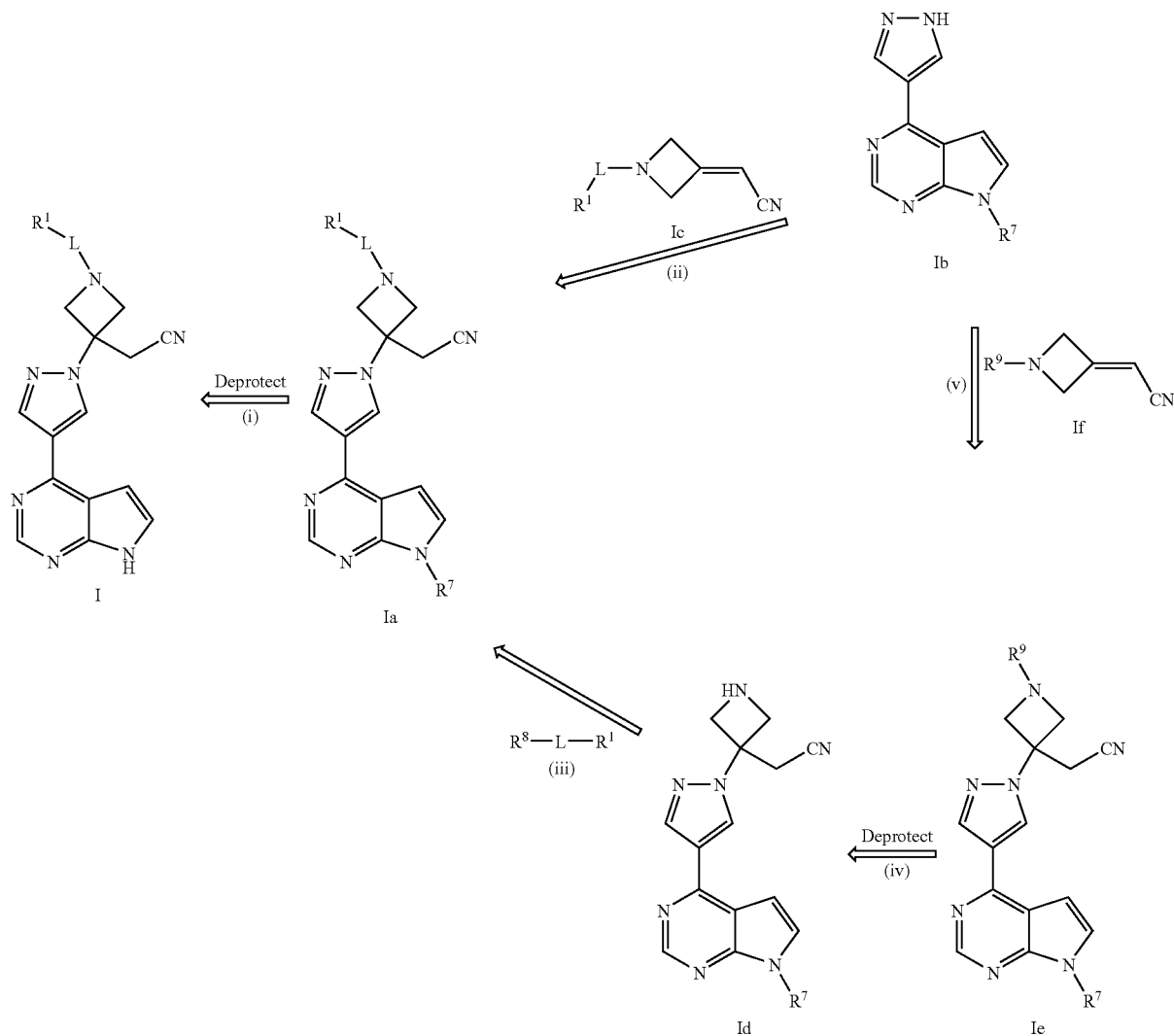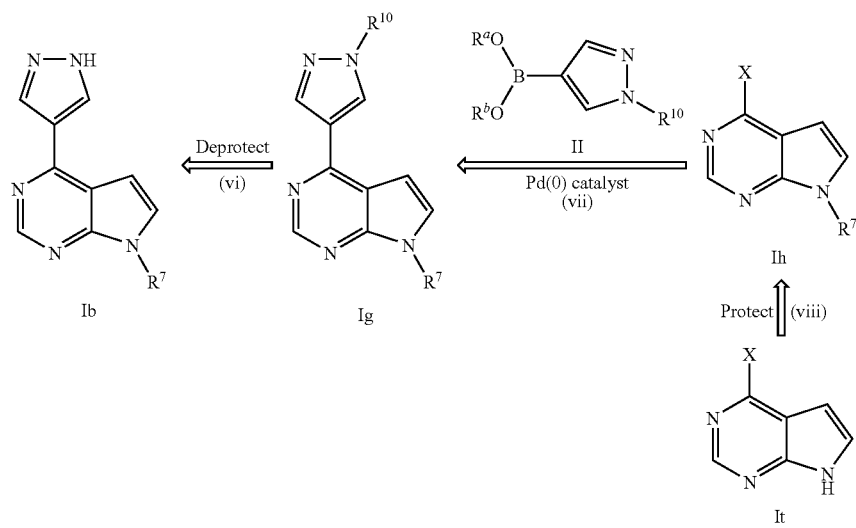

In step (ii), the compound of Formula Ia is formed by a method comprising reacting a compound of Formula Ib:

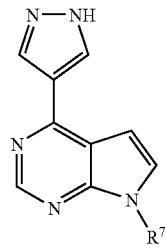

with a compound of Formula Ic:

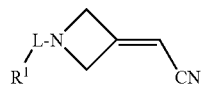

to form the compound of Formula Ia.

Step (ii) of Scheme 1 is a Michael addition reaction between the compound of Formula Ib and the compound of Formula Ic. The Michael addition may be promoted by a Michael addition catalyst, such as base. In some embodiments, the Michael addition catalyst is a tetraalkylammonium halide, tetraalkylammonium hydroxide, guanidine, amidine, hydroxide, alkoxide, silicate, alkali metal phosphate, oxide, tertiary amine, alkali metal carbonate, alkali metal bicarbonate, alkali metal hydrogen phosphate, phosphine, or alkali metal salt of a carboxylic acid. In some embodiments, the Michael addition catalyst is tetramethyl guanidine, 1,8-diazabicyclo(5.4.0)undec-7-ene, 1,5-diazabicyclo(4.3.0)non-5-ene, 1,4-diazabicyclo(2.2.2)octane, tert-butyl ammonium hydroxide, sodium hydroxide, potassium hydroxide, sodium methoxide, sodium ethoxide, tripotassium phosphate, sodium silicate, calcium oxide, triethylamine, sodium carbonate, potassium carbonate, sodium bicarbonate, potassium bicarbonate, potassium hydrogen phosphate, triphenyl phosphine, triethyl phosphine, potassium acetate, or potassium acrylate. In some embodiments, the Michael addition catalyst is 1,8-diazabicyclo(5.4.0)undec-7-ene (DBU). In some embodiments, a stoichiometric or a catalytical amount of base is used to facilitate the Michael addition reaction.

In some embodiments, the reaction is conducted in an organic solvent, such as acetonitrile or dimethylacetamide, at room temperature for two to six hours. Under the optimized reaction conditions, the desired Michael adduct, the compound of Formula Ia, may be obtained in high yield and purity.

Alternatively, the compound of Formula Ia can be formed by the process shown in step (iii) of Scheme 1. Accordingly, the compound of Formula Ia is formed by a method comprising reacting a compound of Formula Id:

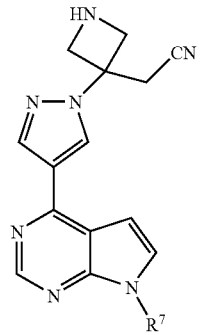

with a compound of formula $R^8$-L-$R^1$ to form the compound of Formula Ia; wherein $R^8$ is a leaving group.

In some embodiments, $R^8$ is any good leaving group known in the art. In some embodiments, $R^8$ is halogen or $C_{1-4}$ alkoxy. In some embodiments, $R^8$ is chloro.

In some embodiments, the reacting of the compound of Formula Id with the compound of formula $R^8$-L-$R^1$ is performed in the presence of a base. In some embodiments, the base is a tertiary amine, such as triethylamine, diisopropylethylamine, N-methylmorpholine, and the like. In some embodiments, the base is diisopropylethylamine.

In step (iv) of Scheme 1, the compound of Formula Id is formed by a method comprising treating a compound of Formula Ie:

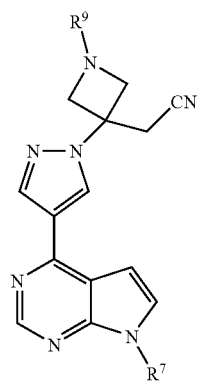

to remove the $R^9$ group thereby forming the compound of Formula Id; wherein $R^9$ is a protecting group.

Appropriate $R^9$ protecting groups include, but are not limited to the protecting groups for amines delineated in Wuts and Greene, Protective Groups in Organic Synthesis, 4th ed., John Wiley & Sons: New Jersey, pages 696-887 (and, in particular, pages 872-887) (2007), which is incorporated herein by reference in its entirety. $R^9$ is a protecting group which can be selectively removed under conditions which do not displace the $R^7$ protecting group. In some embodiments, the $R^9$ is a protecting group which can be removed under acidic conditions at room temperature, at a temperature from about 15° C. to about 40° C., or at a temperature from about 15° C. to about 30° C. In some embodiments, $R^9$ is $C_{1-6}$ alkoxycarbonyl. In some embodiments, $R^9$ is tert-butoxycarbonyl. As used herein, "alkoxycarbonyl" refers to a group of formula —C(=O)O-alkyl.

Treatment of the compound of Formula Ie to remove the $R^9$ group can be accomplished by methods known in the art for the removal of particular protecting groups for amines, such as those in Wuts and Greene, Protective Groups in Organic Synthesis, 4th ed., John Wiley & Sons: New Jersey, pages 696-887 (and, in particular, pages 872-887) (2007), which is incorporated herein by reference in its entirety. Appropriate treatment conditions do not displace the $R^7$ protecting group. In some embodiments, the treating comprises subjecting the compound of Formula Ie to acidic conditions at room temperature, at a temperature from about 15° C. to about 40° C., or at a temperature from about 15° C. to about 30° C. In some embodiments, the treating of the compound of Formula Ie comprises treating with hydrochloric acid in 1,4-dioxane.

In step (v) of Scheme 1, the compound of Formula Ia ie is formed by a method comprising reacting a compound of Formula Ib:

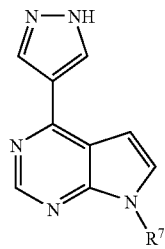

Ib with a compound of Formula If:

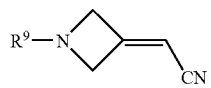

If to form the compound of Formula Ie.

Step (v) of Scheme 1 is a Michael addition reaction between the compound of Formula Ib and the compound of Formula If. The Michael addition may be promoted by a Michael addition catalyst, such as base. In some embodiments, the Michael addition catalyst is a tetraalkylammonium halide, tetraalkylammonium hydroxide, guanidine, amidine, hydroxide, alkoxide, silicate, alkali metal phosphate, oxide, tertiary amine, alkali metal carbonate, alkali metal bicarbonate, alkali metal hydrogen phosphate, phosphine, or alkali metal salt of a carboxylic acid. In some embodiments, the Michael addition catalyst is tetramethyl guanidine, 1,8-diazabicyclo(5.4.0)undec-7-ene, 1,5-diazabicyclo(4.3.0)non-5-ene, 1,4-diazabicyclo(2.2.2)octane, tert-butyl ammonium hydroxide, sodium hydroxide, potassium hydroxide, sodium methoxide, sodium ethoxide, tripotassium phosphate, sodium silicate, calcium oxide, triethylamine, sodium carbonate, potassium carbonate, sodium bicarbonate, potassium bicarbonate, potassium hydrogen phosphate, triphenyl phosphine, triethyl phosphine, potassium acetate, or potassium acrylate. In some embodiments, the Michael addition catalyst is 1,8-diazabicyclo(5.4.0)undec-7-ene (DBU). In some embodiments, a stoichiometric or a catalytical amount of base is used to facilitate the Michael addition reaction.

In some embodiments, the reaction is conducted in an organic solvent, such as acetonitrile or dimethylacetamide, at room temperature for two to six hours. Under the optimized reaction conditions, the desired Michael adduct, the compound of Formula Ia, may be obtained in high yield and purity.

In step (vi) of Scheme 2, the compound of Formula Ig is formed by a method comprising treating a compound of Formula Ig:

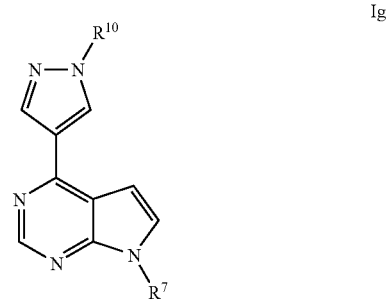

Ig to remove the $R^{10}$ group thereby forming the compound of Formula Ib; wherein $R^{10}$ is a protecting group.

Appropriate $R^{10}$ protecting groups include, but are not limited to the protecting groups for amines delineated in Wuts and Greene, Protective Groups in Organic Synthesis, 4th ed., John Wiley & Sons: New Jersey, pages 696-887 (and, in particular, pages 872-887) (2007), which is incorporated herein by reference in its entirety. $R^{10}$ is a protecting group which can be selectively removed under conditions which do not displace the $R^7$ protecting group. In some embodiments, the $R^{10}$ is a protecting group which can be removed under acidic conditions at room temperature, at a temperature from about 15° C. to about 40° C., or at a temperature from about 15° C. to about 30° C. In some embodiments, $R^{10}$ is a group which is deprotected under room temperature acidic conditions. In some embodiments, $R^{10}$ is 1-(ethoxy)ethyl, tri($C_{1-6}$ alkyl)silyl (e.g., t-butyldimethylsilyl or triisopropylsilyl), p-methoxybenzyl (PMB), triphenylmethyl (Tr), diphenylmethyl, hydroxymethyl, methoxymethyl (MOM), diethoxymethyl, or t-butyldimethylsilylmethyl. In some embodiments, $R^{10}$ is 1-(ethoxy)ethyl.

Treatment of the compound of Formula Ig to remove the $R^{10}$ group can be accomplished by methods known in the art for the removal of particular protecting groups for amines, such as those in Wuts and Greene, Protective Groups in Organic Synthesis, 4th ed., John Wiley & Sons: New Jersey, pages 696-887 (and, in particular, pages 872-887) (2007), which is incorporated herein by reference in its entirety. In some embodiments, the treating comprises treating the compound of Formula Ig under acidic conditions (e.g., hydrochloric acid or trifluoroacetic acid) at room temperature, at a temperature from about 15° C. to about 40° C., or at a temperature from about 15° C. to about 30° C. In some embodiments, the treating comprises treating the compound of Formula Ig with an aqueous solution of from about 1 N to about 5 N hydrochloric acid at a temperature of from about 10° C. to about 30° C.

In step (vii) of Scheme 2, the compound of Formula 1 g is formed by a method comprising reacting a compound of Formula Ih:

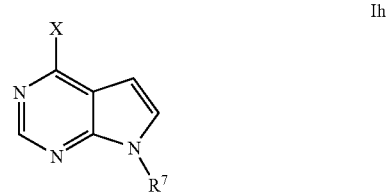

Ih with a compound of Formula Il:

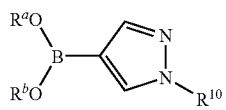

in the presence of a palladium catalyst and a base to form the compound of Formula Ig; wherein:

X is a tosylate group, a triflate group, iodo, chloro, or bromo; and $R^a$ and $R^b$ are each independently H or $C_{1-6}$ alkyl; or $R^a$ and $R^b$, together with the oxygen atoms to which they are attached and the boron atom, form a 5- to 6-membered heterocyclic ring, which is optionally substituted with 1, 2, 3, or 4 $C_{1-4}$ alkyl groups.

Step (vii) is a Suzuki coupling reaction, which can be initiated using a number of palladium(0) and palladium(II) catalysts and performed under conditions known in the art (see, e.g., Miyaura and Suzuki, *Chem. Rev.* 1995, 95, 2457-2483, which is hereby incorporated in its entirety). In some embodiments, the palladium catalyst is $Pd(PPh_3)_4$ and $Pd(dppf)_2Cl_2$. In some embodiments, the palladium catalyst is tetrakis(triphenylphosphine)palladium(0) or tetrakis(tri(o-tolyl)phosphine)palladium(0). In some embodiments, the palladium catalyst is tetrakis(triphenylphosphine)palladium (0).

In some embodiments, the palladium catalyst loading is from about $1 \times 10^{-4}$ to about 0.1 equivalents. In some embodiments, the palladium catalyst loading is from about 0.0010 to about 0.0015 equivalents. In some embodiments, the stoichiometric ratio of the compound of Formula Ih to the compound of Formula Il is from about 1 to about 1.05, or from about to 1 to about 1.35.

In some embodiments, the solvent for step (vii) comprises water and an organic solvent. In some embodiments, the organic solvent is 1,4-dioxane, 1-butanol, 1,2-dimethoxyethane (DME), 2-propanol, toluene or ethanol, or a combination thereof. In some embodiments, the organic solvent comprises a combination of 1-butanol and DME.

In some embodiments, the base is an inorganic base. In some embodiments, the base is an organic base. In some embodiments, the base is an alkali metal carbonate or an alkali metal hydrogen carbonate. In some embodiments, the base is potassium carbonate ($K_2CO_3$). In some embodiments, two to five equivalents of base (e.g., $K_2CO_3$) are used. In some embodiments, two to five equivalents of base (e.g., $NaHCO_3$) are used.

In some embodiments, the Suzuki coupling reaction is conducted at a temperature of about 80 to about 100° C. In some embodiments, the reaction is carried out for two to twelve hours.

In some embodiments, $R^a$ and $R^b$, together with the oxygen atoms to which they are attached and the boron atom, form the moiety:

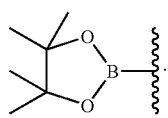

In some embodiments, X is chloro, bromo, or iodo. In some embodiments, X is chloro.

In step (viii) of Scheme 2, the compound of Formula Ih is formed by protecting a compound of Formula It:

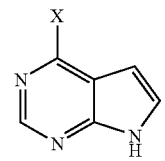

with a $R^7$ group.

The $R^7$ group is chosen as described above. In some embodiments, $R^7$ is 2-(trimethylsilyl)ethoxymethyl. In some embodiments, $R^7$ is N-pivaloyloxymethyl.

Addition of the $R^7$ protecting groups can be added by methods known in the art for attachment of protecting groups for amines (see e.g., Wuts and Green referred to above). For example, the indole nitrogen can be deprotonated with a base (e.g., with sodium hydride (NaH)) in an organic solvent (e.g., THF, 1,4-dioxane, 1,2-dimethoxyethane (DME), or N,N-dimethylacetamide (DMAC)) at low temperature (e.g., from about 0 to about 5° C.) before being treated with an electrophile, such as trimethylsilylethoxymethyl chloride (SEM-Cl) or pivaloyloxymethyl chloride (POM-Cl). The SEM- or POM-protected 4-chloro-7H-pyrrolo[2,3-d]pyrimidine can then isolated or in-situ generated as the starting materials for subsequent Suzuki reaction with or without further purification.

The compound of Formula Ic can be formed by the methods shown in Scheme 3 below. Accordingly, in step (ix) of Scheme 3, the compound of Formula Ic is formed by a method comprising reacting the compound of Formula Ik:

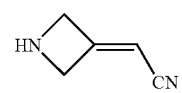

or salt thereof, with a compound of formula $R^8$-L-$R^1$ in the presence of a base to form the compound of Formula Ic; wherein $R^8$ is a leaving group.

The $R^8$ group can be any appropriate leaving group known in the art for adding a sulfonyl or carbonyl containing moiety. In some embodiments, $R^8$ is halogen or $C_{1-4}$ alkoxy. In some embodiments, $R^8$ is chloro, bromo, or iodo. In some embodiments, $R^8$ is chloro.

In some embodiments, the base is a tertiary amine, such as triethylamine, diisopropylethylamine, N-methylmorpholine, and the like. In some embodiments, the base is diisopropylethylamine. In some embodiments, the salt of the compound of Formula Ik is the hydrochloride salt.

A compound of Formula If can be formed by protecting the amino group of a compound of Formula Ik with an appropriate $R^9$ group by methods known in the art (see e.g., Wuts and Green above). Alternatively, a compound of Formula Im may be used in place of the compound of Formula If.

In step (x) of Scheme 3, the compound of Formula Ik is formed by a method comprising treating a compound of Formula Im:

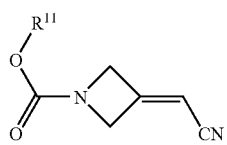

to remove the —C(=O)OR$^{11}$ moiety thereby forming the compound of Formula Ik; wherein R$^{11}$ is is C$_{1-6}$ alkoxycarbonyl.

In some embodiments, R$^{11}$ is tert-butoxycarbonyl (BOC). In some embodiments, the treating of the compound of Formula Im comprises any method known in the art for removing an alkoxycarbonyl group from an amine (e.g., a BOC group) (see e.g., Wuts and Greene, Protective Groups in Organic Synthesis, 4th ed., John Wiley & Sons: New Jersey, pages 696-887 (and, in particular, pages 872-887) (2007), which is incorporated herein by reference in its entirety). In some embodiments, the treating of the compound of Formula Im comprises treating with aqueous hydrochloric acid.

demic/Plenum Publishers:New York, pages 111-119 (2001); and March, Advanced Organic Chemistry: Reactions, Mechanisms, and Structure, 3rd ed., John Wiley & Sons:New York, pages 845-855 (1985), each of which is incorporated herein by references in its entirety). Exemplative Wittig-type reagents containing a cyanomethyl or cyanomethyl ylide group include, but are not limited to, compounds of general formula (R'O)$_2$P(=O)-L-R$^1$, R"$_3$P(+)-L(-)-R$^1$, R"$_2$P(=O)-L-R$^1$, and (R'N)$_2$P(=O)-L-R$^1$, wherein R' is C$_{1-6}$ alkoxy or optionally substituted phenyl; R" is optionally substituted phenyl; L is —CH$_2$— or —CH—; and R$^1$ is cyano. In some embodiments, the Wittig-type reagent is diethyl cyanomethyl phosphate. In some embodiments, the reacting of the com-

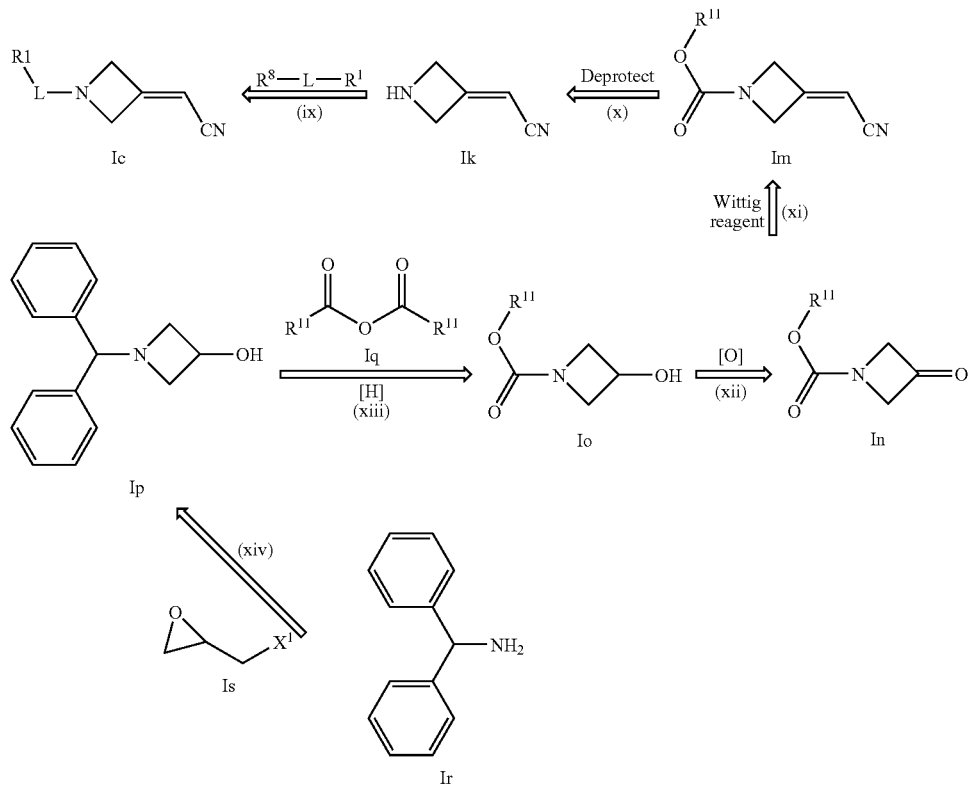

Scheme 3

In step (xi) of Scheme 3, the compound of Formula Im is formed by a method comprising reacting a compound of Formula In:

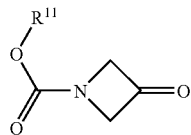

In with a Wittig-type reagent containing a cyanomethyl or cyanomethyl ylide group to form the compound of Formula Im.

As used herein, the term "Wittig-type reagent" refers to reagents used in the Wittig reaction, the Wadsworth-Emmons reaction, and the Horner-Wittig reaction as described in the art (see e.g., Carey and Sundberg, Advanced Organic Chemistry, Part B: Reactions and Synthesis, 4th ed., Kluwer Acapound of Formula In with the Wittig-type reagent in the presence of a base. In some embodiments, the base is a strong base. In some embodiments, the base is potassium t-butoxide, sodium t-butoxide, sodium hydride, sodium ethoxide, sodium hydroxide, potassium carbonate, or sodium carbonate. In some embodiments, the base is an alkali metal alkoxide. In some embodiments, the base is an alkali metal t-butoxide. In some embodiments, the base is potassium t-butoxide. In some embodiments, the olefination of the azetidine ketone of Formula In with a Wittig reagent is conducted in an organic solvent, such as THF, under the influence a base, such as potassium tert-butoxide, at a temperature from about 0 to about 5° C.

The azetidinones of Formula In can be prepared by a modified procedure reported by Gaertner (J. Org. Chem., 1967, 32, 2972) (see e.g., steps (xii) to (xiv)). In one embodiment, the "one-part" formation of the corresponding carbamate protected azetidinols of Formula Io from the compounds of Formula Ip under the catalytic hydrogenolysis conditions in the presence an electrophile, such as di-tert-butyl dicarbonate, simplifies the process to prepare the protected azetidinols compared to other modified procedures (Zhengming, Chen et al, WO 00/63168). TEMPO-catalyzed oxidation of the protected azetidinols of Formula Io to the corresponding ketones of Formula In provides almost quantitative yield under the mild reaction conditions. As the di-funtionalized compounds, N-protected azetidinones of Formula Io are very useful synthetic intermediates for the preparation of complex organic molecules.

Accordingly, in step (xii) of Scheme 3, the compound of Formula In is formed by a method comprising treating a compound of Formula Io:

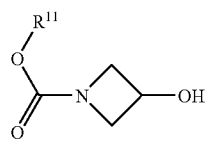

Io with an oxidizing agent component to form the compound of Formula In.

As used herein, the term "oxidizing agent component" refers to one or more oxidizing agents known in the art for oxidizing a secondary alcohol to a ketone (see, e.g., Carey and Sundberg, Advanced Organic Chemistry, Part B: Reactions and Synthesis, 4th ed., Kluwer Academic/Plenum Publishers: New York, pages 747-757), which is incorporated herein by references in its entirety). In some embodiments, the oxidizing agent component comprises a transition-metal oxidant, including, but not limited to, a chromium (VI) reagent (e.g., a Collins reagent, pyridinium dichromate (PDC), or pyridinium chlorochromate (PCC)), potassium permanganate, manganese(IV) dioxide, a ruthenium (II) reagent (e.g., $RuCl_2$ (p-cymene)$_2$), ruthenium tetraoxide, or a combination of a manganese(IV) dioxide, a ruthenium (II) reagent and benzoquinone; DMSO and an electrophilic reagent such as a carbodiimide reagent (e.g., dicyclohexylcarbodiimide), acetic anhydride, trifluoroacetic anhydride, oxalyl chloride, or sulfur trioxide; dimethyl sulfide and N-chlorosuccinimide; DMSO and chlorine; or a Dess-Martin reagent. In some embodiments, the oxidizing agent component comprises 2,2, 6,6-tetramethylpiperidine-1-oxyl (TEMPO) and a stoichiometric oxidant (e.g., sodium hypochlorite or N-chlorosuccinimide (NCS)). In some embodiments, the oxidizing agent component comprises TEMPO and sodium hypochlorite.

In step (xiii) of Scheme 3, the compound of Formula Io is formed by a method comprising reacting a compound of Formula Ip:

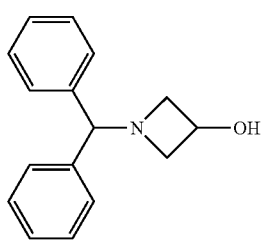

Ip with a compound of Formula Iq:

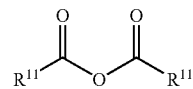

Iq under catalytic hydrogenation conditions to form the compound of Formula Io.

In some embodiments, the catalytic hydrogenation conditions comprises hydrogen gas and a palladium on carbon catalyst.

In step (xiv) of Scheme 3, the compound of Formula Ip is prepared by a method comprising the steps of:

(a) reacting a compound of Formula Ir:

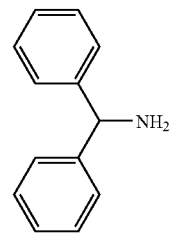

Ir with a compound of Formula Is:

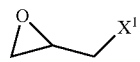

Is to form the halide salt of the compound of Formula Ip; and (b) treating the salt of the compound of Formula Ip with a base to form the compound of Formula Ip;

wherein $X^1$ is halogen.

In some embodiments, $X^1$ is chloro.

The present invention further provides a method of forming a compound of Formula I comprising:

(a) reacting a compound of Formula Ih:

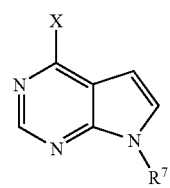

Ih with a compound of formula:

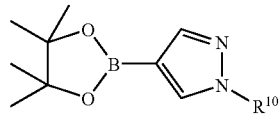

in the presence of tetrakis(triphenylphosphine)palladium(0) and an alkali metal carbonate or alkali metal hydrogen carbonate base to form a compound of Formula Ig:

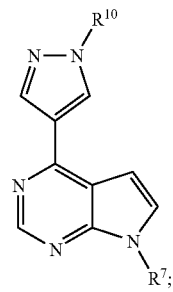

Ig (b) treating the compound of Formula Ig to remove the R¹⁰ group to form a compound of Formula Ib:

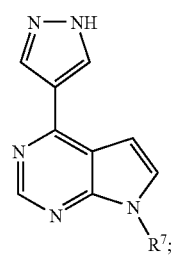

Ib (c) reacting the compound of Formula Ib with a compound of Formula Ic:

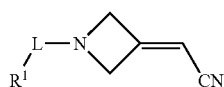

Ic in the presence of a catalytic or stoichiometric amount of 1,8-diazabicyclo(5.4.0)undec-7-ene to form the compound of Formula Ia:

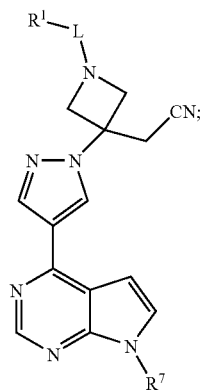

Ia (d) treating the compound of Formula Ia to remove the R⁷ moiety to form a compound of Formula I:

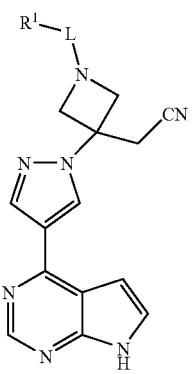

I wherein:
L is SO₂;
R¹ is C₁₋₆ alkyl;
R⁷ is 2-(trimethylsilyl)ethoxyethyl or 2-pivaloyloxymethyl;
R¹⁰ is 1-(ethoxy)ethyl; and
X is chloro.

The present invention further provides a method of forming a compound of Formula I comprising:
(a) reacting a compound of Formula Ih:

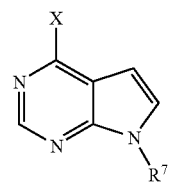

Ih with a compound of formula:

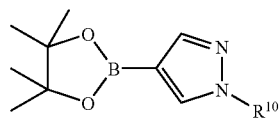

in the presence of tetrakis(triphenylphosphine)palladium(0) and an alkali metal carbonate base to form a compound of Formula Ig:

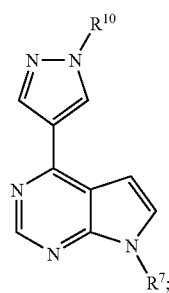

Ig (b) treating the compound of Formula Ig to remove the $R^{10}$ group to form a compound of Formula Ib:

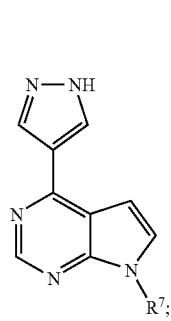
Ib (c) reacting a compound of Formula Ib:

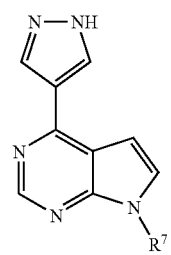
Ib with a compound of Formula If:

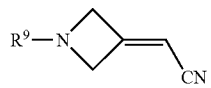
If in the presence of a catalytic or stoichiometric amount of 1,8-diazabicyclo(5.4.0)undec-7-ene to form a compound of Formula Ie:

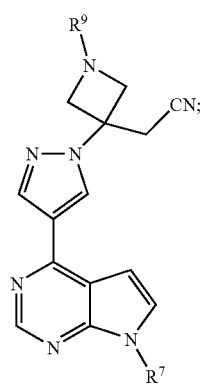
Ie (d) treating the compound of Formula Ie to remove the $R^9$ group thereby forming a compound of Formula Id:

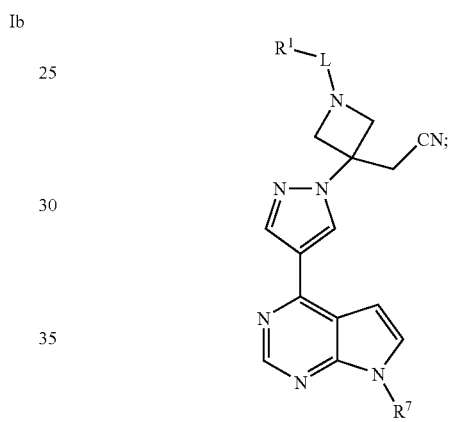
Id (e) reacting the compound of Formula Id with a compound of formula $R^8$-L-$R^1$ to form a compound of Formula Ia:

Ia (f) treating the compound of Formula Ia to remove the $R^7$ moiety to form a compound of Formula I:

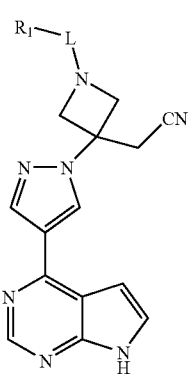
I wherein:
L is $SO_2$;
$R^1$ is $C_{1-6}$ alkyl;
$R^7$ is 2-(trimethylsilyl)ethoxyethyl or 2-pivaloyloxymethyl;
$R^8$ is chloro;
$R^9$ is tert-butoxycarbonyl;
$R^{10}$ is 1-(ethoxy)ethyl; and
X is chloro.

The methods may be used to produce any of the compounds described in the embodiments herein, or combinations thereof, or any of the compounds of the examples. The present invention provides any combination of the individual methods for forming compounds of Formula I, compounds of Formula Ia, etc. The present invention further provides any of the intermediates above, or salts thereof.

In some embodiments, the compound of Formula I produced by the methods, or combination thereof, is {1-(Ethylsulfonyl)-3-[4-(7H-pyrrolo[2,3-d]pyrimidin-4-yl)-1H-pyrazol-1-yl]azetidin-3-yl}acetonitrile. The present invention further provides each of the corresponding intermediates of Formula Ia, Ib, Ic, etc., for producing {1-(Ethylsulfonyl)-3-[4-(7H-pyrrolo[2,3-d]pyrimidin-4-yl)-1H-pyrazol-1-yl]azetidin-3-yl}acetonitrile.

In some embodiments, the methods further comprise reacting the compound of Formula I with phosphoric acid to form the phosphate salt. The phosphoric acid salt of the compound of Formula I may be produced by treating a solution of the corresponding free base in an organic solvent, such as ethanol (EtOH), with a solution of phosphoric acid in an organic solvent, such as ethanol, at room temperature or at an elevated temperature (e.g., from about 60 to about 70° C.). The produced crude phosphate salt may then be further purified by recrystallization or re-slurry in an organic solvent or a mixed organic solvent system.

In some embodiments, the compound produced by the method is {1-(ethylsulfonyl)-3-[4-(7H-pyrrolo[2,3-d]pyrimidin-4-yl)-1H-pyrazol-1-yl]azetidin-3-yl}acetonitrile phosphoric acid salt.

In some embodiments, the compounds of Formulas I, II, III, and IV can be prepared according to the synthetic procedures described below in the Example section.

Methods

Compounds of the invention can modulate activity of one or more Janus kinases (JAKs). The term "modulate" is meant to refer to an ability to increase or decrease the activity of one or more members of the JAK family of kinases. Accordingly, compounds of the invention can be used in methods of modulating a JAK by contacting the JAK with any one or more of the compounds or compositions described herein. In some embodiments, compounds of the present invention can act as inhibitors of one or more JAKs. In further embodiments, the compounds of the invention can be used to modulate activity of a JAK in an individual in need of modulation of the receptor by administering a modulating amount of a compound of Formula I or II.

JAKs to which the present compounds bind and/or modulate include any member of the JAK family. In some embodiments, the JAK is JAK1, JAK2, JAK3 or TYK2. In some embodiments, the JAK is JAK1 or JAK2. In some embodiments, the JAK is JAK2. In some embodiments, the JAK is JAK3.

Another aspect of the present invention pertains to methods of treating a JAK-associated disease or disorder in an individual (e.g., patient) by administering to the individual in need of such treatment a therapeutically effective amount or dose of a compound of the present invention or a pharmaceutical composition thereof. A JAK-associated disease can include any disease, disorder or condition that is directly or indirectly linked to expression or activity of the JAK, including overexpression and/or abnormal activity levels. A JAK-associated disease can also include any disease, disorder or condition that can be prevented, ameliorated, or cured by modulating JAK activity.

Examples of JAK-associated diseases include diseases involving the immune system including, for example, organ transplant rejection (e.g., allograft rejection and graft versus host disease).

Further examples of JAK-associated diseases include autoimmune diseases such as multiple sclerosis, rheumatoid arthritis, juvenile arthritis, psoriatic arthritis, type I diabetes, lupus, psoriasis, inflammatory bowel disease, ulcerative colitis, Crohn's disease, myasthenia gravis, immunoglobulin nephropathies, autoimmune thyroid disorders, and the like. In some embodiments, the autoimmune disease is an autoimmune bullous skin disorder such as pemphigus vulgaris (PV) or bullous pemphigoid (BP).

Further examples of JAK-associated diseases include allergic conditions such as asthma, food allergies, atopic dermatitis and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated diseases or conditions include skin disorders such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one JAK inhibitor of the invention together with the agent causing unwanted sensitization can be helpful in treating such unwanted sensitization or dermatitis. In some embodiments, the skin disorder is treated by topical administration of at least one JAK inhibitor of the invention.

In further embodiments, the JAK-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, melanoma etc.), hematological cancers (e.g., lymphoma, leukemia such as acute lymphoblastic leukemia, acute myelogenous leukemia (AML) or multiple myeloma), and skin cancer such as cutaneous T-cell lymphoma (CTCL) and cutaneous B-cell lymphoma. Example cutaneous T-cell lymphomas include Sezary syndrome and mycosis fungoides.

JAK-associated diseases can further include those characterized by expression of a mutant JAK2 such as those having at least one mutation in the pseudo-kinase domain (e.g., JAK2V617F).

JAK-associated diseases can further include myeloproliferative disorders (MPDs) such as polycythemia vera (PV), essential thrombocythemia (ET), myelofibrosis with myeloid metaplasia (MMM), chronic myelogenous leukemia (CML), chronic myelomonocytic leukemia (CMML), hypereosinophilic syndrome (HES), systemic mast cell disease (SMCD), and the like. In some embodiments, the myeloproliferative disorder is primary myelofibrosis (PMF) or post polycythemia vera/essential thrombocythemia myelofibrosis (Post-PV/ET MF).

Further JAK-associated diseases include inflammation and inflammatory diseases. Example inflammatory diseases include inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases.

The JAK inhibitors described herein can further be used to treat ischemia reperfusion injuries or a disease or condition related to an inflammatory ischemic event such as stroke or cardiac arrest. The JAK inhibitors described herein can further be used to treat anorexia, cachexia, or fatigue such as that resulting from or associated with cancer. The JAK inhibitors described herein can further be used to treat restenosis, sclerodermitis, or fibrosis. The JAK inhibitors described herein can further be used to treat conditions associated with hypoxia or astrogliosis such as, for example, diabetic retinopathy, cancer, or neurodegeneration. See, e.g., Dudley, A. C. et al. *Biochem. J.* 2005, 390(Pt 2):427-36 and Sriram, K. et al. *J. Biol. Chem.* 2004, 279(19):19936-47. Epub Mar. 2, 2004. The JAK inhibitors described herein can be used to treat Alzheimer's disease.

The JAK inhibitors described herein can further be used to treat other inflammatory diseases such as systemic inflammatory response syndrome (SIRS) and septic shock.

The JAK inhibitors described herein can further be used to treat gout and increased prostate size due to, e.g., benign prostatic hypertophy or benign prostatic hyperplasia.

The JAK inhibitors described herein, as well as other JAK inhibitors capable of influencing IL-6/STAT3 signalling, can further be used to treat inflammation-associated proliferative diseases. Inflammation has been shown to be linked to the development of certain types of cancers. For example, patients suffering from inflammatory bowel disease such as ulcerative colitis have been shown to have a much higher risk of developing colorectal cancer. These types of inflammation-linked cancers have been termed colitis-associated cancer (CAC). Several studies have shown that the IL-6/STAT3 signaling is involved in promoting CAC. For example, mice deficient in STAT3 intestinal epithelial cells had decreased tumor size and incidence in an animal model of CAC. Bromberg, et al., "Inflammation and cancer: IL-6 and STAT3 complete the link", *Cancer Cell,* 15:79-80 (2009). Similar results were obtained with IL-6 deficient mice, which developed fewer and smaller adenomas than wild-type mice. Grivennikov, et al., "IL-6 and STAT3 are required for survival of intestinal epithelial cells and the development of colitis-associated cancer", *Cancer Cell,* 15:103-111 (2009). See also, Bollrath, et al., "gp130-Mediated STAT3 activation in enterocytes regulatres cell survival and cell-cycle progression during colitis-associated tumorigenesis", *Cancer Cell,* 15:91-102 (2009); and Kortylewski, et al., "Regulation of the IL-23 and IL-12 balance by Stat3 signaling in the tumor microenvironment", *Cancer Cell,* 15:114-123 (2009).

Accordingly, in some embodiments, JAK inhibitors of the invention and those which influence IL-6/STAT3 signaling, can be used to treat inflammation-associated cancers. In some embodiments, the cancer is associated with inflammatory bowel disease. In some embodiments, the inflammatory bowel disease is ulcerative colitis. In some embodiments, the inflammatory bowel disease is Crohn's disease. In some embodiments, the inflammation-associated cancer is colitis-associated cancer. In some embodiments, the inflammation-associated cancer is colon cancer or colorectal cancer. In some embodiments, the cancer is gastric cancer, gastrointestinal carcinoid tumor, gastrointestinal stromal tumor (GIST), adenocarcinoma, small intestine cancer, or rectal cancer. In addition to the compounds provided herein, example JAK inhibitors that can be used in the treatment of inflammation-associated cancers include those described in US 2006/0106020; US 2006/0183906; US 2007/0149506; US 2007/0135461; US 2008/0188500; US 2008/0312258; US 2008/0312259; and U.S. Ser. No. 12/270,135.

JAK inhibitors can be tested in animal models for potential efficacy in treating inflammation-associated cancers. For example, CAC can be induced in treated (e.g., with JAK inhibitors) or untreated mice by the method summarized in Grivennikov, et al., "IL-6 and STAT3 are required for survival of intestinal epithelial cells and the development of colitis-associated cancer", *Cancer Cell,* 15:103-111 (2009). Progression of the disease can be followed by measuring body weight and monitoring for signs of rectal bleeding and diarrhea. After sacrifice of the animals, portions of the distal colon are removed for analysis.

In some embodiments, the JAK inhibitors described herein can further be used to treat a dry eye disorder. As used herein, "dry eye disorder" is intended to encompass the disease states summarized in a recent official report of the Dry Eye Workshop (DEWS), which defined dry eye as "a multifactorial disease of the tears and ocular surface that results in symptoms of discomfort, visual disturbance, and tear film instability with potential damage to the ocular surface. It is accompanied by increased osmolarity of the tear film and inflammation of the ocular surface." Lemp, "The Definition and Classification of Dry Eye Disease: Report of the Definition and Classification Subcommittee of the International Dry Eye WorkShop", The Ocular Surface, 5(2), 75-92 April 2007, which is incorporated herein by reference in its entirety. Dry eye is also sometimes referred to as keratoconjunctivitis sicca. In some embodiments, the treatment of the dry eye disorder involves ameliorating a particular symptom of dry eye disorder, such as eye discomfort, visual disturbance, tear film instability, tear hyperosmolarity, and inflammation of the ocular surface.

As summarized in the DEWS report, dry eye can be classified into two different classes: aqueous tear-deficient dry eye and evaporative dry eye, which in turn encompass various subclasses. Accordingly, in some embodiments, the dry eye disorder is aqueous tear-deficient dry eye (ADDE). In further embodiments, the dry eye disorder is evaporative dry eye. In further embodiments, the dry eye disorder is selected from any of the subclasses of ADDE or evaporative dry eye disorder, or appropriate combinations thereof. As noted by the author of the DEWS report, however, the various classes and subclasses are not mutually exclusive. Hence, dry eye can occur via different mechanism in different subclasses or a dry eye disease state originating in one subclass can lead to events that cause dry eye by a mechanism in another subclass.

The first class of dry eye, aqueous tear-deficient dry eye (ADDE), is also known as tear deficient dry eye and lacrimal tear deficiency. In ADDE, dry eye is believed to be due to a failure of lacrimal tear secretion. While not wishing to be bound by any theory, it is believed that dryness results from reduced lacrimal tear secretion and volume, causing tear hyperosmolarity. Tear film hyperosmolarity can cause hyperosmolarity of the ocular surface epithelial cells, stimulating inflammatory events involving various kinases and signaling pathways.

Two subclasses of ADDE are Sjogren syndrome dry eye (SSDE), where the lacrimal glands are targeted by an autoimmune process, and non-Sjogren syndrome dry eye (NSSDE). Accordingly, in some embodiments, the eye disorder is SSDE. In other embodiments, dry eye disorder is non-Sjogren syndrome dry eye. In SSDE, it is believed that activated T-cells can infiltrate the lacrimal glands, causing cell death of acinar and ductular cells and hyposecretion of tears. The effects of locally released cytokines or circulating antibodies can amplify the effects of hyposecretion. The two major forms of SSDE are primary and secondary forms. Primary SS can occur in combination with dry mouth (xerostomia). Secondary SSDE occurs with the symptoms of primary SSDE together with an autoimmune connective disease such as rheumatoid arthritis (RA), systemic lupus erythematosis, polyarteritis nodosa, Wegener's granulomatosis, systemic sclerosis, primary bilary sclerosis, or mixed connective tissue disease. Diagnostic criteria for each of these connective diseases is known in the art. Further, primary SSDE may be associated with systemic manifestations of disease which may involve the lungs, kidneys, liver, blood vessels and joints.

In NSSDE, the systemic autoimmune characteristics of Sjogren syndrome dry eye are excluded. Forms of NSSDE include primary lacrimal gland deficiencies (including age-related dry eye, congenital alacrima, and familial dysautonomia), secondary lacrimal deficiencies (including inflammatory infiltration of the lacrimal gland by sarcoid granulomata, lymphomatous cells, and AIDS related T-cells; that associated with graft vs. host disease; and that resulting from lacrimal gland ablation or lacrimal gland denervation), obstruction of the lacrimal gland ducts (including that caused by cicatrizing conjunctivitis including trachoma, cicatricial pemphigoid and mucous membrane pemphigoid, erythema multiforme, and chemical or thermal burns), and reflex hyposecretion (including reflex sensory block, such as that associated with contact lens wear, diabetes mellitus, and neurotrophic keratitis, and reflex motor block, including that associated with VII cranial nerve damage, multiple neuromatosis, and exposure to systemic drugs such as antihistamines, beta blockers, antispasmodics, diuretics, tricyclic antidepressants, selective serotonin reuptake inhibitors, and other psychotropic drugs).

The second major class of dry eye disorder is evaporative dry eye, which is caused by excessive water loss from the exposed ocular surface in the presence of normal lacrimal secretory function. Intrinsic causes of evaporative dry eye include Meibomian gland dysfunction (MGD) (including that caused by a reduced number of glands due to congenital deficiency acquired-MGD; MGD associated with dystichiasis, dystichiasis lymphedema syndrome, and metaplasia; hypersecretory MGD associated with Meibomian seborrhea, hypersecretory MGD associated with retinoid therapy, primary and secondary obstructive MGD, focal or diffuse obstructive MGD, simple or cicatricial obstructive MGD, atrophic or inflammatory obstructive MGD; Simple MGD primary or secondary to anterior blepharitis, acne rosacea, seborrhoeic dermatitis, ectrodactyly syndrome, Turner syndrome, systemic toxicity from 13-cis retinoic acid, polychlorinated biphenyls, and epinephrine; and cicatricial MGD primary or secondary to chemical burns, pemphigoid, acne rosacea, erythema multiforms, VKC and AKC), disorders of the lid aperture and lid/globe congruity or dynamic (such as that occurring with craniostenosis, endocrine and other forms of proptosis, myopia, and after plastic surgery on the lids), and low blink rate (including that caused by an extrapyramidal disorder such as Parkinson's disease). Extrinsic causes of evaporative dry eye include ocular surface disorders (including xerophthalmia caused by vitamin A deficiency; and that associated with topical drugs and preservatives such as topical anesthesia and benzalkonium chloride), contact lens wear, ocular surface disease (including allergic eye disease), allergic conjunctivitis (including aseasonal allergic conjunctivitis, vernal keratoconjunctivitis, and atopic keratoconjunctivitis), and the use of anti-histamines.

Patients in need of treatment of a dry eye disorder can be identified by a variety of diagnostic methods known in the art, including the diagnostic methods summarized in Bron, et al., "Methodologies to Diagnose and Monitor Dry Eye Disease: Report of the Diagnostic Methodology Subcommittee of the International Dry Eye Workshop (2007)", The Ocular Surface, 5(2), 108-152 (April 2007), which is hereby incorporated herein by reference in its entirety. These include, but are not limited to: (1) symptom questionnaires (e.g., Begley, et al., "Use of the dry eye questionnaire to measure symptoms of ocular irritation in patients with aqueous tear deficient dry eye", Cornea, 2002:21:664-70); (2) staining of the ocular surface to check for surface damage (e.g., Rose Bengal or fluorescein staining or other staining method such as those techniques summarized in Barr et al., "Corneal scarring in the Collaborative Longitudinal Evaluation of Keratoconus (CLEK) Study: baseline prevalence and repeatability of detection", Cornea 1999;18(1):34-46; Lemp, "Report of the National Eye Institute/Industry Workshop on clinical trials in dry eyes", CLAO J 1995;21(4):221-31; Nichols, et al., "The repeatability of clinical measurements of dry eye", Cornea 2004;23:272-85; Bron, et al., "Grading of corneal and conjunctival staining in the context of other dry eye tests", Cornea 2003;22(7):640-50); (3) measurement of tear film break-up time to test for tear film stability (e.g., Abelson, et al., "Alternate reference values for tear film break-up time in normal and dry eye populations", Adv Exp Med Biol 2002;506,Part B:1121-1125; Bron A J, et al., "Grading of corneal and conjunctival staining in the context of other dry eye tests", Cornea 2003;22:640-50; Cho et al, "Review of the tear break-up time and a closer look at the tear break-up time of Hong Kong Chinese", Optom Vis Sci 1993;70(1):30-8; Craig et al. "Tear lipid layer structure and stability following expression of the meibomian glands. Ophthalmic Physiol Opt 1995, 15(6):569-74; Eliason, et al., "Staining of the conjunctiva and conjunctival tear film", Br J Ophthalmol 1990;74:519-22; Farrell et al., "A classification for dry eyes following comparison of tear thinning time with Schirmer tear test", Acta Ophthalmol (Copenh) 1992; 70(3):357-60; Johnson et al., "The effect of instilled fluorescein solution volume on the values and repeatability of TBUT measurements", Cornea 2005;24:811-7; Lemp et al., "Corneal desiccation despite normal tear volume", Ann Ophthalmol 1970;284:258-261; Lemp "Report of National Eye Institute/Industry Workshop on clinical trials in dry eyes", CLAO J 1995;21 :221-232; Madden et al. Comparative study of two non-invasive tear film stability techniques. Curr Eye Res 1994; 13(4):263-9; Marquardt et al., "Modification of tear film break-up time test for increased reliability" in Holly ed. The Preocular Tear Film in Health, Disease and Contact Lens Wear. Lubbock, Tex.: Dry Eye Institute, 1986:57-63; Mengher et al., "Non-invasive tear film break-up time: sensitivity and specificity", Acta Ophthalmol (Copenh) 1986; 64(4):441-4; Nichols et al., "The repeatability of clinical measurements of dry eye" Cornea 2004;23:272-85; Pflugfelder et al. "Evaluation of subjective assessments and objective diagnostic tests for diagnosing tear-film disorders known to cause ocular irritation. Cornea 1998; 17(1):38-56; Vitali et al. "The European Community Study Group on diagnostic criteria for Sjogren's syndrome. Sensitivity and specificity of tests for ocular and oral involvement in Sjogren's syndrome." 1992; Ann Rheum Dis 53(10): 637-47; Welch et al., "An approach to a more standardized method of evaluating tear film break-up time" Invest Ophthalmol Vis Sci 2003; 2485/B324.); (4) the Schirmer test (an estimation of tear flow stimulated reflexly by insertion of a filter paper into the conjunctival sac) (e.g., van Bijsterveld, "Diagnostic tests in the sicca syndrome" Arch Ophthalmol 1969;82: 10-14; Holly et al., "Lacrimation kinetics as determined by a novel technique", in Holly F J (ed). The preocular tear film. Lubbock Tex., Lubbock Dry Eye Institute, 1986, pp 76-88); (5) measurement of tear osmolarity (e.g., Farris, "Tear osmolarity—a new gold standard?" Adv Exp Med Biol 350:495-503, 1994; Nelson et al., "Tear film osmolality determination: an evaluation of potential errors in measurement" Curr Eye Res September;5(9):677-81, 1986; Sullivan et al., "4th International Conference on the Lacrimal Gland, Tear Film & Ocular Surface and Dry Eye Syndromes, Nov. 20, 2004"; White et al., "Human basic tear fluid osmolality. I. Importance of sample collection strategy", Acta Ophthalmol (Copenh) August;71(4):524-9, 1993; (6) measurement of tear meniscus radius, height and cross sectional area to diagnose aqueous tear deficiency (e.g., Cermak et al, "Is complete androgen insensitivity syndrome associated with alterations in the meibomium gland and ocular surface", Cornea 2003; 22:516-521; Farrell et al., "A clinical procedure to predict the value of temporary occlusion therapy in keratoconjunctivitis sicca" Ophthal Physiol Opt 2003;23:1-8; Glasson et al., "Differences in clinical parameters and tear film of tolerant and intolerant contact lens wearers", Invest Ophthalmol Vis Sci 2003;44:5116-5124; Mainstone et al., "Tear meniscus measurement in the diagnosis of dry eye", Curr Eye Res 1996; 15:653-661; Nichols et al., "The repeatability of clinical measurements of dry eye", Cornea 2004a; 23:272-285; Nichols et al., "The lack of association between signs and symptoms in patients with dry eye disease", Cornea 2004b; 23:762-770; Oguz et al., "The height and radius of the tear meniscus and methods for examining these parameters", Cornea 2000;19: 497-500; Yokoi et al., "Non-invasive methods of assessing the tear film", Exp Eye Res 2004;78:399-407); (7) tear film lipid layer interferometry to diagnose aqueous tear deficient dry eye (ATD) or precorneal lipid tear deficiency (Danjo et al., "Observation of precorneal tear film in patients with Sjogren's syndrome", Acta Ophthalmol Scand 1995;73:501-5; Doane, "An instrument for in vivo tear film interferometry", Optom Vis Sci 1989; 66: 383-8; Goto et al., "Computer-synthesis of an interference color chart of human tear lipid layer by a colorimetric approach", Invest Ophthalmol Vis Sci 2003;44:4693-7; Goto et al., "Differentiation of lipid tear deficiency dry eye by kinetic analysis of tear interference images", Arch Ophthalmol 2003;121:173-80; Goto E, et al., "Kinetic analysis of tear interference images in aqueous tear deficiency dry eye before and after punctal occlusion. Invest Ophthalmol Vis Sci 2003;44: 1897-905; Goto et al., "Color mapping of tear lipid layer thickness distribution from the image analysis in DR-1 tear lipid layer interference images (ARVO abstract). ARVO 2004; Guillon, "Tear film photography and contact lens wear", J Br Contact Lens Assoc 1982; 5:84-7; King-Smith et al., "Three interferometric methods for measuring the thickness of layers of the tear film", Optom Vis Sci 1999;76:19-32; Korb, et al., "Increase in tear film lipid layer thickness following treatment of meibomian gland dysfunction", Adv Exp Med Biol 1994;350:293-8; Korb et al., "The effect of two novel lubricant eye drops on tear film lipid layer thickness in subjects with dry eye symptoms", Optom Vis Sci 2005; 82: 594-601; Mathers et al., "Assessment of the tear film with tandem scanning confocal microscopy", Cornea 1997; 16:162-8; Maruyama et al., "Effect of environmental conditions on tear dynamics in soft contact lens wearers", Invest Ophthalmol Vis Sci 2004;45(8):2563-8; Tiffany, "Refractive index of meibomian and other lipids", Curr Eye Res 1986;5:887-9; Tiffany et al., "Meniscometry using the Tearscope-plus (ARVO abstract). Invest Ophthalmol Vis Sci 2001;42, s37; Yokoi et al., "Correlation of tear lipid layer interference patterns with the diagnosis and severity of dry eye", Am J Ophthalmol 1996;122:818-24; Yokoi et al., "Assessment of meibomian gland function in dry eye using meibometry", Arch Ophthalmol 1999;117:723-9); (8) Tear Stability Analyses System (TSAS) to diagnose tear instability (e.g., Goto et al., "Tear Film Stability Analysis System: Introducing a new application for videokeratography", Cornea 2004a; November;23(8):S65-S70; Goto et al., "Evaluation of the tear film stability after laser in situ keratomileusis using the tear film stability analysis system", Am J Ophthalmol January, 2004b; 137(1):116-20; Kojima et al., "A new noninvasive tear stability analysis system for the assessment of dry eyes" Invest Ophthalmol Vis Sci 2004;May;45(5):1369-74); (9) meibometry to assess Meibomian gland dysfunction (e.g., Chew et al., "An instrument for quantifying meibomian lipid on the lid margin: the Meibometer", Curr Eye Res 1993a;12: 247-254; Chew et al., "The casual level of meibomian lipids in humans", Current Eye Research 1993b;12:255-259; Komuro et al., "Assessment of meibomian gland function by a newly developed laser meibometer", Adv Exp Med Biol 2002;506:517-520; Yokoi et al., "Assessment of meibomian gland function in dry eye using meibometry" Arch Ophthalmol 1999;117:723-729); (10) meibography or meiboscopy to measure Meibomian gland dysfunction (e.g., Kaercher, "Ocular symptoms and signs in patients with ectodermal dysplasia symdromes", Grafes Arch Clin Exp Ophthalmol 2004;495-500; Jester et al., "In vivo biomcroscopy and photography of meibomian glands in a rabbit model of meibomian gland dysfunction", Invest Ophthalmol Vis Sci 1982; 22:660-7; Mathers et al., "Video imaging of the meibomian gland", Arch Ophthalmol 1994;112:448-9; Pflugfelder, et al., "Evaluation of subjective assessments and objective diagnostic tests for diagnosing tear-film disorders known to cause ocular irritation", Cornea 1998;17(1):38-56; Robin et al., "In vivo transillumination biomicroscopy and photography of meibomian gland dysfunction. Ophthalmology 1985;92:1423-6; Shimazaki et al., "Meibomian gland dysfunction in patients with Sjogren syndrome", Ophthalmology 1998;105(8):1485-8; Yokoi et al., "A newly developed videomeibography system featuring a newly designed probe", Jpn J Ophthalmol 2007; 51: 53-6); (11) Brush Cytology Technique (e.g., Fukagawa et al., "Histological evaluation of brush cytology of rabbit conjunctiva", Nippon Ganka Gakkai Zasshi 1993;97:1173-8; Fujihara et al., "Evaluation of human conjunctival epithelium by a combination of brush cytology and flow cytometry: an approach to the quantitative technique", Diagn Cytopathol 1997;17:456-60; Miyoshi et al., "Interleukin-8 concentrations in conjunctival epithelium brush cytology samples correlate with neutrophil, eosinophil infiltration, and corneal damage", Cornea 2001;20:743-7; Takano et al., "Inflammatory cells in brush cytology samples correlate with the severity of corneal lesions in atopic keratoconjunctivitis", Br J Ophthalmol 2004;88:1504-5; Tsubota et al., "Brush cytology for the evaluation of dry-eye", Nippon Ganka Gakkai Zasshi 1990a ;94:224-30; Tsubota et al., "Conjunctival brush cytology", Acta Cytol 1990 b;34:233-5; Tsubota et al., "Detection by brush cytology of mast cells and eosinophils in allergic and vernal conjunctivitis"; Cornea 1991;10:525-31); (12) Flow cytometry in impression cytology to detect conjuctivial inflammation (e.g., Baudouin et al., "Flow cytometry in impression cytology specimens. A new method for evaluation of conjunctival Inflammation", Invest Ophthalmol Vis Sci 1997a;38:1458-1464; Bourcier et al., "Expression of CD40 and CD40 ligand in the human conjunctival epithelium", Invest Ophthalmol Vis Sci 2000;41: 120-126; Brignole et al., "Expression of Fas antigen (CD95) in the human conjunctival epithelium. Positive correlation with class II HLA DR expression in inflammatory conditions", Exp Eye Res 1998;67:687-697; Brignole et al., "Flow cytometric analysis of inflammatory markers in conjunctival epithelial cells of patients with dry eyes" Invest Ophthalmol Vis Sci 2000; 41:1356-1363; Brignole et al., "Flow cytometric analysis of inflammatory markers in KCS: 6-month treatment with topical cyclosporin A", Invest Ophthalmol Vis Sci 2001;42:90-95; Brignole et al., "Flow cytometry in conjunctival impression cytology: a new tool for exploring ocular surface pathologies", Exp Eye Res 2004;78:473-481; Fujihara et al., "Evaluation of human conjunctival epithelium by a combination of brush cytology and flow cytometry: an approach to the quantitative technique" Diagn Cytopathol 1997;17:456-460; Pisella et al., "Flow cytometric analysis of conjunctival epithelium in ocular rosacea and keratoconjunctivitis sicca. Ophthalmology 2000; 107:1841-1849; Pisella, et al., "Conjunctival proinflammatory and proapoptotic effects of latanoprost, preserved timolol and unpreserved timolol: an ex vivo and in vitro study. Invest Ophthalmol Vis Sci 2004; 45:1360-1368); (13) the Ferning test to diagnose the quality of tears (electrolyte concentration), KCS, and hyperosmolarity (e.g., Albach et al., "Diagnosis of keratoconjunctivitis sicca in rheumatoid arthritis. The value of various tests", Ophthalmologe April 1994;91(2):229-34; Golding et al., "X-ray and scanning electron microscopic analysis of the structural composition of tear ferns", Cornea January 1994; 13(1):58-66; Norn, "Quantitative tear ferning. Clinical investigations", Acta Ophthalmol (Copenh) June 1994;72(3):369-72; Pearce et al., "Spatial location studies on the chemical composition of human tear ferns", Ophthalmic Physiol Opt 2000;July;20(4):306-13; Pensyl et al., "The repeatability of tear mucus ferning grading", Optom Vis Sci August 1998;75 (8):600-4; Rolando, "Tear mucus ferning test in normal and keratoconjunctivitis sicca eyes. Chibret Int J Ophthalmol 1984;2(4):32-41; Rolando et al., "Tear mucus ferning test in keratoconjunctivitis sicca", in: Holly F J, Lamberts D W, MacKeen D L (eds.): The preocular tear film in health, disease, and contact lens wear,. 1st Intern Tear Film Symposium. Lubbok (Tex., USA), Dry Eye Institute, 1986, 203-210; Rolando et al., "The effect of hyperosmolarity on tear mucus ferning", Fortschr Ophthalmol 1986;83:644-646; Rolando et al., "Tear mucus crystallization in children with cystic fibrosis", Ophthalmologica 1988;197(4):202-6); (14) Ocular Protection Index (OPI) to assess ocular surface protection and risk of ocular surface damage (e.g., Ousler et al., "Factors that influence the inter-blink interval (IBI) as measured by the ocular protection index (OPI)", (Poster presentation) ARVO 2002; Nally et al., "Ocular discomfort and tear film break-up time in dry eye patients: A correlation", Invest Ophthalmol Vis Sci 2000;41 :4:1436; Abelson et al., "Alternate reference values for tear film break-up time in normal and dry eye populations", Lacrimal Gland, Tear Film, and Dry Eye Syndromes 3 Part B", Adv Exp Med Biol 2002; 506:1121-1125; Abelson et al., "Dry eye syndrome: diagnosis, clinical trials, and pharmaceutical treatment—'improving clinical trials'. Lacrimal Gland, Tear Film, and Dry Eye Syndromes 3 Part B", Adv Exp Med Biol 2002; 506:1079-86); (15) fluorophotometry (fluorimetry) of tear flow to assess changes in tear flow in aqueous tear deficiency (ATD) (e.g., Gobbels et al., "Tear secretion in dry eyes as assessed by objective fluorophotometry. Ger J Ophthalmol 1992; 1:350-353; Kuppens et al., "Basal tear turnover and topical timolol in glaucoma patients and healthy controls by Fluorophotometry", Invest Ophthalmol Vis Sci 1992; 33:3442-3448; Mishima, "Some physiological aspects of the precorneal tear film", Arch Ophthalmol 1965;73:233-241; Mishima S, "Determination of tear volume and tear flow", Invest Ophthalmol 1966; 5:264-275; Mathers et al., "Tear film and evaporation in patients with and without dry eye", Ophthalmology 1996; 103:664-669; Mathers et al., "Tear film changes associated with normal aging", Cornea 1996; 15:229-334; Mathers, "Evaporation from the ocular surface", Exp Eye Res 2004; 78:389-394; Van Best et al., "Measurement of basal tear turnover using a standardized protocol", Graefe's Arch Clin Exp Ophthalmol 1995; 233:1-7; McNamara et al., "Fluorometry in contact lens research: The next step", Optom Vis Sci 1998; 75:316-322; Pearce, "An improved fluorophotometric method for tear turnover assessment", Optom Vis Sci 2001; 78:30-36), and combinations of these diagnostic tests, the disclosures of each reference are incorporated herein by reference in their entireties. These methods can also be used to assess the clinical efficacy of the compounds described herein in treating dry eye disorders.

In a further aspect, the present invention provides a method of treating conjunctivitis, uveitis (including chronic uveitis), chorioditis, retinitis, cyclitis, sclieritis, episcleritis, or iritis; treating inflammation or pain related to corneal transplant, LASIK (laser assisted in situ keratomileusis), photorefractive keratectomy, or LASEK (laser assisted sub-epithelial keratomileusis); inhibiting loss of visual acuity related to corneal transplant, LASIK, photorefractive keratectomy, or LASEK; or inhibiting transplant rejection in a patient in need thereof, comprising administering to the patient a therapeutically effective amount of a compound of Formula I, or pharmaceutically acceptable salt or N-oxide thereof. In some embodiments, the compound, or pharmaceutically acceptable salt or N-oxide thereof, is administered preoperatively to a patient about to undergo a procedure selected from corneal transplant, LASIK, photorefractive keratectomy, and LASEK. In some embodiments, the compound, or pharmaceutically acceptable salt or N-oxide thereof, suppresses or lessens inflammation or pain during and after the procedure. In some embodiments, the compound, or pharmaceutically acceptable salt or N-oxide thereof, is administered about 1 day to about 2 days prior to the procedure. In some embodiments, the compound, or pharmaceutically acceptable salt or N-oxide thereof, is administered postoperatively to a patient who has undergone a procedure selected from corneal transplant, LASIK, photorefractive keratectomy, and LASEK. In some embodiments, inhibiting loss of visual acuity means lessening the loss of visual acuity. In some embodiments, the postoperative or preoperative treatment lessens the amount of scarring and fibrous deposits following the procedure. In some embodiments, inhibiting loss of visual acuity means that the patient retains visual acuity. In some embodiments, inhibiting transplant rejection means that the compound, or pharmaceutically acceptable salt or N-oxide thereof, is immunosuppressive, thereby preventing total rejection of the corneal transplant.

As used herein, the term "contacting" refers to the bringing together of indicated moieties in an in vitro system or an in vivo system. For example, "contacting" a JAK with a compound of the invention includes the administration of a compound of the present invention to an individual or patient, such as a human, having a JAK, as well as, for example, introducing a compound of the invention into a sample containing a cellular or purified preparation containing the JAK.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, as well as Bcr-Abl, Flt-3, RAF and FAK kinase inhibitors such as, for example, those described in WO 2006/056399, or other agents can be used in combination with the compounds of the present invention for treatment of JAK-associated diseases, disorders or conditions. The one or more additional pharmaceutical agents can be administered to a patient simultaneously or sequentially.

Example chemotherapeutic include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, one or more of the compounds of the invention can be used in combination with one or more other kinase inhibitors including imatinib, particularly for treating patients resistant to imatinib or other kinase inhibitors.

In some embodiments, one or more JAK inhibitors of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a JAK inhibitor of the present invention with an additional agent. Furthermore, resistance of multiple myeloma cells to agents such as dexamethasone may be reversible upon treatment with a JAK inhibitor of the present invention. The agents can be combined with the present compounds in a single or continuous dosage form, or the agents can be administered simultaneously or sequentially as separate dosage forms.

In some embodiments, a corticosteroid such as dexamethasone is administered to a patient in combination with at least one JAK inhibitor where the dexamethasone is administered intermittently as opposed to continuously.

In some further embodiments, combinations of one or more JAK inhibitors of the invention with other therapeutic agents can be administered to a patient prior to, during, and/or after a bone marrow transplant or stem cell transplant.

In some embodiments, at least one additional therapeutic agent can be used in connection with treatment of dry eye disorders and other disorders of the eye. In some embodiments, the additional therapeutic agent is fluocinolone acetonide (Retisert®), or rimexolone (AL-2178, Vexol, Alcon). In some embodiments, the additional therapeutic agent is cyclosporine (Restasis®). In some embodiments, the additional therapeutic agent is a corticosteroid. In some embodiments, the corticosteroid is triaminolone, dexamethasone, fluocinolone, cortisone, prednisolone, or flumetholone.

In some embodiments, the additional therapeutic agent is selected from Dehydrex™ (Holles Labs), Civamide (Opko), sodium hyaluonate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-m ethyl-oxolane-2-carbamyl, Can-Fite Biopharma), voclosporin (LX212 or LX214, Lux Biosciences), ARG103 (Agentis), RX-10045 (synthetic resolvyn analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), or thalidomide.

In some embodiments, the additional therapeutic agent is an anti-angiogenic agent, cholinergic agonist, TRP-1 receptor modulator, a calcium channel blocker, a mucin secretagogue, MUC1 stimulant, a calcineurin inhibitor, a corticosteroid, a P2Y2 receptor agonist, a muscarinic receptor agonist, another JAK inhibitor, Bcr-Abl kinase inhibitor, Flt-3 kinase inhibitor, RAF kinase inhibitor, and FAK kinase inhibitor such as, for example, those described in WO 2006/056399. In some embodiments, the additional therapeutic agent is a tetracycline derivative (e.g., minocycline or doxycline).

In some embodiments, the additional therapeutic agent(s) are demulcent eye drops (also known as "artificial tears"), which include, but are not limited to, compositions containing polyvinylalcohol, hydroxypropyl methylcellulose, glycerin, polyethylene glycol (e.g. PEG400), or carboxymethyl cellulose. Artificial tears can help in the treatment dry eye by compensating for reduced moistening and lubricating capacity of the tear film. In some embodiments, the additional therapeutic agent is a mucolytic drug, such as N-acetyl-cysteine, which can interact with the mucoproteins and, therefore, to decrease the viscosity of the tear film.

In some embodiments, the additional therapeutic agent includes an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; comolyn; lodoxamide; levocabastin; naphazoling; antazoline; pheniramimane; or azalide antibiotic.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain, as the active ingredient, one or more of the compounds of the invention above in combination with one or more pharmaceutically acceptable carriers (excipients). In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, for example see International Patent Application No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

In some embodiments, the compound of the invention, or pharmaceutically acceptable salt thereof, is administered as an ophthalmic composition. Accordingly, in some embodiments, the methods comprise administration of the compound, or pharmaceutically acceptable salt thereof, and an ophthalmically acceptable carrier. In some embodiments, the ophthalmic composition is a liquid composition, semi-solid composition, insert, film, microparticles or nanooparticles.

In some embodiments, the ophthalmic composition is a liquid composition. In some embodiments, the ophthalmic composition is a semi-solid composition. In some embodiments, the ophthalmic composition is an topical composition. The topical compositions include, but are not limited to liquid and semi-solid compositions. In some embodiments, the ophthalmic composition is a topical composition. In some embodiments, the topical composition comprises aqueous solution, an aqueous suspension, an ointment or a gel. In some embodiments, the ophthalmic composition is topically applied to the front of the eye, under the upper eyelid, on the lower eyelid and in the cul-de-sac. In some embodiments, the ophthalmic composition is sterilized. The sterilization can be accomplished by known techniques like sterilizing filtration of the solution or by heating of the solution in the ampoule ready for use. The ophthalmic compositions of the invention can further contain pharmaceutical excipients suitable for the preparation of ophthalmic formulations. Examples of such excipients are preserving agents, buffering agents, chelating agents, antioxidant agents and salts for regulating the osmotic pressure.

As used herein, the term "ophthalmically acceptable carrier" refers to any material that can contain and release the compound, or pharmaceutically acceptable salt or N-oxide thereof, and that is compatible with the eye. In some embodiments, the ophthalmically acceptable carrier is water or an aqueous solution or suspension, but also includes oils such as those used to make ointments and polymer matrices such as used in ocular inserts. In some embodiments, the composition may be an aqueous suspension comprising the compound, or pharmaceutically acceptable salt or N-oxide thereof. Liquid ophthalmic compositions, including both ointments and suspensions, may have a viscosity that is suited for the selected route of administration. In some embodiments, the ophthalmic composition has a viscosity in the range of from about 1,000 to about 30,000 centipoise.

In some embodiments, the liquid composition further comprises a polymer. These polymers may be used to improve the bioavailability, raise viscosity, or reduce drainage from the eye for a liquid formulation. In some embodiments, the polymers include, but are not limited to, those described in Wagh, et al., "Polymers used in ocular dosage form and drug delivery systems", *Asian J. Pharm.*, pages 12-17 (January 2008), which is incorporated herein by reference in its entirety. In some embodiments, the polymer is sodium hyaluronase, chitosan, a cyclodextrin (e.g., hydroxypropyl β-cyclodextrin), polygalactoronic acid, xyloglucan, xanthan gum, gellan gum, a thiomer, a poly(ortho ester) (e.g., as described in Einmahl, *Adv. Drug. Deliv. Rev.* 53:45-73 (2001), which is incorporated herein by reference in its entirety), or a tamarind seed polysaccharide (e.g., as described in Ghelardi, et al., Antimicrob. Agents Chemother. 48:3396-3401 (2004), which is incorporated herein by reference in its entirety).

In some embodiments, the ophthalmic compositions may further comprise one or more of surfactants, adjuvants, buffers, antioxidants, tonicity adjusters, preservatives (e.g., EDTA, BAK (benzalkonium chloride), sodium chlorite, sodium perborate, polyquaterium-1), thickeners or viscosity modifiers (e.g., carboxymethyl cellulose, hydroxymethyl cellulose, polyvinyl alcohol, polyethylene glycol, glycol 400, propylene glycol hydroxymethyl cellulose, hydroxpropylguar, hyaluronic acid, and hydroxypropyl cellulose) and the like. Additives in the formulation may include, but are not limited to, sodium chloride, sodium bicarbonate, sorbic acid, methyl paraben, propyl paraben, chlorhexidine, castor oil, and sodium perborate.

Aqueous ophthalmic compositions (solutions or suspensions) generally do not contain physiologically or ophthalmically harmful constituents. In some embodiments, purified or deionized water is used in the composition. The pH may be adjusted by adding any physiologically and ophthalmically acceptable pH adjusting acids, bases or buffers to within the range of about 5.0 to 8.5. Ophthalmically acceptable examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, trishydroxymethylamino-methane, and the like. Salts and buffers include citrate/dextrose, sodium bicarbonate, ammonium chloride and mixtures of the aforementioned acids and bases.

In some embodiments, the osmotic pressure of the ophthalmic composition may be from about 10 milliosmolar (mOsM) to about 400 mOsM, or from 260 to about 340 mOsM. In some embodiments, the osmotic pressure can be adjusted by using appropriate amounts of physiologically and ophthalmically acceptable salts or excipients. In further embodiments, sodium chloride may be used to approximate physiologic fluid. In other embodiments, the composition comprises sodium chloride ranging from about 0.01% to about 1% by weight, or from about 0.05% to about 0.45% by weight, based on the total weight of the composition. Equivalent amounts of one or more salts made up of cations such as potassium, ammonium and the like and anions such as chloride, citrate, ascorbate, borate, phosphate, bicarbonate, sulfate, thiosulfate, bisulfate, sodium bisulfate, ammonium sulfate, and the like can also be used in addition to or instead of sodium chloride to achieve osmolalities within the above stated range. Similarly, a sugar such as mannitol, dextrose, sorbitol, glucose and the like can also be used to adjust osmolality.

In some embodiments, the methods involve forming or supplying a depot of the therapeutic agent in contact with the external surface of the eye. A depot refers to a source of therapeutic agent that is not rapidly removed by tears or other eye clearance mechanisms. This allows for continued, sustained high concentrations of therapeutic agent be present in the fluid on the external surface of the eye by a single application. Without wishing to be bound by any theory, it is believed that absorption and penetration may be dependent on both the dissolved drug concentration and the contact duration of the external tissue with the drug containing fluid. As the drug is removed by clearance of the ocular fluid and/or absorption into the eye tissue, more drug is provided, e.g. dissolved, into the replenished ocular fluid from the depot. Accordingly, the use of a depot may more easily facilitate loading of the ocular tissue for more insoluble therapeutic agents. In some embodiments, the depot can remain for up to eight hours or more. In some embodiments, the ophthalmic depot forms includes, but is not limited to, aqueous polymeric suspensions, ointments, and solid inserts.

In some embodiments, a semi-solid composition is a liquid formulation which increases in viscosity upon application to the eye, usually because of a polymer in the liquid formulation. This viscosity increase may be triggered by a change in temperature, pH, or electrolyte concentration. In some embodiments, the polymer include, but are not limited to, those described for semi-solid dosage forms in Wagh, et al., "Polymers used in ocular dosage form and drug delivery systems", *Asian J. Pharm.*, pages 12-17 (January 2008), which is incorporated herein by reference in its entirety. In some embodiments, the polymer is celluloseacetophthalate, polyacrylic acid, gellan gum, hyaluronase, chitosan, salts of alginic acid (e.g., sodium alginate), or a block copolymer of ethylene oxide and propylene oxide (e.g., Pluronic®, BASF; poloxamer). In some embodiment, the polyacrylic acid is crosslinked acrylic acid (e.g., Carbopol®). In some embodiments, the semi-solid composition comprises a mixture of carbopol and a block copolymer of ethylene oxide and propylene oxide; a mixture of methyl cellulose and hydroxyethyl cellulose; or a mixture of polyethylene glycol and a block copolymer of ethylene oxide and propylene oxide.

In some embodiments, the ophthalmic composition is an ointment or gel. In some embodiment, the ophthalmic composition is an oil-based delivery vehicle. In some embodiments, the composition comprises a petroleum or lanolin base to which is added the active ingredient, usually as 0.1 to 2%, and excipients. Common bases may include, but are not limited to, mineral oil, petrolatum and combinations thereof In some embodiments, the ointment is applied as a ribbon onto the lower eyelid.

In some embodiment, the ophthalmic composition is an ophthalmic insert. In some embodiments, the ophthalmic insert is biologically inert, soft, bio-erodible, viscoelastic, stable to sterilization after exposure to therapeutic agents, resistant to infections from air borne bacteria, bio-erodible, biocompatible, and/or viscoelastic. In some embodiments, the insert comprises an ophthalmically acceptable matrix, e.g., a polymer matrix. The matrix is typically a polymer and the therapeutic agent is generally dispersed therein or bonded to the polymer matrix. In some embodiments, the therapeutic agent may slowly released from the matrix through dissolution or hydrolysis of the covalent bond. In some embodiments, the polymer is bioerodible (soluble) and the dissolution rate thereof can control the release rate of the therapeutic agent dispersed therein. In another form, the polymer matrix is a biodegradable polymer that breaks down such as by hydrolysis to thereby release the therapeutic agent bonded thereto or dispersed therein. In further embodiments, the matrix and therapeutic agent can be surrounded with an additional polymeric coating to further control release. In some embodiments, the insert comprises a biodegradable polymer such as polycaprolactone (PCL), an ethylene/vinyl acetate copolymer (EVA), polyalkyl cyanoacrylate, polyurethane, a nylon, or poly (dl-lactide-co-glycolide) (PLGA), or a copolymer of any of these. In some embodiments, the therapeutic agent is dispersed into the matrix material or dispersed amongst the monomer composition used to make the matrix material prior to polymerization. In some embodiments, the amount of therapeutic agent is from about 0.1 to about 50%, or from about 2 to about 20%. In further embodiments, the biodegradable or bioerodible polymer matrix is used so that the spent insert does not have to be removed. As the biodegradable or bioerodible polymer is degraded or dissolved, the therapeutic agent is released.

In further embodiments, the ophthalmic insert comprises a polymer, including, but are not limited to, those described in Wagh, et al., "Polymers used in ocular dosage form and drug delivery systems", *Asian J. Pharm.*, pages 12-17 (January 2008), which is incorporated herein by reference in its entirety. In some embodiments, the insert comprises a polymer selected from polyvinylpyrrolidone (PVP), an acrylate or methacrylate polymer or copolymer (e.g., Eudragit® family of polymers from Rohm or Degussa), hydroxymethyl cellulose, polyacrylic acid, poly(amidoamine) dendrimers, poly(dimethyl siloxane), polyethylene oxide, poly(lactide-co-glycolide), poly(2-hydroxyethylmethacrylate), poly(vinyl alcohol), or poly(propylene fumarate). In some embodiments, the insert comprises Gelfoam® R. In some embodiments, the insert is a polyacrylic acid of 450 kDa-cysteine conjugante.

In some embodiments, the ophthalmic composition is a ophthalmic film. Polymers suitable for such films include, but are not limited to, those described in Wagh, et al., "Polymers used in ocular dosage form and drug delivery systems", *Asian J. Pharm.*, pages 12-17 (January 2008), In some embodiments, the film is a soft-contract lense, such as ones made from copolymers of N,N-diethylacrylamide and methacrylic acid crosslinked with ethyleneglycol dimethacrylate.

In some embodiments, the insert comprises a core comprising the therapeutic agent and an outer tube (see e.g., U.S. Patent Pub. No. 20040009222, which is incorporated herein by reference in its entirety). In some embodiments, the outer tube may be permeable, semi-permeable, or impermeable to the drug. In some embodiments, the drug core may include a polymer matrix which does not significantly affect the release rate of the drug. In some embodiments, the outer tube, the polymer matrix of the drug core, or both may be bioerodible. In some embodiments, the co-extruded product can be segmented into drug delivery devices. In some embodiments, the devices may be left uncoated so that their respective ends are open, or the devices may be coated with, for example, a layer that is permeable to the therapeutic agent, semi-permeable to the therapeutic agent, or bioerodible. In certain embodiments, the therapeutic agent and at least one polymer are admixed in powder form. In some embodiments, the insert is formed by forwarding a polymeric material to a first extrusion device, forwarding an therapeutic agent to a second extrusion device, co-extruding a mass including the polymeric material and the therapeutic agent, and forming the mass into at least one co-extruded drug delivery device which comprises a core including the therapeutic agent and an outer layer including the polymeric material. In certain embodiments, the therapeutic agent forwarded to the second extrusion device is in admixture with at least one polymer. In certain embodiments, the therapeutic agent and at least one polymer are admixed in powder form. In certain embodiments, this act includes forwarding more than one drug to the second extrusion device. In certain embodiments, the polymeric material is one of impermeable, semi-permeable, or permeable to the therapeutic agent. The polymeric material may be bioerodible and/or radiation curable. In latter instances, the insert may be irradiated.

In certain embodiments, the insert is in a tubular form, and may be segmented into a plurality of shorter products. In certain embodiments, the insert further comprises a coating of the plurality of shorter products with one or more layers including at least one of a layer that is permeable to the therapeutic agent, a layer that is semi-permeable to the therapeutic agent, and a layer that is bioerodible. The polymeric material may include any biocompatible polymer, such as polycaprolactone (PCL), an ethylene/vinyl acetate copolymer (EVA), polyalkyl cyanoacrylate, polyurethane, a nylon, or poly (dl-lactide-co-glycolide) (PLGA), or a copolymer of any of these.

In some embodiments, the insert comprises a therapeutically effective amount of at least one therapeutic agent coated by or dispersed in a polymer matrix, wherein the therapeutic agent is in granular or particulate form. In some embodiments, the therapeutic agent is released from the formulation as drug from the granules dissolves into or within the matrix, diffuses through the matrix, and is released into the surrounding physiological fluid. In some embodiments, the rate of release is limited primarily by the rate of dissolution of the therapeutic agent from the granules/particles into the matrix; the steps of diffusion through the matrix and dispersion into the surrounding fluid are primarily not release-rate-limiting. In certain embodiments, the polymer matrix is non-bioerodible, while in other embodiments it is bioerodible. Exemplary non-bioerodible polymer matrices can be formed from polyurethane, polysilicone, poly(ethylene-co-vinyl acetate) (EVA), polyvinyl alcohol, and derivatives and copolymers thereof. Exemplary bioerodible polymer matrices can be formed from polyanhydride, polylactic acid, polyglycolic acid, polyorthoester, polyalkylcyanoacrylate, and derivatives and copolymers thereof.

In some embodiments, the insert comprises a collagenous material. In some embodiments, the insert may be a soluble ophthalmic drug insert (SODI, e.g., a polymeric oval film that can be introduced in the upper conjuctival sac for drug delivery; an elliptical insert such as OCUSERT® (Pilocarpine ocular therapeutic system, developed by Alza Corporation) which is made of ethylene vinyl acetate; OCUFIT® (developed by Escalon Ophthalmics Inc., Skillman, N S), which is a rod shaped silicone elastomer; Lacrisert®, a rod shaped insert made of cellulose; New Ophthalmic Drug Delivery Systems (NODS), made of poly (vinyl alcohol); and the inserts described in Fabrizio, *Advanced Drug Delivery Reviews* 16: 95-106, 1998, which is incorporated herein by reference in its entirety. In further embodiments, the insert can be placed, depending on the location and the mechanism used to hold the insert in position, by either the patient or the doctor. In further embodiments, the insert comprises collagen, gelatin, or a polymer, wherein the polymer is selected from polycaprolactone (PCL), an ethylene/vinyl acetate copolymer (EVA), polyalkyl cyanoacralate, polyurethane, a nylon, poly(dl-lactide-co-glycolide) (PLGA), or a copolymer of any of the aforementioned. In some embodiments, the insert is implanted under the upper eyelid. In some embodiments, the insert is implanted in the posterior segment of the eye, in the chroidal space, or in the sclera. In some embodiments, the insert is implanted intravitreally or sub-retinally. In some embodiments, the insert is injected sub-retinally. Methods of administration and techniques for their preparation are set forth in Remington's Pharmaceutical Sciences, which is incorporated herein by reference in it entirety.

In other embodiments, the insert provides a sustained release of the therapeutic agent to the vitreous of the eye. As used herein, "sustained release" means that the composition releases the therapeutic agent over an extended period of time in a controlled fashion. In some embodiments, the insert releases the therapeutic agent at a rate such that the aqueous therapeutic agent concentration remains less than the vitreous therapeutic agent concentration during the release. In some embodiments, the aqueous therapeutic agent concentration is from about 0.002 µg/mL to about 0.01 µg/mL, or from about 0.01 µg/mL to about 0.05 µg/mL, or less than about 0.05 µg/mL. In some embodiments, the therapeutic agent is released at a rate of about 1 µg/day to about 50 µg/day, or from about 1 µg/day to about 10 µg/day. In some embodiments, the insert further comprises an additional therapeutic agent, as detailed above, e.g., fluocinolone acetonide (such as that found in the ophthalmic insert Retisert®).

In some embodiments, the ophthalmic composition comprises microspheres or nanoparticles. In some embodiment, the microspheres comprise gelatin. In some embodiments, the microspheres are injected to the posterior segment of the eye, in the chroidal space, in the sclera, intravitreally or subretinally. In some embodiments, the microspheres or nanoparticles comprises a polymer including, but not limited to, those described in Wagh, et al., "Polymers used in ocular dosage form and drug delivery systems", *Asian J. Pharm., pages* 12-17 (January 2008), which is incorporated herein by reference in its entirety. In some embodiments, the polymer is chitosan, a polycarboxylic acid such as polyacrylic acid, albumin particles, hyaluronic acid esters, polyitaconic acid, poly(butyl)cyanoacrylate, polycaprolactone, poly(isobutyl) caprolactone, poly(lactic acid-co-glycolic acid), or poly(lactic acid). In some embodiments, the microspheres or nanoparticles comprise solid lipid particles.

In some embodiments, the ophthalmic composition comprises an ion-exchange resin. In some embodiments, the ion-exchange resin is an inorganic zeolite or synthetic organic resin. In some embodiments, the ion-exchange resin includes, but is not limited to, those described in Wagh, et al., "Polymers used in ocular dosage form and drug delivery systems", *Asian J. Pharm., pages* 12-17 (January 2008), which is incorporated herein by reference in its entirety. In some embodiments, the ion-exchange resin is a partially neutralized polyacrylic acid.

In some embodiments, the ophthalmic composition is an aqueous polymeric suspension. In some embodiments, the therapeutic agent or a polymeric suspending agent is suspended in an aqueous medium (e.g., having the properties as described above). In some embodiment, the therapeutic agent is suspended. In some embodiments, the therapeutic agent is in solution. In further embodiments, the suspending agent serves to provide stability to the suspension, to increase the residence time of the dosage form on the eye, or to enhance the sustained release of the drug in terms of both longer release times and a more uniform release curve. Examples of polymeric suspending agents include, but are not limited to, dextrans, polyethylene glycols, polyvinylpyrolidone, polysaccharide gels, Gelrite®, cellulosic polymers like hydroxypropyl methylcellulose, and carboxy-containing polymers such as polymers or copolymers of acrylic acid, as well as other polymeric demulcents. In some embodiments, the polymeric suspending agent is a water swellable, water insoluble polymer, especially a crosslinked carboxy-containing polymer. In some embodiments, the polymeric suspending agent comprises from at least about 90% to about 99.9%, or from about 95% to about 99.9%, by weight based on the total weight of monomers present, of one or more carboxy-containing monoethylenically unsaturated monomers. In some embodiments, the carboxy-containing monoethylenically unsaturated monomer includes acrylic acid, methacrylic acid, ethacrylic acid, methylacrylic acid (crotonic acid), cis-α-methylcrotonic acid (angelic acid), trans-α-methylcrotonic acid (tiglic acid), α-butylcrotonic acid, α-phenylacrylic acid, α-benzylacrylic acid, α-cyclohexylacrylic acid, phenylacrylic acid (cinnamic acid), coumaric acid (o-hydroxycinnamic acid), and umbellic acid (p-hydroxycoumaric acid). In some embodiments, the polymers may be crosslinked by a polyfunctional crosslinking agent (e.g., a difunctional crosslinking agent). In further embodiments, the amount of crosslinking should be sufficient to form insoluble polymer particles, but not so great as to unduly interfere with sustained release of the therapeutic agent. In some embodiment, the polymers are only lightly crosslinked. In some embodiments, the crosslinking agent is contained in an amount of from about 0.01% to about 5%, or from about 0.1% to about 5.0%, or from about 0.2% to about 1%, based on the total weight of monomers present. In some embodiments, the crosslinking agents are nonpolyalkenyl polyether difunctional crosslinking monomers such as divinyl glycol, 2,3-dihydroxyhexa-1,5-diene, 2,5-dimethyl-1,5-hexadiene, divinylbenzene, N,N-diallylacrylamide, N,N-diallymethacrylamide; polyalkenyl polyether crosslinking agents containing two or more alkenyl ether groupings per molecule, e.g., alkenyl ether groupings containing terminal $H_2C=C<$groups, prepared by etherifying a polyhydric alcohol containing at least four carbon atoms and at least three hydroxyl groups with an alkenyl halide such as allyl bromide or the like, e.g., polyallyl sucrose, polyallyl pentaerythritol, or the like; diolefinic non-hydrophilic macromeric crosslinking agents having molecular weights of from about 400 to about 8,000, such as insoluble diacrylates and polyacrylates and methacrylates of diols and polyols, diisocyanate hydroxyalkyl acrylate or methacrylate reaction products of isocyanate terminated prepolymers derived from polyester diols, polyether diols or polysiloxane diols with hydroxyalkylmethacrylates, and the like.

In some embodiments, the crosslinked polymers may be made from a carboxy-containing monoethylenically unsaturated monomer or monomers as the sole monoethylenically unsaturated monomer present, together with a crosslinking agent or agents. In some embodiments, the polymers are ones in which up to about 40%, and preferably from about 0% to about 20% by weight, of the carboxy-containing monoethylenically unsaturated monomer or monomers has been replaced by one or more non-carboxyl-containing monoethylenically unsaturated monomer or monomers containing only physiologically and ophthalmically innocuous substituents, including acrylic and methacrylic acid esters such as methyl methacrylate, ethyl acrylate, butyl acrylate, 2-ethylhexylacrylate, octyl methacrylate, 2-hydroxyethylmethacrylate, 3-hydroxypropylacrylate, and the like, vinyl acetate, N-vinylpyrrolidone, and the like (see Mueller et al. U.S. Pat. No. 4,548,990, the entire contents of which are incorporated herein by reference, for a more extensive listing of such additional monoethylenically unsaturated monomers). In some embodiments, the polymers include polycarbophil (Noveon AA-1), Carbopol®, and DuraSite®. In some embodiments, the crosslinked polymers are prepared by suspension or emulsion polymerizing the monomers, using conventional free radical polymerization catalysts, to a dry particle size of not more than about 50 μm in equivalent spherical diameter. In some embodiments, the average dry particle size is from about 1 to about 30 μm, or from about 3 to about 20 μm in equivalent spherical diameter. In some embodiments, the polymer particles are obtained by mechanically milling larger polymer particles. In further embodiments, such polymers will have a molecular weight from about 250,000 to about 4,000,000, and from 3,000,000,000 to 4,000,000,000. In other embodiments, the particles of crosslinked polymer are monodisperse, meaning that they have a particle size distribution such that at least about 80%, about 90% or about 95%, of the particles fall within a μm band of major particle size distribution. In further embodiments, the monodisperse particle size means that there is no more than about 20%, about 10%, or about 5% particles of a size below 1 μm. In some embodiments, the aqueous polymeric suspension comprises from about 0.05 to about 1%, from about 0.1 to about 0.5%, or from about 0.1 to about 0.5%, of the therapeutic agent and from about 0.1 to about 10%, from about 0.5 to about 6.5%, from about 0.5 to about 2.0%, from about 0.5% to about 1.2%, from about 0.6 to about 0.9%, or from about 0.6 to about 0.8% of a polymeric suspending agent. Although referred to in the singular, it should be understood that one or more species of polymeric suspending agent can be used with the total amount falling within the stated ranges. In one embodiment, the amount of insoluble lightly crosslinked polymer particles, the pH, and the osmotic pressure can be correlated with each other and with the degree of crosslinking to give a composition having a viscosity in the range of from about 500 to about 100,000 centipoise, and preferably from about 1,000 to about 30,000 or about 1,000 to about 10,000 centipoise, as measured at room temperature (about 25° C.) using a Brookfield Digital LVT Viscometer equipped with a number 25 spindle and a 13R small sample adapter at 12 rpm. In some embodiments, the viscosity is from about 10 to about 400 centipoise, from about 10 to about 200 centipoises or from about 10 to about 25 centipoise.

In some embodiments, the aqueous polymeric suspensions may be formulated so that they retain the same or substantially the same viscosity in the eye that they had prior to administration to the eye. In some embodiments, they may be formulated so that there is increased gelation upon contact with tear fluid. For instance, when a formulation containing DuraSite® or other similar polyacrylic acid-type polymer is administered to the eye at a pH of less than about 6.7, the polymer may swell upon contact with tear fluid since it has a higher pH (around 7). This gelation or increase in gelation may lead to entrapment of the suspended particles, thereby extending the residence time of the composition in the eye. In some embodiments, the therapeutic agent is released slowly as the suspended particles dissolve over time. In some embodiments, this delivery route increases patient comfort and increased therapeutic agent contact time with the eye tissues, thereby increasing the extent of drug absorption and duration of action of the formulation in the eye. The therapeutic agents contained in these drug delivery systems may be released from the gels at rates that depend on such factors as the drug itself and its physical form, the extent of drug loading and the pH of the system, as well as on any drug delivery adjuvants, such as ion exchange resins compatible with the ocular surface, which may also be present.

The compositions of the invention can further include one or more additional pharmaceutical agents such as a chemotherapeutic, steroid, anti-inflammatory compound, or immunosuppressant, examples of which are listed hereinabove.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

{1-(ethylsulfonyl)-3-[4-(7H-pyrrolo[2,3-d]pyrimidin-4-yl)-1H-pyrazol-1-y]azetidin-3-yl}acetonitrile trifluoroacetic acid salt

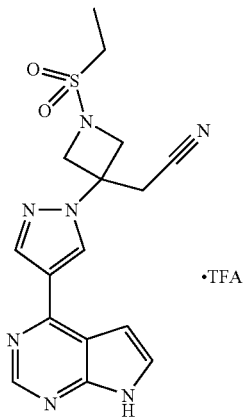

Step 1. tert-butyl 3-(cyanomethylene)azetidine-1-carboxylate

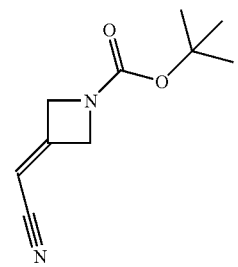

To a suspension of sodium hydride (60% dispersion in mineral oil, 0.257 g, 6.42 mmol) in tetrahydrofuran (32 mL) at 0° C. under a nitrogen atmosphere was added diethyl cyanomethylphosphonate (1.19 g, 6.72 mmol) (purchased from Aldrich). The reaction was then stirred for 45 minutes at room temperature. A solution of tert-butyl 3-oxoazetidine-1-carboxylate (1.00 g, 5.84 mmol) (purchased from Alfa Aesar) in tetrahydrofuran (8.8 mL) was introduced dropwise and the mixture was stirred for 16 hours. Brine and ethyl acetate were added and the layers separated. The aqueous layer was extracted with three portions of ethyl acetate. The combined extracts were dried over sodium sulfate, filtered and concentrated to afford product, used without further purification in Step 2 (1.12 g, 99%).

$^1$H NMR (300 MHz, CDCl$_3$): δ 5.38 (p, 1H), 4.73-4.68 (m, 2H), 4.64-4.59 (m, 2), 1.46 (s, 9H).

Step 2. tert-butyl 3-(cyanomethyl)-3-[4-(7-[2-(trimethylsilyl)ethoxy]methyl-7H-pyrrolo[2,3-d]pyrimidin-4-yl)-1H-pyrazol-1-yl]azetidine-1-carboxylate

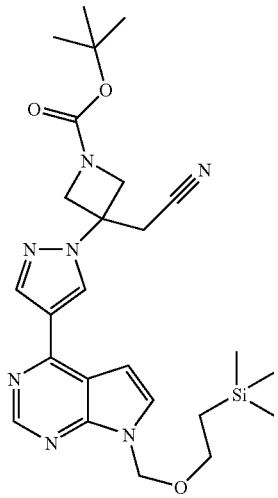

To a solution of 4-(1 H-pyrazol-4-yl)-7-[2-(trimethylsilyl)ethoxy]methyl-7H-pyrrolo[2,3-d]pyrimidine (4.61 g, 14.6 mmol) (prepared according to the method of WO 2007/070514 in Example 65, Step 2) and tert-butyl 3-(cyanomethylene)azetidine-1-carboxylate (2.84 g, 14.6 mmol) in acetonitrile (100 mL) was added 1,8-diazabicyclo[5.4.0]undec-7-ene (2.19 mL, 14.6 mmol). The reaction was stirred at room temperature for 16 hours. The acetonitrile was removed in vacuo and the residue was dissolved in ethyl acetate. This solution was sequentially washed with 1N HCl and brine, dried over sodium sulfate, filtered and concentrated. The residue was purified by flash column chromatography, eluting with 80% ethyl acetate/hexanes to afford desired product (5.36 g, 72%).

$^1$H NMR (300 MHz, CDCl$_3$): δ 8.86 (s, 1H), 8.44 (s, 1H), 8.34 (s, 1H), 7.42 (d, 1H), 6.80 (d, 1H), 5.68 (s, 2H), 4.54 (d, 2H), 4.29 (d, 2H), 3.59-3.51 (m, 2H), 3.33 (s, 2H), 1.47 (s, 9H), 0.96-0.89 (m, 2H), −0.06 (s, 9H); LCMS (M+H)$^+$: 510.2.

Step 3. 3-[4-(7-[2-(trimethylsilyl)ethoxy]methyl-7H-pyrrolo[2,3-d]pyrimidin-4-yl)-1H-pyrazol-1-yl]azetidin-3-ylacetonitrile

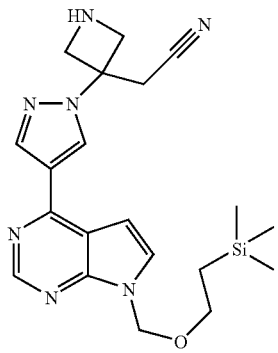

To a solution of tert-butyl 3-(cyanomethyl)-3-[4-(7-[2-(trimethylsilyl)ethoxy]methyl-7H-pyrrolo[2,3-d]pyrimidin-4-yl)-1H-pyrazol-1-yl]azetidine-1-carboxylate (5.36 g, 10.5 mmol) in 1,4-dioxane (100 mL) was added 4.00 M of hydrogen chloride in 1,4-dioxane (40 mL, 160 mmol) and the mixture was stirred at room temperature for 16 hours. The reaction was poured into saturated sodium bicarbonate solution sufficient to neutralize. The product was extracted with three portions of ethyl acetate. The combined extracts were washed with brine, dried over sodium sulfate, filtered and concentrated to afford product which was used without further purification (3.0 g, 69%).

$^1$H NMR (400 MHz, CDCl$_3$): δ 8.85 (s, 1H), 8.42 (s, 1H), 8.32 (s, 1H), 7.41 (d, 1H), 6.80 (d, 1H), 5.68 (s, 2H), 4.30 (d, 2H), 3.88 (d, 2H), 3.58-3.51 (m, 2H), 3.42 (s, 2H), 0.96-0.89 (m, 2H), −0.06 (s, 9H); LCMS (M+H)$^+$: 410.2.

Step 4. 1-(ethylsulfonyl)-3-[4-(7-[2-(trimethylsilyl)ethoxy]methyl-7H-pyrrolo[2,3-d]pyrimidin-4-yl)-1H-pyrazol-1-yl]azetidin-3-ylacetonitrile

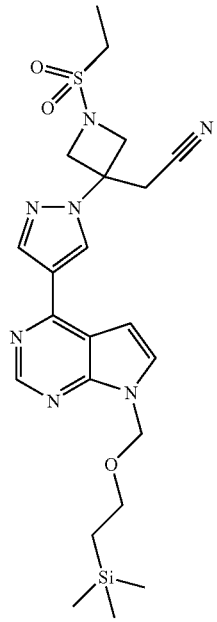

To a solution of 3-[4-(7-[2-(trimethylsilyl)ethoxy]methyl-7H-pyrrolo[2,3-d]pyrimidin-4-yl)-1H-pyrazol-1-yl]azetidin-3-ylacetonitrile (0.100 g, 0.244 mmol) in tetrahydrofuran (2 mL) containing N,N-diisopropylethylamine (0.085 mL, 0.49 mmol) was added ethanesulfonyl chloride (0.023 mL, 0.24 mmol). After stirring for 1.5 hours, the reaction mixture was poured into dilute HCl and extracted with three portions of ethyl acetate. The combined extracts were washed with brine, dried over sodium sulfate, decanted and concentrated to afford product, used without further purification in Step 5 (111 mg, 91%).

$^1$H NMR (300 MHz, CDCl$_3$): δ 8.86 (s, 1H), 8.63 (s, 1H), 8.35 (s, 1H), 7.45 (d, 1H), 6.83 (d, 1H), 5.68 (s, 2H), 4.63 (d, 2H), 4.26 (d, 2H), 3.54 (t, 2H), 3.42 (s, 2H), 3.09 (q, 2H), 1.41 (t, 3H), 0.92 (t, 2H), −0.06 (s, 9H); LCMS (M+H)$^+$: 502.1.

Step 5. 1-(ethylsulfonyl)-3-[4-(7H-pyrrolo[2,3-d]pyrimidin-4-yl)-1H-pyrazol-1-yl]azetidin-3-ylacetonitrile trifluoroacetate salt To a solution of 1-(ethylsulfonyl)-3-[4-(7-[2-(trimethylsilyl)ethoxy]methyl-7H-pyrrolo[2,3-d]pyrimidin-4-yl)-1H-pyrazol-1-yl]azetidin-3-ylacetonitrile (0.111 g, 0.22 mmol) in methylene chloride (3 mL) was added trifluoroacetic acid (2 mL) and the solution was stirred for 1.5 hours. The solvents were removed in vacuo and the residue was dissolved in methanol (3 mL) and ethylenediamine (0.1 mL) was added. After stirring for 3 hours, the volume was reduced in vacuo and the product was purified by preparative-HPLC/MS, (SunFire C18 column, eluting with a gradient of MeCN/H$_2$O containing 0.1% TFA) to afford the product as the trifluoroacetic acid salt (50 mg, 47%).

$^1$H NMR (400 MHz, d$_6$-dmso): δ 12.55 (br d, 1H), 9.03 (s, 1H), 8.83 (s, 1H), 8.56 (s, 1H), 7.79-7.75 (m, 1H), 7.24-7.19 (m, 1H), 4.59 (d, 2H), 4.26 (d, 2H), 3.71 (s, 2H), 3.25 (q, 2H), 1.24 (t, 3H); LCMS (M+H)$^+$: 372.1.

Alternatively, the deprotection and sulfonylation steps could be performed in the reverse order, as in Example 2.

Example 2

1-(cyclopropylsulfonyl)-3-[4-(7H-pyrrolo[2,3-d]pyrimidin-4-yl)-1H-pyrazol-1-yl]azetidin-3-ylacetonitrile trifluoroacetic acid salt

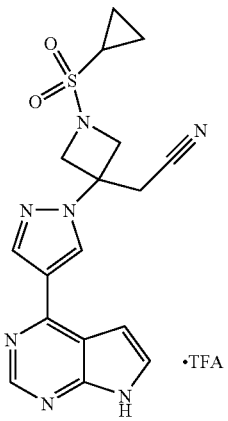

Step 1. 3-[4-(7H-pyrrolo[2,3-d]pyrimidin-4-yl)-1H-pyrazol-1-yl]azetidin-3-ylacetonitrile trifluoroacetic acid salt

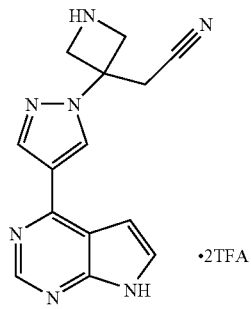

A solution of tert-butyl 3-(cyanomethyl)-3-[4-(7-[2-(trimethylsilyl)ethoxy]methyl-7H-pyrrolo[2,3-d]pyrimidin-4-yl)-1H-pyrazol-1-yl]azetidine-1-carboxylate, as prepared in Example 1, Step 2 (0.60 g, 1.2 mmol) in trifluoroacetic acid (10 mL) and methylene chloride (40 mL) was stirred for 5 hours. The solvents were removed in vacuo and the residue stirred in a solution of methanol (40 mL) and 14.50 M of ammonium hydroxide in water (10 mL) overnight. The solvent was evaporated, the residue reconstituted in methanol and purified by preparative-HPLC/MS (SunFire C18 column, eluting with a gradient of MeCN/H$_2$O containing 0.1% TFA) to afford the product as the trifluoroacetic acid salt (526 mg, 88%).

$^1$H NMR (400 MHz, d$_6$-dmso): δ 12.36 (br s, 1H), 9.37 (br s, 1H), 9.15 (br s, 1H), 9.05 (s, 1H), 8.77 (s, 1H), 8.56 (s, 1H), 7.71 (dd, 1H), 7.14 (dd, 1H), 4.75-4.65 (m, 2H), 4.48-4.39 (m, 2H), 3.74 (s, 2H); LCMS (M+H)$^+$: 280.1.

Step 2. 1-(cyclopropylsulfonyl)-3-[4-(7H-pyrrolo[2,3-d]pyrimidin-4-yl)-1H-pyrazol-1-yl]azetidin-3-ylacetonitrile trifluoroacetate salt To 3-[4-(7H-pyrrolo[2,3-d]pyrimidin-4-yl)-1 H-pyrazol-1-yl]azetidin-3-ylacetonitrile bis(trifluoroacetate) (0.400 g, 0.788 mmol) in tetrahydrofuran (38 mL) and triethylamine (0.55 mL, 3.9 mmol) was added cyclopropanesulfonyl chloride (0.084 mL, 0.83 mmol). The reaction was stirred at room temperature for a few hours with periodic addition of cyclopropanesulfonyl chloride until the starting amine was consumed as evidenced by LCMS. To dissolve insolubles, methanol (0.16 mL) was added. The THF was removed in vacuo and MeOH was used to reconstitute the sample for purification by preparative-HPLC/MS (SunFire C18 column, eluting with a gradient of MeCN/H$_2$O containing 0.1% TFA) to afford the product as the trifluoroacetate salt (193 mg, 49%).

$^1$H NMR (300 MHz, d$_6$-dmso): δ 12.53 (br s, 1H), 9.05 (s, 1H), 8.82 (s, 1H), 8.55 (s, 1H), 7.76 (dd, 1H), 7.21 (dd, 1H), 4.65 (d, 2H), 4.31 (d, 2H), 3.70 (s, 2H), 2.90-2.80 (m, 1H), 1.07-0.97 (m, 4H); LCMS (M+H)$^+$: 384.1.

Example 3

1-[(1-methylcyclopropyl)carbonyl-3-[4-(7H-pyrrolo[2,3-d]pyrimidin-4-yl)-1H-pyrazol-1-yl]azetidin-3-ylacetonitrile trifluoroacetic acid salt

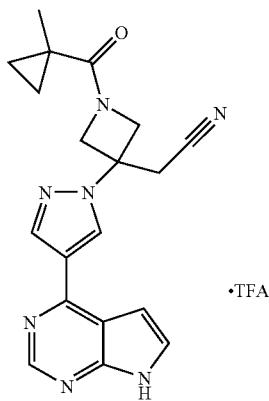

To a solution of 1-methylcyclopropanecarboxylic acid (4.3 mg, 0.043 mmol) and N,N-diisopropylethylamine (0.018 g, 0.14 mmol) in N,N-dimethylformamide (1.5 mL) was added N,N,N',N'-tetramethyl-O-(7-azabenzotriazol-1-yl)uronium hexafluorophosphate (0.016 g, 0.043 mmol) (purchased from Aldrich). The reaction was stirred for 15 minutes followed by the addition of 3-[4-(7H-pyrrolo[2,3-d]pyrimidin-4-yl)-1 H-pyrazol-1-yl]azetidin-3-ylacetonitrile bis(trifluoroacetate) salt from Example 2, Step 1 (0.014 g, 0.029 mmol). The reaction was stirred for 16 hours. The product was purified by preparative-HPLC/MS, (SunFire C18 column, eluting with a gradient of MeCN/H$_2$O containing 0.1% TFA) to afford the product as the trifluoroacetate salt (6 mg, 45%).

$^1$H NMR (300 MHz, d$_6$-dmso): δ 12.82 (br s, 1H), 9.10 (s, 1H), 8.91 (s, 1H), 8.59 (s, 1H), 7.86 (s, 1H), 7.31 (s, 1H), 5.07-4.07 (br, 4H), 3.72 (s, 2H), 1.28 (s, 3H), 0.98 (s, 2H), 0.54 (s, 2H); LCMS(M+H)$^+$: 362.2.

In some cases, a modification to Example 3 was used where THF was substituted for DMF as the solvent. In Table 1, this is indicated by modification A.

Example 4

1-[(1-methylcyclopropyl)sulfonyl]-3-[4-(7H-pyrrolo[2,3-d]pyrimidin-4-yl)-1H-pyrazol-1-yl]azetidin-3-ylacetonitrile trifluoroacetic acid salt

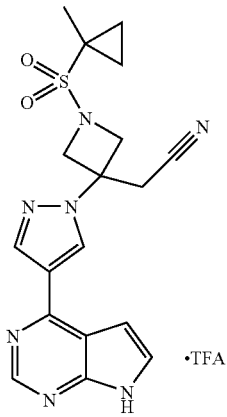

Step 1. 1-(cyclopropylsulfonyl)azetidin-3-ol

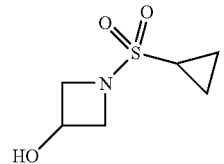

To a solution of azetidin-3-ol hydrochloride (1.00 g, 9.13 mmol) (purchased from Matrix) and N,N-diisopropylethylamine (4.77 mL, 27.4 mmol) in tetrahydrofuran (100 mL) at 0° C. was added cyclopropanesulfonyl chloride (0.930 mL, 9.13 mmol) and the reaction was stirred for 16 hours. Water was added and the product was extracted with ethyl acetate. The combined extracts were washed with 1N HCl, saturated sodium bicarbonate, and brine, dried over sodium sulfate, decanted and concentrated to afford a yellow oil used without further purification (1.04 g, 64%).

$^1$H NMR (300 MHz, CDCl$_3$): δ 4.61 (p, 1H), 4.14-4.07 (m, 2H), 3.93-3.86 (m, 2H), 2.69 (br s, 1H), 2.42-2.32 (m, 1H), 1.20-1.11 (m, 2H), 1.06-0.98 (m, 2H).

Step 2. 1-(cyclopropylsulfonyl)-3-[(triethylsilyl)oxy]azetidine

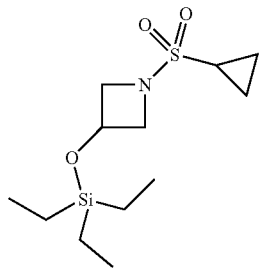

To a solution of 1-(cyclopropylsulfonyl)azetidin-3-ol (1.04 g, 5.87 mmol) and triethylamine (3.11 mL, 22.3 mmol) in tetrahydrofuran (20 mL) was added 4-dimethylaminopyridine (0.090 g, 0.73 mmol) followed by chlorotriethylsilane (1.00 M in THF, 8.0 mL, 8.0 mmol). The reaction was stirred at room temperature for 16 hours. To the reaction was added saturated sodium bicarbonate solution and the product was extracted with a 1:1 mix of ethyl acetate:hexanes three times. The combined organic extracts were washed with dilute HCl and brine, then dried over sodium sulfate, decanted and concentrated. Flash column chromatography, eluting with a gradient of 0-50% ethyl acetate in hexanes afforded desired product (1.0 g, 58%).

$^1$H NMR (300 MHz, CDCl$_3$): δ 4.56 (p, 1H), 4.05-3.98 (m, 2H), 3.90-3,83 (m, 2H), 2.41-2.32 (m, 1H), 1.20-1.12 (m, 2H), 1.05-0.96 (m, 2H), 0.93 (t, 9H), 0.57 (q, 6H).

Step 3. 1-[(1-methylcyclopropyl)sulfonyl]-3-[(triethylsilyl)oxy]azetidine

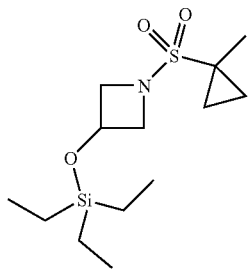

To a solution of 1-(cyclopropylsulfonyl)-3-[(triethylsilyl)oxy]azetidine (1.0 g, 3.4 mmol) in tetrahydrofuran (20 mL) at −78° C. was added 2.50 M of n-butyllithium in hexane (1.37 mL, 3.43 mmol) dropwise. After stirring at this temperature for 1 hour, methyl iodide (0.224 mL, 3.60 mmol) was added. After 30 minutes, the reaction temperature was raised to 0° C. and stirred for 50 minutes. The reaction was quenched by the addition of saturated sodium bicarbonate, followed by brine and the product was extracted with ethyl acetate. The extracts were dried over sodium sulfate, decanted and concentrated. Flash column chromatography eluting with a gradient of 0-30% ethyl acetate in hexanes afforded product (890 mg, 85%).

$^1$H NMR (300 MHz, CDCl$_3$): δ 4.57 (p, 1H), 4.00-3.94 (m, 2H), 3.92-3.86 (m, 2H), 1.49 (s, 3H), 1.35-1.29 (m, 2H), 0.93 (t, 9H), 0.73 (dt, 2H), 0.57 (q, 6H).

Step 4.
1-[(1-methylcyclopropyl)sulfonyl]azetidin-3-ol

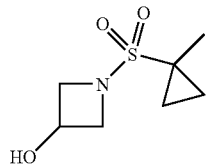

A solution of 1-[(1-methylcyclopropyl)sulfonyl]-3-[(triethylsilyl)oxy]azetidine (0.125 g, 0.41 mmol) in tetrahydrofuran (3 mL), water (1 mL) and acetic acid (1 mL) was stirred at room temperature for four hours. The mixture was neutralized by pouring into a solution of sodium bicarbonate. The product was extracted with ethyl acetate, the extracts were washed with brine, dried over sodium sulfate, decanted and concentrated to afford product, used without further purification (64 mg, 82%).

$^1$H NMR (300 MHz, CD$_3$OD): δ 4.56-4.47 (m, 1H), 4.02-3.95 (m, 2H), 3.83-3.75 (m, 2H), 1.47 (s, 3H), 1.26-1.19 (m, 2H), 0.84-0.77 (m, 2H).

Step 5.
1-[(1-methylcyclopropyl)sulfonyl]azetidin-3-one

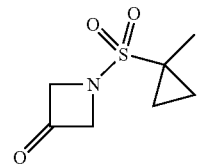

To a solution of oxalyl chloride (59 μL, 0.69 mmol) in methylene chloride (1.5 mL) at −78° C. was added dimethyl sulfoxide (0.10 mL, 1. 5 mmol) slowly dropwise. The reaction was stirred for 15 minutes following complete addition. A solution of 1-[(1-methylcyclopropyl)-sulfonyl]azetidin-3-ol (64 mg, 0.33 mmol) in methylene chloride (1.0 mL) was added dropwise and the reaction mixture was stirred for 45 min at −60° C. Triethylamine (0.28 mL, 2.0 mmol) was added dropwise and the reaction was stirred for 15 minutes and the bath was removed and the solution allowed to warm to ambient temperature. The solvent was removed in vacuo and ethyl acetate was added. The solution was washed sequentially with saturated sodium bicarbonate solution, water and brine, dried over sodium sulfate, decanted and concentrated. The crude product was used without further purification in Step 6.

$^1$H NMR (300 MHz, CDCl$_3$): δ 4.07 (d, 2H), 3.93 (d, 2H), 1.58 (s, 3H), 1.44-1.38 (m, 2H), 0.87 (dt, 2H).

Step 6. 1-[(1-methylcyclopropyl)sulfonyl]azetidin-3-ylideneacetonitrile

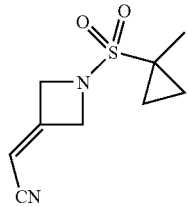

To a mixture of sodium hydride (60% dispersion in mineral oil, 17 mg, 0.42 mmol) in tetrahydrofuran (2 mL) at 0° C. was added diethyl cyanomethylphosphonate (70 μL, 0.43 mmol) dropwise. The mixture was then allowed to reach room temperature and stir for a further 45 minutes. A solution of 1-[(1-methylcyclopropyl)sulfonyl]azetidin-3-one (prepared in Step 5) in tetrahydrofuran (1.0 mL) was added and the mixture was allowed to stir at ambient temperature for 16 hours. Into the reaction was added water and solid NaCl, and the product was extracted with three portions of ethyl acetate. The combined extracts were dried over sodium sulfate, decanted and concentrated to afford product (71 mg, 100%), used without further purification in Step 7.

¹H NMR (300 MHz, CDCl₃): δ 5.44-5.39 (m, 1H), 4.76-4.71 (m, 2H), 4.69-4.64 (m, 2H), 1.49 (s, 3H), 1.36-1.30 (m, 2H), 0.80 (dt, 2H).

Step 7. 1-[(1-methylcyclopropyl)sulfonyl]-3-[4-(7-[2-(trimethylsilyl)ethoxy]ethyl-7H-pyrrolo[2,3-d]pyrimidin-4-yl)-1H-pyrazol-1-yl]azetidin-3-ylacetonitrile

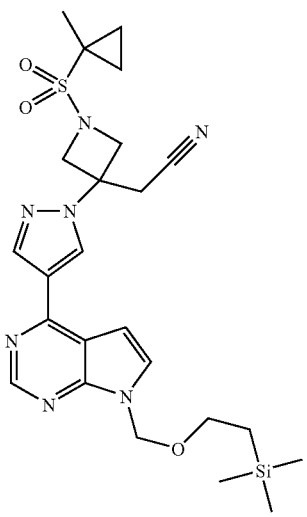

To a solution of 4-(1H-pyrazol-4-yl)-7-[2-(trimethylsilyl)ethoxy]methyl-7H-pyrrolo[2,3-d]pyrimidine (0.108 g, 0.344 mmol) and 1-[(1-methylcyclopropyl)sulfonyl]azetidin-3-ylideneacetonitrile (71 mg, 0.33 mmol) in acetonitrile (3 mL) was added 1,8-diazabicyclo[5.4.0]undec-7-ene (51 μL, 0.34 mmol). After a reaction time of 1.5 hours, the acetonitrile was removed in vacuo and the residue was partitioned between ethyl acetate and 1N HCl. The layers were separated and the organic layer was washed with brine, dried over sodium sulfate, filtered and concentrated. Flash column chromatography, eluting with a gradient of 0-80% ethyl acetate in hexanes afforded product (135 mg, 77%).

¹H NMR (300 MHz, CDCl₃): δ 8.86 (s, 1H), 8.46 (s, 1H), 8.35 (s, 1H), 7.42 (d, 1H), 6.80 (d, 1H), 5.68 (s, 2H), 4.62 (d, 2H), 4.22 (d, 2H), 3.59-3.50 (m, 2H), 3.42 (s, 2H), 1.55 (s, 3H), 1.42-1.36 (m, 2H), 0.96-0.89 (m, 2H), 0.85 (dt, 2H), -0.06 (s, 9H); LCMS (M+H)⁺: 528.1.

Step 8. 1-[(1-methylcyclopropyl)sulfonyl]-3-[4-(7H-pyrrolo[2,3-d]pyrimidin-4-yl)-1H-pyrazol-1-yl]azetidin-3-ylacetonitrile trifluoroacetic acid salt A solution of 1-[(1-methylcyclopropyl)sulfonyl]-3-[4-(7-[2-(trimethylsilyl)ethoxy]methyl-7H-pyrrolo[2,3-d]pyrimidin-4-yl)-1H-pyrazol-1-yl]azetidin-3-ylacetonitrile (44 mg, 0.083 mmol) in methylene chloride (10 mL) and trifluoroacetic acid (5 mL) was stirred for 2 hours. The solvents were removed in vacuo. The residue was stirred with 14.50 M of ammonium hydroxide solution (3 mL) in methanol (10 mL) for 16 hours. Solvents were removed in vacuo and the residue was purified by preparative HPLC-MS (SunFire C18 column, eluting with a gradient of H₂O and MeCN containing 0.1% TFA) to afford product as the trifluoroacetate salt (0.02 g, 50%).

¹H NMR (300 MHz, d₆-dmso): δ 12.56 (br s, 1H), 9.03 (s, 1H), 8.83 (s, 1H), 8.55 (s, 1H), 7.77 (dd, 1H), 7.21 (dd, 1H), 4.58 (d, 2H), 4.23 (d, 2H), 3.71 (s, 2H), 1.46 (s, 3H), 1.22-1.16 (m, 2H), 0.93-0.87 (m, 2H); LCMS (M+H)⁺: 398.1.

Acid chlorides, isocyanates or chloroformates were used in place of sulfonyl chlorides in either the method of Example 1 or Example 2 to afford amides (Ex. Nos. 22, 24, 26-30 & 33 of Table 1), ureas (Ex. No. 38 of Table 1) or carbamates (Ex. Nos. 35-37 of Table 1), respectively, as products. Additionally, triethylamine and diisopropylethylamine were used interchangeably. Some amides in Table 1 were prepared by an alternative method illustrated in Example 3, by coupling the amine of Example 2, Step 1 with carboxylic acids.

TABLE 1

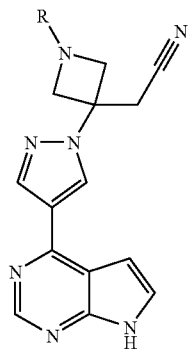

| Ex. No. | —R | Name | MS (M + H)⁺ | ¹H NMR (δ) | Method of Preparation |
|---|---|---|---|---|---|
| 5 | —SO₂Me | {1-(methylsulfonyl)-3-[4-(7H-pyrrolo[2,3-d]pyrimidin-4-yl)-1H-pyrazol-1-yl]azetidin-3-yl}acetonitrile trifluoroacetic acid salt | 358.1 | (400 MHz, d₆-dmso): 12.35 (br s, 1H), 8.99 (s, 1H), 8.77 (s, 1H), 8.52 (s, 1H), 7.70 (t, 1H), 7.16 (dd, 1H), 4.62 (d, 2H), 4.28 (d, 2H), 3.70 (s, 2H), 3.02 (br s, 3 H). | Ex. # 1 |

TABLE 1-continued

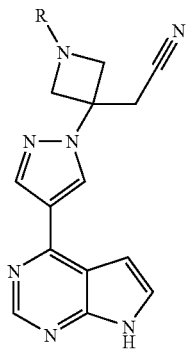

| Ex. No. | —R | Name | MS (M + H)+ | 1H NMR (δ) | Method of Preparation |
|---|---|---|---|---|---|
| 6 | —SO$_2$Ph | {1-(phenylsulfonyl)-3-[4-(7H-pyrrolo[2,3-d]pyrimidin-4-yl)-1H-pyrazol-1-yl]azetidin-3-yl}acetonitrile trifluoroacetic acid salt | 420.1 | (400 MHz, d$_6$-dmso): 12.55 (br s, 1H), 8.80 (s, 1H), 8.78 (s, 1H), 8.34 (s, 1H), 7.88-7.83 (m, 2H), 7.79-7.74 (m, 1H), 7.66-7.56 (m, 3H), 7.15-7.11 (m, 1H), 4.40 (d, 2H), 4.23 (d, 2H), 3.55 (s, 2 H). | Ex. # 2 |
| 7 | —SO$_2$$^i$Pr | {1-(isopropylsulfonyl)-3-[4-(7H-pyrrolo[2,3-d]pyrimidin-4-yl)-1H-pyrazol-1-yl]azetidin-3-yl} acetonitrile | 386.1 | (300 MHz, d$_6$-dmso): 12.16 (br s, 1H), 8.93 (s, 1H), 8.71 (s, 1H), 8.48 (s, 1H), 7.63 (t, 1H), 7.09 (d, 1H), 4.59 (d, 2H), 4.21 (d, 2H), 3.71 (s, 2H), 3.41-3.29 (m, 1H), 1.26 (d, 6 H). | Ex. # 2 |
| 8 | —SO$_2$$^n$Pr | {1-(propylsulfonyl)-3-[4-(7H-pyrrolo[2,3-d]pyrimidin-4-yl)-1H-pyrazol-1-yl]azetidin-3-yl} acetonitrile | 386.1 | (300 MHz, d$_6$-dmso): 12.17 (br s, 1H), 8.94 (s, 1H), 8.71 (s, 1H), 8.48 (s, 1H), 7.63 (dd, 1H), 7.09 (dd, 1H), 4.60 (d, 2H), 4.24 (d, 2H), 3.69 (s, 2H), 3.26-3.18 (m, 2H), 1.79-1.65 (m, 2H), 0.99 (t, 3 H). | Ex. # 2 |
| 9 | —SO$_2$$^n$Bu | {1-(butylsulfonyl)-3-[4-(7H-pyrrolo[2,3-d]pyrimidin-4-yl)-1H-pyrazol-1-yl]azetidin-3-yl}acetonitrile | 400.1 | (300 MHz, d$_6$-dmso): 12.17 (br s, 1H), 8.94 (s, 1H), 8.71 (s, 1H), 8.48 (s, 1H), 7.63 (dd, 1H), 7.09 (dd, 1H), 4.60 (d, 2H), 4.24 (d, 2H), 3.69 (s, 2H), 3.28-3.20 (m, 2H), 1.73-1.61 (m, 2H), 1.47-1.33 (m, 2H), 0.89 (t, 3 H). | Ex. # 2 |
| 10 | —SO$_2$$^t$Bu | {1-(tert-butylsulfonyl)-3-[4-(7H-pyrrolo[2,3-d]pyrimidin-4-yl)-1H-pyrazol-1-yl]azetidin-3-yl}acetonitrile trifluoroacetic acid salt | 400.1 | (400 MHz, d$_6$-dmso): 12.48 (br s, 1H), 8.99 (s, 1H), 8.80 (s, 1H), 8.54 (s, 1H), 7.74 (s, 1H), 7.21-7.16 (m, 1H), 4.61 (d, 2H), 4.20 (d, 2H), 3.73 (s, 2H), 1.32 (s, 9 H). | Ex. # 2 |
| 11 | —SO$_2$NMe$_2$ | 3-(cyanomethyl)-N,N-dimethyl-3-[4-(7H-pyrrolo[2,3-d]pyrimidin-4-yl)-1H-pyrazol-1-yl]azetidine-1-sulfonamide trifluoroacetic acid salt | 387.1 | (400 MHz, d$_6$-dmso): 12.59 (br s, 1H), 9.03 (s, 1H), 8.84 (s, 1H), 8.56 (s, 1H), 7.80-7.76 (m, 1H), 7.24-7.20 (m, 1H), 4.53 (d, 2H), 4.20 (d, 2H), 3.70 (s, 2H), 2.79 (s, 6 H). | Ex. # 2 |

TABLE 1-continued

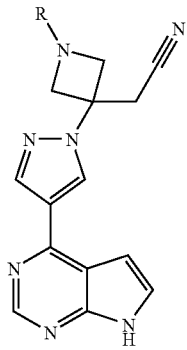

| Ex. No. | —R | Name | MS (M + H)+ | 1H NMR (δ) | Method of Preparation |
|---|---|---|---|---|---|
| 12 | —SO₂-(1-methyl-1H-pyrazol-3-yl) | {1-[(1-methyl-1H-pyrazol-3-yl)sulfonyl]-3-[4-(7H-pyrrolo[2,3-d]pyrimidin-4-yl)-1H-pyrazol-1-yl]azetidin-3-yl}acetonitrile trifluoroacetic acid salt | 424.1 | (400 MHz, d₆-dmso): 12.56 (br s, 1H), 8.83 (s, 1H), 8.82 (s, 1H), 8.44 (s, 1H), 7.88 (d, 1H), 7.77 (t, 1H), 7.19-7.15 (m, 1H), 6.79 (d, 1H), 4.53 (d, 2H), 4.28 (d, 2H), 3.77 (s, 3H), 3.52 (s, 2 H). | Ex. # 2 |
| 13 | —SO₂-CH₂CH₂-CF₃ | {3-[4-(7H-pyrrolo[2,3-d]pyrimidin-4-yl)-1H-pyrazol-1-yl]-1-[(3,3,3-trifluoropropyl)sulfonyl]azetidin-3-yl}acetonitrile | 440.1 | (300 MHz, d₆-dmso): 12.17 (br s, 1H), 8.94 (s, 1H), 8.71 (s, 1H), 8.49 (s, 1H), 7.63 (dd, 1H), 7.09 (dd, 1H), 4.68 (d, 2H), 4.31 (d, 2H), 3.72 (s, 2H), 3.63-3.55 (m, 2H), 2.85-2.67 (m, 2 H). | Ex. # 2 |
| 14 | —SO₂-isobutyl | {1-(isobutylsulfonyl)-3-[4-(7H-pyrrolo[2,3-d]pyrimidin-4-yl)-1H-pyrazol-1-yl]azetidin-3-yl}acetonitrile | 400.1 | (300 MHz, d₆-dmso): 12.17 (br s, 1H), 8.94 (s, 1H), 8.71 (s, 1H), 8.48 (s, 1H), 7.63 (dd, 1H), 7.09 (dd, 1H), 4.60 (d, 2H), 4.24 (d, 2H), 3.68 (s, 2H), 3.16 (d, 2H), 2.22-2.06 (m, 1H), 1.05 (d, 6 H). | Ex. # 2 |
| 15 | —SO₂-sec-butyl | {1-(sec-butylsulfonyl)-3-[4-(7H-pyrrolo[2,3-d]pyrimidin-4-yl)-1H-pyrazol-1-yl]azetidin-3-yl}acetonitrile | 400.1 | (300 MHz, d₆-dmso): 12.16 (br s, 1H), 8.93 (s, 1H), 8.71 (s, 1H), 8.48 (s, 1H), 7.63 (dd, 1H), 7.08 (dd, 1H), 4.58 (d, 2H), 4.20 (d, 2H), 3.70 (s, 2H), 3.21-3.08 (m, 1H), 1.98-1.82 (m, 1H), 1.55-1.37 (m, 1H), 1.26 (d, 3H), 0.95 (t, 3 H). | Ex. # 2 |
| 16 | —SO₂-(5-methyl-2-thienyl) | {1-[(5-methyl-2-thienyl)sulfonyl]-3-[4-(7H-pyrrolo[2,3-d]pyrimidin-4-yl)-1H-pyrazol-1-yl]azetidin-3-yl}acetonitrile trifluoroacetic acid salt | 440.1 | (400 MHz, d₆-dmso): 12.59 (br s, 1H), 8.82 (s, 2H), 8.41 (s, 1H), 7.78 (t, 1H), 7.59 (d, 1H), 7.17 (dd, 1H), 6.89 (dd, 1H), 4.45 (d, 2H), 4.30 (d, 2H), 3.56 (s, 2H), 2.30 (s, 3 H). | Ex. # 2 |
| 17 | —SO₂-(4-fluorophenyl) | {1-[(4-fluorophenyl)sulfonyl]-3-[4-(7H-pyrrolo[2,3-d]pyrimidin-4-yl)-1H-pyrazol-1-yl]azetidin-3-yl}acetonitrile trifluoroacetic acid salt | 438.1 | (400 MHz, d₆-dmso): 12.60 (br s, 1H), 8.83 (s, 1H), 8.78 (s, 1H), 8.38 (s, 1H), 7.97-7.91 (m, 2H), 7.80-7.77 (m, 1H), 7.44-7.38 (m, 2H), 7.18-7.14 (m, 1H), 4.42 (d, 2H), 4.25 (d, 2H), 3.57 (s, 2 H). | Ex. # 2 |

TABLE 1-continued

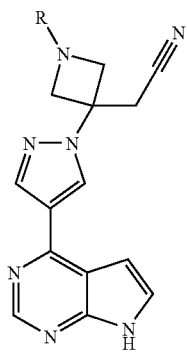

| Ex. No. | —R | Name | MS (M + H)+ | $^1$H NMR (δ) | Method of Preparation |
|---|---|---|---|---|---|
| 18 | —SO$_2$—(3-fluorophenyl) | {1-[(3-fluorophenyl)sulfonyl]-3-[4-(7H-pyrrolo[2,3-d]pyrimidin-4-yl)-1H-pyrazol-1-yl]azetidin-3-yl} acetonitrile trifluoroacetic acid salt | 438.1 | (400 MHz, d$_6$-dmso): 12.50 (br s, 1H), 8.79 (s, 1H), 8.78 (s, 1H), 8.34 (s, 1H), 7.78-7.68 (m, 3H), 7.64 (dt, 1H), 7.53-7.46 (m, 1H), 7.14-7.11 (m, 1H), 4.48 (d, 2H), 4.28 (d, 2H), 3.58 (s, 2 H). | Ex. # 2 |
| 19 | —SO$_2$—(2-fluorophenyl) | {1-[(2-fluorophenyl)sulfonyl]-3-[4-(7H-pyrrolo[2,3-d]pyrimidin-4-yl)-1H-pyrazol-1-yl]azetidin-3-yl} acetonitrile trifluoroacetic acid salt | 438.1 | (400 MHz, d$_6$-dmso): 12.65 (br s, 1H), 8.94 (s, 1H), 8.84 (s, 1H), 8.41 (s, 1H), 7.86 (dt, 1H), 7.80 (dd, 1H), 7.75-7.68 (m, 1H), 7.46 (dd, 1H), 7.43 (dd, 1H), 7.20-7.17 (m, 1H), 4.56 (d, 2H), 4.35 (d, 2H), 3.64 (s, 2 H). | Ex. # 2 |
| 20 | —SO$_2$—(pyridin-3-yl) | {1-(pyridin-3-ylsulfonyl)-3-[4-(7H-pyrrolo[2,3-d]pyrimidin-4-yl)-1H-pyrazol-1-yl]azetidin-3-yl} acetonitrile trifluoroacetic acid salt | 421.1 | (400 MHz, d$_6$-dmso): 12.75 (br s, 1H), 9.01 (d, 1H), 8.86 (s, 2H), 8.80 (dd, 1H), 8.35 (s, 1H), 8.29 (dq, 1H), 7.83 (dd, 1H), 7.63 (ddd, 1H), 7.19 (dd, 1H), 4.49 (d, 2H), 4.32 (d, 2H), 3.62 (s, 2 H). | Ex. # 2 |
| 21 | —SO$_2$—(pyridin-2-yl) | {1-(pyridin-2-ylsulfonyl)-3-[4-(7H-pyrrolo[2,3-d]pyrimidin-4-yl)-1H-pyrazol-1-yl]azetidin-3-yl} acetonitrile trifluoroacetic acid salt | 421.1 | (400 MHz, d$_6$-dmso): 12.66 (br s, 1H), 9.02 (d, 1H), 8.85 (s, 1H), 8.84 (s, 1H), 8.81 (dd, 1H), 8.34 (s, 1H), 8.29 (dt, 1H), 7.82-7.78 (m, 1H), 7.63 (dd, 1H), 7.19-7.15 (m, 1H), 4.49 (d, 2H), 4.31 (d, 2H), 3.62 (s, 2 H). | Ex. # 2 |
| 22 | cyclopropylcarbonyl | {1-(cyclopropylcarbonyl)-3-[4-(7H-pyrrolo[2,3-d]pyrimidin-4-yl)-1H-pyrazol-1-yl]azetidin-3-yl} acetonitrile trifluoroacetic acid salt | 348.1 | (400 MHz, d$_6$-dmso): 12.59 (br s, 1H), 9.05 (s, 1H), 8.83 (s, 1H), 8.56 (s, 1H), 7.79-7.75 (m, 1H), 7.25-7.22 (m, 1H), 4.92 (d, 1H), 4.65 (d, 1H), 4.50 (d, 1H), 4.25 (d, 1H), 3.75 (s, 2H), 1.67-1.60 (m, 1H), 0.83-0.71 (m, 4H). | Ex. # 2 |
| 23 | (1-methylcyclopropyl)carbonyl | {1-[(1-methylcyclopropyl)carbonyl]-3-[4-(7H-pyrrolo[2,3-d]pyrimidin-4-yl)-1H-pyrazol-1-yl]azetidin-3-ylacetonitrile trifluoroacetic acid salt | 362.2 | (300 MHz, d$_6$-dmso): 12.82 (br s, 1H), 9.10 (s, 1H), 8.91 (s, 1H), 8.59 (s, 1H), 7.86 (s, 1H), 7.31 (s, 1H), 5.07-4.07 (br, 4H), 3.72 (s, 2H), 1.28 (s, 3H), 0.98 (s, 2H), 0.54 (s, 2 H). | Ex. # 3 |

TABLE 1-continued

| Ex. No. | —R | Name | MS (M + H)⁺ | ¹H NMR (δ) | Method of Preparation |
|---|---|---|---|---|---|
| 24 | (benzoyl) | {1-benzoyl-3-[4-(7H-pyrrolo[2,3-d]pyrimidin-4-yl)-1H-pyrazol-1-yl]azetidin-3-yl}acetonitrile trifluoroacetic acid salt | 384.1 | (400 MHz, d₆-dmso): 12.59 (br s, 1H), 9.07 (s, 1H), 8.84 (s, 1H), 8.55 (s, 1H), 7.78 (t, 1H), 7.74-7.69 (m, 2H), 7.60-7.47 (m, 3H), 7.26-7.22 (m, 1H), 5.05 (d, 1H), 4.68 (d, 2H), 4.46 (d, 1H), 3.74 (s, 2H). | Ex. # 2 |
| 25 | (6-methylpyridin-2-yl)carbonyl | {1-[(6-methylpyridin-2-yl)carbonyl]-3-[4-(7H-pyrrolo[2,3-d]pyrimidin-4-yl)-1H-pyrazol-1-yl]azetidin-3-yl}acetonitrile | 399.2 | (300 MHz, d₆-dmso): 12.23 (br s, 1H), 9.00 (s, 1H), 8.73 (s, 1H), 8.49 (s, 1H), 7.91-7.79 (m, 2H), 7.65 (dd, 1H), 7.44 (dd, 1H), 7.13 (dd, 1H), 5.25 (d, 1H), 5.02 (d, 1H), 4.76 (d, 1H), 4.46 (d, 1H), 3.78 (s, 2H), 2.55 (s, 3H). | Ex. # 3 |
| 26 | (pyridin-3-ylcarbonyl) | {1-(pyridin-3-ylcarbonyl)-3-[4-(7H-pyrrolo[2,3-d]pyrimidin-4-yl)-1H-pyrazol-1-yl]azetidin-3-yl}acetonitrile | 385.1 | (300 MHz, d₆-dmso): 12.16 (br s, 1H), 8.98 (s, 1H), 8.90 (s, 1H), 8.74 (d, 1H), 8.70 (s, 1H), 8.48 (s, 1H), 8.11 (d, 1H), 7.65-7.60 (m, 1H), 7.57-7.50 (m, 1H), 7.12-7.07 (m, 1H), 5.13 (d, 1H), 4.76-4.72 (m, 2H), 4.46 (d, 1H), 3.73 (s, 2H). | Ex. # 2 |
| 27 | (3-methylbenzoyl) | {1-(3-methylbenzoyl)-3-[4-(7H-pyrrolo[2,3-d]pyrimidin-4-yl)-1H-pyrazol-1-yl]azetidin-3-yl}acetonitrile trifluoroacetic acid salt | 398.2 | (400 MHz, d₆-dmso): 12.67 (br s, 1H), 9.09 (s, 1H), 8.86 (s, 1H), 8.57 (s, 1H), 7.80 (t, 1H), 7.54-7.48 (m, 2H), 7.39-7.35 (m, 2H), 7.26 (dd, 1H), 5.03 (d, 1H), 4.68 (d, 2H), 4.45 (d, 1H), 3.74 (s, 2H), 2.37 (s, 3H). | Ex. # 2 |
| 28 | (4-methylbenzoyl) | {1-(4-methylbenzoyl)-3-[4-(7H-pyrrolo[2,3-d]pyrimidin-4-yl)-1H-pyrazol-1-yl]azetidin-3-yl}acetonitrile trifluoroacetic acid salt | 398.2 | (400 MHz, d₆-dmso): 12.62 (br s, 1H), 9.08 (s, 1H), 8.85 (s, 1H), 8.56 (s, 1H), 7.79 (t, 1H), 7.62 (d, 2H), 7.30 (d, 2H), 7.24 (dd, 1H), 5.04 (d, 1H), 4.73-4.63 (m, 2H), 4.44 (d, 1H), 3.74 (s, 2H), 2.37 (s, 3H). | Ex. # 2 |

TABLE 1-continued

| Ex. No. | —R | Name | MS (M + H)+ | 1H NMR (δ) | Method of Preparation |
|---|---|---|---|---|---|
| 29 | (3-cyanobenzoyl) | 3-({3-(cyanomethyl)-3-[4-(7H-pyrrolo[2,3-d]pyrimidin-4-yl)-1H-pyrazol-1-yl]azetidin-1-yl}carbonyl)benzonitrile trifluoroacetic acid salt | 409.2 | (400 MHz, d6-dmso): 12.52 (br s, 1H), 9.06 (s, 1H), 8.82 (s, 1H), 8.54 (s, 1H), 8.16 (t, 1H), 8.06-8.01 (m, 2H), 7.77-7.74 (m, 1H), 7.72 (t, 1H), 7.24-7.19 (m, 1H), 5.11 (d, 1H), 4.72 (d, 1H), 4.71 (d, 1H), 4.47 (d, 1H), 3.74 (s, 2 H). | Ex. # 2 |
| 30 | (2-thienylcarbonyl) | [3-[4-(7H-pyrrolo[2,3-d]pyrimidin-4-yl)-1H-pyrazol-1-yl]-1-(2-thienylcarbonyl)azetidin-3-yl]acetonitrile trifluoroacetic acid salt | 390.1 | (400 MHz, d6-dmso): 12.64 (br s, 1H), 9.11 (s, 1H), 8.85 (s, 1H), 8.58 (s, 1H), 7.89 (dd, minor rotamer 1H), 7.88 (dd, major rotamer, 1H), 7.81-7.77 (m, 1H), 7.73 (dd, minor rotamer, 1H), 7.62 (dd, major rotamer, 1H), 7.27-7.25 (m, 1H), 7.22 (dd, major rotamer, 1H), 7.18 (dd, minor rotamer, 1H), 5.23-5.14 (br d, 1H), 4.87 (br d, 1H), 4.69 (br d, 1H), 4.46 (br d, 1H), 3.79 (s, 2 H). | Ex. # 2 |
| 31 | (1H-pyrrol-2-ylcarbonyl) | [3-[4-(7H-pyrrolo[2,3-d]pyrimidin-4-yl)-1H-pyrazol-1-yl]-1-(1H-pyrrol-2-ylcarbonyl)azetidin-3-yl]acetonitrile trifluoroacetic acid salt | 373.2 | (400 MHz, d6-dmso): 13.07 (br s, 1H), 11.69 (br s, 1H), 9.21 (s, 1H), 8.99 (s, 1H), 8.66 (s, 1H), 7.96 (s, 1H), 7.41 (s, 1H), 6.96 (s, 1H), 6.59 (s, 1H), 6.20-6.17 (m, 1H), 5.15-4.35 (br, 4H), 3.78 (s, 2 H). | Ex. # 3 Modification A |
| 32 | (1H-indol-2-ylcarbonyl) | {1-(1H-indol-2-ylcarbonyl)-3-[4-(7H-pyrrolo[2,3-d]pyrimidin-4-yl)-1H-pyrazol-1-yl]azetidin-3-yl}acetonitrile trifluoroacetic acid salt | 423.1 | (400 MHz, d6-dmso): 12.91 (br s, 1H), 11.75 (d, 1H), 9.20 (s, 1H), 8.94 (s, 1H), 8.64 (s, 1H), 7.92-7.87 (m, 1H), 7.65 (d, 1H), 7.46 (d, 1H), 7.38-7.34 (m, 1H), 7.25-7.20 (m, 1H), 7.10-7.05 (m, 1H), 6.98 (d, 1H), 5.26 (d, 1H), 4.96 (d, 1H), 4.73 (d, 1H), 4.53 (d, 1H), 3.82 (s, 2 H). | Ex. # 3 |

TABLE 1-continued

| Ex. No. | —R | Name | MS (M + H)+ | 1H NMR (δ) | Method of Preparation |
|---|---|---|---|---|---|
| 33 | (isoxazol-5-ylcarbonyl) | {1-(isoxazol-5-ylcarbonyl)-3-[4-(7H-pyrrolo[2,3-d]pyrimidin-4-yl)-1H-pyrazol-1-yl]azetidin-3-yl}acetonitrile trifluoroacetic acid salt | 375.0 | (400 MHz, d6-dmso): 12.50 (br s, 1H), 9.09 (s, 1H), 8.83 (d, major rotamer 1H), 8.80 (d, minor rotamer, 1H), 8.81 (s, 1H), 8.55 (s, 1H), 7.76-7.73 (m, 1H), 7.24-7.20 (m, 1H), 7.19 (d, minor rotamer, 1H), 7.15 (d, major rotamer, 1H), 5.22 (d, 1H), 4.91 (d, 1H), 4.73 (d, 1H), 4.48 (d, 1H), 3.79 (s, 2 H). | Ex. # 2 |
| 34 | (1H-pyrazol-3-ylcarbonyl) | {1-(1H-pyrazol-3-ylcarbonyl)-3-[4-(7H-pyrrolo[2,3-d]pyrimidin-4-yl)-1H-pyrazol-1-yl]azetidin-3-yl} acetonitrile trifluoroacetic acid salt | 374.2 | (400 MHz, d6-dmso): 12.77 (br s, 1H), 9.14 (s, 1H), 8.89 (s, 1H), 8.59 (s, 1H), 7.87-7.82 (m, 2H), 7.33-7.29 (m, 1H), 6.71 (d, 1H), 5.11 (d, 1H), 4.91 (d, 1H), 4.68 (d, 1H), 4.44 (d, 1H), 3.78 (s, 2 H) | Ex. # 3 Modification A |
| 35 | isobutyl ester | isobutyl 3-(cyanomethyl)-3-[4-(7H-pyrrolo[2,3-d]pyrimidin-4-yl)-1H-pyrazol-1-yl]azetidine-1-carboxylate trifluoroacetic acid salt | 380.1 | (400 MHz, d6-dmso): 12.53 (br s, 1H), 9.02 (s, 1H), 8.82 (s, 1H), 8.53 (s, 1H), 7.78-7.74 (m, 1H), 7.23-7.20 (m, 1H), 4.57 (br s, 2H), 4.30 (br s, 2H), 3.80 (d, 2H), 3.71 (s, 2H), 1.87 (sept, 1H), 0.89 (d, 6 H). | Ex. # 2 |
| 36 | phenyl ester (OPh) | phenyl 3-(cyanomethyl)-3-[4-(7H-pyrrolo[2,3-d]pyrimidin-4-yl)-1H-pyrazol-1-yl]azetidine-1-carboxylate trifluoroacetic acid salt | 400.1 | (400 MHz, d6-dmso): 12.52 (br s, 1H), 9.08 (s, 1H), 8.83 (s, 1H), 8.57 (s, 1H), 7.79-7.75 (m, 1H), 7.44-7.37 (m, 2H), 7.28-7.22 (m, 2H), 7.20-7.12 (m, 2H), 4.85 (br m, 1H), 4.66 (br m, 1H), 4.56 (br m, 1H), 4.39 (br m, 1H), 3.79 (s, 2 H). | Ex. # 2 |
| 37 | benzyl ester (OBn) | benzyl 3-(cyanomethyl)-3-[4-(7H-pyrrolo[2,3-d]pyrimidin-4-yl)-1H-pyrazol-1-yl]azetidine-1-carboxylate trifluoroacetic acid salt | 414.2 | (400 MHz, d6-dmso): 12.56 (br s, 1H), 9.03 (s, 1H), 8.83 (s, 1H), 8.54 (s, 1H), 7.79-7.75 (br m, 1H), 7.40-7.30 (m, 5H), 7.24-7.21 (br m, 1H), 5.10 (s, 2H), 4.60 (br, 2H), 4.34 (br, 2H), 3.72 (s, 2 H). | Ex. # 2 |

US 8,158,616 B2

TABLE 1-continued

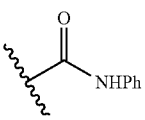

| Ex. No. | —R | Name | MS (M + H)+ | 1H NMR (δ) | Method of Preparation |
|---|---|---|---|---|---|
| 38 | (structure with C(=O)NHPh) | 3-(cyanomethyl)-N-phenyl-3-[4-(7H-pyrrolo[2,3-d]pyrimidin-4-yl)-1H-pyrazol-1-yl]azetidine-1-carboxamide trifluoroacetic acid salt | 399.2 | (400 MHz, $d_6$-dmso): 12.61 (br s, 1H), 9.06 (s, 1H), 8.85 (s, 1H), 8.75 (s, 1H), 8.57 (s, 1H), 7.79 (br t, 1H), 7.53-7.48 (m, 2H), 7.29-7.22 (m, 3H), 6.95 (t, 1H), 4.61 (d, 2H), 4.36 (d, 2H), 3.75 (s, 2H). | Ex. # 2 |

Where products in Table 1 are referred to as the free base, they were purified using preparative-HPLC/MS (XBridge C18 column, eluting with a gradient of MeCN/$H_2O$ containing 0.15% $NH_4OH$ rather than containing 0.1% TFA).

Example 39 cis-3-(cyanomethyl)-N,N-dimethyl-3-[4-(7H-pyrrolo[2,3-d]pyrimidin-4-yl)-1H-pyrazol-1-yl]cyclobutanesulfonamide and trans-3-(cyanomethyl)-N,N-dimethyl-3-[4-(7H-pyrrolo[2,3-d]pyrimidin-4-yl)-1H-pyrazol-1-yl]cyclobutanesulfonamide

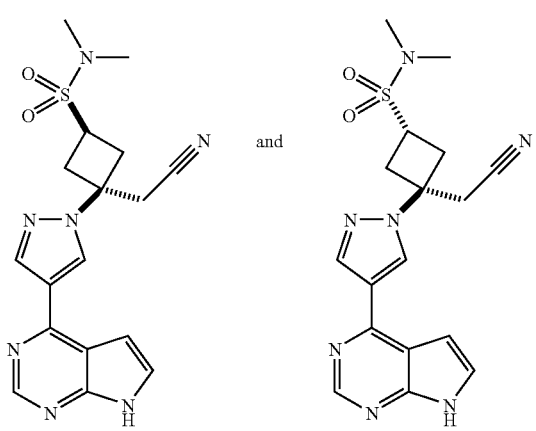

Step 1. cis- and trans-3-(benzyloxy)-N,N-dimethyl-cyclobutanesulfonamide

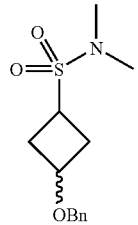

To a solution of methanesulfonamide, N,N-dimethyl-(7.45 g, 60.5 mmol) in tetrahydrofuran (190 mL) at −78° C. was added a solution of 2.50 M of n-butyllithium in hexane (31 mL, 77.5 mmol). The reaction was stirred at −78° C. for 45 minutes, was then warmed to 0° C. and stirred for 15 minutes, then was re-cooled to −78° C. A solution of 2-(benzyloxy)-propane-1,3-diyl bis(4-methylbenzenesulfonate) (prepared as described in Chemical Communications v. 30, pp. 3190-3192 (2006); 29.1 g, 59.3 mmol) in tetrahydrofuran (120 mL) was added dropwise, rapidly. The reaction was stirred at −78° C. for 15 minutes following complete addition, then the bath was removed and the reaction allowed to warm to ambient temperature over 1.5 hours. The solution was re-cooled to −78° C. and 2.50 M of n-butyllithium in hexane (31 mL, 77.5 mmol) was added. After 15 min, the bath was removed and the reaction again allowed to reach ambient temperature and stir for 16 hours. As the reaction was judged incomplete by TLC, it was cooled again to −78° C. and a further portion of 2.50 M of n-butyllithium in hexane (10 mL, 25 mmol) was added. Upon warming to room temperature, the reaction was quenched by the addition of water and the mixture was extracted with three portions of ethyl acetate. The combined organic extracts were washed with saturated sodium bicarbonate solution followed by brine, dried over sodium sulfate, filtered and concentrated. Flash chromatography, eluting with a gradient of 20-50% ethyl acetate in hexanes afforded desired product. The isomers were characterized separately but were recombined for the subsequent transformation as a mixture of cis and trans isomers (7.06 g, 44%).

Isomer 1: $^1$H NMR (400 MHz, CDCl$_3$): δ 7.38-7.27 (m, 5H), 4.42 (s, 2H), 4.41-4.33 (m, 1H), 3.83-3.74 (m, 1H), 2.87 (s, 6H), 2.79-2.71 (m, 2H), 2.47-2.38 (m, 2H).

Isomer 2: $^1$H NMR (400 MHz, CDCl$_3$): δ 7.37-7.26 (m, 5H), 4.44 (s, 2H), 4.02-3.93 (m, 1H), 3.34-3.24 (m, 1H), 2.85 (s, 6H), 2.61-2.46 (m, 4H).

Step 2. cis- and trans-3-hydroxy-N,N-dimethylcyclobutanesulfonamide

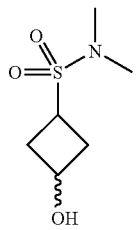

To a mixture of cis- and trans-3-(benzyloxy)-N,N-dimethylcyclobutanesulfonamide (7.06 g, 26.2 mmol) in ethanol (100 mL) was added palladium (2.8 g, 2.6 mmol) (10% on C, wet Degussa type). The mixture was degassed and shaken under 50 psi of hydrogen for 16 hours. The reaction mixture was filtered, and the palladium on carbon was rinsed with ethanol. The filtrate was concentrated to afford a white solid, used without further purification (4.60 g, 98%).

$^1$H NMR (400 MHz, CDCl$_3$): δ 4.71-4.63 (m, 1H, minor isomer), 4.22 (p, 1H, major isomer), 3.83-3.74 (m, 1H, minor isomer), 3.37-3.27 (m, 1H, major isomer), 2.87 (s, 6H, minor isomer), 2.86 (s, 6H, major isomer), 2.85-2.77 (m, 2H, minor isomer), 2.76-2.68 (m, 2H, major isomer), 2.48-2.40 (m, 2H, major isomer), 2.40-2.32 (m, 2H, minor isomer).

Step 3. N,N-dimethyl-3-oxocyclobutanesulfonamide

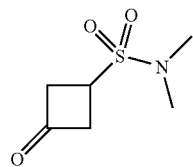

To a solution of Dess-Martin periodinane (14.3 g, 33.7 mmol) in methylene chloride (200 mL) was added cis- and trans-3-hydroxy-N,N-dimethylcyclobutanesulfonamide (5.75 g, 32.1 mol) in methylene chloride (200 mL). The reaction was stirred at ambient temperature for 16 hours. The volume of DCM was reduced to 100 mL in vacuo. This solution was filtered through a plug of basic alumina, rinsing with further DCM. The filtrate was evaporated. The resulting yellow sticky solid was extracted by stirring vigorously with several portions of diethyl ether in succession. The extracts were filtered through a plug of solid sodium carbonate and again filtered through another plug of basic alumina, rinsing finally with an additional small portion of ethyl acetate to afford clean product (4 g, 70%).

$^1$H NMR (400 MHz, CDCl$_3$): δ 3.89-3.80 (m, 1H), 3.68-3.59 (m, 2H), 3.44-3.34 (m, 2H), 2.93 (s, 6H).

Step 4. cis-3-(cyanomethyl)-N,N-dimethyl-3-[4-(7H-pyrrolo[2,3-d]pyrimidin-4-yl)-1H-pyrazol-1-yl]cyclobutanesulfonamide and trans-3-(cyanomethyl)-N,N-dimethyl-3-[4-(7H-pyrrolo[2,3-d]pyrimidin-4-yl)-1H-pyrazol-1-yl]cyclobutanesulfonamide A mixture of N,N-dimethyl-3-oxocyclobutanesulfonamide (4.0 g, 22 mmol) and (triphenylphosphoranylidene)acetonitrile (6.80 g, 22.6 mmol) in toluene (150 mL) was heated to reflux for 1 hour. The reaction solution was decanted away from insolubles and the solvent removed in vacuo to afford crude product, used without further purification in conjugate addition.

$^1$H NMR (300 MHz, CDCl$_3$): δ 5.31-5.25 (m, 1H), 3.91-3.78 (m, 1H), 3.50-3.10 (m, 4H), 2.89 (s, 6H).

To a solution of 4-(1 H-pyrazol-4-yl)-7-[2-(trimethylsilyl)ethoxy]methyl-7H-pyrrolo[2,3-d]pyrimidine (7.09 g, 22.5 mmol) and crude 3-(cyanomethylene)-N, N-dimethylcyclobutanesulfonamide (prepared above) in acetonitrile (200 mL) was added 1,8-diazabicyclo[5.4.0]undec-7-ene (3.36 mL, 22.5 mmol). The reaction was stirred for 16 hours. The crude product was purified by flash column chromatography, eluting with a gradient of 0-10% MeOH in DCM (dichloromethane). The product collected from this pre-purification was further purified using preparative-HPLC/MS (XBridge C18 column, eluting with a gradient of MeCN/H$_2$O containing 0.15% NH$_4$OH) to afford a mixture of isomers. The cis- and trans-isomers were separated using a portion of this mixture by the following method: Chiral Technologies Chiralcel OJ column, 30×250 mm, 5 µ packing material, eluting with 60% ethanol in hexanes at a flow rate of 14.5 mL/min and column loading of 65 mg/injection. Peak 1 so obtained was deprotected by stirring with 20% TFA/DCM for 2 hours, followed by evaporation and dissolving the residue in 4 mL MeOH to which 0.25 mL of ethylenediamine was then added. After stirring for 1 hour, the solvents were removed in vacuo, the crude product reconstituted and purified by preparative-HPLC/MS (XBridge C18 column, eluting with a gradient of MeCN/H$_2$O containing 0.15% NH$_4$OH) to afford cis-3-(cyanomethyl)-N,N-dimethyl-3-[4-(7H-pyrrolo[2,3-d]pyrimidin-4-yl)-1H-pyrazol-1-yl]cyclobutanesulfonamide.

$^1$H NMR (500 MHz, d$_6$-dmso): δ 12.10 (br s, 1H), 8.78 (s, 1H), 8.69 (s, 1H), 8.42 (s, 1H), 7.60 (d, 1H), 7.06 (d, 1H), 4.25 (p, 1H), 3.59 (s, 2H), 3.14-3.07 (m, 2H), 2.85-2.79 (m, 2H), 3.80 (s, 6H); LCMS: 386.1.

Peak 2 obtained from the separation of isomers was deprotected and purified by the same method as for Peak 1 to afford trans-3-(cyanomethyl)-N,N-dimethyl-3-[4-(7H-pyrrolo[2,3-d]pyrimidin-4-yl)-1 H-pyrazol-1-yl]cyclobutanesulfonamide.

$^1$H NMR (500 MHz, d$_6$-dmso): δ 12.10 (br s, 1H), 8.90 (s, 1H), 8.70 (s, 1H), 8.45 (s, 1H), 7.60 (d, 1H), 7.09 (d, 1H), 4.18 (p, 1H), 3.46 (s, 2H), 3.35-3.28 (m, 2H), 2.89-2.82 (m, 2H), 2.79 (s, 6H); LCMS: 386.0.

Example 40 cis-3-isoxazol-3-yl-1-[4-(7H-pyrrolo[2,3-d]pyrimidin-4-yl)-1H-pyrazol-1-yl]cyclobutylacetonitrile and trans-3-isoxazol-3-yl-1-[4-(7H-pyrrolo[2,3-d]pyrimidin-4-yl)-1H-pyrazol-1-yl]cyclobutylacetonitrile

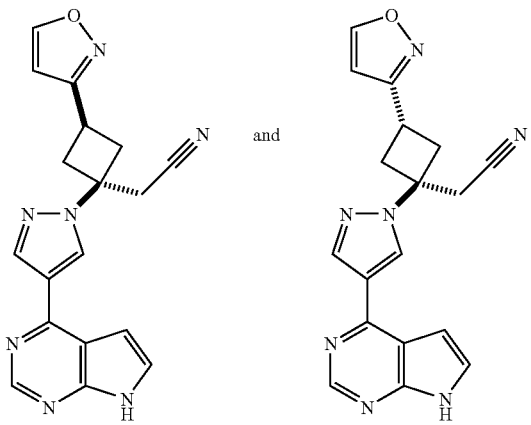

Step 1. diethyl 3-(benzyloxy)cyclobutane-1,1-dicarboxylate

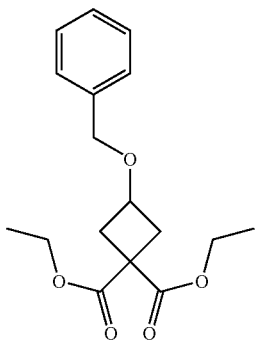

To a suspension of sodium hydride (60% dispersion in mineral oil, 4.67 g, 0.117 mol) in 1,4-dioxane (69 mL) was added diethyl malonate (17.7 mL, 0.117 mol) dropwise. The mixture was stirred for 1.5 hours at ambient temperature after complete addition. To this mixture was added [2-bromo-1-(chloromethyl)ethoxy]methylbenzene (prepared according to the procedure found in Organic Letters (2004), 6(11), pp. 1853-1856; 32.0 g, 0.121 mol) dropwise and the resulting mixture was stirred for 1 hour at ambient temperature, then heated at reflux for 16 hours. The mixture was cooled briefly in an ice bath and sodium hydride (60% dispersion in mineral oil, 4.67 g, 0.117 mol) was added portionwise. The mixture was heated to reflux for a further 24 hours. Upon cooling to room temperature, the mixture was poured into pH 7 buffer and brine, and the product was extracted with three portions of ethyl acetate. The combined extracts were washed with brine, dried over sodium sulfate, decanted and concentrated. Flash column chromatography, eluting with a gradient of 5-60% ethyl acetate in hexanes afforded product (26.9 g, 75%).

$^1$H NMR (400 MHz, CDCl$_3$): δ 7.37-7.25 (m, 5H), 4.42 (s, 2H), 4.24-4.10 (m, 5H), 2.83-2.75 (m, 2H), 2.58-2.50 (m, 2H), 1.31-1.24 (m, 6H).

Step 2. cis- and trans-3-(benzyloxy)cyclobutanecarboxylic acid

A solution of diethyl 3-(benzyloxy)cyclobutane-1,1-dicarboxylate (20.0 g, 0.0653 mol) and potassium hydroxide (18 g, 0.32 mol) in ethanol (110 mL) and water (10 mL) was heated to reflux for 2 hours. The basic mixture was washed once with diethyl ether. The ether wash was back extracted with two portions of 1N NaOH. The combined aqueous layers were acidified by the addition of c.HCl and were then extracted with ethyl ether three times. The combined extracts were washed with brine, dried over sodium sulfate, decanted and concentrated to afford the intermediate diacid as a sticky yellow solid which was subsequently azeotroped with toluene. The diacid was heated neat under hyvac (<5 mm Hg) at 190° C. for 1.5 hours to effect decarboxyation to a mixture of cis- and trans-monoacids, used without further purification (13.5 g, 92%).

$^1$H NMR(400 MHz, CDCl$_3$): δ 7.38-7.26 (m, 10H), 4.44 (s, 2H), 4.43 (s, 2H), 4.31 (p, 1H), 4.02-3.93 (m, 1H), 3.12-3.04 (m, 1H), 2.72-2.62 (m, 1H), 2.59-2.48 (m, 4H), 2.38-2.24 (m, 4H).

Step 3. cis- and trans-3-(benzyloxy)-N-methoxy-N-methylcyclobutanecarboxamide

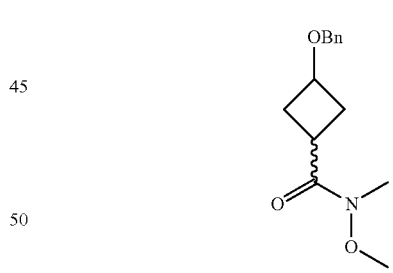

A mixture of 3-(benzyloxy)cyclobutanecarboxylic acid (2.50 g, 12.1 mmol), N,O-dimethylhydroxylamine hydrochloride (1.18 g, 12.1 mmol), benzotriazol-1-yloxytris(dimethylamino)phosphonium hexafluorophosphate (5.9 g, 13 mmol) (Advanced ChemTech) and triethylamine (3.7 mL, 27 mmol) in methylene chloride (80 mL) was stirred at room temperature for 16 hours. The solution was then washed with twice with water, once with brine, dried over sodium sulfate, decanted and concentrated. Flash column chromatography, eluting with a gradient of 20-50% ethyl acetate in hexanes afforded product as a mixture of cis- and trans-isomers (1.7 g, 56%).

$^1$H NMR(400 MHz, CDCl$_3$): δ 7.35-7.24 (m, 10H), 4.43 (s, 2H), 4.42 (s, 2H), 4.31-4.24 (m, 1H), 4.03-3.95 (m, 1H), 3.64

(s, 3H), 3.63 (s, 3H), 3.47 (br s, 1H), 3.19 (s, 3H), 2.18 (s, 3H), 2.95 (br s, 1H), 2.57-2.48 (m, 2H), 2.47-2.38 (m, 2H), 2.34-2.23 (m, 4H).

Step 4. cis- and trans-1-[3-(benzyloxy)cyclobutyl]prop-2-yn-1-one

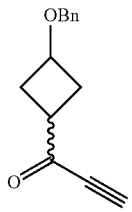

To a solution of 3-(benzyloxy)-N-methoxy-N-methylcyclobutanecarboxamide (1.7 g, 6.8 mmol) in tetrahydrofuran (40 mL) at −78° C. was added 0.5 M of ethynylmagnesium bromide in tetrahydrofuran (14.3 mL, 7.15 mmol) and the reaction was allowed to warm to ambient temperature over a period of 1 hour. The reaction was quenched by the addition of satd. NH$_4$Cl solution and the product was extracted with ethyl acetate. The extracts were dried over sodium sulfate, decanted and concentrated to afford product used without further purification in Step 5.

$^1$H NMR(400 MHz, CDCl$_3$): δ 7.39-7.21 (m, 10H), 4.43 (s, 2H), 4.41 (s, 2H), 4.19-4.09 (m, 1H), 4.06-3.95 (m, 1H), 3.36-3.24 (m, 1H), 3.29 (s, 1H), 3.26 (s, 1H), 2.90-2.79 (m, 1H), 2.67-2.59 (m, 2H), 2.56-2.47 (m, 2H), 2.36-2.26 (m, 4H).

Step 5. cis-3-[3-(benzyloxy)cyclobutyl]isoxazole and trans-3-[3-(benzyloxy)cyclobutyl]isoxazole

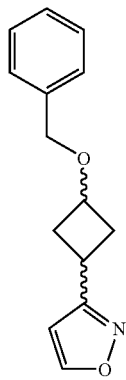

To a solution of 1-[3-(benzyloxy)cyclobutyl]prop-2-yn-1-one (prepared in Step 4) in ethanol (40 mL) was added hydroxylamine hydrochloride (0.54 g, 7.7 mmol) followed by sodium carbonate (1.48 g, 14.0 mmol). The reaction was stirred for 16 hours. The reaction was then heated to reflux for 4 hours and cooled. Into the reaction mixture was added water and ethyl acetate. The layers were separated, and the aqueous layer was extracted with two further portions of ethyl acetate. The combined extracts were washed with brine, dried over sodium sulfate, decanted and concentrated. Flash column chromatography, eluting with a gradient of 15-50% ethyl acetate in hexanes afforded the product as a mixture of cis- and trans-isomers (520 mg, 33% over the two steps).

$^1$H NMR (400 MHz, CDCl$_3$): δ 8.32 (dd, 1H), 8.31 (dd, 1H), 7.36-7.26 (m, 10H), 6.30 (d, 1H), 6.21 (d, 1H), 4.47 (s, 2H), 4.45 (s, 2H), 4.38-4.30 (m, 1H), 4.12-4.04 (m, 1H), 3.62-3.53 (m, 1H), 3.23-3.13 (m, 1H), 2.75-2.14 (m, 8H).

Step 6. cis- and trans-3-isoxazol-3-ylcyclobutanol

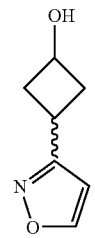

A mixture of cis- and trans-3-[3-(benzyloxy)cyclobutyl]isoxazole (0.520 g, 2.27 mmol) and 20% palladium hydroxide on carbon (0.14 g, 0.20 mmol) in tetrahydrofuran (30 mL) and acetic acid (8 mL) was degassed and stirred under an atmosphere of hydrogen (provided by a balloon) for 3 hours. The mixture was filtered, neutralized by the addition of NaOH and extracted with three portions of ethyl acetate. The combined extracts were washed with brine, dried over sodium sulfate, decanted and concentrated to afford product as a mixture of cis- and trans-isomers (320 mg, 100%).

$^1$H NMR (400 MHz, CD$_3$OD): δ 8.55 (dd, 1H), 8.54 (dd, 1H), 6.44 (d, 1H), 6.42 (d, 1H), 4.50-4.41 (m, 1H), 4.26-4.17 (m, 1H), 3.55-3.46 (m, 1H), 3.14-3.03 (m, 1H), 2.73-2.64 (m, 2H), 2.54-2.46 (m, 2H), 2.44-2.35 (m, 2H), 2.13-2.03 (m, 2H).

Step 7. 3-isoxazol-3-ylcyclobutanone

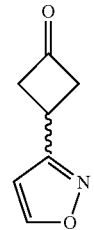

3-Isoxazol-3-ylcyclobutanol (0.316 g, 2.27 mmol), as a mixture of cis- and trans-isomers, was dissolved in methylene chloride (10 mL) and Dess-Martin periodinane (0.96 g, 2.3 mmol) was added. After stirring for 2 hours, satd. NaHCO$_3$ solution and brine were added, and the mixture was extracted with three portions of ethyl acetate. The combined extracts were dried over sodium sulfate, decanted and concentrated. Flash column chromatography, eluting with a gradient of 20-50% ethyl acetate in hexanes, afforded product (258 mg, 83%).

¹H NMR (400 MHz, CDCl₃): δ 8.40 (dd, 1H), 6.31 (d, 1H), 3.81-3.72 (m, 1H), 3.59-3.48 (m, 2H), 3.46-3.37 (m, 2H).

Step 8. (3-isoxazol-3-ylcyclobutylidene)acetonitrile

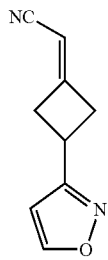

Sodium hydride (60% dispersion in mineral oil, 75 mg, 1.88 mmol) was added at once to a solution of diethyl cyanomethylphosphonate (0.33 mL, 2.1 mmol) in tetrahydrofuran (8 mL). After stirring for 5 minutes, a solution of 3-isoxazol-3-ylcyclobutanone (258 mg, 1.88 mmol) in tetrahydrofuran (20 mL) was added. After 2 hours reaction time, the reaction mixture was partitioned between ethyl acetate and brine and the layers separated. The aqueous layer was extracted with two further portions of ethyl acetate and the combined extracts were dried over sodium sulfate, decanted and concentrated. The residue was then azeotroped with toluene and the product was used without further purification in Step 9.

¹H NMR (400 MHz, CDCl₃): δ 8.38 (dd, 1H), 6.28 (d, 1H), 5.27 (p, 1H), 3.81-3.72 (m, 1H), 3.50-3.15 (m, 4H).

Step 9. cis-3-isoxazol-3-yl-1-[4-(7H-pyrrolo[2,3-d]pyrimidin-4-yl)-1H-pyrazol-1-yl]cyclobutylacetonitrile and trans-3-isoxazol-3-yl-1-[4-(7H-pyrrolo[2,3-d]pyrimidin-4-yl)-1H-pyrazol-1-yl]cyclobutylacetonitrile To a solution of (3-isoxazol-3-ylcyclobutylidene)acetonitrile (prepared in Step 8) in acetonitrile (8 mL) was added 4-(1H-pyrazol-4-yl)-7-[2-(trimethylsilyl)ethoxy]methyl-7H-pyrrolo[2,3-d]pyrimidine (0.59 g, 1.9 mmol) followed by 1,8-diazabicyclo[5.4.0]undec-7-ene (280 μL, 1.9 mmol). The reaction was stirred for 72 hours. The acetonitrile was removed in vacuo. Flash column chromatography, eluting with a gradient of 50-100% ethyl acetate in hexanes, afforded a mixture of cis- and trans-isomers. The mixture was stirred with 20% TFA/DCM (8 mL/32 mL) for 3 hours, and the excess solvents were removed in vacuo. The residue was stirred with ethylenediamine (2 mL) in MeOH (40 mL) for 16 hours. Solvents were again removed in vacuo. The mixture was purified by preparative-HPLC/MS (XBridge C18 column, mobile phases 20.5-25.5% of MeCN/H₂O containing 0.1% NH₄OH). Peak 1, cis-3-isoxazol-3-yl-1-[4-(7H-pyrrolo[2,3-d]pyrimidin-4-yl)-1H-pyrazol-1-yl]cyclobutylacetonitrile (185 mg, 28%), Peak 2, trans-3-isoxazol-3-yl-1-[4-(7H-pyrrolo[2,3-d]pyrimidin-4-yl)-1H-pyrazol-1-yl]cyclobutylacetonitrile (85 mg, 13%).

Peak 1, (cis-): ¹H NMR (400 MHz, d₆-dmso): δ 12.13 (br s, 1H), 8.85 (d, 1H), 8.76 (s, 1H), 8.69 (s, 1H), 8.42 (s, 1H), 7.60 (d, 1H), 7.07 (d, 1H), 6.67 (d, 1H), 3.85 (p, 1H), 3.67 (s, 2H), 3.04-2.95 (m, 2H), 2.89-2.81 (m, 2H); LCMS (M+H)⁺: 346.1.

Peak 2, (trans-): ¹H NMR (400 MHz, d₆-dmso): δ 12.14 (br s, 1H), 8.94 (s, 1H), 8.89 (d, 1H), 8.71 (s, 1H), 8.47 (s, 1H), 7.62 (dd, 1H), 7.11 (dd, 1H), 6.73 (d, 1H), 3.71 (p, 1H), 3.46 (s, 2H), 3.34-3.27 (m, 2H), 2.80-2.71 (m, 2H); LCMS (M+H)⁺: 346.1.

Example 41

{cis-3-(3-methyl-1,2,4-oxadiazol-5-yl)-1-[4-(7H-pyrrolo[2,3-d]pyrimidin-4-yl)-1H-pyrazol-1-yl]cyclobutyl}acetonitrile trifluoroacetate salt and {trans-3-(3-methyl-1,2,4-oxadiazol-5-yl)-1-[4-(7H-pyrrolo[2,3-d]pyrimidin-4-yl)-1H-pyrazol-1-yl]cyclobutyl}acetonitrile trifluoroacetic acid salt

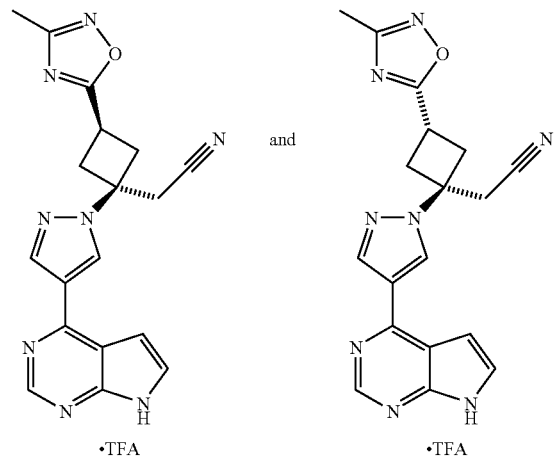

Step 1. cis- and trans-ethyl 3-(benzyloxy)cyclobutanecarboxylate

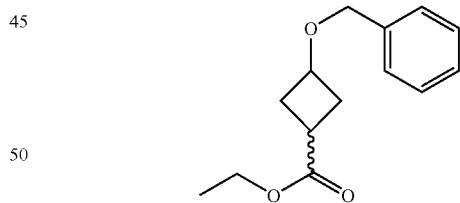

To a solution of 3-(benzyloxy)cyclobutanecarboxylic acid (5.00 g, 24.2 mmol) (prepared as in Example 6, Step 2) in ethanol (60 mL) was added 0.08 mL c.H₂SO₄. The mixture was heated at gentle reflux for 48 hours. After cooling to room temperature, the solvent was evaporated in vacuo. Flash column chromatography, eluting with a gradient of 0-20% ethyl acetate in hexanes afforded desired product as a mixture of cis- and trans-isomers (3.91 g, 69%).

¹H NMR(400 MHz, CDCl₃): δ 7.37-7.26 (m, 10H), 4.43 (s, 2H), 4.41 (s, 2H), 4.29 (p, 1H), 4.14 (q, 2H), 4.13 (q, 2H), 3.99-3.91 (m, 1H), 3.07-2.98 (m, 1H), 2.66-2.55 (m, 1H), 2.54-2.44 (m, 4H), 2.34-2.20 (m, 4H), 1.26 (t, 3H), 1.25 (t, 3H).

Step 2. cis- and trans-ethyl 3-hydroxycyclobutanecarboxylate

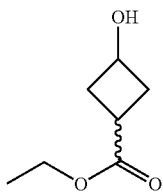

To a solution of cis- and trans-ethyl 3-(benzyloxy)cyclobutanecarboxylate (3.91 g, 16.7 mmol) in ethanol (40 mL) was added palladium (10% on carbon, wet Degussa type) (270 mg, 0.25 mmol). The mixture was degassed and shaken under 50 psi of hydrogen for 16 hours. The reaction mixture was filtered and the solvent removed in vacuo to afford product as a mixture of cis- and trans-isomers used without further purification (2.40 g, 99%).
$^1$H NMR (400 MHz, CDCl$_3$): δ 4.60-4.52 (m, 1H), 4.22-4.12 (m, 1H), 4.14 (q, 2H), 4.13 (q, 2H), 3.04-2.96 (m, 1H), 2.64-2.51 (m, 5H), 2.25-2.11 (m, 4H), 2.02 (br s, 2H), 1.25 (t, 3H), 1.25 (t, 3H).

Step 3. ethyl 3-oxocyclobutanecarboxylate

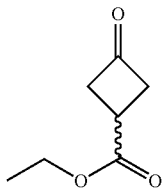

To methylene chloride (100 mL) at −78° C. was added oxalyl chloride (1.79 mL, 21.2 mmol), followed by dimethyl sulfoxide (2.51 mL, 35.3 mmol). After 30 minutes, cis- and trans-ethyl 3-hydroxycyclobutanecarboxylate (2.68 g, 17.6 mol) in methylene chloride (46 mL) was added. The mixture was stirred for 30 minutes at −78° C. Triethylamine (9.84 mL, 70.6 mmol) was added. The mixture was then allowed to warm to room temperature over 2 hours. Water was added to the reaction mixture, and the layers separated. The organic phase was washed sequentially with 1N HCl, water, saturated sodium bicarbonate solution, brine, dried over sodium sulfate, decanted and concentrated. The product (2.36 g, 94%) was used without further purification.
$^1$H NMR (400 MHz, CDCl$_3$): δ 4.21 (q, 2H), 3.45-3.37 (m, 2H), 3.33-3.17 (m, 3H), 1.29 (t, 3H).

Step 4. ethyl 3-(cyanomethylene)cyclobutanecarboxylate

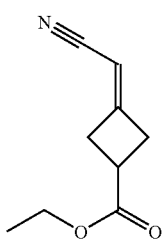

To a suspension of sodium hydride (60% dispersion in mineral oil, 0.730 g, 18.3 mmol) in tetrahydrofuran (100 mL) at 0° C. was added diethyl cyanomethylphosphonate (3.22 mL, 19.9 mmol), dropwise. The cooling bath was removed and the reaction was allowed to reach room temperature and was stirred at this temperature for 45 minutes. The solution was re-cooled to 0° C. and a solution of ethyl 3-oxocyclobutanecarboxylate (2.36 g, 16.6 mmol) in tetrahydrofuran (50 mL) was introduced dropwise. After stirring for 2 hours, water and ethyl ether were added into the reaction. The layers were separated and the aqueous portion extracted with two further portions of ether. The combined extracts were washed with brine, dried over sodium sulfate, decanted and concentrated. The residue was azeotroped once with toluene to afford product, used without further purification in Step 5.
$^1$H NMR (400 MHz, CDCl$_3$): δ 5.23-5.20 (m, 1H), 4.18 (q, 2H), 3.25-3.02 (m, 5H), 1.28 (t, 3H).

Step 5. ethyl 3-(cyanomethyl)-3-[4-(7-[2-(trimethylsilyl)ethoxy]methyl-7H-pyrrolo[2,3-d]pyrimidin-4-yl)-1H-pyrazol-1-yl]cyclobutanecarboxylate

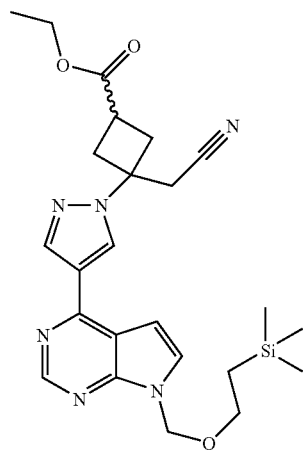

To a solution of 4-(1H-pyrazol-4-yl)-7-[2-(trimethylsilyl)ethoxy]methyl-7H-pyrrolo[2,3-d]pyrimidine (5.23 g, 16.6 mmol) and ethyl 3-(cyanomethylene)cyclobutanecarboxylate (prepared in Step 4) in acetonitrile (40 mL) was added 1,8-diazabicyclo[5.4.0]undec-7-ene (2.48 mL, 16.6 mmol). The mixture was stirred for 136 hours at room temperature. The solvent was removed in vacuo. Flash column chromatography, eluting with a gradient of 50-90% ethyl acetate in hexanes afforded product as a mixture of cis- and trans-isomers (4.53 g, 52% over the two steps).
$^1$H NMR (400 MHz, CDCl$_3$): δ 8.85 (s, 1H), 8.84 (s, 1H), 8.45 (s, 1H), 8.41 (s, 1H), 8.33 (s, 1H), 8.31 (s, 1H), 7.41 (d, 1H), 7.40 (d, 1H), 6.81 (d, 1H), 6.80 (d, 1H), 5.68 (s, 4H), 4.17 (q, 2H), 4.12 (q, 2H), 3.54 (t, 4H), 3.27 (s, 2H), 3.28-2.80 (m, 10H), 3.19 (s, 2H), 1.26 (t, 3H), 1.25 (t, 3H), 0.92 (t, 4H), −0.06 (s, 18H); LCMS (M+H)$^+$: 481.1.

Step 6. {cis-3-(3-methyl-1,2,4-oxadiazol-5-yl)-1-[4-(7H-pyrrolo[2,3-d]pyrimidn-4-yl)-1H-pyrazol-1-yl]cyclobutyl}acetonitrile trifluoroacetate salt and {trans-3-(3-m ethyl-1,2,4-oxadiazol-5-yl)-1-[4-(7H-pyrrolo[2,3-d]pyrimidn-4-yl)-1H-pyrazol-1-yl]cyclobutyl}acetonitrile trifluoroacetate salt To a solution of cis- and trans-ethyl 3-(cyanomethyl)-3-[4-(7-[2-(trimethylsilyl)ethoxy]methyl-7H-pyrrolo[2,3-d]pyrimidin-4-yl)-1H-pyrazol-1-yl]cyclobutanecarboxylate (2.25 g, 3.98 mmol) in tetrahydrofuran (55 mL) and water (18 mL)

was added a solution of lithium hydroxide (0.48 g, 20 mmol) in a small amount of water. The reaction was stirred at room temperature for 4 hours. The reaction mixture was cooled in an ice bath and c.HCl was added to achieve a pH of 5. The product was extracted with three portions of ethyl acetate. The extracts were dried over sodium sulfate, decanted and concentrated to afford the product as a mixture of cis- and trans-isomers, which was used without further purification. LCMS (M+H)$^+$: 453.1.

To a mixture of 3-(cyanomethyl)-3-[4-(7-[2-(trimethylsilyl)ethoxy]methyl-7H-pyrrolo[2,3-d]pyrimidin-4-yl)-1H-pyrazol-1-yl]cyclobutanecarboxylic acid prepared above (50.0 mg, 0.11 mmol), 1-Hydroxybenzotriazole (3.0 mg, 0.022 mmol), and N-hydroxyethanimidamide (prepared according to the procedure found in J. Org. Chem., 2003, 68(19), pp. 7316-7321) (8.2 mg, 0.11 mmol) in N,N-dimethylformamide (0.5 mL) and N,N-diisopropylethylamine (96 µL, 0.55 mmol) was added O-(Benzotriazol-1-yl)-N,N,N',N'-tetramethyluronium hexafluorophosphate (42 mg, 0.110 mmol) (Advanced ChemTech) and the mixture was stirred at room temperature for 16 hours. Additional sub-stoichiometric quantities of O-(benzotriazol-1-yl)-N,N,N',N'-tetramethyluronium hexafluorophosphate and N-hydroxyethanimidamide were added and the reaction was continued for a further 24 hours. The reaction was then heated to 110° C. for 1 hour to complete cyclization. Into the reaction was added saturated sodium bicarbonate solution and the product was extracted with four portions of ethyl acetate. The extracts were dried over sodium sulfate, decanted and concentrated. The crude product mixture was stirred in DCM containing 20% TFA for 2 hours, and the solvents were removed in vacuo. The residue was dissolved in 1.5 mL of methanol and 0.3 mL ethylenediamine and was stirred for 2 hours. The reaction mixture was purified by preparative-HPLC/MS (SunFire C18 column, eluting with a gradient of H$_2$O/MeCN containing 0.1% TFA), which resolved the cis-(6 mg, 10%) and trans-(5 mg, 8%) isomers and afforded each product as the trifluoroacetic acid salt.

Cis-isomer: $^1$H NMR (300 MHz, d$_6$-dmso): δ 12.39 (br s, 1H), 8.86 (s, 1H), 8.77 (s, 1H), 8.48 (s, 1H), 7.86 (br s, 1H), 7.73-7.68 (m, 1H), 7.19-7.14 (m, 1H), 4.12-3.96 (m, 1H), 3.70 (s, 2H), 3.22-3.08 (m, 2H), 2.99-2.85 (m, 2H), 2.31 (s, 3H); LCMS (M+H)$^+$: 361.1.

Trans-isomer: $^1$H NMR (300 MHz, d$_6$-dmso): δ 12.36 (br s, 1H), 8.99 (s, 1H), 8.77 (s, 1H), 8.52 (s, 1H), 7.90 (br s, 1H), 7.72-7.67 (m, 1H), 7.21-7.17 (m, 1H), 4.03-3.88 (m, 1H), 3.52 (s, 2H), 3.47-3.31 (m, 2H), 2.93-2.84 (m, 2H), 2.36 (s, 3H); LCMS (M+H)$^+$: 361.0.

Additional oxadiazoles were prepared according to Example 41, using different amidoximes (prepared according to the procedure found in J. Org. Chem. 2003, 68(19), pp. 7316-7321) in Step 6, and are found in Table 2.

TABLE 2

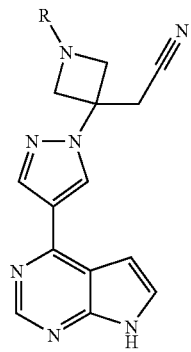

| Ex. No. | —R | Name | MS (M + H)$^+$ | $^1$H NMR (δ) | Method of Preparation |
|---|---|---|---|---|---|
| 42a | (cis-) | {cis-3-(3-tert-butyl-1,2,4-oxadiazol-5-yl)-1-[4-(7H-pyrrolo[2,3-d]pyrimidin-4-yl)-1H-pyrazol-1-yl]cyclobutyl}acetonitrile trifluoroacetate salt | 403.1 | (300 MHz, d$_6$-dmso): 12.61 (br s, 1H), 8.92 (s, 1H), 8.83 (s, 1H), 8.53 (s, 1H), 7.80-7.74 (m, 1H), 7.25-7.20 (m, 1H), 4.06 (p, 1H), 3.68 (s, 2H), 3.19-3.09 (m, 2H), 3.01-2.90 (m, 2H), 1.27 (s, 9 H). | Ex. # 41 |
| 42b | (trans-) | {trans-3-(3-tert-butyl-1,2,4-oxadiazol-5-yl)-1-[4-(7H-pyrrolo[2,3-d]pyrimidin-4-yl)-1H-pyrazol-1-yl]cyclobutyl}acetonitrile trifluoroacetate salt | 403.1 | (300 MHz, d$_6$-dmso): 12.54 (br s, 1H), 9.03 (s, 1H), 8.83 (s, 1H), 8.55 (s, 1H), 7.79-7.73 (m, 1H), 7.27-7.22 (m, 1H), 3.96 (p, 1H), 3.51 (s, 2H), 3.45-3.33 (m, 2H), 2.98-2.87 (m, 2H), 1.33 (s, 9 H). | Ex. # 41 |

Example 43

1-[4-(7H-pyrrolo[2,3-d]pyrimidin-4-yl)-1H-pyrazol-1-yl]cyclobutylacetonitrile trifluoroacetic acid salt

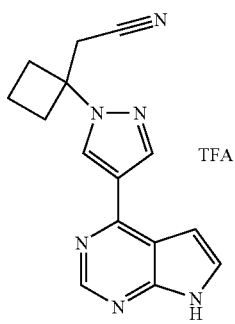

Step 1. cyclobutylideneacetonitrile

To a solution of 1.0000 M of potassium tert-butoxide in tetrahydrofuran (19.2 ML) at 0° C. was added dropwise a solution of diethyl cyanomethylphosphonate (3.26 mL, 0.0202 mol) in tetrahydrofuran (24.52 mL, 0.3023 mol). The reaction was warmed to rt and then cooled to 0° C. again. To the reaction mixture was added a solution of cyclobutanone (1.37 mL, 0.0183 mol) in tetrahydrofuran (4.90 mL, 0.0605 mol). The reaction was allowed to warm up to rt and stirred at rt overnight. After quenching with water, the mixture was extracted with EtOAc. The combined organic layers were washed with brine, dried and evaporated to dryness. The crude mixture was used directly in next step (1.30 g, 76.25%).

Step 2. 1-[4-(7H-pyrrolo[2,3-d]pyrimidin-4-yl)-1H-pyrazol-1-yl]cyclobutylacetonitrile To a solution of 4-(1H-pyrazol-4-yl)-7-[2-(trimethylsilyl)ethoxy]methyl-7H-pyrrolo[2,3-d]pyrimidine (0.030 g, 0.000095 mol) in acetonitrile (0.60 mL, 0.011 mol) was added cyclobutylideneacetonitrile (0.0177 g, 0.000190 mol), followed by 1,8-diazabicyclo[5.4.0]undec-7-ene (0.0142 mL, 0.0000951 mol). The resulting mixture was stirred at rt overnight. After evaporation to dryness, the residue was purified on silica gel to give the desired Micheal addition product. LCMS (M+H) 409.1.

The crude residue made above was dissolved in 0.2 mL of dichloromethane and treated with 0.4 mL of TFA at rt for 30 min. After evaporation to dryness, the residue was treated with 50 μL of ethylenediamine in 1 mL of methanol at rt for 30 min. The resulting mixture was purified on RP-HPLC (XBridge C18 column, eluting with a gradient of acetonitrile/water containing 0.1% TFA) to give the tilted product as TFA salt, LCMS calculated for $C_{15}H_{15}N_6(M+H)^+$: 279.1; Found: 279.0. $^1$H NMR (400 MHz, DMSO-$d_6$): δ 12.68(1H, br s), 8.88 (1H, s), 8.84 (1H, s), 8.51 (1H, s), 7.78 (1H, m), 7.25 (1H, m), 3.49 (2H, s), 2.78 (2H, m), 2.39 (2H, m), 2.06 (1H, m), 1.93 (1H, m) ppm.

Example 44 cis- and trans-3-(hydroxymethyl)-1-[4-(7H-pyrrolo[2,3-d]pyrimidin-4-yl)-1H-pyrazol-1-yl]cyclobutylacetonitrile

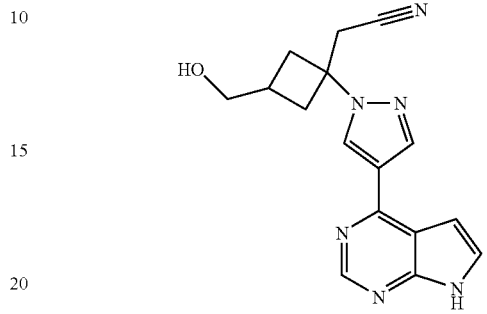

Step 1. diisopropyl 3,3-dimethoxycyclobutane-1,1-dicarboxylate

Diisopropyl malonate (72 g, 0.38 mol) was added dropwise, under nitrogen, to a stirred suspension of sodium hydride (17 g, 0.42 mol) in dry N,N-dimethylformamide (140 mL, 1.8 mol) at a rate such that the temperature was maintained below 70° C. On cessation of hydrogen evolution, 1,3-dibromo-2,2-dimethoxypropane (50 g, 0.2 mol) was added in one portion and the mixture heated at 140° C. for 48 h. The cooled mixture was poured into sat. solution of ammonium chloride (300 mL), extracted with hexane. The organic layer was washed with sat. sodium bicarbonate, brine, dried over sodium sulfate, and evaporated to dryness. The residue was distilled under vacuum (oil pump) to afford the desired cyclobutane compound (31 g, 56.32%). bp 92-94° C./0.01 mm). $^1$H NMR (400 MHz, CDCl$_3$): δ 5.02 (2H, sept., J=6.4 Hz), 3.12 (6H, s), 2.66 (4H, s), 1.11 (12H, d, J=6.4 Hz.) ppm.

Step 2. 3-oxocyclobutanecarboxylic acid

Diisopropyl 3,3-dimethoxycyclobutane-1,1-dicarboxylate (31 g, 0.11 mol) was heated with 78 mL of 20% HCl at reflux for 60 h. After cooling, the solution was continuously extracted with ether for 18 h. The ether was removed at a reduced pressure, leaving a yellow oil, which crystallized on standing to give the titled acid (10.4 g, 84.78%).

Step 3. methyl 3-oxocyclobutanecarboxylate

A solution of N,N'-dicyclohexylcarbodiimide (7.17 g, 0.0347 mol) in methylene chloride (8 mL, 0.1 mol) was added dropwise to a stirred mixture of 3-oxocyclobutanecarboxylic acid (3.6 g, 0.032 mol), methanol (2.6 mL, 0.063 mol) and 4-dimethylaminopyridine (3.08 g, 0.0252 mol) in methylene chloride (20 mL, 0.2 mol). The mixture was stirred at rt for 24 h, then filtered through Celite. The filtrate was washed with 0.5 M HCl and sat. sodium bicarbonate, dried and concentrated to dry. The residue was purified on silica gel, eluting with 0 to 40% EtOAc in hexane, to give the desired ester (3.26 g, 80.64%). $^1$H NMR (CDCl$_3$, 400 MHz): δ 3.78 (s, 3H), 3.43~3.20 (5H, m) ppm.

Step 4. methyl 3-(cyanomethylene)cyclobutanecarboxylate

To a solution of 1.0000 M of potassium tert-butoxide in tetrahydrofuran (26.7 mL) at 0° C. was added dropwise a solution of diethyl cyanomethylphosphonate (4.53 mL, 0.0280 mol) in tetrahydrofuran (50 mL, 0.6 mol). The reaction was warmed to rt and then cooled at 0° C. again. To the reaction mixture was a solution of methyl 3-oxocyclobutanecarboxylate (3.26 g, 0.0254 mol) in tetrahydrofuran (20 mL, 0.3 mol). The reaction was allowed to warm up to rt and stirred at rt overnight. After quenching with water, the mixture was extracted with ether. The combined organic layers were washed with water, brine, dried and evaporated to dryness. The crude mixture was purified on silica gel, eluting with 0 to 40% EtOAc in hexane, to give the desired product (3.12 g, 81.12%). LCMS calculated for C$_8$H$_{10}$NO$_2$(M+H)$^+$: 152.1; Found: 152.3.

Step 5. methyl 3-(cyanomethyl)-3-[4-(7-[2-(trimethylsilyl)ethoxy]methyl-7H-pyrrolo[2,3-d]pyrimidin-4-yl)-1H-pyrazol-1-yl]cyclobutanecarboxylate To a solution of 4-(1H-pyrazol-4-yl)-7-[2-(trimethylsilyl)ethoxy]methyl-7H-pyrrolo[2,3-d]pyrimidine (2.01 g, 0.00637 mol) in acetonitrile (4.0E1 mL, 0.77 mol) was added methyl 3-(cyanomethylene)cyclobutanecarboxylate (1.93 g, 0.0127 mol), followed by 1,8-diazabicyclo[5.4.0]undec-7-ene (0.953 mL, 0.00637 mol). The resulting mixture was stirred at 50° C. overnight. After evaporation to dryness, the residue was purified on silica gel, eluting with 0 to 100% EtOAc in hexane, to give the desired Micheal addition product as a mixture of cis- and trans-isomers (2.12 g, 71.3%). LCMS calculated for C$_{23}$H$_{31}$N$_6$O$_3$Si(M+H)$^+$: 467.2; Found: 467.4.

Step 6. 3-(hydroxymethyl)-1-[4-(7-[2-(trimethylsilyl)ethoxy]methyl-7H-pyrrolo[2,3-d]pyrimidin-4-yl)-1H-pyrazol-1-yl]cyclobutylacetonitrile To a mixture of methyl 3-(cyanomethyl)-3-[4-(7-[2-(trimethylsilyl)ethoxy]methyl-7H-pyrrolo[2,3-d]pyrimidin-4-yl)-1H-pyrazol-1-yl]cyclobutanecarboxylate (7.0 g, 0.015 mol) in tetrahydrofuran (100 mL, 1 mol) was added lithium tetrahydroborate (0.327 g, 0.0150 mol) at 0° C. The reaction was then heated at 50° C. for 3 h. To the reaction was added 60 mL of methanol. The resulting mixture was heated at 50° C. for another 15 min, then evaporated to dryness. The residue was treated with 1 N HCl, then neutralized with solid sodium bicarbonate, extracted with EtOAc. The combined organic layers were washed with brine, dried over sodium sulfate and evaporated to dryness. The residue was purified on silica gel, eluting with 0 to 100% EtOAc, to give the desired product as cis- and trans-mixture (5.85 g, 88.91%). LCMS calculated for C$_{22}$H$_{31}$N$_6$O$_2$Si(M+H)$^+$: 439.2; Found: 439.4.

Step 7. 3-(hydroxymethyl)-1-[4-(7H-pyrrolo[2,3-d]pyrimidin-4-yl)-1H-pyrazol-1-yl]cyclobutylacetonitrile To 3-(hydroxymethyl)-1-[4-(7-[2-(trimethylsilyl)ethoxy]methyl-7H-pyrrolo[2,3-d]pyrimidin-4-yl)-1H-pyrazol-1-yl]cyclobutylacetonitrile (0.030 g, 0.000068 mol) was added 1.5 mL of TFA. The reaction was stirred at rt for 30 min, then evaporated to dryness. The crude mixture was dissolved in 1 mL of methanol and treated with 60 μL of ethylenediamine at rt for 5 h. The resulting mixture was purified on RP-HPLC (XBridge C18 column, eluting with a gradient of acetonitrile/water containing 0.15% NH$_4$OH) to give the desired products as free bases. First peak retention time 0.766 min, LCMS calculated for C$_{1-6}$H$_{71}$N$_6$O(M+H)$^+$: 309.1; Found: 309.3. $^1$H NMR (400 MHz, DMSO-d$_6$): δ 12.11(1H, br s), 8.67 (1H, s), 8.65 (1H, s), 8.37 (1H, s), 7.58 (1H, d, J=3.6), 7.02 (1H, d, J=3.6 Hz), 4.69 (1H, br s), 3.47 (2H, s), 3.41 (2H, br s), 2.53 (2H, m), 2.37 (2H, m) ppm. Second peak retention time 0.805 min, LCMS calculated for C$_{16}$H$_{17}$N$_6$O(M+H)$^+$: 309. 1; Found: 309.3. $^1$H NMR (400 MHz, DMSO-d$_6$): δ 12.11(1H, br s), 8.80 (1H, s), 8.68 (1H, s), 8.40 (1H, s), 7.58 (1H, d, J=3.6 Hz), 7.07 (1H, d J=3.6 Hz), 4.78 (1H, br t, J=5.2 Hz), 3.47 (2H, br t, J=5.2 Hz), 3.36 (2H, s), 2.85 (2H, m), 2.29 (2H, m), ppm.

Example 45 cis- and trans-3-(fluoromethyl)-1-[4-(7H-pyrrolo[2,3-d]pyrimidin-4-yl)-1H-pyrazol-1-yl]cyclobutylacetonitrile

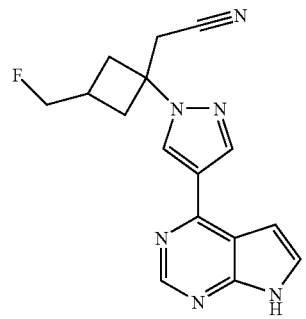

To a mixture of 3-(hydroxymethyl)-1-[4-(7-[2-(trimethylsilyl)ethoxy]methyl-7H-pyrrolo[2,3-d]pyrimidin-4-yl)-1H-pyrazol-1-yl]cyclobutylacetonitrile (0.050 g, 0.00011 mol) in methylene chloride (3.10 mL, 0.0483 mol) in a plastic bottle was added 2-methoxy-N-(2-methoxyethyl)-N-(trifluoro-λ(4)-sulfanyl)ethanamine (63.0 μL, 0.000342 mol) followed by ethanol (1 μL, 0.00002 mol). The reaction was stirred at rt overnight, then evaporated to drynes to yield the fluorinated product. LCMS (M+H) 441.1.

To the residue from above was added 3 mL of TFA. The reaction was stirred at rt for 30 min, then evaporated to dryness. The crude mixture was dissolved in 1 mL of methanol and treated with 60 μL of ethylenediamine at rt for 5 h. The resulting mixture was purified on RP-HPLC (XBridge C18 column, eluting with a gradient of acetonitrile/water containing 0.15% NH$_4$OH) to give the desired products as free bases. First peak retention time 0.973 min on analytic LCMS [Waters SunFire HPLC column (C18, 2.1×50 mm, 5 μM), injection volumn 2 μL, flow rate 3 mL/min, gradient from 2 to 80% B in 3 minutes (A=water with 0.025% TFA; B=acetonitrile)], LCMS calculated for C$_{16}$H$_{16}$FN$_6$(M+H)$^+$: 311.1; Found: 311.3. Second peak retention time 1.006 min on analytic LCMS, LCMS calculated for C$_{16}$H$_{16}$FN$_6$(M+H)$^+$: 311.1; Found: 311.3. $^1$H NMR (500 MHz, DMSO-d$_6$): δ 12.09(1H, br s), 8.84 (1H, s), 8.70 (1H, s), 8.43 (1H, s), 7.59 (1H, d, J=4.0 Hz), 7.08 (1H, d, J=4.0 Hz), 4.53 (2H, dd, J=5.5 and 47.5 Hz), 3.38 (2H, s), 2.97 (2H, m), 2.68 (1H, m), 2.39 (2H, m) ppm. $^{19}$F NMR (500 MHz, DMSO-d$_6$) δ -221.84 (td, J=47.5 and 21.0 Hz) ppm.

Example 46 cis- and trans-3-(difluoromethyl)-1-[4-(7H-pyrrolo[2,3-d]pyrimidin-4-yl)-1H-pyrazol-1-yl]cyclobutylacetonitrile

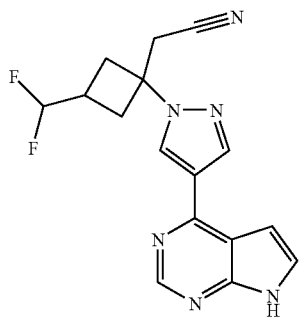

Step 1. 3-formyl-1-[4-(7-[2-(trimethylsilyl)ethoxy]methyl-7H-pyrrolo[2,3-d]pyrimidin-4-yl)-1H-pyrazol-1-yl]cyclobutylacetonitrile Dimethyl sulfoxide (0.194 mL, 0.00274 mol) was added to a solution of oxalyl chloride (0.145 mL, 0.00171 mol) in methylene chloride (6.384 mL, 0.09959 mol) at −78° C. After 10 min, 3-(hydroxymethyl)-1-[4-(7-[2-(trimethylsilyl)ethoxy]methyl-7H-pyrrolo[2,3-d]pyrimidin-4-yl)-1H-pyrazol-1-yl]cyclobutylacetonitrile (0.500 g, 0.00114 mol) in methylene chloride (12.77 mL, 0.1992 mol) was added and the resultant mixture was stirred at −78° C. for 30 min. Triethylamine (0.794 mL, 0.00570 mol) was then added and the mixture was stirred for 5 h with the temperature allowed to gradually warm up to rt. After quenching with water, the mixture was extracted with methylene chloride. The organic layers were combined, washed with brine, dried and evaporated to dry. The residue was purified on silica gel, eluting with 0 to 100% EtOAc in hexane, to give the desired aldehyde (430 mg, 86%). LCMS calculated for C$_{22}$H$_{29}$N$_6$O$_2$Si(M+H)$^+$: 437.2; Found: 437.4.

Step 2. 3-(difluoromethyl)-1-[4-(7H-pyrrolo[2,3-d]pyrimidin-4-yl)-1H-pyrazol-1-yl]cyclobutylacetonitrile To a mixture of 3-formyl-1-[4-(7-[2-(trimethylsilyl)ethoxy]methyl-7H-pyrrolo[2,3-yl]pyrimidin-4-yl)-1H-pyrazol-1-yl]cyclobutylacetonitrile (0.285 g, 0.000653 mol) in methylene chloride (6 mL, 0.09 mol) in a plastic bottle was added 2-methoxy-N-(2-methoxyethyl)-N-(trifluoro-λ(4)-sulfanyl)ethanamine (0.481 mL, 0.00261 mol) followed by ethanol (8 µL, 0.0001 mol). The reaction was stirred at rt overnight, then evaporated to dryness. LCMS (M+H) 459.4. To the residue made above was added 3 mL of TFA. The reaction was stirred at rt for 30 min, then evaporated to dryness. The crude mixture was dissolved in 3 mL of methanol and treated with ethylenediamine (0.22 mL, 0.0033 mol) at rt for 5 h. The resulting mixture was purified on RP-HPLC (XBridge C18 column, eluting with a gradient of acetonitrile/water containing 0.15% NH$_4$OH) to give the desired products as free bases. First peak retention time 0.935 min, LCMS calculated for C$_{16}$H$_{15}$F$_2$N$_6$(M+H)$^+$: 329.1; Found: 329.1. $^1$H NMR (500 MHz, DMSO-d$_6$): δ 12.10(1H, br s), 8.74 (1H, s), 8.69 (1H, s), 8.40 (1H, s), 7.59 (1H, d, J=3.5 Hz), 7.06 (1H, d, J=3.5 Hz), 6.20 (1H, td, J=57.0 and 4.0 Hz), 3.57 (2H, s), 2.98 (1H, m), 2.81 (2H, m), 2.52 (2H, m) ppm. Second peak retention time 0.974 min, LCMS calculated for C$_{16}$H$_{15}$F$_2$N$_6$ (M+H)$^+$: 329.1; Found: 329.1. $^1$H NMR (500 MHz, DMSO-d$_6$): δ 12.10(1H, br s), 8.78 (1H, s), 8.70 (1H, s), 8.44 (1H, s), 7.60 (1H, d, J=3.5 Hz), 7.09 (1H, d, J=3.5 Hz), 6.25 (1H, td, J=57.0 and 4.5 Hz), 3.41 (2H, s), 3.01 (2H, m), 2.90 (1H, m), 2.56 (2H, m) ppm.

Example 47 cis- and trans-2,2'-[1-[4-(7H-pyrrolo[2,3-d]pyrimidin-4-yl)-1H-pyrazol-1-yl]cyclobutane-1,3-diyl]diacetonitrile

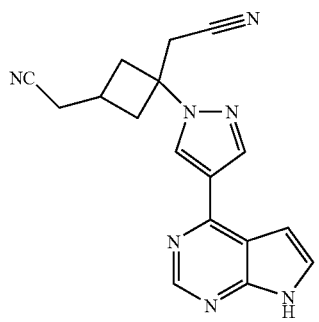

Step 1. 3-(cyanomethyl)-3-[4-(7-[2-(trimethylsilyl)ethoxy]methyl-7H-pyrrolo[2,3-d]pyrimidin-4-yl)-1H-pyrazol-1-yl]cyclobutylmethyl methanesulfonate To a mixture of 3-(hydroxymethyl)-1-[4-(7-[2-(trimethylsilyl)ethoxy]methyl-7H-pyrrolo[2,3-d]pyrimidin-4-yl)-1H-pyrazol-1-yl]cyclobutylacetonitrile (0.122 g, 0.000278 mol) in methylene chloride (2 mL, 0.04 mol) was added triethylamine (0.0775 mL, 0.000556 mol) followed by methanesulfonyl chloride (0.0478 g, 0.000417 mol) at 0° C. The reaction was stirred at rt overnight, quenched with water, extracted with dichloromethane. The organic layers were washed with brine, dried over magnesium sulfate, then evaporated to dryness. The crude mixture was used directly in next step (138 mg, 96.02%). LCMS calculated for C$_{23}$H$_{33}$N$_6$O$_4$SSi(M+H)$^+$: 517.2; Found: 517.4.

Step 2. 2,2'-[1-[4-(7H-pyrrolo[2,3-d]pyrimidin-4-yl)-1H-pyrazol-1-yl]cyclobutane-1,3-diyl]diacetonitrile A mixture of 3-(cyanomethyl)-3-[4-(7-[2-(trimethylsilyl)ethoxy]methyl-7H-pyrrolo[2,3-d]pyrimidin-4-yl)-1H-pyrazol-1-yl]cyclobutylmethyl methanesulfonate (0.138 g, 0.000267 mol) and potassium cyanide (0.0870 g, 0.00134 mol) in N,N-dimethylformamide (1.0 mL, 0.013 mol) was heated at 65° C. overnight. After cooled to rt, the mixture was extracted with EtOAc. The combined organic layers were washed with water, brine, dried over magnesium sulfate, then evaporated to dryness. LCMS (M+H) 448.4.

The crude product made above was treated with 1 mL of TFA at rt for 30 min, then evaporated to dryness. The resulting residue was treated with 0.1 mL of ethylenediamine in 1 mL of MeOH at rt overnight. The mixture was applied on RP-HPLC (XBridge C18 column, eluting with a gradient of acetonitrile/water containing 0.15% NH₄OH) to give two isomers at a ratio of 3:2. First peak retention time 0.869 min, LCMS calculated for $C_{17}H_{16}N_7(M+H)^+$: 318. 1; Found 318.3. ¹H NMR (500 MHz, DMSO-d₆): δ 12.09(1H, br s), 8.72 (1H, s), 8.69 (1H, s), 8.39 (1H, s), 7.60 (1H, d, J=3.5 Hz), 7.05 (1H, d, J=3.5 Hz), 3.52 (2H, s), 2.79 (2H, br s), 2.68 (1H, m), 2.61 (2H, br s), 2.60 (2H, br s) ppm. Second peak retention time 0.919 min, LCMS calculated for $C_{17}H_{16}N_7(M+H)^+$: 318.1; Found 318.3. ¹H NMR (500 MHz, DMSO-d₆): δ 12.09 (1H, br s), 8.85 (1H, s), 8.70 (1H, s), 8.43 (1H, s), 7.59 (1H, d, J=3.5 Hz), 7.08 (1H, d, J=3.5 Hz), 3.40 (2H, s), 3.07 (2H, m), 2.80 (2H, d, J=7.0 Hz), 2.70 (1H, m), 2.34 (2H, m) ppm.

Example 48 cis- and trans-3-(cyanomethyl)-1-methyl-3-[4-(7H-pyrrolo[2,3-d]pyrimidin-4-yl)-1H-pyrazol-1-yl]cyclobutanecarbonitrile

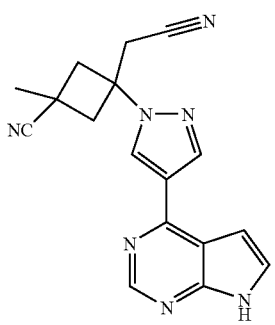

Step 1.
1-methyl-3-methylenecyclobutanecarbonitrile

To a mixture of 3-methylenecyclobutanecarbonitrile (5.00 g, 0.0537 mol) (from Bepharm Ltd., China) in tetrahydrofuran (200 mL, 2 mol) was added 2.00 M of lithium diisopropylamide in tetrahydrofuran (32.2 mL) at −78° C. After stirring at '178° C. for 30 min, methyl iodide (4.18 mL, 0.0671 mol) was added. The reaction was stirred at −78° C. for 30 min, then allowed to warm up to rt, quenched with ammonium chloride, then extracted with ether. The combined organic layers were washed with water, brine, dried, and evaporated to dryness. The crude residue was used directly in next step.

Step 2. 1-methyl-3-oxocyclobutanecarbonitrile

A mixture of water (60 mL, 3 mol) and 1,4-dioxane (200 mL, 2 mol), 1-methyl-3-methylenecyclobutanecarbonitrile (5.75 g, 0.0537 mol), and 0.2 M of osmium tetraoxide in water (1 mL) was stirred for 5 min, during which time the mixture became brown. While the temperature was maintained at room temperature, sodium periodate (24.1 g, 0.113 mol) was added in portions over a period of 30 min. The mixture was stirred overnight. The mixture was extracted with dichloromethane and combined organic layers were dried over MgSO₄. After removal of the solvents, the crude product was used directly in next step (5.50 g, 93.92%). ¹H NMR (CDCl₃, 400 MHz): δ 3.74 (2H, m), 3.16 (2H, m), 1.75 (3H, s) ppm.

Step 3.
3-(cyanomethylene)-1-methylcyclobutanecarbonitrile

To a solution of 1.0 M of potassium tert-butoxide in tetrahydrofuran (52.9 mL) at 0° C. was added dropwise a solution of diethyl cyanomethylphosphonate (8.98 mL, 0.0555 mol) in tetrahydrofuran (90 mL, 1 mol). The reaction was warmed to rt and then cooled at 0° C. again. To the reaction mixture was added a solution of 1-methyl-3-oxocyclobutanecarbonitrile (5.50 g, 0.0504 mol) in tetrahydrofuran (40 mL, 0.6 mol). The reaction was allowed to warm up to rt and stirred at rt overnight. After quenching with water, the mixture was extracted with ether. The combined organic layers were washed with water, brine, dried and evaporated to dryness. The crude mixture was purified on silica gel, eluting with 0 to 60% EtOAc in hexane, to give the desired product (3.12 g, 46.84%). LCMS calculated for $C_8H_9N_2(M+H)^+$: 133.1; Found: 133.1.

Step 4. 3-(cyanomethyl)-1-methyl-3-[4-(7H-pyrrolo [2,3-d]pyrimidin-4-yl)-1H-pyrazol-1-yl]cyclobutanecarbonitrile To a solution of 4-(1H-pyrazol-4-yl)-7-[2-(trimethylsilyl) ethoxy]methyl-7H-pyrrolo[2,3-d]pyrimidine (0.030 g, 0.000095 mol) in acetonitrile (0.5 mL, 0.01 mol) was added 3-(cyanomethylene)-1-methylcyclobutanecarbonitrile (0.0126 g, 0.0000951 mol), followed by 1,8-diazabicyclo [5.4.0]undec-7-ene (0.0142 mL, 0.0000951 mol). The resulting mixture was stirred at rt overnight, then evaporated to dryness. LCMS (M+H) 448.4.

The crude mixture was treated with 1 mL of TFA (trifluoroacetic acid) at rt for 1 h, and evaporated to dryness. The residue was stirred with 0.050 mL of ethylenediamine in 1 mL of methanol at rt overnight. The reaction mixture was applied on RP-HPLC (XBridge C18 column, eluting with a gradient of acetonitrile/water containing 0.15% NH₄OH) to give the desired products as free bases. First peak retention time 0.916 min, LCMS calculated for $C_{17}H_{16}N_7(M+H)^+$: 318.1; Found 318.4. ¹H NMR (500 MHz, DMSO-d₆): δ 12.10 (1H, br s), 8.93 (1H, s), 8.71 (1H, s), 8.46 (1H, s), 7.61 (1H, d, J=3.5 Hz), 7.08 (1H, d, J=3.5 Hz), 3.48 (2H, dd, J=2.0 and 12.5 Hz), 3.45 (2H, s), 2.74 (2H, dd, J=2.0 and 12.5 Hz), 1.62 (3H, s) ppm. Second peak retention time 0.988 min, LCMS calculated for $C_{17}H_{16}N_7(M+H)^+$: 318. 1; Found 318.4. ¹H NMR (500 MHz, DMSO-d₆): δ 12.10(1H, br s), 8.84 (1H, s), 8.70 (1H, s), 8.43 (1H, s), 7.61 (1H, d, J=3.5 Hz), 7.06 (1H, d, J=3.5 Hz), 3.52 (2H, s), 3.12 (4H, m), 1.45 (3H, s) ppm.

Example 49 cis- and trans-3-(cyanomethyl)-1-(methoxymethyl)-3-[4-(7H-pyrrolo[2,3-d]pyrimidin-4-yl)-1H-pyrazol-1-yl]cyclobutanecarbonitrile

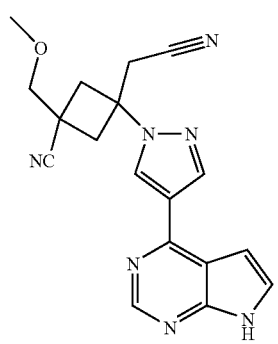

Step 1. 1-(methoxymethyl)-3-methylenecyclobutanecarbonitrile

To a mixture of 3-methylenecyclobutanecarbonitrile (1.00 g, 0.0107 mol) in tetrahydrofuran (40 mL, 0.5 mol) was added 2.00 M of lithium diisopropylamide in tetrahydrofuran (6.44 mL) at −78° C. After stirred at −78° C. for 30 min, to the resulting mixture was added chloromethyl methyl ether (1.02 mL, 0.0134 mol). The reaction was stirred at −78° C. for 30 min, then allowed to warm up to rt, quenched with ammonium chloride, then extracted with ether. The combined organic layers were washed with water, brine, dried, and evaporated to dryness. The crude residue was used directly in next step.

Step 2. 1-(methoxymethyl)-3-oxocyclobutanecarbonitrile

A mixture of water (2 mL, 0.1 mol) and 1,4-dioxane (7 mL, 0.08 mol), 1-(methoxymethyl)-3-methylenecyclobutanecarbonitrile (0.294 g, 0.00214 mol), and 0.2 M of osmium tetraoxide in water (0.04 mL) was stirred for 5 min, during which time the mixture became brown. While the temperature was maintained at room temperature, sodium periodate (0.963 g, 0.00450 mol) was added in portions over a period of 30 min. The mixture was stirred overnight. The mixture was extracted with EtOAc and the combined organic layers were dried over MgSO$_4$. After removal of the solvents, the crude product was used directly in next step (298 mg, 99.92%). $^1$H NMR (400 MHz, CDCl$_3$): δ 3.70 (2H, s), 3.68 (3H, s), 3.58 (2H, m), 3.38 (2H, m) ppm.

Step 3. 3-(cyanomethylene)-1-(methoxymethyl)cyclobutanecarbonitrile

To a solution of 1.0000 M of potassium tert-butoxide in tetrahydrofuran (2.25 mL) at 0° C. was added dropwise a solution of diethyl cyanomethylphosphonate (0.381 mL, 0.00236 mol) in tetrahydrofuran (4 mL, 0.05 mol). The reaction was warmed to rt and then cooled to 0° C. again. To the reaction mixture was added a solution of 1-(methoxymethyl)-3-oxocyclobutanecarbonitrile (0.298 g, 0.00214 mol) in tetrahydrofuran (2 mL, 0.02 mol). The reaction was allowed to warm up to rt and stirred at rt overnight. After quenching with water, the mixture was extracted with ether. The combined organic layers were washed with water, brine, dried and evaporated to dryness. The crude mixture was used directly in next step. LCMS calculated for C$_9$H$_{11}$N$_2$O(M+H)$^+$:163.1; Found: 163.1.

Step 4. 3-(cyanomethyl)-1-(methoxymethyl)-3-[4-(7H-pyrrolo[2,3-d]pyrimidin-4-yl)-1H-pyrazol-1-yl]cyclobutanecarbonitrile To a solution of 4-(1H-pyrazol-4-yl)-7-[2-(trimethylsilyl)ethoxy]methyl-7H-pyrrolo[2,3-d]pyrimidine (0.256 g, 0.000812 mol) in acetonitrile (5 mL, 0.1 mol) was added 3-(cyanomethylene)-1-(methoxymethyl)cyclobutanecarbonitrile (0.166 g, 0.00102 mol), followed by 1,8-diazabicyclo[5.4.0]undec-7-ene (0.153 mL, 0.00102 mol). The resulting mixture was stirred at rt overnight, and evaporated to dryness. LCMS (M+H) 478.4.
The crude mixture from above was treated with 1 mL of TFA at rt for 1 h, then evaporated to dryness. The residue was stirred with 0.050 mL of ethylenediamine in 1 mL of methanol at rt overnight. The reaction mixture was applied on RP-HPLC (XBridge C18 column, eluting with a gradient of acetonitrile/water containing 0.15% NH$_4$OH) to give the desired products as free bases. First peak retention time 0.969 min, LCMS calculated for C$_{18}$H$_{18}$N$_7$O(M+H)$^+$: m/z=348.2; Found: 348.4. Second peak retention time 0.986 min, LCMS calculated for C$_{18}$H$_{18}$N$_7$O(M+H)$^+$: 348.2; Found: 348.4.

Example 50 cis- and trans-3-(cyanomethyl)-1-(fluoromethyl)-3-[4-(7H-pyrrolo[2,3-d]pyrimidin-4-yl)-1H-pyrazol-1-yl]cyclobutanecarbonitrile

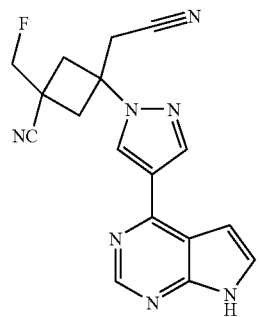

Step 1. 1-(hydroxymethyl)-3-methylenecyclobutanecarbonitrile

To a mixture of 1-(methoxymethyl)-3-methylenecyclobutanecarbonitrile (1.40 g, 0.0102 mol) in methylene chloride (30 mL, 0.4 mol) was added 1.0 M of boron tribromide in methylene chloride (12.8 mL) at −78° C. The reaction was stirred at rt for 2 h, quenched with aq. sodium bicarbonate, and extracted with dichloromethane. The combined organic layers were dried over magnesium sulfate and evaporated to dryness to give the desired product (1.26 g, 100%). $^1$H NMR (400 MHz, CDCl$_3$): δ4.81 (2H, m), 3.66 (2H, s), 3.10 (2H, m), 2.59 (2H, m) ppm.

Step 2. 1-(fluoromethyl)-3-methylenecyclobutanecarbonitrile

To a mixture of 1-(hydroxymethyl)-3-methylenecyclobutanecarbonitrile (0.252 g, 0.00205 mol) in methylene chloride (20 mL, 0.3 mol) in a plastic bottle was added 2-methoxy-N-(2-methoxyethyl)-N-(trifluoro-λ(4)-sulfanyl)ethanamine (1. 13 mL, 0.00614 mol) followed by ethanol (20 μL, 0.0004 mol). The reaction was stirred at rt overnight, then quenched with aq. sodium bicarbonate, and extracted with dichloromethane. The extracts were combined and washed with water, brine, and dried over magnesium sulfate, and evaporated to dryness. The residue was used directly in next step.

Step 3. 1-(fluoromethyl)-3-oxocyclobutanecarbonitrile

A mixture of water (2 mL, 0.1 mol) and 1,4-dioxane (6 mL, 0.08 mol), 1-(fluoromethyl)-3-methylenecyclobutanecarbonitrile (0.256 g, 0.00204 mol), and 0.2 M of osmium tetraoxide in water (0.04 mL) was stirred for 5 min, during which time the mixture became brown. While the temperature was maintained at room temperature, sodium periodate (0.919 g, 0.00430 mol) was added in portions over a period of 30 min. The mixture was stirred overnight. The mixture was extracted with EtOAc and combined organic layers were dried over MgSO$_4$. After removal of the solvents, the crude product was used directly in next step.

Step 4. 3-(cyanomethylene)-1-(fluoromethyl)cyclobutanecarbonitrile

To a solution of 1.0 M of potassium tert-butoxide in tetrahydrofuran (2.15 mL) at 0° C. was added dropwise a solution of diethyl cyanomethylphosphonate (0.364 mL, 0.00225 mol) in tetrahydrofuran (4 mL, 0.04 mol). The reaction was warmed to rt and then cooled to 0° C. again. To the reaction mixture was added a solution of 1-(fluoromethyl)-3-oxocyclobutanecarbonitrile (0.260 g, 0.00204 mol) in tetrahydrofuran (2 mL, 0.02 mol). The reaction was allowed to warm up to rt and stirred at rt overnight. After quenching with water, the mixture was extracted with ether. The combined organic layers were washed with water then brine, dried, and evaporated to dryness. The crude mixture was used directly in next step.

Step 5. 3-(cyanomethyl)-1-(fluoromethyl)-3-[4-(7H-pyrrolo[2,3-d]pyrimidin-4-yl)-1H-pyrazol-1-yl]cyclobutanecarbonitrile To a solution of 4-(1H-pyrazol-4-yl)-7-[2-(trimethylsilyl)ethoxy]methyl-7H-pyrrolo[2,3-d]pyrimidine (0.256 g, 0.000812 mol) in acetonitrile (5 mL, 0.1 mol) was added 3-(cyanomethylene)-1-(fluoromethyl)cyclobutanecarbonitrile (0.153 g, 0.00102 mol), followed by 1,8-diazabicyclo[5.4.0]undec-7-ene (0.153 mL, 0.00102 mol). The resulting mixture was stirred at rt overnight, evaporated to dry. LCMS (M+H) 465.4.

The crude mixture was treated with 1 mL of TFA at rt for 1 h, and evaporated to dryness. The residue was stirred with 0.050 mL of ethylenediamine in 1 mL of methanol at rt overnight. The reaction mixture was applied on RP-HPLC (XBridge C18 column, eluting with a gradient of acetonitrile/water containing 0.15% NH$_4$OH) to give the desired products as free bases. First peak retention time 0.939 min, LCMS calculated for C$_{17}$H$_{15}$FN$_7$(M+H)$^+$: 336.1; Found: 336.3. $^1$H NMR (400 MHz, DMSO-d$_6$): δ 12.08(1H, br s), 8.97 (1H, s), 8.70 (1H, s), 8.49 (1H, s), 7.61 (1H, d, J=3.6 Hz), 7.09 (1H, d, J=3.6 Hz), 4.81 (2H, d, J=46.4 Hz), 3.48 (2H, s), 3.44 (2H, m), 2.90 (2H, m) ppm. Second peak retention time 0.978 min, LCMS calculated for C$_{17}$H$_{15}$FN$_7$(M+H)$^+$: 336.1; Found: 336.3. $^1$H NMR (400 MHz, DMSO-d$_6$): δ 12.08(1H, br s), 8.85 (1H, s), 8.68 (1H, s), 8.43 (1H, s), 7.61 (1H, d, J=4.4 Hz), 7.06 (1H, d, J=4.4 Hz), 4.58 (2H, d, J=46.4 Hz), 3.58 (2H, s), 3.26 (2H, m), 3.09 (2H, m) ppm.

Example 51 cis- and trans-1,3-bis(cyanomethyl)-3-[4-(7H-pyrrolo[2,3-d]pyrimidin-4-yl)-1H-pyrazol-1-yl]cyclobutanecarbonitrile

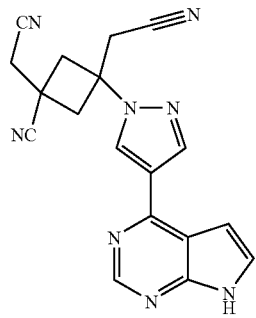

Step 1. (1-cyano-3-methylenecyclobutyl)methyl methanesulfonate

To a mixture of 1-(hydroxymethyl)-3-methylenecyclobutanecarbonitrile (0.756 g, 0.00614 mol) in methylene chloride (20 mL, 0.3 mol) was added triethylamine (1.28 mL, 0.00921 mol) followed by methanesulfonyl chloride (0.594 mL, 0.00767 mol) at 0° C. The reaction was stirred at rt for 1 h, quenched with water, and extracted with dichloromethane. The combined organic layers were washed with water, brine, and then dried over magnesium sulfate and evaporated to dryness. The residue was used directly in next step.

Step 2. 1-(cyanomethyl)-3-methylenecyclobutanecarbonitrile

A mixture of (1-cyano-3-methylenecyclobutyl)methyl methanesulfonate (0.41 g, 0.0020 mol) and potassium cyanide (0.66 g, 0.010 mol) in N,N-dimethylformamide (5 mL, 0.06 mol) was heated at 65° C. overnight. After diluting with water, the resulting mixture was extracted with EtOAc. The combined organic layers were washed with water, brine, dried and evaporated to dry. The residue was used directly in next step.

Step 3. 1-(cyanomethyl)-3-oxocyclobutanecarbonitrile

A mixture of water (2 mL, 0.1 mol) and 1,4-dioxane (6 mL, 0.08 mol), 1-(cyanomethyl)-3-methylenecyclobutanecarbonitrile (0.270 g, 0.00204 mol), and 0.2 M of osmium tetraoxide in water (0.04 mL) was stirred for 5 min, during which time the mixture became brown. While the temperature was maintained at room temperature, sodium periodate (0.919 g, 0.00430 mol) was added in portions over a period of 30 min. The mixture was stirred overnight. The mixture was extracted with EtOAc and the combined organic layers were dried over MgSO$_4$. After removal of the solvents, the crude product was used directly in next step.

Step 4. 1-(cyanomethyl)-3-(cyanomethylene)cyclobutanecarbonitrile

To a solution of 1.0 M of potassium tert-butoxide in tetrahydrofuran (2.15 mL) at 0° C. was added dropwise a solution of diethyl cyanomethylphosphonate (0.364 mL, 0.00225 mol) in tetrahydrofuran (4 mL, 0.04 mol). The reaction was warmed to rt and then cooled to 0° C. again. To the reaction mixture was added a solution of 1-(cyanomethyl)-3-oxocyclobutanecarbonitrile (0.274 g, 0.00204 mol) in tetrahydrofuran (2 mL, 0.02 mol). The reaction was allowed to warm up to rt and stirred at rt overnight. After quenching with water, the mixture was extracted with ether. The combined organic layers were washed with water and brine, then dried and evaporated to dryness. The crude mixture was used directly in next step.

Step 5. 1,3-bis(cyanomethyl)-3-[4-(7H-pyrrolo[2,3-d]pyrimidin-4-yl)-1H-pyrazol-1-yl]cyclobutanecarbonitrile To a solution of 4-(1 H-pyrazol-4-yl)-7-[2-(trimethylsilyl)ethoxy]methyl-7H-pyrrolo[2,3-d]pyrimidine (0.256 g, 0.000812 mol) in acetonitrile (5 mL, 0.1 mol) was added 1-(cyanomethyl)-3-(cyanomethylene)cyclobutanecarbonitrile (0.161 g, 0.00102 mol), followed by 1,8-diazabicyclo[5.4.0]undec-7-ene (0.153 mL, 0.00102 mol). The resulting mixture was stirred at rt overnight, evaporated to dry. LCMS (M+H) 473.4.

The crude mixture was treated with 1 mL of TFA at rt for 1 h, then evaporated to dryness. The residue was stirred with 0.050 mL of ethylenediamine in 1 mL of methanol at rt overnight. The reaction mixture was applied on RP-HPLC (XBridge C18 column, eluting with a gradient of acetonitrile/water containing 0.15% $NH_4OH$) to give the desired products as free bases. First peak retention time 0.883 min, LCMS calculated for $C_{18}H_{15}N_8(M+H)^+$: 343.1; Found: 343.4. $^1H$ NMR (400 MHz, DMSO-$d_6$): δ 12.12(1H, br s), 8.98 (1H, s), 8.70 (1H, s), 8.48 (1H, s), 7.61 (1H, d, J=4.0 Hz), 7.10 (1H, d, J=4.0 Hz), 3.56 (2H, d, J=13.2), 3.46 (2H, s), 3.42 (2H, m), 2.92 (2H, d, J=13.2 Hz) ppm. Second peak retention time 0.897 min, LCMS calculated for $C_{18}H_{15}N_8(M+H)^+$: 343.1; Found: 343.4. $^1H$ NMR (400 MHz, DMSO-$d_6$): δ 12.08(1H, br), 8.85 (1H, s), 8.69 (1H, s), 8.43 (1H, s), 7.61 (1H, m), 7.07 (1H, m), 3.38 (2H, s), 3.27 (2H, m), 3.14 (2H, m), 2.88 (2H, m) ppm.

Example 52 cis and trans-3-(cyanomethyl)-3-[4-(7H-pyrrolo[2,3-d]pyrimidin-4-yl)-1H-pyrazol-1-yl]cyclobutanecarbonitrile

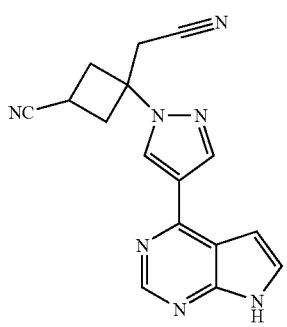

Step 1. 3-oxocyclobutanecarbonitrile

A mixture of water (40 mL, 2 mol) and 1,4-dioxane (100 mL, 1 mol), 3-methylenecyclobutanecarbonitrile (3.30 g, 0.0354 mol) (commercially available from Bepharma Ltd., China), and 0.2 M of osmium tetraoxide in water (0.7 mL) was stirred for 5 min, during which time the mixture became brown. While the temperature was maintained at room temperature, sodium periodate (15.9 g, 0.0744 mol) was added in portions over a period of 30 min. The mixture was stirred for an additional 1.5 h, then extracted with dichloromethane. The combined organic layers were dried over magnesium sulfate and concentrated to give a solid (2.04 g, 60.54%). $^1H$ NMR (300 MHz, CDCl$_3$): δ 3.58 (4H, m), 3.25 (1H, m) ppm.

Step 2. 3-(cyanomethylene)cyclobutanecarbonitrile

To a solution of 1 M of potassium tert-butoxide in THF (67.4 mL) at 0° C. was added dropwise a solution of diethyl cyanomethylphosphonate (11.4 mL, 0.0706 mol) in tetrahydrofuran (100 mL, 1 mol). The reaction mixture was warmed up to room temperature and cooled to 0° C. again. To the resulting mixture, a solution of 3-oxocyclobutanecarbonitrile (6.10 g, 0.0641 mol) in tetrahydrofuran (20 mL, 0.2 mol) was added. The reaction mixture was allowed to warm up to room temperature and stirred for 2 hours. After quenching with water, the mixture was extracted with EtOAc. The combined organic layers were dried and concentrated. The residue was purified by flash silica gel column, eluting with 0-10% MeOH/dichloromethane to give the titled product (5.40 g, 71.26%). LCMS (M+Na) 141.3. $^1H$ NMR (400 MHz, CDCl$_3$): δ 5.30 (1H, m), 3.40 (2H, m), 3.14 (3H, m) ppm.

Step 3. 3-(cyanomethyl)-3-[4-(7-[2-(trimethylsilyl)ethoxy]methyl-7H-pyrrolo[2,3-d]pyrimidin-4-yl)-1H-pyrazol-1-yl]cyclobutanecarbonitrile 3-(Cyanomethylene)cyclobutanecarbonitrile (120 mg, 0.0010 mol) was combined with 4-(1H-pyrazol-4-yl)-7-[2-(trimethylsilyl)ethoxy]methyl-7H-pyrrolo[2,3-d]pyrimidine (0.1 g, 0.0003 mol) in acetonitrile (2 mL, 0.04 mol) and 1,8-diazabicyclo[5.4.0]undec-7-ene (6 μL, 0.00004 mol) under nitrogen. The mixture was stirred at room temperature over the weekend. After evaporation to dryness, the crude mixture was purified by flash column, eluting with 0 to 10% MeOH in dichloromethane, to give the desired product. LCMS (M+H) 434.4.

Step 4. 3-(cyanomethyl)-3-[4-(7H-pyrrolo[2,3-d]pyrimidin-4-yl)-1H-pyrazol-1-yl]cyclobutanecarbonitrile A 500 mL round bottom flask fitted with stir bar, condenser, and nitrogen inlet, was charged with acetonitrile (16.3 mL, 0.311 mol), water (1.4 mL, 0.078 mol) and 3-(cyanomethyl)-3-[4-(7-[2-(trimethylsilyl)ethoxy]methyl-7H-pyrrolo[2,3-d]pyrimidin-4-yl)-1H-pyrazol-1-yl]cyclobutanecarbonitrile (1.00 g, 0.00231 mol). The solution was homogeneous. After adding lithium tetrafluoroborate (2.21 g, 0.0231 mol), the resulting mixture was heated to reflux overnight, then charged with 7.2 M of ammonium hydroxide in water (1.2 mL) in portions over a period of 5 minutes at room temperature to adjust pH to 9-10. The reaction was stirred for 2 h at room temperature. Solid was removed by filtration and the filtrate was diluted with acetonitrile, water, and MeOH. The resultant mixture was purified on Waters XBridge HPLC column (C18, 30×100 mm, 5 μM), with injection volume 5 mL (~50 mg/injection) and flow rate 60 mL/min, at gradient 10-28% B in 12 minutes (A=water with 0.15% $NH_4OH$; B=acetonitrile with 0.15% $NH_4OH$), to give the desired products as free bases. First peak retention time 0.826 min at Waters SunFire HPLC column (C18, 2.1×50 mm, 5 μM) with injection volumn 2 μL and flow rate 3 mL/min, at gradient from 2 to 80% B in 3 minutes (A=water with 0.025% TFA; B=acetonitrile). LCMS calculated for $C_{16}H_{14}N_7(M+H)^+$: 304.1; Found 304.3. $^1H$ NMR (500 MHz, DMSO-$d_6$): δ 12.10 (1H, br s), 8.82 (1H, s), 8.70 (1H, s), 8.44 (1H, s), 7.61 (1H, d, J=4.0 Hz), 7.08 (1H, d, J=4.0 Hz), 3.59 (1H, m), 3.57 (2H, s), 3.19 (2H, m), 2.86 (2H, m) ppm. Second peak retention time 0.864 min at the same SunFire column HPLC condition, LCMS calculated for $C_{16}H_{14}N_7(M+H)^-$: 304.1; Found 304.3. $^1H$ NMR (400 MHz, CD$_3$OD): δ 8.67 (1H, s), 8.66 (1H, s), 8.40 (1H, s), 7.51 (1H, d, J=3.6 Hz), 6.99 (1H, d, J=3.6 Hz), 3.50 (1H, m), 3.42 (2H, s), 3.24 (2H, m), 3.00 (2H, m) ppm.

Example 53

3,3-bis(hydroxymethyl)-1-[4-(7H-pyrrolo[2,3-d]pyrimidin-4-yl)-1H-pyrazol-1-yl]cyclobutylacetonitrile

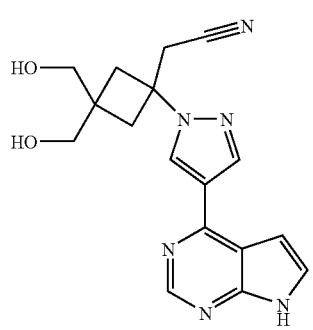

Step 1. diisopropyl 3-oxocyclobutane-1,1-dicarboxylate

A mixture of diisopropyl 3,3-dimethoxycyclobutane-1,1-dicarboxylate (3 g, 0.01 mol) in 20 mL of trifluoroacetic acid-water (95:5) was stirred at 0° C. for 4 h. The reaction was diluted with EtOAc, washed with water, saturated NaHCO$_3$ solution, and brine, dried over MgSO$_4$ and evaporated to give crude product (2.4 g) as yellow oil, which was used directly in the next step.

H NMR (CDCl$_3$, 400 MHz) δ 5.07 (2H, h, J=6.8 Hz), 3.54 (4H, s), 1.23 (12H, d, J=6.8 Hz) ppm.

Step 2. diisopropyl 3-(cyanomethylene)cyclobutane-1,1-dicarboxylate

To a mixture of 1.0000 M of potassium tert-butoxide in tetrahydrofuran (17 mL) and THF (10 mL) was added dropwise, at 0° C., diethyl cyanomethylphosphonate (2.7 mL, 0.017 mol). The reaction was warmed to rt and 30 min later cooled to 0° C. again. To the reaction mixture was added a solution of diisopropyl 3-oxocyclobutane-1,1-dicarboxylate (2.7 g, 0.011 mol) in THF (10 mL). The reaction was allowed to warm up to rt gradually and stirred at rt for 2 h. The reaction was quenched with saturated aq. NH$_4$Cl and the organic solvent was reduced. The mixture was extracted with EtOAc. The combined organic layers were washed with brine, dried over MgSO$_4$, concentrated and purified with Combiflash (silica gel, 0-35% EtOAc/Hex) to give the desired product (2.65 g) as light yellow oil.

Step 3. diisopropyl 3-(cyanomethyl)-3-[4-(7-[2-(trimethylsilyl)ethoxy]methyl-7H-pyrrolo[2,3-d]pyrimidin-4-yl)-1H-pyrazol-1-yl]cyclobutane-1,1-dicarboxylate Diisopropyl 3-(cyanomethylene)cyclobutane-1,1-dicarboxylate (2.65 g, 0.00999 mol) was combined with 4-(1H-pyrazol-4-yl)-7-[2-(trimethylsilyl)ethoxy]methyl-7H-pyrrolo[2,3-d]pyrimidine (1 g, 0.003 mol) in acetonitrile (10 mL) and 1,8-diazabicyclo[5.4.0]undec-7-ene (0.5 mL, 0.003 mol) was added under N$_2$. The mixture was heated at 50° C. overnight. The reaction was concentrated and purified with Combiflash (silica gel, 0-50% EtOAc/Hex) to give the desired product (0.3 g) as colorless oil. LCMS calculated for C$_{29}$H$_{41}$N$_6$O$_5$Si(M+H): 581.3; Found: 581.4.

Step 4. 3,3-bis(hydroxymethyl)-1-[4-(7-[2-(trimethylsilyl)ethoxy]methyl-7H-pyrrolo[2,3-d]pyrimidin-4-yl)-1H-pyrazol-1-yl]cyclobutylacetonitrile Diisopropyl 3-(cyanomethyl)-3-[4-(7-[2-(trimethylsilyl)ethoxy]methyl-7H-pyrrolo[2,3-d]pyrimidin-4-yl)-1H-pyrazol-1-yl]cyclobutane-1,1-dicarboxylate (0.3 g, 0.5 mmol) was dissolved in tetrahydrofuran (15 mL, 180 mmol) and lithium tetrahydroborate (0.017 g, 0.77 mmol) was added at 0° C. The reaction was then heated to 50° C. for 30 min. To the reaction was added MeOH (10 mL). The reaction was held at 50° C. for 15 min, then stripped to near dryness. The residue was treated with 1N HCl, then neutralized with solid NaHCO$_3$. The mixture was partitioned between water and EtOAc. The phases were separated and the aq. phase was washed with EtOAc. The combined organic phases were washed with water, then brine, dried over MgSO$_4$, concentrated and purified with Combiflash (silica gel, 0-100% EtOAc/Hex) to give the desired product (0.145 g, 60%) as colorless oil. LCMS calculated for C$_{23}$H$_{33}$N$_6$O$_3$Si(M+H)$^+$: 469.2; Found: 469.4.

Step 5. 3,3-bis(hydroxymethyl)-1-[4-(7H-pyrrolo[2,3-d]pyrimidin-4-yl)-1H-pyrazol-1-yl]cyclobutylacetonitrile 3,3-Bis(hydroxymethyl)-1-[4-(7-[2-(trimethylsilyl)ethoxy]methyl-7H-pyrrolo[2,3-d]pyrimidin-4-yl)-1H-pyrazol-1-yl]cyclobutylacetonitrile (0.022 g, 0.000046 mol) was treated with trifluoroacetic acid (0.5 mL, 0.006 mol) at rt for 30 min and evaporated to dryness. The residue was then mixed with ethylenediamine (0.2 mL, 0.003 mol) in MeOH (1 mL) for 2 h. The reaction was concentrated and purified on prep. LCMS (XBridge C18 column, eluting with a gradient of acetonitrile/water containing 0.15% NH$_4$OH) to give the desired product as free base. LCMS calculated for C$_{17}$H$_{19}$N$_6$O$_2$(M+H)$^+$: 339.2; Found: 339.3. $^1$H NMR (300 MHz, CD$_3$OD): δ 8.72 (1H, s), 8.67 (1H, s), 8.39 (1H, s), 7.51 (1H, d, J=3.3 Hz), 6.97 (1H, d, J=3.3 Hz), 3.62 (2H, s), 3.46 (2H, s), 3.36 (2H, s), 2.80 (2H, d, J=13.8 Hz), 2.54 (2H, d, J=13.8 Hz) ppm.

Example 54

3,3-bis(fluoromethyl)-1-[4-(7-[2-(trimethylsilyl)ethoxy]methyl-7H-pyrrolo[2,3-d]pyrimidin-4-yl)-1H-pyrazol-1-yl]cyclobutylacetonitrile

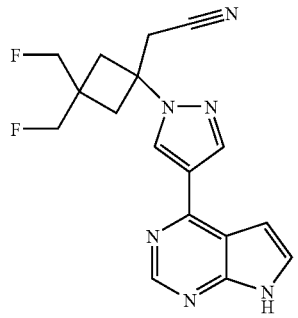

A solution of 3,3-bis(hydroxymethyl)-1-[4-(7-[2-(trimethylsilyl)ethoxy]methyl-7H-pyrrolo[2,3-d]pyrimidin-4-yl)-1H-pyrazol-1-yl]cyclobutylacetonitrile (0.03 g, 0.00006 mol) in dichloromethane (3 mL), contained in a Teflon bottle equipped with a nitrogen inlet tube and stirring bar, was treated with 2-methoxy-N-(2-methoxyethyl)-N-(trifluoro-λ(4)-sulfanyl)ethanamine (0.06 mL, 0.0004 mol) at rt. Ethanol (0.003 mL, 0.00006 mol) was added, and the mixture was stirred at rt overnight. The resultant mixture was concentrated and purified with prep LCMS (XBridge C18 column, eluting with a gradient of acetonitrile/water containing 0.15% NH$_4$OH) to give the corresponding fluorinated product, which was treated with trifluoroacetic acid (0.5 mL, 0.006 mol) at rt for 30 min. After evaporation to dryness, the resultant residue was mixed with ethylenediamine (0.2 mL, 0.003 mol) in MeOH (1 mL) at rt for 2 h. The reaction was evaporated to dry and the residue was purified with prep. LCMS (pH=10) to give the desired product. LCMS calculated for C$_{17}$H$_{17}$F$_2$N$_2$ (M+H)$^+$: 343.1; Found: 343.4. $^1$H NMR (300 MHz, CDCl$_3$): δ 9.55 (1H, br s), 8.86 (1H, s), 8.49 (1H, s), 8.35 (1H, s), 7.40 (1H, m), 6.82 (1H, m), 4.54 (2H, d, J=47.7

Hz), 4.38 (2H, d, J=47.4 Hz), 3.14 (2H, s), 2.96 (2H, d, J=13.8 Hz), 2.72 (2H, d, J=13.8 Hz) ppm.

Example 55

2,2',2''-[1-(4-(7H-pyrrolo[2,3-d]pyrimidin-4-yl)-1H-pyrazol-1-yl]cyclobutane-1,3,3-triyl]triacetonitrile

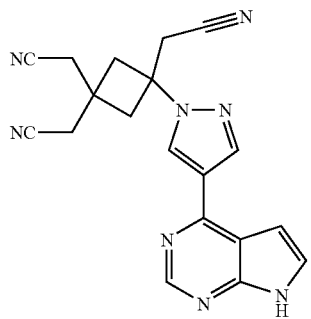

Step 1. (3,3-dimethoxycyclobutane-1,1-diyl)dimethanol

At 0° C., to a solution of diisopropyl 3,3-dimethoxycyclobutane-1,1-dicarboxylate (3.0 g, 0.010 mol) in THF (20 mL) was added 2.0 M of lithium tetrahydroaluminate in tetrahydrofuran (16 mL) slowly with stirring. The mixture was stirred for 2 h, allowing warm up to rt. At 0° C., to the reaction was added dropwise water (1.2 mL), 15% NaOH solution (1.2 mL) and water (3.6 mL) successively and the resultant mixture was stirred for 20 min at rt. The mixture was filtered and the filtrate was concentration to give the desired product (1.64 g, 89%) as colorless oil which was used directly in the next step without purification.

Step 2. (3,3-dimethoxycyclobutane-1,1-iyl)bis(methylene)dimethanesulfonate

To a mixture of (3,3-dimethoxycyclobutane-1,1-diyl)dimethanol (1.64 g, 0.00931 mol) and triethylamine (7.8 mL, 0.056 mol) in dichloromethane (10 mL) was added methanesulfonyl chloride (2.2 mL, 0.028 mol) dropwise at 0° C. The resultant mixture was stirred at rt for 1 h. The reaction was diluted with dichloromethane, washed with water and brine, dried over $MgSO_4$ and concentrated to give crude mesylate product (2.95 g, 95.4%) as brown oil. $^1$H NMR (400 MHz, $CDCl_3$): δ 4.38 (4H, s), 3.14 (6H, s), 3.02 (6H, s), 2.10 (4H, s) ppm.

Step 3. 2,2'-(3,3-dimethoxycyclobutane-1,1-diyl)diacetonitrile

To a solution of (3,3-dimethoxycyclobutane-1,1-diyl)bis(methylene)dimethanesulfonate (2.9 g, 0.0087 mol) in DMSO (10 mL) was added potassium cyanide (1.7 g, 0.026 mol) and 1,4,7,10,13,16-hexaoxacyclooctadecane (6.9 g, 0.026 mol). The reaction was stirred at 60° C. over night. The reaction was quenched with water, extracted with EtOAc. The combined organic layers were washed with brine, dried over $MgSO_4$ and concentrated to give crude product (2 g) as brown oil. $^1$H NMR (400 MHz, $CDCl_3$): δ 3.14 (6H, s), 2.78 (4H, s), 2.11 (4H, s) ppm.

Step 4. 2,2'-(3-oxocyclobutane-1,1-diyl)diacetonitrile

To a mixture of 2,2'-(3,3-dimethoxycyclobutane-1,1-diyl)diacetonitrile (2 g, 0.01 mol) in acetone (5 mL) was added p-toluenesulfonic acid (1 g, 0.006 mol). The mixture was stirred at rt over weekend. The reaction was neutralized with aq. saturated $NaHCO_3$ solution, extracted with EtOAc. The combined organic layers were washed with brine, dried over $MgSO_4$ and evaporated to give a crude product as brown oil.

Step 5. 2,2',2''-cyclobutane-1,1-diyl-3-ylidenetriacetonitrile

To a solution of 1.0 M of potassium tert-butoxide in tetrahydrofuran (5.1 mL) was added dropwise at 0° C. diethyl cyanomethylphosphonate (0.82 mL, 0.0051 mol). The reaction was warmed to rt and 30 min later cooled to 0° C. again. To the reaction mixture was added a solution of 2,2'-(3-oxocyclobutane-1,1-diyl)diacetonitrile (0.5 g, 0.003 mol) in THF (5 mL). The reaction was allowed to warm up to rt gradually and stirred at rt for 2 h. The reaction was quenched with saturated aq. $NH_4Cl$, then extracted with EtOAc. The combined organic layers were washed with brine, dried over $MgSO_4$ and concentrated to give a brown oily crude product, which was used directly in the next step.

Step 6. 2,2',2''-1-[4-(7-[2-(trimethylsilyl)ethoxy]methyl-7H-pyrrolo[2,3-d]pyrimidin-4-yl)-1H-pyrazol-1-yl]cyclobutane-1,3,3-triyltriacetonitrile The crude 2,2',2''-cyclobutane-1,1-diyl-3-ylidenetriacetonitrile (1 g, 0.006 mol) was combined with 4-(1H-pyrazol-4-yl)-7-[2-(trimethylsilyl)ethoxy]methyl-7H-pyrrolo[2,3-d]pyrimidine (0.2 g, 0.0006 mol) in acetonitrile (10 mL) and 1,8-diazabicyclo[5.4.0]undec-7-ene (0.1 mL, 0.001 mol) was added under nitrogen. The mixture was heated at 50° C. over night. The reaction was concentrated and purified with Combiflash (silica gel, 0-100% EtOAc/Hex) to give the desired product as light brown oil. LCMS calculated for $C_{25}H_{31}N_8OSi(M+H)^+$: 487.2; Found: 487.4.

Step 7. 2,2',2''-1-[4-(7H-pyrrolo[2,3-d]pyrimidin-4-yl)-1H-pyrazol-1-yl]cyclobutane-1,3,3-triyltriacetonitrile 2,2',2''-1-[4-(7-[2-(Trimethylsilyl)ethoxy]methyl-7H-pyrrolo[2,3-d]pyrimidin-4-yl)-1H-pyrazol-1-yl]cyclobutane-1,3,3-triyltriacetonitrile (0.03 g, 0.00006 mol) was treated with trifluoroacetic acid (0.5 mL, 0.006 mol) at rt for 30 min and then evaporated to dryness. The residue was mixed with ethylenediamine (0.2 mL, 0.003 mol) in MeOH (1 mL) at rt for 1 h. The reaction was evaporated to dryness and the residue was purified with prep. LCMS (pH=10) to give the desired product. LCMS calculated for $C_{19}H_{17}N_8(M+H)^+$: m/z=357.1; Found: 357.4. $^1$H NMR (400 MHz, DMSO-$d_6$): δ 12.06 (1H, br s), 8.79 (1H, s), 8.63 (1H, s), 8.38 (1H, s), 7.55 (1H, d, J=3.6 Hz), 7.01 (1H, d, J=3.6 Hz), 3.46 (2H, s), 3.03 (2H, s), 2.97 2H, d, J=15.2 Hz), 2.76 (2H, s), 2.57 (2H, d, J=15.2 Hz) ppm.

Example 56 cis- and trans-3-hydroxy-1-[4-(7H-pyrrolo[2,3-d]pyrimidin-4-yl)-1H-pyrazol-1-yl]cyclobutylacetonitrile

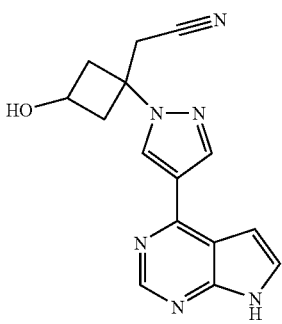

Step 1.
N-methoxy-N-methyl-3-oxocyclobutanecarboxamide

To a mixture of N,O-dimethylhydroxylamine hydrochloride (5.2 g, 0.054 mol), and 3-oxocyclobutanecarboxylic acid (4.0 g, 0.035 mol) in dichloromethane (30 mL) was added N-(3-dimethylaminopropyl)-N'-ethylcarbodiimide hydrochloride (10.0 g, 0.052 mol), 1-hydroxybenzotriazole (7.1 g, 0.052 mol) followed by triethylamine (34 mL, 0.24 mol) at 0° C. The mixture was stirred at rt over night, then quenched with water. The mixture was extracted with EtOAc. The organic layers were dried over MgSO$_4$, concentrated and purified with Combiflash (silica gel, 0-5% for 30 min followed by 5-20% EtOAc/Hex) to give the desired product (4.3 g, 78%) as light yellow oil. LCMS calculated for C$_7$H$_{12}$NO$_3$ (M+H)$^+$: 158.1; Found: 158.3.

Step 2.
3-hydroxy-N-methoxy-N-methylcyclobutanecarboxamide

N-Methoxy-N-methyl-3-oxocyclobutanecarboxamide (1 g, 0.006 mol) was dissolved in methanol (8 mL, 0.2 mol). To the mixture, sodium borohydride (0.2 g, 0.006 mol) was added. The reaction was stirred at rt for 1 h. To the reaction mixture was added 1N aq. HCl to adjust the pH to 2. The mixture was concentrated, then extracted with EtOAc. The combined organic layers were dried over MgSO$_4$ and concentrated to give crude product (1.4 g) as light yellow oil. LCMS calculated for C$_7$H$_{14}$NO$_3$(M+H)$^+$: 160.0; Found: 160.3.

Step 3. 3-[tert-butyl(diphenyl)silyl]oxy-N-methoxy-N-methylcyclobutanecarboxamide Into a solution of 3-hydroxy-N-methoxy-N-methylcyclobutanecarboxamide (0.6 g, 0.004 mol in DMF (10 mL) was added tert-butylchlorodiphenylsilane (3 mL, 0.01 mol), followed by 1H-imidazole (1 g, 0.02 mol). The mixture was stirred at rt over night. The reaction was diluted with dichloromethane and washed with sat. NaHCO$_3$, water and brine. The organic layers were dried over MgSO$_4$, concentrated and purified with Combiflash (silica gel, 0-30% EtOAc/Hex) to give the desired product (0.7 g, 50%) as cis- and trans-isomer mixtures. LCMS calculated for C$_{23}$H$_{32}$NO$_3$Si(M+H)$^+$: 398.2; Found: 398.1.

Step 4. 1-(3-[tert-butyl(diphenyl)silyl]oxycyclobutyl)ethanone

A solution of 3-[tert-butyl(diphenyl)silyl]oxy-N-methoxy-N-methylcyclobutanecarboxamide (0.7 g, 0.002 mol) in ether (10 mL) was added into 3.0 M of methylmagnesium iodide in ether (3 mL) slowly under N$_2$. The reaction was stirred and heated to reflux for 2 h. The mixture was quenched with ice and the ether layer separated. The aq. layer was acidified with 1N HCl and extracted several times with ether. The organic layers were combined, dried over MgSO$_4$, concentrated and purified with Combiflash (silica gel, 0-30% EtOAc/Hex) to give the desired product (0.6 g) as colorless oil. LCMS calculated for C$_{22}$H$_{29}$O$_2$Si(M+H)$^+$: 353.2; Found: 353.3.

Step 5. 3-[tert-butyl(diphenyl)silyl]oxycyclobutyl acetate

To a stirred solution of 1-(3-[tert-butyl(diphenyl)silyl]oxycyclobutyl)ethanone (0.65 g, 0.0018 mol) in dichloromethane (10 mL) at 0° C. was added sodium bicarbonate (0.39 g, 0.0046 mol) and m-chloroperbenzoic acid (1.0 g, 0.0046 mol) with stirring. The reaction was stirred at rt over night. LCMS showed incomplete reaction, another 2.5 eq. of mCPBA and NaHCO$_3$ were added and the reaction was stirred for another day. The reaction was quenched with 20% aq. Na$_2$S$_2$O$_3$ solution (50 mL) and stirred for a further 30 min at rt, then extracted with dichloromethane. The combined organic layers were washed with brine, dried over MgSO$_4$, concentrated and purified on silica gel with Combiflash (silica gel, 0-10% EtOAc/Hex) to give the desired product (0.3 g, 40%) as colorless oil. LCMS calculated for C$_{22}$H$_{29}$O$_3$Si(M+H)$^+$: 369.2; Found: 369.4.

Step 6. 3-[tert-butyl(diphenyl)silyl]oxycyclobutanol

To a solution of 3-[tert-butyl(diphenyl)silyl]oxycyclobutyl acetate (0.27 g, 0.00073 mol) in THF (5 mL) and MeOH (3 mL) was added 1.0 M of lithium hydroxide in water (10 mL). The reaction was stirred at rt for 1 h. The mixture was quenched with water and extracted with EtOAc. The combined organic layers were dried over MgSO$_4$ and concentrated to give crude alcohol product (0.3 g) as colorless oil, which was directly used in next step without further purification. LCMS calculated for C$_{20}$H$_{26}$O$_2$NaSi(M+Na)$^+$: 349.2; Found: 349.3.

Step 7.
3-[tert-butyl(diphenyl)silyl]oxycyclobutanone

A solution of oxalyl chloride (0.1 mL, 0.001 mol) in dichloromethane (2 mL) under N$_2$ was cooled to −78° C. Dimethyl sulfoxide (0.2 mL, 0.002 mol) was added dropwise. On complete addition, the reaction was stirred for 15 min. A solution of crude 3-[tert-butyl(diphenyl)silyl]oxycyclobutanol (0.2 g, 0.0006 mol) in dichloromethane (3 mL) was added dropwise and the reaction mixture was stirred for 45 min at −78° C. Triethylamine (0.5 mL, 0.004 mol) was added dropwise and the reaction was stirred for 15 minutes. The reaction was then allowed to warm to rt, quenched with water and extracted with dichloromethane. The organic layers were combined, washed with brine, dried over MgSO$_4$ and evaporated to give crude ketone (0.27 g) as yellow oil, which was directly used in the next step without further purification. LCMS calculated for C$_{20}$H$_{25}$O$_2$Si(M+H)$^+$: 325.12; Found: 325.3.

Step 8. (3-[tert-butyl(diphenyl)silyl]oxycyclobutyl-idene)acetonitrile

To 1.0 M of potassium tert-butoxide in tetrahydrofuran (1.2 mL) was added dropwise, at 0° C., diethyl cyanomethylphosphonate (0.19 mL, 0.0012 mol). The reaction was warmed to rt and 30 min later cooled to 0° C. again. To the reaction mixture was added a solution of 3-[tert-butyl(diphenyl)silyl]oxycyclobutanone (0.25 g, 0.00077 mol) in THF (5 mL). The reaction was allowed to warm up to rt gradually and stirred at rt for 2 h. The reaction was quenched with saturated aq. NH4Cl, extracted with EtOAc. The combined organic layers were washed with brine, dried over MgSO4, concentrated. The resultant residue was purified with Combiflash (silica gel, 0-20% EtOAc/Hex) to give the desired product (0.2 g) as colorless oil. LCMS calculated for $C_{22}H_{26}NOSi(M+H)^+$: 348.1 Found: 348.3.

Step 9. {3-Hydroxy-1-[4-(1H-pyrrolo[2,3-d]pyrimidin-4-yl)-1H-pyrazol-1-yl]cyclobutyl}acetonitrile (3-[tert-Butyl(diphenyl)silyl]oxycyclobutylidene)acetonitrile (0.15 g, 0.00043 mol) was combined with 4-(1H-pyrazol-4-yl)-7-[2-(trimethylsilyl)ethoxy]methyl-7H-pyrrolo[2,3-d]pyrimidine (0.14 g, 0.00043 mol) in acetonitrile (5 mL) and 1,8-diazabicyclo[5.4.0]undec-7-ene (0.064 mL, 0.00043 mol) was added under nitrogen. The mixture was heated to 50° C. over night. LCMS showed a peak with m/z of 425.4, indicating a de-silyl reaction occurred simultaneously during the Micheal addition. The reaction was concentrated and purified on combiflash (silica gel, 0-100% EtOAc/Hex) to yield the desired produt. LCMS (M+H) 425.4.

Step 10. 3-hydroxy-1-[4-(7H-pyrrolo[2,3-d]pyrimidin-4-yl)-1H-pyrazol-1-yl]cyclobutylacetonitrile 3-Hydroxy-1-[4-(7-[2-(trimethylsilyl)ethoxy]methyl-7H-pyrrolo[2,3-d]pyrimidin-4-yl)-1H-pyrazol-1-yl]cyclobutylacetonitrile (0.020 g, 0.000046 mol) was treated with trifluoroacetic acid (0.5 mL, 0.006 mol) at rt for 30 min and evaporated to dry. The resultant residue was mixed with ethylenediamine (0.2 mL, 0.003 mol) in MeOH (1 mL) for 2 h. The reaction was concentrated and purified on prep. LCMS (pH=10) to give 2 isomers of the desired products. First peak retention time 0.714 min, LCMS calculated for $C_{15}H_{15}N_6O$ $(M+H)^+$: 295.1; Found: 295.3. Second peak retention time 0.750 min, LCMS calculated for $C_{15}H_{15}N_6O(M+H)^+$: 295.1; Found: 295.3. $^1$H NMR (400 MHz, CD$_3$OD): δ 8.67 (1H, s), 8.66 (1H, s), 8.38 (1H, s), 7.51 (1H, d, J=3.6 Hz), 6.98 (1H, d, J=3.6 Hz), 4.37 (1H, s), 3.34 (2H, s), 3.22 (2H, m), 2.48 (2H, m) ppm.

Example 57

3-fluoro-1-[4-(7H-pyrrolo[2,3-d]pyrimidin-4-yl)-1H-pyrazol-1-yl]cyclobutylacetonitrile

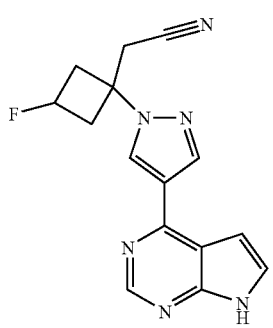

A solution of 3-hydroxy-1-[4-(7H-pyrrolo[2,3-d]pyrimidin-4-yl)-1H-pyrazol-1-yl]cyclobutylacetonitrile (0.01 g, 0.00003 mol) (a mixture of cis/trans isomers) in dichloromethane (3 mL), contained in a Teflon bottle equipped with a nitrogen inlet tube and stirring bar, was treated with 2-methoxy-N-(2-methoxyethyl)-N-(trifluoro-λ(4)-sulfanyl)ethanamine (0.03 mL, 0.0002 mol) at rt. Ethanol (0.002 mL, 0.00003 mol) was added, and the mixture was stirred at rt over weekend. The reaction was evaporated to dry and the residue was purified with prep. HPLC (pH=10) to give a mixture of two isomers. LCMS calculated for $C_{15}H_{14}FN_6(M+H)^+$: 297.1; Found: 297.3.

Example 58

3-methyl-1-[4-(7H-pyrrolo[2,3-d]pyrimidin-4-yl)-1H-pyrazol-1-yl]cyclobutylacetonitrile

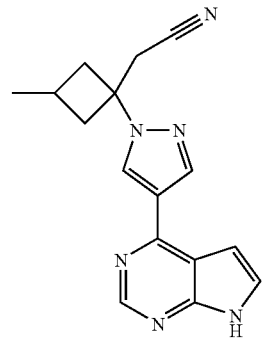

Step 1. 3-(bromomethyl)-1-[4-(7-[2-(trimethylsilyl)ethoxy]methyl-7H-pyrrolo[2,3-d]pyrimidin-4-yl)-1H-pyrazol-1-yl]cyclobutylacetonitrile To an ice-cooled mixture of 3-(hydroxymethyl)-1-[4-(7-[2-(trimethylsilyl)ethoxy]methyl-7H-pyrrolo[2,3-d]pyrimidin-4-yl)-1H-pyrazol-1-yl]cyclobutylacetonitrile (1.0 g, 0.0023 mol) and carbon tetrabromide (1.1 g, 0.0034 mol) in DMF (7 mL) was added triphenylphosphine (0.90 g, 0.0034 mol) and the mixture was stirred at this temp. for 30 min. To the resulting dark brown solution was added saturated aq. NaHCO$_3$ (5 mL) followed by water (5 mL) and the mixture was extracted with dichloromethane. The organic layers were combined, washed with water, dried over Na$_2$SO$_4$, concentrated and purified with combiflash (silica gel, 0-40% EtOAc/Hex) to give the desired product (1.0 g, 87%) as light yellow solid. LCMS calculated for $C_{22}H_{30}BrN_6OSi(M+H)^+$: 501.1: Found: 501.3.

Step 2. 3-methyl-1-[4-(7-[2-(trimethylsilyl)ethoxy]methyl-7H-pyrrolo[2,3-d]pyrimidin-4-yl)-1H-pyrazol-1-yl]cyclobutylacetonitrile 3-(Bromomethyl)-1-[4-(7-[2-(trimethylsilyl)ethoxy]methyl-7H-pyrrolo[2,3-d]pyrimidin-4-yl)-1H-pyrazol-1-yl]cyclobutylacetonitrile (0.65 g, 0.0013 mol) was reacted with sodium tetrahydroborate (0.096 g, 0.0026 mol) in DMF (5.2 mL) (~0.5 M) at rt under nitrogen for 3h. The reaction was quenched with water and extracted with dichloromethane. The organic layers were washed with water, brine, dried over MgSO$_4$ and concentrated to give a yellow oil, the desired product as cis- and trans-isomer mixtures. LCMS calculated for $C_{22}H_{31}N_6OSi(M+H)^+$: 423.2; Found: 423.4.

Step 3. 3-methyl-1-[4-(7H-pyrrolo[2,3-d]pyrimidin-4-yl)-1H-pyrazol-1-yl]cyclobutylacetonitrile To a mixture of 3-methyl-1-[4-(7-[2-(trimethylsilyl)ethoxy]methyl-7H-pyrrolo[2,3-d]pyrimidin-4-yl)-1H-pyrazol-1-yl]cyclobutylacetonitrile (0.5 g, 0.001 mol) in acetonitrile (8.07 mL, 0.154 mol) and water (0.70 mL, 0.039 mol) was added lithium tetrafluoroborate (1.10 g, 0.0114 mol). The solution was warmed to reflux at 100° C. over 5 days. Charged 7.2 M of ammonium hydroxide in water (0.59 mL) in portions over a period of 5 minutes at rt adjusting pH to 9-10. The reaction mixture was stirred for 2 h at rt. The reaction was filtered and the filtrate was diluted with acetonitrile, water and MeOH and purified with prep. HPLC (XBridge C18 column, eluting with a gradient of acetonitrile/water containing 0.15% NH$_4$OH) to give the first isomer with retention time 1.057 min, LCMS calculated for $C_{16}H_{17}N_6$(M+H)$^+$: 293.2; Found: 293.3. $^1$H NMR (500 MHz, CDCl$_3$): δ 10.07(1H, br s), 8.88 (1H, s), 8.45 (1H, s), 8.34 (1H, s), 7.43 (1H, d, J=3.5 Hz), 6.85 (1H, d, J=3.5 Hz), 3.16 (2H, s), 2.77 (2H, m), 2.55 (1H, m), 2.43 (2H, m), 1.24 (3H, d, J=6.5 Hz) ppm; then the second isomer with retention time 1.107 min; LCMS calculated for $C_{16}H_{17}N_6$(M+H)$^+$: 293.2; Found: 293.3. $^1$H NMR (500 MHz, CDCl$_3$): δ 10.21(1H, br s), 8.89 (1H, s), 8.61 (1H, s), 8.37 (1H, s), 7.44 (1H, d, J=3.5 Hz), 6.86 (1 H, d, J=3.5 Hz), 3.07 (2H, s), 3.05 (2H, m), 2.61 (1H, m), 2.26 (2H, m), 1.25 (3H, d, J=7.0 Hz) ppm.

Example 59

3,3-dimethyl-1-[4-(7H-pyrrolo[2,3-d]pyrimidin-4-yl)-1H-pyrazol-1-yl]cyclobutylacetonitrile

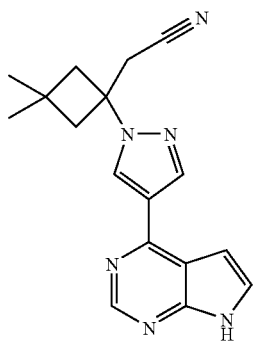

Step 1. 3-(cyanomethyl)-3-[4-(7-[2-(trimethylsilyl)ethoxy]methyl-7H-pyrrolo[2,3-d]pyrimidin-4-yl)-1H-pyrazol-1-yl]cyclobutane-1,1-diylbis(methylene) dimethanesulfonate To a mixture of 3,3-bis(hydroxymethyl)-1-[4-(7-[2-(trimethylsilyl)ethoxy]methyl-7H-pyrrolo[2,3-d]pyrimidin-4-yl)-1H-pyrazol-1-yl]cyclobutylacetonitrile (0.06 g, 0.0001 mol) and triethylamine (0.1 mL, 0.0008 mol) in dichloromethane (3 mL) was added methanesulfonyl chloride (0.03 mL, 0.0004 mol) slowly. The resultant mixture was stirred at rt for 30 min. The reaction was diluted with dichloromethane, washed with water and brine, dried over MgSO$_4$, concentrated. The residue was purified on Combiflash (silica gel, 0-100% EtOAc/Hex) to give the desired product (60 mg, 75%) as white solid. LCMS calculated for $C_{25}H_{37}N_6O_7S_2Si$ (M+H)$^+$: 625.2; Found: 625.3.

Step 2. 3,3-dimethyl-1-[4-(7-[2-(trimethylsilyl)ethoxy]methyl-7H-pyrrolo[2,3-d]pyrimidin-4-yl)-1H-pyrazol-1-yl]cyclobutylacetonitrile 3-(Cyanomethyl)-3-[4-(7-[2-(trimethylsilyl)ethoxy]methyl-7H-pyrrolo[2,3-d]pyrimidin-4-yl)-1H-pyrazol-1-yl]cyclobutane-1,1-diylbis(methylene) dimethanesulfonate (0.06 g, 0.0001 mol) was reacted with sodium tetrahydroborate (0.02 g, 0.0004 mol) in DMF (0.8 mL) (~0.5 M) at 65° C. under nitrogen for 2 h. The reaction was quenched with water, and extracted with dichloromethane. The organic layers were washed with water, dried over MgSO$_4$, concentrated. The residue was purified with Combiflash (silica gel, 0-60% EtOAc/Hex) to give the desired product. LCMS calculated for $C_{23}H_{33}N_6OSi$(M+H)$^+$: 437.2; Found: 437.4.

Step 3. 3,3-dimethyl-1-[4-(7H-pyrrolo[2,3-d]pyrimidin-4-yl)-1H-pyrazol-1-yl]cyclobutylacetonitrile 3,3-Dimethyl-1-[4-(7-[2-(trimethylsilyl)ethoxy]methyl-7H-pyrrolo[2,3-d]pyrimidin-4-yl)-1H-pyrazol-1-yl]cyclobutylacetonitrile (0.020 g, 0.000046 mol) was treated with trifluoroacetic acid (0.5 mL, 0.006 mol) at rt for 30 min and then evaporated to dry. The residue was then shaked with ethylenediamine (0.2 mL, 0.003 mol) in MeOH (1 mL) for 2 h. The reaction was concentrated and purified on prep HPLC (XBridge C18 column, eluting with a gradient of acetonitrile/water containing 0.15% NH$_4$OH) to give the desired prodcut. LCMS calculated for $C_{17}H_{19}N_6$(M+H)$^+$: 307.2; Found: 307.3. $^1$H NMR (400 MHz, DMSO-d$_6$): δ 12.10 (1H, br s), 8.76 (1H, s), 8.67 (1H, s), 8.40 (1H, s), 7.58 (1H, d, J=3.6 Hz), 7.05 (1H, d, J=3.6 Hz), 3.35 (2H, s), 2.75 (2H, d, J=14 Hz), 2.33 (2H, d, J=14.0 Hz), 1.22 (3H, s), 1.02 (3H, s) ppm.

Example 60 cis- and trans-3-(benzyloxy)-1-[4-(7H-pyrrolo[2,3-d]pyrimidin-4-yl)-1H-pyrazol-1-yl]cyclobutylacetonitrile

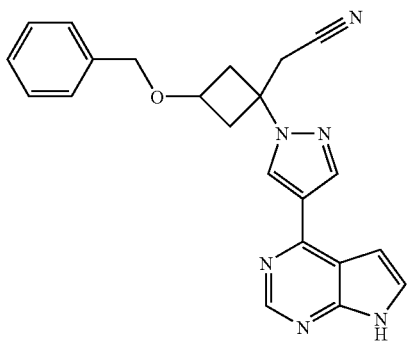

Step 1. [2-bromo-1-(bromomethyl)ethoxy]methylbenzene

1-Bromo-2,3-epoxypropane (28 mL, 0.33 mol) and benzyl bromide (39 mL, 0.33 mol) was mixed with mercury(II) chloride (0.04 g, 0.0002 mol). The mixture was heated slowly to 155-160° C. and stirred over night. The reaction mixture was then cooled to room temperature, purified with Combiflash (silica gel, 100% hexanes) to give the desired product (63 g, 62%) as a clear oil. $^1$H NMR (400 MHz, CDCl$_3$): δ 7.40 (5H, m), 4.71 (2H, s), 3.82 (1H, t, J=4.8 Hz), 3.60 (4H, d, J=4.8 Hz) ppm.

Step 2. ([3-(methylsulfinyl)-3-(methylthio)cyclobutyl]oxymethyl)benzene 2.5 M of n-butyllithium in hexane (19 mL) was added to a solution of (methylsulfinyl)(methylthio)methane (5.0 g, 0.040 mol) in THF (10 mL) dropwise at −10° C. and the mixture was stirred for 3 h. To the resultant solution was added dropwise [2-bromo-1-(bromomethyl)ethoxy]methylbenzene (4.9 g, 0.016 mol) at −70° C. over 30 min. The mixture was stirred at this temperature for 3 h and then at rt over night. The reaction was diluted with dichloromethane and washed with water. The aqueous phases were extracted with dichloromethane. The organic layers were combined, washed with brine, dried over MgSO$_4$, concentrated and purified with Combiflash (silica gel, 0-55% EtOAc/Hex) to give the desired product (2.4 g, 56%) as brown oil. LCMS (M+Na) 293.3. $^1$H NMR (400 MHz, CDCl$_3$): δ 7.30 (5H, m), 4.45 (2H, s), 4.33 (1H, m), 2.75 (2H, m), 2.65 (2H, m), 2.41 (3H, s), 2.12 (3H, s) ppm.

Step 3. 3-(benzyloxy)cyclobutanone ([3-(methylsulfinyl)-3-(methylthio)cyclobutyl]oxymethyl)benzene (2.4 g, 0.0089 mol) was dissolved in Et$_2$O (40 mL) and 35% perchloric acid (1.8 mL) was added. The resulting mixture was stirred at rt overnight. To the reaction mixture was added solid NaHCO$_3$ and MgSO$_4$ and stirred for a while. The insoluble solid was filtered off. The filtrate was concentrated and purified with combiflash (silica gel, 100% dichloromethane) to give the desired product (0.7 g) as light yellow oil. LCMS calculated for C$_{11}$H$_{13}$O$_2$(M+H)$^+$: 177.1. Found: 177.3.

Step 4. [3-(benzyloxy)cyclobutylidene]acetonitrile

To a mixture of 1.0000 M of potassium tert-butoxide in tetrahydrofuran (0.68 mL) and THF (5 mL) was added, at 0° C., diethyl cyanomethylphosphonate (0.11 mL, 0.00068 mol) dropwise. The reaction was warmed to rt and 30 min later cooled to 0° C. again. To the reaction mixture was added a solution of 3-(benzyloxy)cyclobutanone (0.1 g, 0.0006 mol) in THF (5 mL). The reaction was stirred over night, allowing warmed up to rt. The reaction was quenched with saturated aq. NH$_4$Cl solution, extracted with EtOAc. The combined organic layers were washed with water and brine, dried over MgSO$_4$ and concentrated to dryness. The crude product was used directly in next step without further purification.

Step 5. 3-(benzyloxy)-1-[4-(7-[2-(trimethylsilyl)ethoxy]methyl-7H-pyrrolo[2,3-d]pyrimidin-4-yl)-1H-pyrazol-1-yl]cyclobutylacetonitrile To a mixture of [3-(benzyloxy)cyclobutylidene]acetonitrile (0.1 g, 0.0005 mol) and 4-(1H-pyrazol-4-yl)-7-[2-(trimethylsilyl)ethoxy]methyl-7H-pyrrolo[2,3-d]pyrimidine (0.1 g, 0.0003 mol) in acetonitrile (5 mL) was added 1,8-diazabicyclo[5.4.0]undec-7-ene (0.05 mL, 0.0003 mol) under nitrogen. The mixture was heated at 50° C. overnight, then concentrated under reduced pressure. The residue was purified with combiflash (silica gel, 0-55% EtOAc/Hex) to give the desired product as cis- and trans-isomer mixture. LCMS calculated for C$_{28}$H$_{35}$N$_6$O$_2$Si(M+H)$^+$: 515.3; Found: 515.4.

Step 6. 3-(benzyloxy)-1-[4-(7H-pyrrolo[2,3-d]pyrimidin-4-yl)-1H-pyrazol-1-yl]cyclobutylacetonitrile 3-(Benzyloxy)-1-[4-(7-[2-(trimethylsilyl)ethoxy]methyl-7H-pyrrolo[2,3-d]pyrimidin-4-yl)-1H-pyrazol-1-yl]cyclobutylacetonitrile (0.024 g, 0.000046 mol) was treated with trifluoroacetic acid (0.5 mL, 0.006 mol) at rt for 30 min, then evaporated to dry. The residue was dissolved in MeOH (1 mL) and treated with ethylenediamine (0.2 mL, 0.003 mol) at rt for 2 h. The reaction mixture was concentrated in vacuo and the resulting residue purified on prep. HPLC (XBridge C18 column, eluting with a gradient of acetonitrile/water containing 0.15% NH$_4$OH) to give 2 isomers of the desired products. First peak retention time 1.406 min; LCMS calculated for C$_{22}$H$_{21}$N$_6$O(M+H)$^+$: 385.2; Found: 385.3. $^1$H NMR (400 MHz, DMSO-d$_6$): δ 12.10 (1H, br s), 8.71 (1H, s), 8.67 (1H, s), 8.38 (1H, s), 7.58 (1H, d, J=3.6 Hz), 7.33 (4H, m), 7.29 (1H, m), 7.05 (1H, d, J=3.6 Hz), 4.43 (2H, s), 4.23 (1H, m), 3.43 (2H, s), 2.78 (2H, m), 2.74 (2H, m) ppm. Second peak retention time 1.474 min, LCMS calculated for C$_{22}$H$_{21}$N$_6$)(M+H)$^+$: 385.2; Found: 385.3. $^1$H NMR (400 MHz, DMSO-d$_6$): δ 12.10 (1H, br s), 8.79 (1H, s), 8.67 (1H, s), 8.39 (1H, s), 7.59 (1H, d, J=3.6 Hz), 7.34 (4H, m), 7.29 (1H, m), 7.06 (1H, d, J=3.6 Hz), 4.44 (2H, s), 4.14 (1H, m), 3.44 (2H, s), 3.16 (2H, m), 2.44 (2H, m) ppm.

Example 61

Large scale preparation of {1-(ethylsulfonyl)-3-[4-(7H-pyrrolo[2,3-d]pyrimidin-4-yl)-1H-pyrazol-1-yl]azetidin-3-yl}acetonitrile phosphoric acid salt

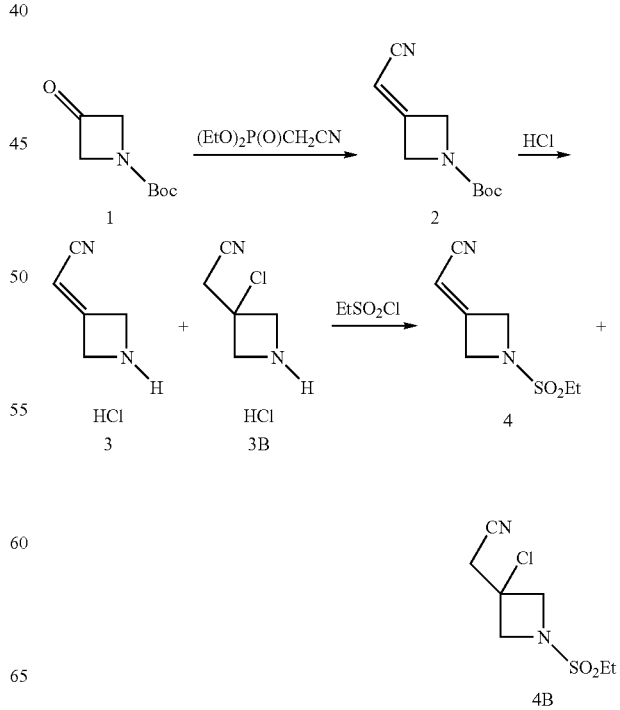

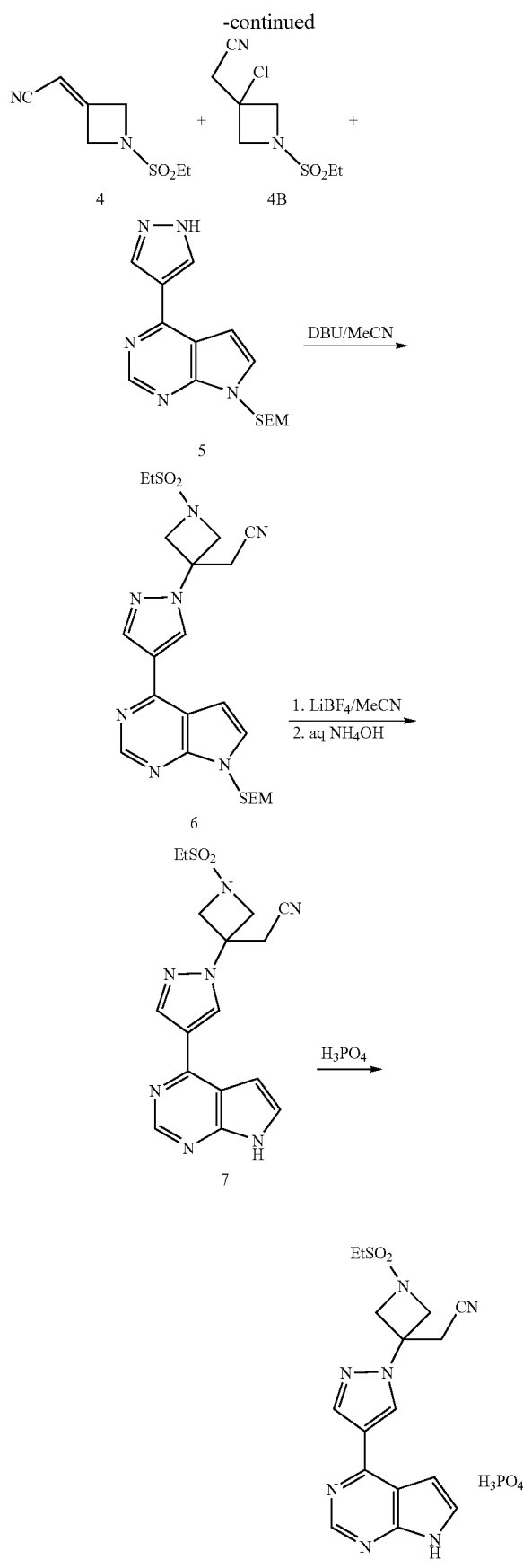

Step. 1 tert-Butyl 3-(cyanomethylene)azetidine-1-carboxylate (2)

Diethyl cyanomethyl phosphonate (745 g, 4.20 mol, 1.20 eqiv) and anhydrous THF (9 L) was added to a four-neck flask equipped with thermowell, addition funnel and nitrogen protection tube. The solution was cooled with an ice-methanol bath to −14° C. and a 1.0 M solution of t-BuOK in THF (3.85 L, 3.85 mol, 1.1 equiv) was added over 20 min keeping the temperature<−5° C. The mixture was stirred for 3 hr at −10° C. and a solution of 1-tert-butoxycarbonyl-3-azetidinone (1, 600 g, 3.50 mol) in THF (2 L) was added over 2 hr while keeping the reaction temperature<−5° C. The reaction mixture was stirred at −5 to −10° C. over 1 hr and then slowly warmed up to room temperature and stirred at room temperature for overnight. The reaction mixture was then diluted with water (4.5 L) and saturated brine (4.5 L) and extracted with ethyl acetate (2×9 L). The combined organic layers were combined and washed with brine (6 L), dried over anhydrous $Na_2SO_4$. The organic solvent was removed under reduced pressure, diluted with dichloromethane (4 L) and adsorbed onto silica gel (1.5 kg). The product was purified by flash column chromatography ($SiO_2$, 3.5 kg×2), each column was eluted with (8 L of heptane, 8 L of 5% AcOEt/heptane, 12 L of 10% AcOEt/heptane, 40 L of 25% AcOEt/heptane) to give the pure tert-butyl 3-(cyanomethylene)azetidine-1-carboxylate (2, 414.7 g, 679.8 g theoretical, 61% yield) as white solid. For 2: $^1$H NMR (300 MHz, $CDCl_3$) δ 1.46 (s, 9H), 4.62 (m, 2H), 4.72 (m, 2H), 5.41 (m, 1H).

Step 2. 2-(1-(Ethylsulfonyl)azetidin-3-ylidene)acetonitrile (4)

tert-Butyl 3-(cyanomethylene)azetidine-1-carboxylate (2, 1000 g, 5.2 mol) was diluted with acetonitrile (7 L) and 3 N aqueous HCl (7 L). This resulting reaction mixture was stirred at room temperature for 18 h. When TLC showed the reaction was deemed complete, the reaction mixture was concentrated under reduced pressure. The residual solids were then suspended in acetonitrile (12 L) and cooled to 5° C. Diisopropyethyl amine (2.7 L, 15. 6 mol, 3 equiv) was slowly added to the suspension while keeping the temperature<15° C. The homogeneous solution was allowed to cool to 5° C. and ethanesulfonyl chloride (730 mL, 7.73 mol, 1.5 equiv) was added over 1 h while keeping the reaction temperature<15° C. The resulting solution was allowed to slowly warm to room temperature and stirred at room temperature for overnight. The additional amount of ethanesulfonyl chloride (100 ml, 1.05 mol, 0.2 equiv) was added and the reaction mixture was stirred for an additional 2 h at room temperature. After the reaction was deemed complete, the reaction mixture was concentrated under reduced pressure to a volume of about 4 L. This solution was then placed in a 50 L separatory funnel, diluted with dichloromethane (10 L) and washed with half saturated brine (10 L). The aqueous phase was extracted with dichloromethane (5 L). The combined organic layers were dried over sodium sulphate and absorbed onto silica gel (1 Kg) under reduced pressure. The material was then loaded onto a silica gel column (2.5 Kg) and eluted with 20% ethyl acetate in heptane (40 L), 40% ethyl acetate in heptane (80 L) and finally 60% ethyl acetate in heptane (40 L) to afford pure 2-(1-(ethylsulfonyl)azetidin-3-ylidene)acetonitrile (4, 567 g, 968.4 g theoretical, 58.6% yield) as a off-white solid. For 4: $^1$H NMR (300 MHz, $CDCl_3$) δ 1.38 (t, 3H), 3.05 (q, 2H), 4.72 (m, 2H), 4.79 (m, 2H), 5.41 (m, 1H); MS: m/z calcd. 187.05; found: 187.1.

Step 3. 2-(1-(Ethylsulfonyl)azetidin-3-ylidene)acetonitrile (4) and 2-(3-chloro-1-(ethylsulfonyl) azetidin-3-yl)acetonitrile (4B)

tert-Butyl 3-(cyanomethylene)azetidine-1-carboxylate (2, 82 g, 0.42 mol) was added to THF (850 mL) and the resulting solution was cooled to 0° C. before a 4 M HCl solution in 1,4-dioxane (850 mL, 3.38 mol, 8.0 equiv) was added over 1 h while keeping the temperature<5° C. The resulting reaction mixture was slowly warmed to room temperature and stirred at room temperature for 18 h. When the reaction was deemed complete, the reaction mixture was concentrated under reduced pressure and the residue was placed under high vacuum for an additional 3 h before being treated with THF (900 mL) and diisopropylethyl amine (183 mL, 1.06 mol, 2.5 equiv) at room temperature. The resulting solution was then cooled to 0° C. and ethanesulfonyl chloride (56 mL, 0.59 mol, 1.4 equiv) was added while keeping the reaction temperature<5° C. The ice bath was removed and the reaction was stirred at room temperature for 18 h. When TLC indicated the reaction was complete, the reaction mixture was diluted with ethyl acetate (1 L) and washed with saturated brine (1 L). The aqueous layer was extracted with ethyl acetate (2×500 mL). The combined organic layers were dried over sodium sulphate and concentrated under reduced pressure. The residue was diluted with dichloromethane and absorbed onto silica gel (150 g). This mixture was purified by column chromatography (1.5 Kg silica gel) eluting with heptane (4 L), 10% EtOAc in heptane (4 L), 20% EtOAc in heptane (8L), 30% EtOAc in heptane (12 L), and finally with 40% EtOAc in heptane (12 L) to afford 2-(1-(ethylsulfonyl)azetidin-3-ylidene)acetonitrile (4) and 2-(3-chloro-1-(ethylsulfonyl) azetidin-3-yl)acetonitrile (4B) as a off-white solid (58.1 g, 68% yield), which was found to be an approximately one to one mixture of compound 4 and 4B. For 4: $^1$H NMR (300 MHz, CDCl$_3$) δ 1.38 (t, 3H), 3.05 (q, 2H), 4.72 (m, 2H), 4.79 (m, 2H), 5.41 (m, 1H); MS: m/z calcd. 187.05; found: 187.1. For 4B: $^1$H NMR (300 MHz, CDCl$_3$) δ 1.38 (t, 3H), 3.05 (q, 2H), 3.1 (s, 2H), 4.15 (d, 2H), 4.37 (d, 2H); MS: m/z calcd. 222.9; found: 222.9.

Step 4. 2-(1-(Ethylsulfonyl)-3-(4-(7-((2-(trimethylsilyl)ethoxy)methyl)-7H-pyrrolo[2,3-d]pyrimidin-4-yl)-1H-pyrazol-1-yl)azetidin-3-yl)acetonitrile (6)

To a solution of 2-(1-(ethylsulfonyl)azetidin-3-ylidene)acetonitrile (4) and 2-(3-chloro-1-(ethylsulfonyl)azetidin-3-yl) acetonitrile (4B) obtained from the previous reaction as an approximate one to one mixture (4 and 4B, 184 g, 919 mmol, 1.2 equiv) and 4-(1H-pyrazol-4-yl)-7-((2-(trimethylsilyl) ethoxy)methyl)-7H-pyrrolo[2,3-d]pyrimidine (5, 241 g, 766 mmol) in acetonitrile (6 L) was added DBU (137 mL, 919 mmol, 1.2 equiv) dropwise over 30 min at room temperature. The resulting reaction mixture was stirred overnight at room temperature. When the reaction was deemed complete, the solvent was removed under reduced pressure. The resulting solid was dissolved in 6 L of ethyl acetate and 2 L of acetonitrile at 40° C. and the solution was washed with a mixture of brine (3 L) and water (1 L). The aqueous layer was extracted with ethyl acetate (3×1.6 L). The combined organic layers were washed with brine (1.6 L) and the solvent was removed under reduced pressure. Toluene (2 L) was added to the residue and the azeotropic distillation was repeated under reduced pressure. The residue was triturated with MTBE (1.5 L, methyl t-butyl ether) and the solids were collected by filtration. The brown solid was dissolved completely in ethyl acetate (3 L) at 50° C. before the solution was treated with charcoal (30 g) and silica gel (30 g). The resulting mixture was stirred at 45° C. for 1 h before being filtered hot through celite. The solvent was removed under reduced pressure and the residue was triturated with MTBE (3 L). The solids were collected by filtration and washed with MTBE (1 L). The solids were then completely dissolved in isopropanol (8.8 L) at 70° C., and the resulting solution was gradually cooled down to room temperature with stirring for overnight. The solids were collected by filtration, washed with isopropanol (1.3 L) and heptane (2×490 mL), and dried in an oven overnight to afford 2-(1-(ethylsulfonyl)-3-(4-(7-((2-(trimethylsilyl)ethoxy)methyl)-7H-pyrrolo[2,3-d]pyrimidin-4-yl)-1H-pyrazol-1-yl)azetidin-3-yl)acetonitrile (6, 327 g, 384.3 g theoretical, 85% yield) as an off-white solid. For 6: $^1$H NMR (300 MHz, CDCl$_3$) δ0.00 (s, 9H), 0.99 (m, 2H), 1.49 (t, 3H), 3.15 (q, 2H), 3.49 (s, 2H), 3.60 (m, 2H), 4.30 (d, 2H), 4.70 (d, 2H), 5.76 (s, 2 H), 6.83 (s, 1H), 7.50 (s, 1H), 8.40 (s, 1H), 8.50 (s, 1H), 8.90 (s, 1H); MS: m/z calcd. 502.20; found: 502.3.

Step 5. 2-(3-(4-(7H-Pyrrolo[2,3-d]pyrimidin-4-yl)-1H-pyrazol-1-yl)-1-(ethylsulfonyl)azetidin-3-yl) acetonitrile (7)

To a solution of 2-(1-(ethylsulfonyl)-3-(4-(7-((2-(trimethylsilyl)ethoxy)methyl)-7H-pyrrolo[2,3-d]pyrimidin-4-yl)-1H-pyrazol-1-yl)azetidin-3-yl)acetonitrile (6, 327 g, 655 mmol) in acetonitrile (3 L) and water (300 mL) was added LiBF$_4$ (614 g, 6.55 mol, 10.0 equiv). The resulting reaction mixture was stirred at 75° C. for overnight. The reaction mixture was cooled to 0° C. before a solution of ammonium hydroxide (NH$_4$OH, 570 mL) in water (2.2 L) was added slowly to keep the temperature below 10° C. (pH 9-10). The mixture was stirred at room temperature for overnight. When the reaction was deemed complete, water (10 L) was added and the resulting mixture was vigorously stirred for 3 h at room temperature. The solids were collected by filtration, washed with water (6.7 L) and heptane (6.7 L), and dried in vacuum oven at 45° C. over the weekend. The dried solid was then dissolved in 20% MeOH in dichloromethane (12 L), and was purified by column chromatography on 1.3 Kg of silica gel eluting with a 20% MeOH in dichloromethane solution (18L) to afford 2-(3-(4-(7H-Pyrrolo[2,3-d]pyrimidin-4-yl)-1H-pyrazol-1-yl)-1-(ethylsulfonyl)azetidin-3-yl)acetonitrile (7, 204 g, 243.3 g theoretical, 83.8% yield) as an off-white solid. For 7: $^1$H NMR (300 MHz, d6-DMSO) δ 1.25 (t, 3H), 3.25 (q, 2H), 3.75 (s, 2H), 4.25 (d, 2H), 4.65 (d, 2H), 7.10 (d, 1H), 7.65 (dd, 1H), 8.50 (s, 1H), 8.70 (s, 1H), 8.95 (s, 1H), 12.2 (bs, 1H); MS: m/z calcd. 372.12; found: 372.0.

Step 6. 2-(3-(4-(7H-Pyrrolo[2,3-d]pyrimidin-4-yl)-1H-pyrazol-1-yl)-1-(ethylsulfonyl)azetidin-3-yl) acetonitrile phosphoric acid salt To a solution of 2-(3-(4-(7H-pyrrolo[2,3-d]pyrimidin-4-yl)-1H-pyrazol-1-yl)-1-(ethylsulfonyl)azetidin-3-yl)acetonitrile (7, 204 g, 550 mmol) in acetonitrile (5.1 L) and ethanol (1.6 L) was added a solution of phosphoric acid (67.4 g, 688 mmol, 1.25 equiv) in ethanol (800 mL) slowly over 30 min at 70° C. The resulting reaction mixture was stirred at 70° C. for 2 h before being gradually cooled to room temperature with stirring for overnight. The solids were collected by filtration, washed with acetonitrile (160 mL) and dried in vacuum oven at 45° C. for 6 h to afford 2-(3-(4-(7H-pyrrolo[2,3-d]pyrimidin-4-yl)-1H-pyrazol-1-yl)-1-(ethylsulfonyl)azetidin-3-yl) acetonitrile phosphoric acid salt (240 g, 258.2 g theoretical, 93% yield) as a white solid. For final product: $^1$H NMR (300 MHz, d$_6$-DMSO) δ 1.25 (t, 3H), 3.25 (q, 2H), 3.75 (s, 2H), 4.20 (d, 2H), 4.61 (d, 2H), 7.10 (d, 1H), 7.60 (dd, 1H),8.50 (s, 1H), 8.70 (s, 1H), 8.95 (s, 1H), 12.2 (bs, 1H); MS: m/z calcd. 372.12; found: 372.0.

Example 62

4-Chloro-7-((2-(trimethylsilyl)ethoxy)methyl)-7H-pyrrolo[2,3-d]pyrimidine(3).

To a flask equipped with a nitrogen inlet, an addition funnel, a thermowell, and the mechanical stirrer was added 4-chloro-7H-pyrrolo[2,3-d]pyrimidine (1, 600 g, 3.91 mol) and N,N-dimethylacetimide (DMAC, 9.6 L) at room temperature. The mixture was cooled to 0-5° C. in an ice/brine bath before solid sodium hydride (NaH, 60 wt %, 174 g, 4.35 mol, 1.1 equiv) was added in portions at 0-5° C. The reaction mixture went to a dark solution during 15 minutes. Trimethylsilylethoxymethyl chloride (2, SEM-Cl, 763 mL, 4.31 mol, 1.1 equiv) was then added slowly via an addition funnel at a rate that the internal reaction temperature did not exceed 5° C. The reaction mixture was then stirred at 0-5° C. for 30 minutes. When the reaction was deemed complete determined by TLC and HPLC, the reaction mixture was quenched by water (1 L). The mixture was then diluted with water (12 L) and MTBE (8 L). The two layers were separated and the aqueous layer was extracted with MTBE (8 L). The combined organic layers were washed with water (2×4 L) and brine (4 L) and dried over sodium sulfate ($Na_2SO_4$). The solvents were removed under reduced pressure. The residue was then dissolved in heptane (2 L), filtered and loaded onto a silica gel ($SiO_2$, 3.5 Kg) column eluting with heptane (6 L), 95% heptane/ethyl acetate (12 L), 90% heptane/ethyl acetate (10 L), and finally 80% heptane/ethyl acetate (10 L). The fractions containing the pure desired product were combined and concentrated under reduced pressure to give 4-chloro-7-((2-(trimethylsilyl)ethoxy)methyl)-7H-pyrrolo[2,3-d]pyrimidine (3, 987 g, 1109.8 g theoretical, 88.9% yield) as a pale yellow oil which partially solidified to an oily solid on standing at room temperature. For 3: $^1$H NMR (DMSO-$d_6$, 300 MHz) δ 8.67 (s, 1H), 7.87 (d, 1H, J=3.8 Hz), 6.71 (d, 1H, J=3.6 Hz), 5.63 (s, 2H), 3.50 (t, 2H, J=7.9 Hz), 0.80 (t, 2H, J=8.1 Hz), 1.24 (s, 9H) ppm; $^{13}$C NMR (DMSO-$d_6$, 100 MHz) δ 151.3, 150.8, 150.7, 131.5, 116.9, 99.3, 72.9, 65.8, 17.1, −1.48 ppm; $C_{12}H_{18}ClN_3OSi$ (MW 283.83), LCMS (EI) m/e 284/286 ($M^+$+H).

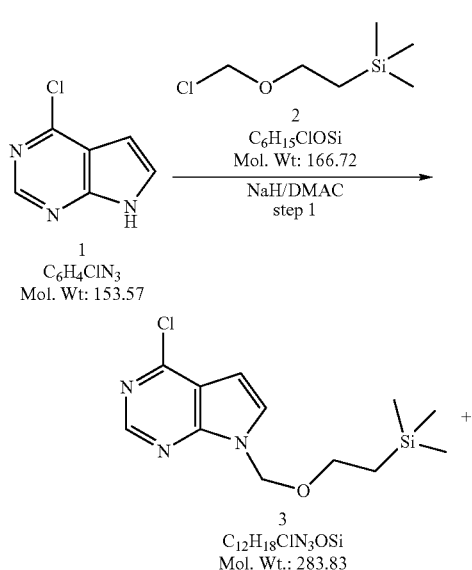

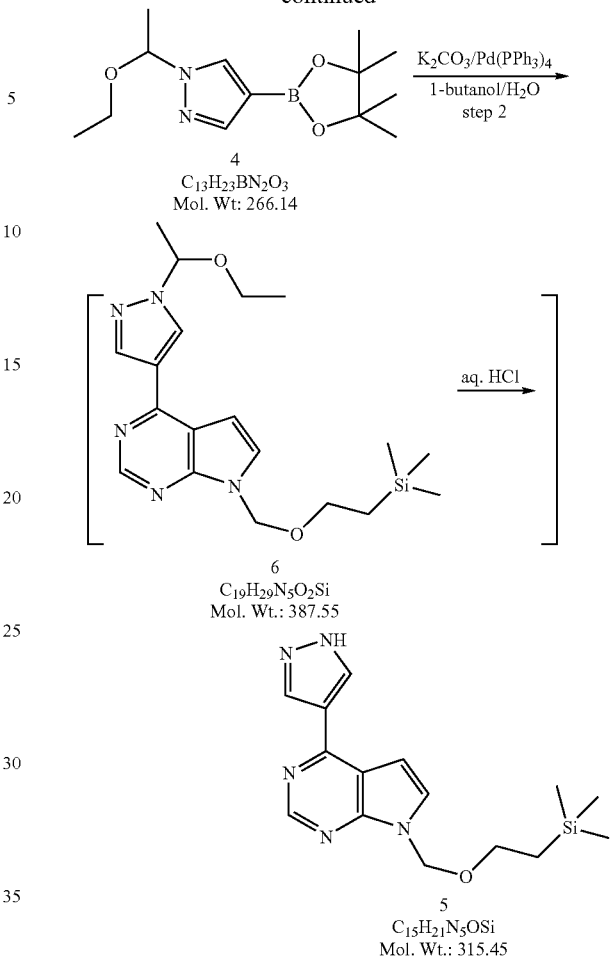

Example 63

4-(1H-Pyrazol-4-yl)-7-((2-(trimethylsilyl)ethoxy)methyl)-7H-pyrrolo[2,3-d]pyrimidine (5)

To a reactor equipped with the overhead stirrer, a condenser, a thermowell, and a nitrogen inlet was charged water ($H_2O$, 9.0 L), solid potassium carbonate ($K_2CO_3$, 4461 g, 32.28 mol, 2.42 equiv), 4-chloro-7-((2-(trimethylsilyl)ethoxy)methyl)-7H-pyrrolo[2,3-d]pyrimidine (3, 3597 g, 12.67 mol), 1-(1-ethoxyethyl)-4-(4,4,5,5-tetramethyl-1,3,2-dioxaborolan-2-yl)-1H-pyrazole (4, 3550 g, 13.34 mol, 1.05 equiv), and 1-butanol (27 L) at room temperature. The resulting reaction mixture was degassed three times backfilling with nitrogen each time before being treated with tetrakis (triphenylphosphine)palladium(0) (Pd(PPh$_3$)$_4$, 46 g, 0.040 mol, 0.003 equiv) at room temperature. The resulting reaction mixture was heated to gentle reflux (about 90° C.) for 1-4 hours. When the reaction was deemed complete determined by HPLC, the reaction mixture was gradually cooled down to room temperature before being filtered through a Celite bed. The Celite bed was washed with ethyl acetate (2×2 L) before the filtrates and washing solution were combined. The two layers were separated, and the aqueous layer was extracted with ethyl acetate (12 L). The combined organic layers were concentrated under reduced pressure to remove solvents, and the crude 4-(1-(1-ethoxyethyl)-1H-pyrazol-4-yl)-7-((2-(trimethylsilyl)ethoxy)methyl)-7H-pyrrolo[2,3-d]pyrimidine (6) was directly charged back to the reactor with tetrahydrofuran (THF, 4.2 L) for the subsequent acid-promoted deprotection reaction without further purification.

To a suspension of crude 4-(1-(1-ethoxyethyl)-1H-pyrazol-4-yl) -7-((2-(trimethylsilyl)ethoxy)methyl)-7H-pyrrolo[2,3-d]pyrimidine (6), made as described above, in tetrahydrofuran (THF, 4.2 L) in the reactor was charged water (H$_2$O, 20.8 L), and a 10% aqueous HCl solution (16.2 L, 45.89 mol, 3.44 equiv) at room temperature. The resulting reaction mixture was stirred at 16-30° C. for 2-5 h. When the reaction was deemed complete by HPLC analysis, the reaction mixture was treated with a 30% aqueous sodium hydroxide (NaOH) solution (4 L, 50.42 mol, 3.78 equiv) at room temperature. The resulting reaction mixture was stirred at room temperature for 1-2 h. The solids were collected by filtration and washed with water (2×5 L). The wet cake was charged back to the reactor with acetonitrile (21.6 L), and resulting suspension was heated to gentle reflux for 1-2 h. The clear solution was then gradually cooled down to room temperature with stirring, and solids were precipitated out from the solution with cooling. The mixture was stirred at room temperature for an additional 1-2 h. The solids were collected by filtration, washed with acetonitrile (2×3.5 L), and dried in oven under reduced pressure at 45-55° C. to constant weight to afford 4-(1H-pyrazol-4-yl)-7-((2-(trimethylsilyl)ethoxy)methyl)-7H-pyrrolo[2,3-d]pyrimidine (5, 3281.7 g, 3996.8 g theoretical, 82.1% yield) as white crystalline solids (99.5 area % by HPLC). For 5: $^1$H NMR (DMSO-d$_6$, 400 MHz) δ 13.41 (br. s, 1H), 8.74 (s, 1H), 8.67 (br. s, 1H), 8.35 (br. s, 1H), 7.72 (d, 1H, J=3.7 Hz), 7.10 (d, 1H, J=3.7 Hz), 5.61 (s, 2H), 3.51 (t, 2H, J=8.2 Hz), 0.81 (t, 2H, J=8.2 Hz), 0.13 (s, 9H) ppm; C$_{15}$H$_{21}$N$_5$OSi (MW, 315.45), LCMS (EI) m/e 316 (M$^+$+H).

Example 64

1-Benzhydrylazetidin-3-ol hydrochloride (23)

A solution of diphenylmethanamine (21, 2737 g, 15.0 mol, 1.04 equiv) in methanol (MeOH, 6 L) was treated with 2-(chloromethyl)oxirane (22, 1330 g, 14.5 mol) from an addition funnel at room temperature. During the initial addition a slight endotherm was noticed. The resulting reaction mixture was stirred at room temperature for 3 days before being warmed to reflux for an additional 3 days. When TLC showed that the reaction was deemed complete, the reaction mixture was first cooled down to room temperature and then to 0-5° C. in an ice bath. The solids were collected by filtration and washed with acetone (4 L) to give the first crop of the crude desired product (23, 1516 g). The filtrate was concentrated under reduced pressure and the resulting semisolid was diluted with acetone (1 L). This solid was then collected by filtration to give the second crop of the crude desired product (23, 221 g). The crude product, 1-benzhydrylazetidin-3-ol hydrochloride (23, 1737 g, 3998.7 g theoretical, 43.4% yield), was found to be sufficiently pure to be used in the subsequent reaction without further purification. For 23: $^1$HNMR (DMSO-d$_6$, 300 MHz), δ 12.28 (br. d, 1H), 7.7 (m, 5H), 7.49 (m, 5H), 6.38 (d, 1H), 4.72 (br. s, 1H), 4.46 (m, 1H), 4.12 (m, 2H), 3.85 (m, 2H) ppm; C$_{16}$H$_{18}$ClNO (free base of 23, C$_{16}$H$_{17}$NO MW, 239.31), LCMS (EI) m/e 240 (M$^+$+H).

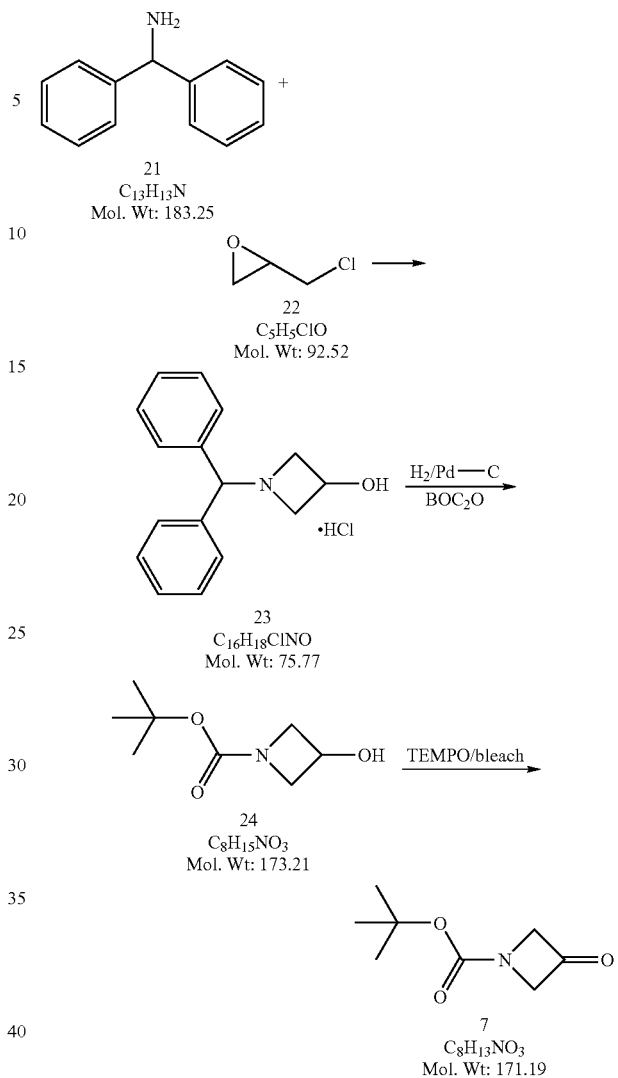

Example 65 tert-Butyl 3-hydroxyazetidine-1-carboxylate (24)

A suspension of 1-benzhydrylazetidin-3-ol hydrochloride (23, 625 g, 2.27 mol) in a 10% solution of aqueous sodium carbonate (Na$_2$CO$_3$, 5 L) and dichloromethane (CH$_2$Cl$_2$, 5 L) was stirred at room temperature until all solids were dissolved. The two layers were separated, and the aqueous layer was extracted with dichloromethane (CH$_2$Cl$_2$, 2 L). The combined organics extracts were dried over sodium sulfate (Na$_2$SO$_4$) and concentrated under reduced pressure. This resulting crude free base of 23 was then dissolved in THF (6 L) and the solution was placed into a large Parr bomb. Di-tert-butyl dicarbonate (BOC$_2$O, 545 g, 2.5 mol, 1.1 equiv) and 20% palladium (Pd) on carbon (125 g, 50% wet) were added to the Parr bomb. The vessel was charged to 30 psi with hydrogen gas (H$_2$) and stirred under steady hydrogen atmosphere (vessel was recharged three times to maintain the pressure at 30 psi) at room temperature for 18 h. When HPLC showed that the reaction was complete (when no more hydrogen was taken up), the reaction mixture was filtered through a Celite pad and the Celite pad was washed with THF (4 L).

The filtrates were concentrated under reduced pressure to remove the solvent and the residue was loaded onto a Biotage 150 column with a minimum amount of dichloromethane ($CH_2Cl_2$). The column was eluted with 20-50% ethyl acetate in heptane and the fractions containing the pure desired product (24) were collected and combined. The solvents were removed under reduced pressure to afford tert-butyl 3-hydroxyazetidine-1-carboxylate (24, 357 g, 393.2 g theoretical, 90.8% yield) as colorless oil, which solidified upon standing at room temperature in vacuum. For 24: $^1$HNMR ($CDCl_3$, 300 MHz), δ 4.56 (m 1H), 4.13 (m, 2H), 3.81 (m, 2H), 1.43 (s, 9H) ppm.

Example 66 tert-Butyl 3-oxoazetidine-1-carboxylate (7)

A solution of tert-butyl 3-hydroxyazetidine-1-carboxylate (24, 50 g, 289 mmol) in ethyl acetate (400 mL) was cooled to 0° C. The resulting solution was then treated with solid TEMPO (0.5 g, 3.2 mmol, 0.011 equiv) and a solution of potassium bromide (KBr, 3.9 g, 33.2 mmol, 0.115 equiv) in water (60 mL) at 0-5° C. While keeping the reaction temperature between 0-5° C. a solution of saturated aqueous sodium bicarbonate ($NaHCO_3$, 450 mL) and an aqueous sodium hypochlorite solution (NaClO, 10-13% available chlorine, 450 mL) were added. Once the solution of sodium hypochlorite was added, the color of the reaction mixture was changed immediately. When additional amount of sodium hypochlorite solution was added, the color of the reaction mixture was gradually faded. When TLC showed that all of the starting material was consumed, the color of the reaction mixture was no longer changed. The reaction mixture was then diluted with ethyl acetate (EtOAc, 500 mL) and two layers were separated. The organic layer was washed with water (500 mL) and the saturated aqueous sodium chloride solution (500 mL) and dried over sodium sulfate ($Na_2SO_4$). The solvent was then removed under reduced pressure to give the crude product, tert-butyl 3-oxoazetidine-1-carboxylate (7, 48 g, 49.47 g theoretical, 97% yield), which was found to be sufficiently pure and was used directly in the subsequent reaction without further purification. For crude 7: $^1$H NMR ($CDCl_3$, 300 MHz), δ 4.65 (s, 4H), 1.42 (s, 9H) ppm.

Example 67 tert-Butyl 3-(cyanomethylene)azetidine-1-carboxylate (9)

Diethyl cyanomethyl phosphonate (8, 745 g, 4.20 mol, 1.20 equiv) and anhydrous tetrahydrofuran (THF, 9 L) was added to a four-neck flask equipped with a thermowell, an addition funnel and the nitrogen protection tube at room temperature. The solution was cooled with an ice-methanol bath to −14° C. and a 1.0 M solution of potassium tert-butoxide (t-BuOK) in anhydrous tetrahydrofuran (THF, 3.85 L, 3.85 mol, 1.1 equiv) was added over 20 min while keeping the reaction temperature below −5° C. The resulting reaction mixture was stirred for 3 h at −10° C. and a solution of 1-tert-butoxycarbonyl-3-azetidinone (7, 600 g, 3.50 mol) in anhydrous tetrahydrofuran (THF, 2 L) was added over 2 h while keeping the internal temperature below −5° C. The reaction mixture was stirred at −5 to −10° C. over 1 h and then slowly warmed up to room temperature and stirred at room temperature for overnight. The reaction mixture was then diluted with water (4.5 L) and saturated aqueous sodium chloride solution (NaCl, 4.5 L) and extracted with ethyl acetate (EtOAc, 2×9 L). The combined organic layers were washed with brine (6 L) and dried over anhydrous sodium sulfate ($Na_2SO_4$). The organic solvent was removed under reduced pressure and the residue was diluted with dichloromethane ($CH_2Cl_2$, 4 L) before being absorbed onto silica gel ($SiO_2$, 1.5 Kg). The crude product, which was absorbed on silica gel, was purified by flash column chromatography ($SiO_2$, 3.5 Kg, 0-25% EtOAc/hexanes gradient elution) to afford tert-butyl 3-(cyanomethylene)azetidine-1-carboxylate (9, 414.7 g, 679.8 g theoretical, 61% yield) as white solid. For 9: $^1$H NMR ($CDCl_3$, 300MHz), δ 5.40 (m, 1H), 4.70 (m, 2H), 4.61 (m, 2H), 1.46 (s, 9H) ppm; $C_{10}H_{14}N_2O_2$ (MW, 194.23), LCMS (EI) m/e 217 (M$^+$+Na).

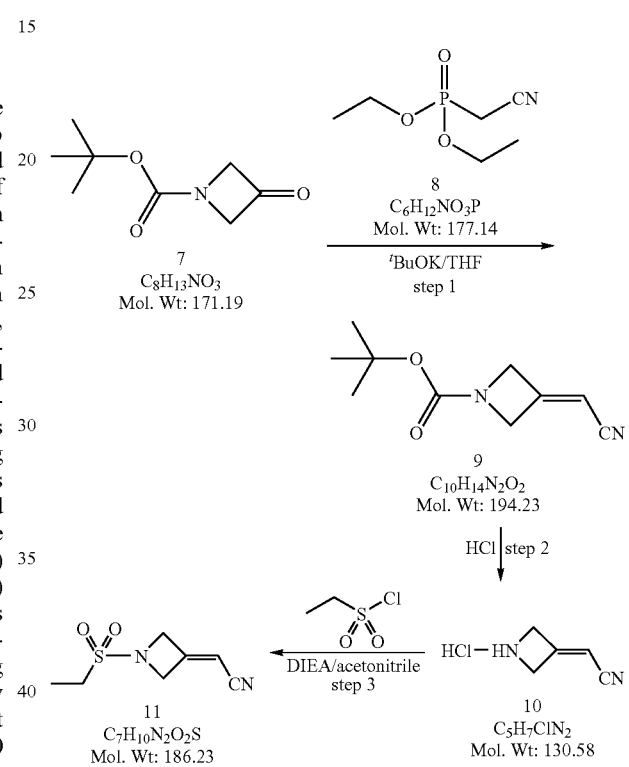

Example 68

2-(1-(Ethylsulfonyl)azetidin-3-ylidene)acetonitrile (11)

A solution of tert-butyl 3-(cyanomethylene)azetidine-1-carboxylate (9, 1000g, 5.2 mol) in acetonitrile (7 L) and a 3 N aqueous HCl solution (7 L) was stirred at room temperature for 18 h. When HPLC showed that all the starting material (9) was consumed, the reaction mixture was concentrated under reduced pressure to dryness. The residue, which contains the crude desired deprotection product (10), was then suspended in acetonitrile (12 L) and the resulting suspension was cooled to 0-5° C. Diisopropyethylamine (DIEA, 3.14 L, 18.03 mol, 3.5 equiv) was then slowly added while keeping the internal temperature below 5° C. The resulting homogeneous solution was allowed to cool down to 0° C. and ethane sulfonyl chloride ($EtSO_2Cl$, 730 mL, 7.73 mol, 1.5 equiv) was added over 1 h while keeping the internal temperature below 5° C. The resulting reaction mixture was allowed to gradually warm to room temperature and stirred at room temperature for overnight. When HPLC showed that the reaction was complete, the reaction mixture was concentrated under reduced pressure to a volume of approximately 2 L. The bath temperature of the rotary evaporator is set to not exceed 45° C. The concentrated residue was then diluted with dichloromethane (CH$_2$Cl$_2$, 10 L) and the resulting dichloromethane solution was washed with aqueous sodium chloride solution (10 L). The aqueous phase was back extracted with dichloromethane (CH$_2$Cl$_2$, 5 L). The combined organic layers were dried over anhydrous sodium sulfate (Na$_2$SO$_4$) and the residue was absorbed onto silica gel (SiO$_2$, 1 Kg) under reduced pressure. The bath temperature of the rotary evaporator was set to not exceed 45° C. The material was then loaded onto a silica gel column (SiO$_2$, 2.5 Kg) and eluted with 20-60 % ethyl acetate in heptane to afford 2-(1-(ethylsulfonyl)azetidin-3-ylidene) acetonitrile (11, 882 g, 968.4 g theoretical, 91% yield) as off-white solids. For 11: $^1$H NMR (CDCl$_3$, 300 MHz) δ 5.46 (m, 1H), 4.77 (m, 2H), 4.70 (m, 2H), 3.05 (q, 2H), 1.39 (t, 3H) ppm; C$_7$H$_{10}$N$_2$O$_2$S (MW, 186.23), LCMS (EI) m/e 187 (M$^+$+H).

Example 69

2-(1-(Ethylsulfonyl)-3-(4-(7-((2-(trimethylsilyl) ethoxy)methyl)-7H-pyrrolo[2,3-d]pyrimidin-4-yl)-1H-pyrazol-1-yl)azetidin-3-yl)acetonitrile (12)

Method A. To a suspension of 4-(1H-pyrazol-4-yl)-7-((2-(trimethylsilyl)ethoxy)methyl)-7H-pyrrolo[2,3-d]pyrimidine (5, 440 g, 1.395 mol) and 2-(1-(ethylsulfonyl)azetidin-3-ylidene)acetonitrile (11, 312.4 g, 1.68 mol, 1.2 equiv) in acetonitrile (4.4 L) was added DBU (249.8 mL, 1.67 mol, 1.2 equiv) drop wise to keep the reaction temperature between 15-25° C. After adding DBU, the reaction mixture became homogeneous, but a precipitate appeared in 30 min. The reaction mixture was stirred for 3 h at room temperature. When HPLC showed that the reaction was deemed complete, the reaction mixture was quenched with water (11 L). The resulting mixture was stirred at room temperature for additional 30 min and then filtered. The solid cake was washed with water (4 L), MTBE (2 L) and dried in vacuum oven at 35° C. for 24 h to afford crude 2-(1-(ethylsulfonyl)-3-(4-(7-((2-(trimethylsilyl)ethoxy)methyl)-7H-pyrrolo[2,3-d]pyrimidin-4-yl)-1H-pyrazol-1-yl)azetidin-3-yl)acetonitrile (12, 681 g, 699.8 g theoretical, 97.3% yield) as white solids, which was found to be sufficiently pure for the subsequent reaction without further purification. For 12: $^1$HNMR (CDCl$_3$, 300 MHz), δ 8.86 (s, 1H), 8.45 (s, 1H), 8.35 (s, 1H), 7.43 (d, 1H), 6.80 (d, 1H), 5.68 (s, 2H), 4.65 (d, 2H), 4.27 (d, 2H), 3.55 (s, 2H), 3.4 (t, 2H), 3.07 (m, 2H), 1.42 (m, 3H), 0.92 (m, 2H), -0.05 (s, 9H) ppm; C$_{22}$H$_{31}$N$_7$O$_3$SSi (MW, 501.68), LCMS (EI) m/e 502 (M$^+$+H).

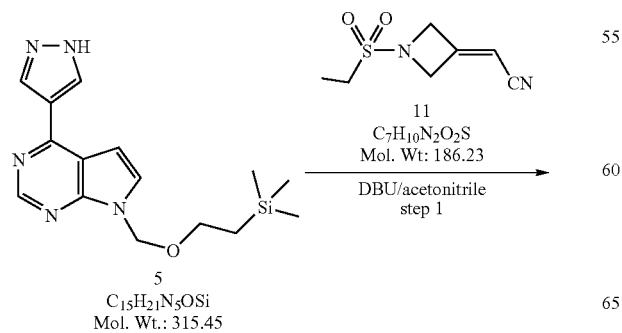

5
C$_{15}$H$_{21}$N$_5$OSi
Mol. Wt.: 315.45

11
C$_7$H$_{10}$N$_2$O$_2$S
Mol. Wt: 186.23

DBU/acetonitrile
step 1

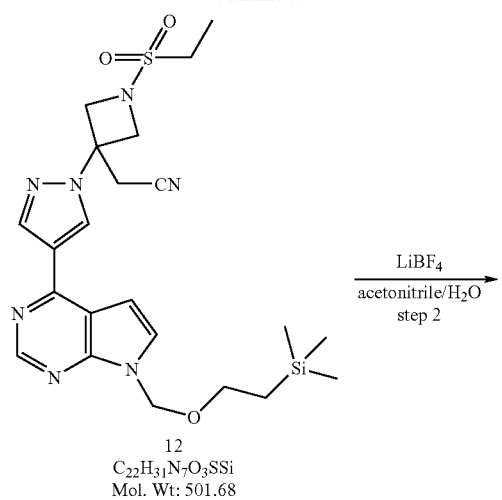

12
C$_{22}$H$_{31}$N$_7$O$_3$SSi
Mol. Wt: 501.68

LiBF$_4$
acetonitrile/H$_2$O
step 2

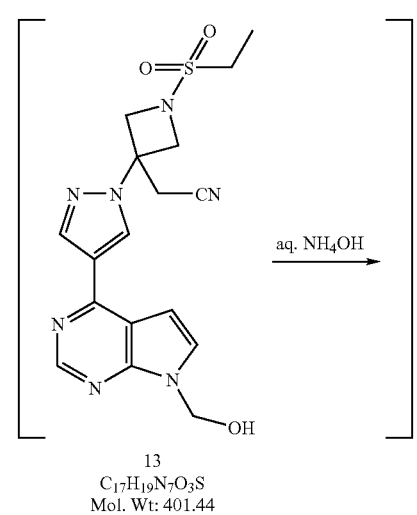

13
C$_{17}$H$_{19}$N$_7$O$_3$S
Mol. Wt: 401.44 aq. NH$_4$OH

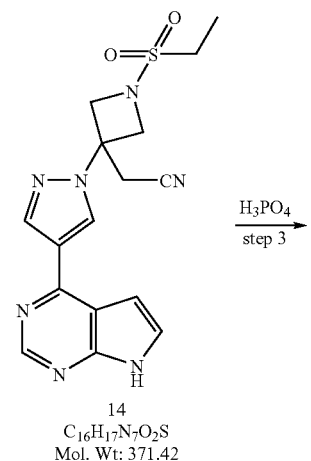

14
C$_{16}$H$_{17}$N$_7$O$_2$S
Mol. Wt: 371.42

H$_3$PO$_4$
step 3

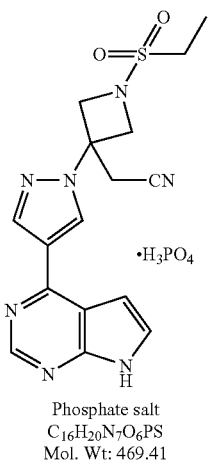

Phosphate salt
C₁₆H₂₀N₇O₆PS
Mol. Wt: 469.41

Example 70

2-(3-(4-(7H-Pyrrolo[2,3-d]pyrimidin-4-yl)-1H-pyrazol-1-yl)-1-(ethylsulfonyl)azetidin-3-yl)acetonitrile (14)

Method A. To a solution of 2-(1-(ethylsulfonyl)-3-(4-(7-((2-(trimethylsilyl)ethoxy)methyl)-7H-pyrrolo[2,3-d]pyrimidin-4-yl)-1H-pyrazol-1-yl)azetidin-3-yl)acetonitrile (12, 400 g, 797 mmol) in acetonitrile (3.6 L) and water (360 mL) was added solid lithium tetrafluoroborate (LiBF$_4$, 747.5 g, 7.97 mol, 10.0 equiv) at room temperature. The resulting reaction mixture was warmed to 80° C. and stirred at 80° C. for overnight. When HPLC showed the first stage of deprotection was complete, which afforded the corresponding hydroxymethyl intermediate 13, the reaction mixture was cooled down to room temperature gradually and subsequently to 0° C. A solution of ammonium hydroxide (28-30% aqueous NH$_4$OH, 680 mL) in water (2.7 L) was added slowly to the reaction mixture to adjust pH to 9-10 while keeping the internal temperature below 10° C. The resulting mixture was stirred at room temperature for overnight. When HPLC showed that the second stage of deprotection was complete, the reaction mixture was added into water (10 L), and the resulting mixture was vigorously stirred at room temperature for 3 h. The solids were collected by filtration, washed with water (8 L) and heptane (8 L), and dried in convection oven at 35° C. over the weekend. The dried solids were dissolved in 20% MeOH in dichloromethane (16 L) before being purified by column chromatography on 1.6 Kg of silica gel (SiO$_2$). The column was eluted with a 20% MeOH in dichloromethane solution (CH$_2$Cl$_2$, 18 L) to give 2-(3-(4-(7H-pyrrolo[2,3-d]pyrimidin-4-yl)-1H-pyrazol-1-yl)-1-(ethylsulfonyl)azetidin-3-yl)acetonitrile (14, 239.5 g, 296.1 g theoretical, 80.9% yield) as off-white solids. For 14: $^1$H NMR (DMSO-d$_6$, 300 MHz) δ12.15 (s, 1H), 8.94 (s, 1H), 8.72 (s, 1H), 8.49 (s, 1H), 7.63 (d, 1H), 7.09 (d, 1H), 4.62 (d, 2H), 4.25 (d, 2H), 3.71 (s, 2H), 3.24 (q, 2H), 1.26 (t, 3H) ppm; C$_{16}$H$_{17}$N$_7$O$_2$S (MW, 371.42), LCMS (EI) m/e 372 (M$^+$+H).

Example 71

2-(3-(4-(7H-Pyrrolo[2,3-d]pyrimidin-4-yl)-1H-pyrazol-1-yl)-1-(ethylsulfonyl)azetidin-3-yl)acetonitrile phosphate salt To a solution of 2-(3-(4-(7H-pyrrolo[2,3-d]pyrimidin-4-yl)-1H-pyrazol-1-yl)-1-(ethylsulfonyl)azetidin-3-yl)acetonitrile (14, 471.2 g, 1268.6 mmol) in acetonitrile (10.86 L) and ethanol (3.75 L) was added an 85% aqueous solution of phosphoric acid (H$_3$PO$_4$, 191.6 g, 1661.7 mmol, 1.31 equiv) in ethanol (EtOH, 1.68 L) slowly over 50 min at 70° C. The resulting reaction mixture was cooled down to room temperature slowly and stirred at room temperature for overnight. The solids were collected by filtration and washed with acetonitrile (500 mL). The resulting wet cake was then suspended in ethanol (EtOH, 7.0 L) before being treated with an aqueous 85% solution of phosphoric acid (H$_3$PO$_4$, 95.1 g, 824.6 mmol, 0.65 equiv) in ethanol (EtOH, 1.23 L) at room temperature. The resulting mixture was then warmed to reflux and stirred at reflux for 1 h before being cooled down to room temperature slowly and stirred at room temperature for overnight. The solids were collected by filtration, washed with ethanol (2 L) and heptane/ethanol (v/v 2/1, 2.1 L), and dried in vacuum oven at 40° C. for overnight to afford 2-(3-(4-(7H-pyrrolo[2,3-d]pyrimidin-4-yl)-1H-pyrazol-1-yl)-1-(ethylsulfonyl)azetidin-3-yl)acetonitrile phosphate salt (534.8 g, 595.5 g theoretical, 89.8% yield) as white crystalline solids. For phosphate salt: mp: 187° C.; elemental analysis for C$_{16}$H$_{20}$N$_7$O$_6$PS, Calcd: C, 40.94; H, 4.29; N, 20.89; P, 6.60; S, 6.83; Found: C, 40.65; H, 4.22; N, 20.71; P, 6.53; S, 6.95; FTIR (vmax, cm$^{-1}$): 3123 (—CH—), 2254 (CN), 1627 and 1441 (heteroaromatic C=N ), 1600 and 1559 (heteroaromatic C=C), 1312 (—SO$_2$—); $^1$H NMR (DMSO-d$_6$, 300 MHz) δ 12.19 (s, 1H), 8.94 (s, 1H), 8.71 (s, 1H), 8.48 (s, 1H), 7.62 (dd, 1H, J=3.5, 2.3 Hz), 7.08 (dd, 1H, J=3.6, 1.5 Hz), 4.60 (d, 2H, J=9.3, 9.2 Hz), 4.23 (d, 2H, J=9.3, 9.2 Hz), 3.69 (s, 2H), 3.23 (q, 2H, J=7.2 Hz), 1.23 (t, 3H, J=7.3 Hz) ppm; $^{13}$C NMR (DMSO-d$_6$, 75 MHz) δ 152.3, 150.9, 149.4, 140.0, 129.7, 127.1, 122.2, 116.8, 113.1, 100.1, 58.6, 56.1, 43.3, 26.9, 7.5 ppm; C$_{16}$H$_{17}$N$_7$O$_2$S (free base, MW, 371.42), LCMS (EI) m/e 372 (M$^+$+H).

Example 72 tert-Butyl 3-(cyanomethyl)-3-(4-(7-((2-(trimethylsilyl)ethoxy)methyl)-7H-pyrrolo[2,3-d]pyrimidin-4-yl)-1H-pyrazol-1-yl)azetidine-1-carboxylate (15)

To a suspension of tert-butyl 3-(cyanomethylene)azetidine-1-carboxylate (9, 417.2 g, 2.15 mol, 1.05 equiv) and 4-(1H-pyrazol-4-yl)-7-((2-(trimethylsilyl)ethoxy)methyl)-7H-pyrrolo[2,3-d]pyrimidine (5, 645 g, 2.04 mol) in acetonitrile (4.9 L) was added DBU (30.5 mL, 0.204 mol, 0.1 equiv) drop wise at room temperature. The resulting reaction mixture was then stirred at room temperature for 3 h. After about 1 h, a clear, brown solution was obtained. When LCMS showed that no starting material remained, silica gel (SiO$_2$, 1 Kg) was added and the mixture was concentrated to dryness under reduced pressure. This material, which contains the crude desired product (15), was then loaded onto a pre-packed silica column (SiO$_2$, 2.5 Kg) and the column was eluted with 60-80% of ethyl acetate/heptane. The fractions containing the pure desired product (15) were combined and concentrated under reduced pressure to give the desired product as thick oil which was then stirred in heptane at room temperature until crystallization occurred. The solids were collected by filtration and washed with heptane to afford tert-butyl 3-(cyanomethyl)-3-(4-(7-((2-(trimethylsilyl)ethoxy) methyl)-7H-pyrrolo[2,3-d]pyrimidin-4-yl)-1H-pyrazol-1-yl)azetidine-1-carboxylate (15, 1014.9 g, 1039.7 g theoretical, 97.6% yield) as white solids. For 15: $^1$H NMR (DMSO-d$_6$, 300 MHz) δ 8.93 (s, 1H), 8.77 (s, 1H), 8.47 (s, 1H), 7.80 (d, 1H, J=3.8 Hz), 7.20 (d, 1H, J=3.7 Hz), 5.63 (s, 2H), 4.50 (d, 2H, J=9.3 Hz), 4.21 (d, 2H, J=9.3 Hz), 3.66 (s, 2H), 3.52 (t, 2H, J=7.8 Hz), 1.40 (s, 9H), 0.82 (t, 2H, J=8.1 Hz), −0.12 (s, 9H) ppm; $C_{25}H_{35}N_7O_3Si$ (MW, 509.68), LCMS (EI) m/e 510 (M⁻+H) and 532 (M⁺+Na).
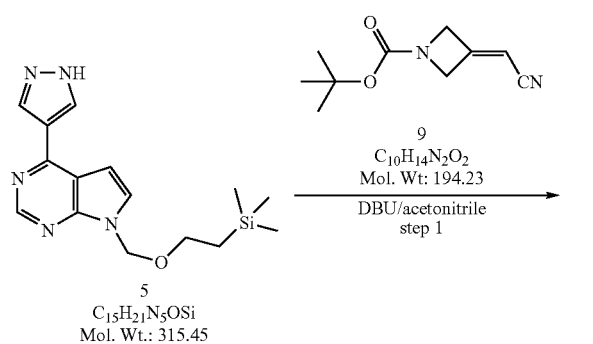
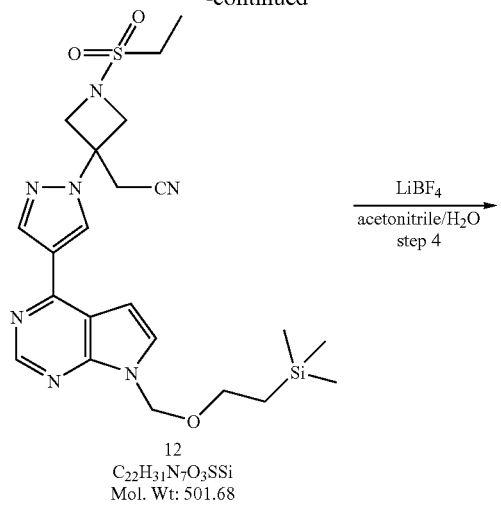
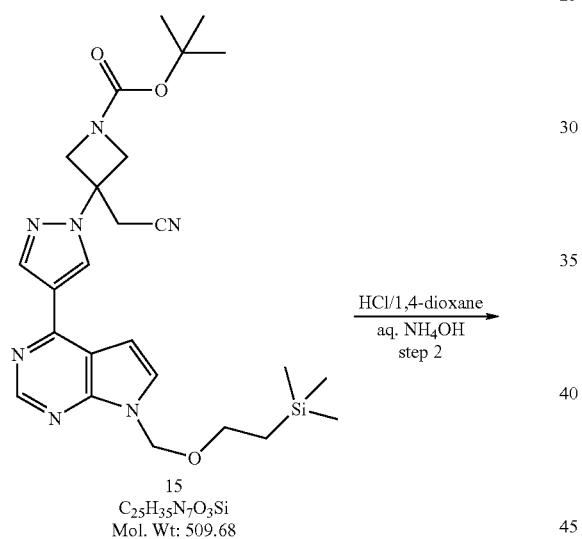
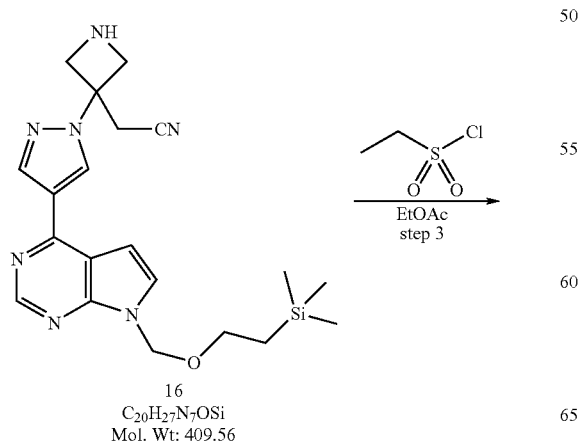
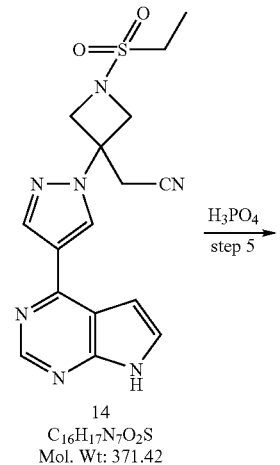

-continued

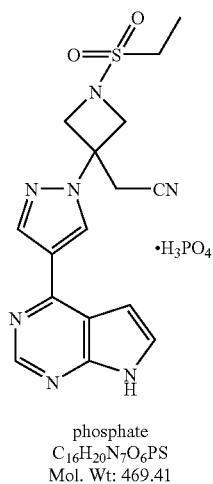

phosphate
C₁₆H₂₀N₇O₆PS
Mol. Wt: 469.41

Example 73

2-(3-(4-(7-((2-(Trimethylsilyl)ethoxy)methyl)-7H-pyrrolo[2,3-d]pyrimidin-4-yl)-1H-pyrazol-1-yl)azetidin-3-yl)acetonitrile (16)

To a solution of tert-butyl 3-(cyanomethyl)-3-(4-(7-((2-(trimethylsilyl)ethoxy)methyl)-7H-pyrrolo[2,3-d]pyrimidin-4-yl)-1H-pyrazol-1-yl)azetidine-1-carboxylate (15, 389.6 g, 0.765 mol) in dichloromethane (CH₂Cl₂, 7 L) was added a solution of hydrogen chloride (HCl) in dioxane (4 M, 1.15 L, 4.6 mol, 6.0 equiv) drop wise at room temperature. The resulting reaction mixture was stirred at room temperature for 48 h. When LCMS showed that all of the starting material had been consumed, the reaction mixture was transferred in portions to a 22 L separation funnel containing aqueous ammonium hydroxide (NH₄OH, about 4% v/v, 2.5 L). Gas was evolved but the funnel stayed cool to the touch. Ice cubes were periodically added as a precaution. Once all of the reaction mixture was added, stirring was continued for about 15 min. The pH of the aqueous layer was found to be close to 11. The two layers were separated and the organic layer was washed with brine (2 L), dried over anhydrous sodium sulfate (Na₂SO₄) and concentrated under reduced pressure to a minimum volume. Heptane (about 3 L) was added to the residue and the resulting suspension was concentrated to dryness under reduced pressure to give crude 2-(3-(4-(7-((2-(trimethylsilyl)ethoxy)methyl)-7H-pyrrolo[2,3-d]pyrimidin-4-yl)-1H-pyrazol-1-yl)azetidin-3-yl)acetonitrile (16, 268.2 g, 313.3 g theoretical, 85.6% yield) as an orange oil which was used directly for the subsequent reaction without further purification. For crude 16: ¹H NMR (300 MHz, CDCl₃): δ 8.92 (s, 1H), 8.45 (s, 1H), 8.39 (s, 1H), 7.47 (d, 1H), 6.87 (d, 1H), 5.74 (s, 2H), 4.36 (d, 2H), 3.95 (d, 2H), 3.77 (s, 2H), 3.62 (t, 2H), 1.9 (br. s, 1H), 0.99 (t, 2 H), 0.01 (s, 9H) ppm; C₂₀H₂₇N₇OSi (MW, 409.56), LCMS (EI) m/e 410 (M⁺+H).

Example 75

2-(1-(Ethylsulfonyl)-3-(4-(7-((2-(trimethylsilyl)ethoxy)methyl)-7H-pyrrolo[2,3-d]pyrimidin-4-yl)-1H-pyrazol-1-yl)azetidin-3-yl)acetonitrile (12)

Method B. To a solution of crude 2-(3-(4-(7-((2-(trimethylsilyl)ethoxy)methyl)-7H-pyrrolo[2,3-d]pyrimidin-4-yl)-1H-pyrazol-1-yl)azetidin-3-yl)acetonitrile (16, 423.7 g, 1.03 mol) in ethyl acetate (EtOAc, 6.5 L) at 0-5° C. was added a solution of ethane sulfonyl chloride (EtSO₂Cl, 117 mL, 1.23 mol, 1.2 equiv) in ethyl acetate (110 mL) drop wise. The resulting reaction mixture was allowed to warm gradually to room temperature and stirred at room temperature for overnight. When LCMS analysis showed that no starting material remained and the reaction mixture was transferred to a 22 L separation funnel and washed with water (4 L), brine (2 L) and saturated aqueous sodium bicarbonate solution (NaHCO₃, 2 L). The combined aqueous layer was back extracted with ethyl acetate (EtOAc, 2 L). The combined organic layers were washed with brine, dried over anhydrous sodium sulfate (Na₂SO₄) and concentrated under reduced pressure. The crude material was purified on silica gel eluted with dichlormethane/ethyl acetate (100/0 to 0/100). The fractions containing the pure desired product (12) were combined and concentrated under reduced pressure to a minimum volume before being treated with heptane at room temperature. The solids were collected by filtration and washed with heptane to afford 2-(1-(ethylsulfonyl)-3-(4-(7-((2-(trimethylsilyl)ethoxy)methyl)-7H-pyrrolo[2,3-d]pyrimidin-4-yl)-1H-pyrazol-1-yl)azetidin-3-yl)acetonitrile (12,397 g, 516.7 g theoretical, 76.8% yield) as white solids, which was found to be identical to the material prepared by method A in every comparable aspect. For 12: ¹H NMR (CDCl₃, 300 MHz), δ 8.86 (s, 1H), 8.45 (s, 1H), 8.35 (s, 1H), 7.43 (d, 1H), 6.80 (d, 1H), 5.68 (s, 2H), 4.65 (d, 2H), 4.27 (d, 2H), 3.55 (s, 2H), 3.4 (t, 2H), 3.07 (m, 2H), 1.42 (m, 3H), 0.92 (m, 2H), −0.05 (s, 9H) ppm; C₂₂H₃₁N₇)₃SSi (MW, 501.68), LCMS (EI) m/e 502 (M⁺+H).

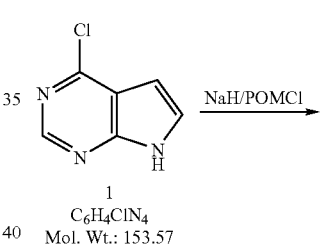

1
C₆H₄ClN₄
Mol. Wt.: 153.57

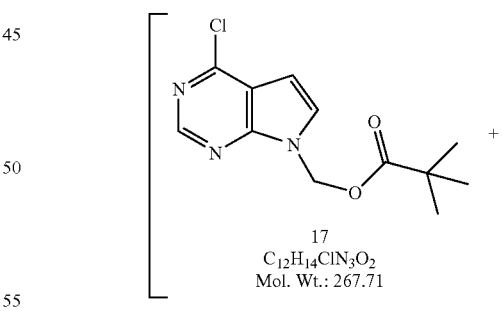

17
C₁₂H₁₄ClN₃O₂
Mol. Wt.: 267.71

4
C₁₃H₂₃BN₂O₃
Mol. Wt: 266.14

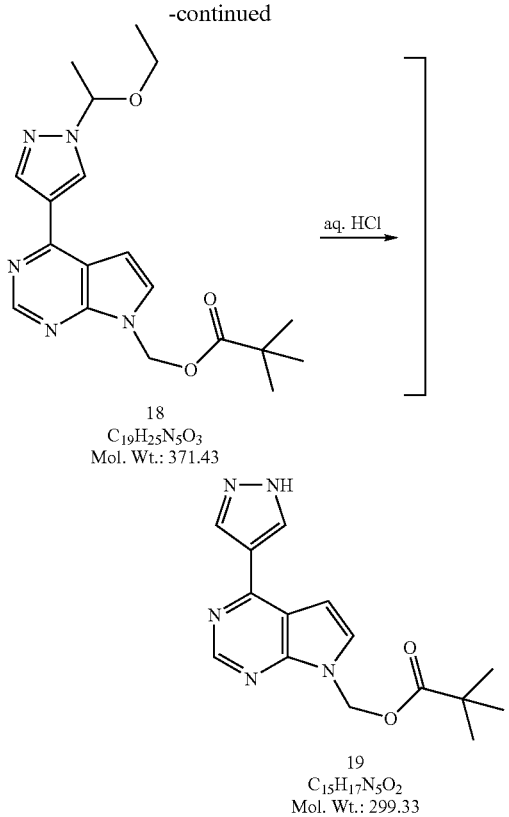

Example 76

[4-(1H-Pyrazol-4-yl)-7H-pyrrolo[2,3-d]pyrimidin-7-yl]methyl pivalate (19)

To a oven dried 3 L 4-neck round bottom flask equipped with a stirring bar, a septa, a thermocouple, a 500 mL addition funnel and the nitrogen inlet was charged solid sodium hydride (NaH, 60 wt % in mineral oil, 32.82 g, 0.82 mol, 1.20 equiv) and anhydrous 1,2-dimethoxyethane (DME, 500 mL, 4.8 mol) and the resulting mixture was cooled to 0-3° C. To a oven dried 1 L round bottom flask was charged 4-chloro-7H-pyrrolo[2,3-d]pyrimidine (1,105.0 g, 0.684 mol) and 1,2-dimethoxyethane (DME, 750 mL, 7.2 mol) and the resulting slurry was then portion wise added to the suspension of sodium hydride in DME via large bore cannula over 30 minutes at 5-12° C. The resulting reaction mixture was heterogeneous. Following the addition, the cold bath was removed and the mixture was gradually warmed to room temperature and allowed to stir at room temperature for 1 hour before being cooled to 0-5° C. Chloromethyl pivalate (pivaloyloxymethyl chloride, POM-Cl, 112 ml, 0.752 mol, 1.1 equiv) was then added drop wise into the reaction mixture over 30 minutes with stirring at 0-5° C. The addition of chloromethyl pivalate was mildly exothermic and the reaction temperature went up to as high as 14° C. After addition of chloromethyl pivalate, the cooling bath was removed and the reaction mixture was allowed to return to room temperature and stirred at room temperature for 90 min. When the reaction was deemed complete after confirmed by HPLC, the reaction mixture was carefully quenched with water (100 mL) and this quenched reaction mixture, which contains crude POM-protected chlorodeazapurine (17), was used directly in the subsequent Suzuki coupling reaction without further work-up and purification.

To the quenched reaction mixture, which contains crude POM-protected chlorodeazapurine (17) made as described above, was added 1-(1-ethoxyethyl)-4-(4,4,5,5-tetramethyl-1,3,2-dioxaborolan-2-yl)-1H-pyrazole (4, 200 g, 0.75 mol, 1.10 equiv) and solid potassium carbonate ($K_2CO_3$, 189 g, 1.37 mol, 2.0 equiv) at room temperature. The resulting mixture was degassed by passing a stream of nitrogen through the solution for 15 minutes before being treated with tetrakis(triphenylphosphine)palladium(0) ($Pd(PPh_3)_4$, 7.9 g, 0.68 mmol, 0.01 equiv) and the resulting reaction mixture was heated at reflux (about 82° C.) for 10 hours. When the reaction was deemed complete by TLC (1:1 hexanes/ethyl acetate) and LCMS, the reaction mixture was cooled to room temperature, diluted with ethyl acetate (2 L) and water (1 L). The two layers were separated, and the aqueous layer was extracted with ethyl acetate (500 mL). The combined organic layers were washed with water (2×1 L) and brine (1 L) before being concentrated under reduced pressure to afford crude {4-[1-(1-ethoxyethyl)-1H-pyrazol-4-yl]-7H-pyrrolo[2,3-d]pyrimidin-7-yl}methyl pivalate (18) as a pale-yellow oil, which was directly used in the subsequent de-protection reaction without further purification.

A solution of crude 18 in THF (1 L, 12.3mol) was treated with a 4 N aqueous HCl solution (500 mL) at room temperature. The resulting reaction mixture was subsequently stirred at room temperature for 5 h. When the reaction was deemed complete, the reaction mixture was cooled to 0-5° C. before the pH was adjusted to 9-10 with a 1 M aqueous sodium hydroxide (NaOH) solution (2 L). The mixture was then concentrated under reduced pressure to remove most of the THF and the resulting suspension was stirred at room temperature for 2 h. The solids were collected by filtration, washed with water (3×500 mL), and dried in vacuum oven to afford [4-(1H-pyrazol-4-yl)-7H-pyrrolo[2,3-d]pyrimidin-7-yl]methyl pivalate (19, 157.5 g, 204.43 g theoretical, 77% yield for three steps) as off-white solids, which was found to be sufficiently pure (>98 area % by HPLC) to do the subsequent reaction without further purification. For 19: $^1$H NMR (DMSO-$d_6$, 400 MHz) δ 13.42 (br s, 1H), 8.76 (s, 1H), 8.67 (s, 1H), 8.33 (s, 1H), 7.68 (d, 1H, J=3.8 Hz), 7.11 (d, 1H, J=3.8 Hz), 6.21 (s, 2H), 1.06 (s, 9H) ppm; $^{13}$C NMR (DMSO-$d_6$, 100 MHz) δ 177.74, 152.31, 152.09, 151.91, 139.52, 130.39, 120.51, 113.93, 101.91, 67.26, 38.98, 27.26 ppm; $C_{15}H_{17}N_5O_2$ (MW, 299.33), LCMS (EI) m/e 300 (M$^+$+H).

Example 77

(4-(1-(3-(Cyanomethyl)-1-(ethylsulfonyl)azetidin-3-yl)-1H-pyrazol-4-yl)-7H-pyrrolo[2,3-d]pyrimidin-7-yl)methyl pivalate (20)

To a suspension of [4-(1H-pyrazol-4-yl)-7H-pyrrolo[2,3-d]pyrimidin-7-yl]methyl pivalate (19, 10.0 g, 33.4 mmol) and 2-(1-(ethylsulfonyl)azetidin-3-ylidene)acetonitrile (11, 6.22 g, 33.4 mmol, 1.0 equiv) in N,N-dimethylformamide (DMF, 20 mL) was added DBU (254 mg, 1.67 mmol, 0.05 equiv) drop wise to keep the reaction temperature between 15-25° C. After adding DBU, the reaction mixture became homogeneous within 90 min. The reaction mixture was stirred for 3 h at room temperature. When HPLC showed that the reaction was deemed complete, the reaction mixture was quenched with water (120 mL) and acetonitrile (80 mL). The resulting mixture was stirred at room temperature for an additional 30 min. The solids were collected by filtration, washed with a mixture of acetonitrile and water (2/3 by volume, 2×20 mL), and dried in vacuum oven at 40-45° C. for 24 h to afford crude (4-(1-(3-(cyanomethyl)-1-(ethylsulfonyl)azetidin-3-yl)-1H-pyrazol-4-yl)-7H-pyrrolo[2,3-d]pyrimidin-7-yl)methyl pivalate (20, 14.5 g, 16.2 g theoretical, 89.5% yield) as white solids, which was found to be sufficiently pure (>98.0% by HPLC) for the subsequent reaction without further purification. For 20: ¹HNMR (CDCl₃, 300 MHz), δ 8.87 (s, 1H), 8.43 (s, 1H), 8.37 (s, 1H), 7.51 (d, 1H, J=3.6 Hz), 6.76 (d, 1H, J=3.6 Hz), 6.26 (s, 2H), 4.64 (d, 2H, J=9.6 Hz), 4.25 (d, 2H, J=9.6 Hz), 3.41 (s, 2H), 3.09 (q, 2H, J=7.6 Hz), 1.42 (t, 3H, J=7.6 Hz), 1.17 (s, 9H) ppm; C₂₂H₂₇N₇O₄S (MW, 485.56), LCMS (EI) m/e 486 (M⁺+H).

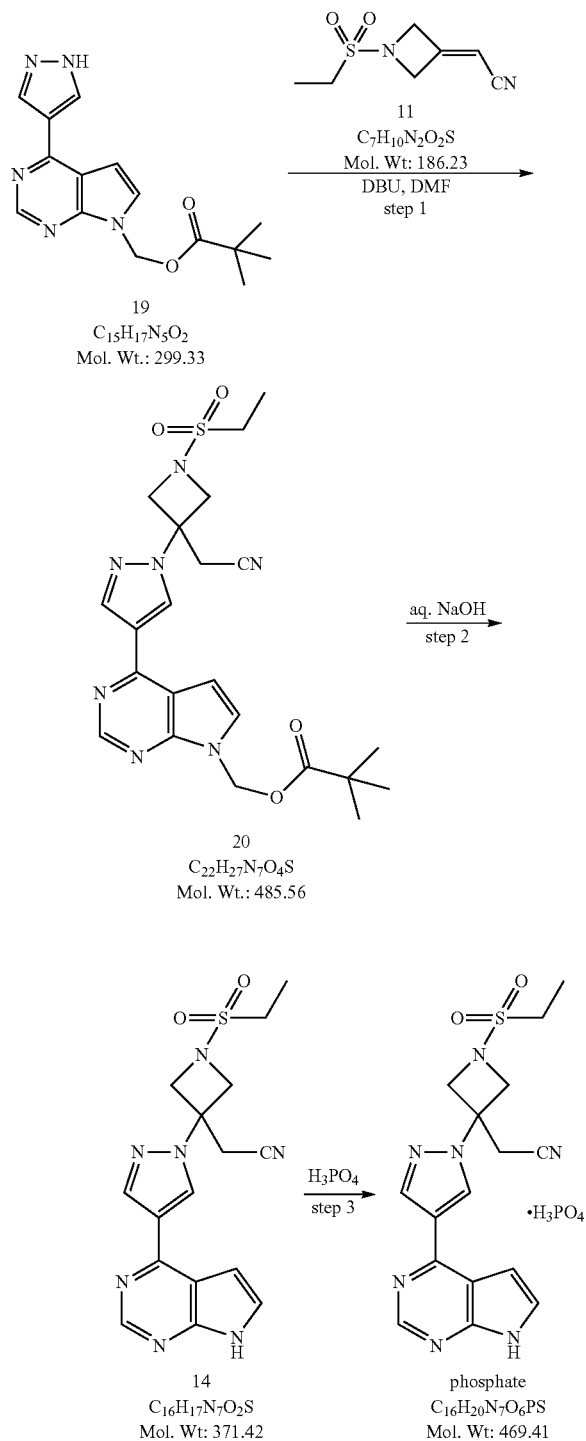

Example 78

2-(3-(4-(7H-Pyrrolo[2,3-d]pyrimidin-4-yl)-1H-pyrazol-1-yl)-1-(ethylsulfonyl)azetidin-3-yl)acetonitrile (14)

Method B. A suspension of (4-(1-(3-(cyanomethyl)-1-(ethylsulfonyl)azetidin-3-yl)-1H-pyrazol-4-yl)-7H-pyrrolo[2,3-d]pyrimidin-7-yl)methyl pivalate (20, 1.0 g, 2.06 mmol) in methanol (MeOH, 5 mL) and tetrahydrofuran (THF, 20 mL) was treated with a 1 M aqueous sodium hydroxide solution (NaOH, 2.3 mL, 2.3 mmol, 1. 12 equiv) at room temperature, and the resulting reaction mixture was stirred at room temperature for 2-3 h. When HPLC showed that the reaction was deemed complete, the reaction mixture was quenched with water (10 mL) and a 1 N aqueous HCl solution (0.2 mL) to adjust pH to 7-7.5 at room temperature. The resulting mixture was stirred at room temperature for 30 min before the solids were collected by filtration. The solids were washed with a mixture of acetonitrile and water (2/3 by volume, 2×4 mL) and dried in vacuum at 40-45° for 24 h to afford crude 2-(3-(4-(7H-pyrrolo[2,3-d]pyrimidin-4-yl)-1H-pyrazol-1-yl)-1-(ethylsulfonyl)azetidin-3-yl)acetonitrile (14, 658 mg, 765 mg theoretical, 86% yield) as off-white solids, which was found to be identical to the material prepared by Method A. For crude 14: ¹H NMR (DMSO-d₆, 300 MHz) δ 12.15 (s, 1H), 8.94 (s, 1H), 8.72 (s, 1H), 8.49 (s, 1H), 7.63 (d, 1H), 7.09 (d, 1H), 4.62 (d, 2H), 4.25 (d, 2H), 3.71 (s, 2H), 3.24 (q, 2H), 1.26 (t, 3H) ppm; C₁₆H₁₇N₇O₂S (MW, 371.42), LCMS (EI) m/e 372 (M⁺+H).

Method C. Alternatively, a suspension of (4-(1-(3-(cyanomethyl)-1-(ethylsulfonyl)azetidin-3-yl)-1H-pyrazol-4-yl)-7H-pyrrolo[2,3-d]pyrimidin-7-yl)methyl pivalate (20, 10.0 g, 20.6 mmol) and lithium hydroxide monohydrate (2.59 g, 61.8 mmol) in acetonitrile (CH₃CN 40 mL) and isopropyl alcohol (10 mL) was heated at 45-50° C. for 6 hours. When HPLC showed that the reaction was deemed complete, the reaction mixture was cooled to room temperature and 1M hydrochloric acid aqueous solution (41 mL) as added to adjust the pH to 6-7 at temperature below 25° C. After the acid addition, the mixture was stirred at room temperature for 1 h and the precipitates were isolated by filtration. The wet cake was washed with water (50 mL) and dried in vacuum oven at 50° C. to give crude 2-(3-(4-(7H-pyrrolo[2,3-d]pyrimidin-4-yl)-1H-pyrazol-1-yl)-1-(ethylsulfonyl)azetidin-3-yl)acetonitrile (14, 6.0 g, 7.65 g theoretical, 78% yield) as off-white solids, which was found to be identical to the material prepared by Method A.

Example 79

{1-(Cyclopropylsulfonyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (25)

To a oven dried 2 L round bottom flask equipped with the overhead stirring, a nitrogen inlet, a septa and a thermocouple was charged anhydrous tetrahydrofuran (THF, 800 mL), {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (16, 38.6 g, 94.2 mmol) and N, N-diisopropylethylamine (DIEA, 22.0 mL, 126 mmol, 1.34 equiv) at room temperature. The resulting solution was then cooled to 0-5° C. before being charged with cyclopropanesulfonyl chloride (14.3 mL, 134 mmol, 1.42 equiv) portion wise over eight minutes via syringe at 0-5° C. After 10 minutes, the ice bath was removed and the reaction mixture was allowed to warm gradually to room temperature. When HPLC showed that the reaction was complete after 22 h, the reaction mixture was concentrated under reduced pressure to remove about 400 mL of solvent. The residue was treated with ethyl acetate (EtOAc, 500 mL) and the resulting solution was washed with 20% aqueous sodium chloride solution (NaCl, 300 mL). The aqueous layer was back extracted with ethyl acetate (EtOAc, 150 mL). The combined organic fractions were dried over magnesium sulfate (MgSO$_4$) and concentrated under reduced pressure to yield the crude product (25) as an amber oil. The crude product was then purified by flash column chromatography (SiO$_2$, 50% to 70% ethyl acetate/hexane gradient elution) to afford {1-(cyclopropylsulfonyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (25, 39.4 g, 48.4 g theoretical, 81.4% yield) as a light yellow oil, which solidified upon standing at room temperature in vacuum. For 25: $^1$H NMR (DMSO-d$_6$, 300 MHz) δ 8.98 (s, 1H), 8.78 (s, 1H), 8.50 (s, 1H), 7.81 (d, 1H, J=3.8 Hz), 7.20 (d, 1H, J=3.6 Hz), 5.63 (s, 2H), 4.66 (d, 2H, J=9.5 Hz), 4.28 (d, 2H, J=9.3 Hz), 3.69 (s, 2H), 3.52 (t, 2H, J=7.8 Hz), 2.84 (m, 1H), 1.01 (m, 4H), 0.82 (t, 2H, J=8.4 Hz), −0.12 (s, 9H) ppm; C$_{23}$H$_{31}$N$_7$O$_3$SSi (MW, 513.69), LCMS (EI) m/e 514 (M$^+$+H) and 536 (M$^+$+Na).

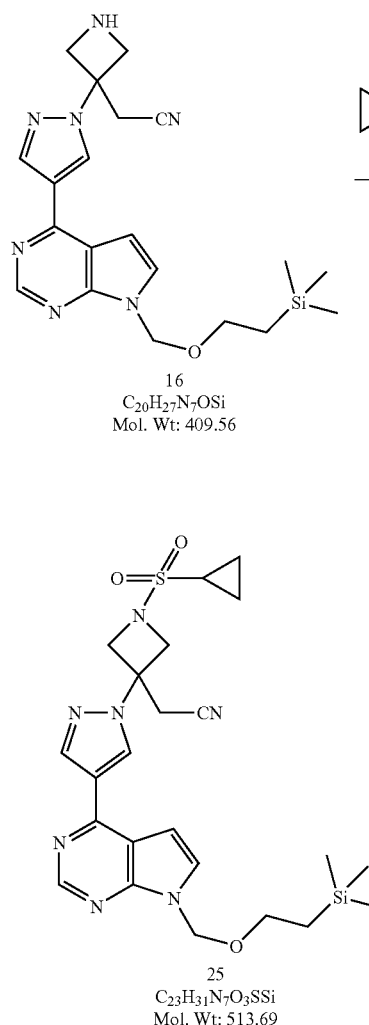

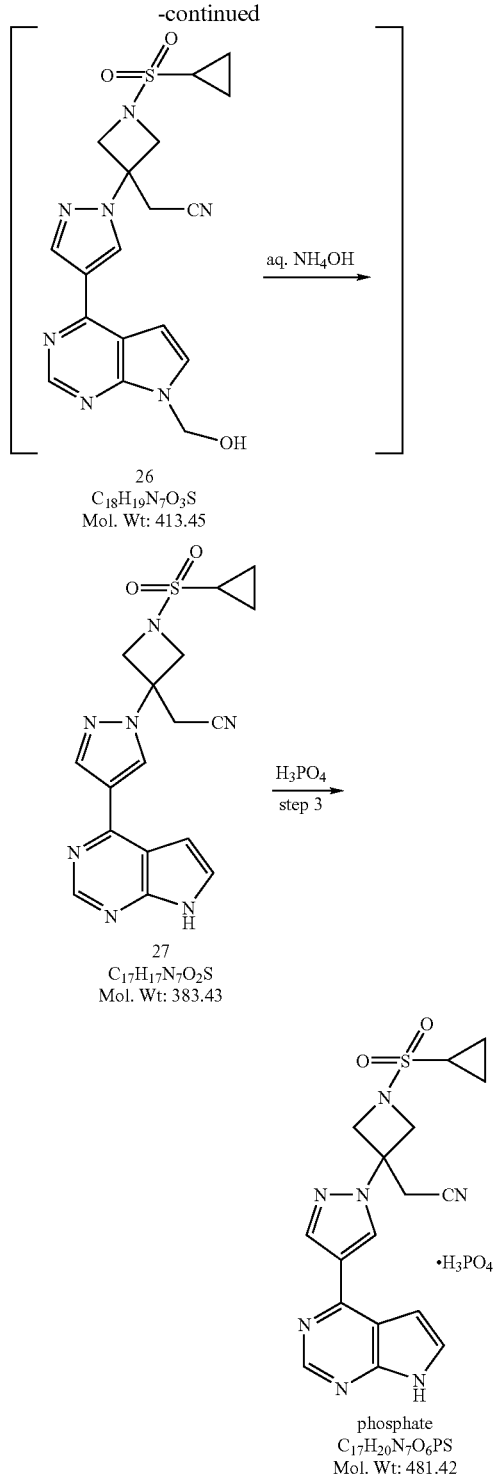

Example 80
2-(3-(4-(7H-Pyrrolo[2,3-d]pyrimidin-4-yl)-1H-pyrazol-1-yl)-1-(cyclopropylsulfonyl)azetidin-3-yl)acetonitrile (27)

To a 500 mL round bottom flask equipped with a stir bar, a condenser, a thermocouple a n d a nitrogen inlet was charged {1-(cyclopropylsulfonyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (25, 17.5 g, 34.1 mmol), acetonitrile (254 mL) and water (23.9 ML) at room temperature. The resulting reaction mixture was charged with solid lithium tetrfluoroborate (LiBF$_4$, 32.6 g, 341 mmol, 10.0 equiv) in one portion at room temperature. The resulting reaction mixture was warmed to reflux and stirred at reflux for 21 h. When HPLC showed that the first stage of deprotection reaction was complete, which produced the corresponding hydroxymethyl intermediate 26, the reaction mixture was allowed to gradually cool to room temperature before the solution pH was adjusted to 9-10 with a 20% aqueous NH$_4$OH solution (45 mL) at room temperature. The resulting reaction mixture was then stirred at room temperature for overnight. When HPLC showed that the second stage of deprotection reaction was complete, the reaction mixture was filtered through a Celite pad and the Celite pad was washed with ethyl acetate (EtOAc, 50 mL). The filtrates were then diluted with a 20% aqueous sodium chloride solution (NaCl, 200 mL) and ethyl acetate (EtOAc, 200 mL). The two layers were separated, and the aqueous layer was extracted with ethyl acetate (EtOAc, 200 mL). The combined organic fractions were washed with 1 M aqueous sodium bicarbonate solution (NaHCO$_3$, 200 mL) and water (200 mL). The combined aqueous solution was back extracted with ethyl acetate (EtOAc, 100 mL). The combined organic fractions were then dried over magnesium sulfate (MgSO$_4$) and concentrated under reduced pressure to give the crude product (27) as light yellow solids. The crude solids were then treated with acetonitrile (200 mL) and the resulting suspension was warmed to 60° C. for 15 minutes before being cooled down to room temperature and stirred at room temperature for 60 minutes. The solids were collected by filtration and washed with a small volume of acetonitrile to give the first crop of the desired product (27, 6.9 g). The combined filtrates were then concentrated to afford yellow solids, which was treated with acetonitrile (100 mL) and warmed to 60° C. for 30 minutes. The suspension was cooled down to room temperature and stirred at room temperature for 60 minutes. The solids were collected by filtration and washed with a small volume of acetonitrile to give the second crop of the desired product (27, 3.0 g). The filtrate was then concentrated and the residue was purified by flash column chromatography (SiO$_2$, 50% ethyl acetate/acetonitrile elution) to give the third crop of the desired product (27, 1.4 g). This reaction afforded 2-(3-(4-(7H-pyrrolo[2,3-d]pyrimidin-4-yl)-1H-pyrazol-1-yl)-1-(cyclopropylsulfonyl)azetidin-3-yl)acetonitrile (27, 11.3 g, 13.07 g theoretical, 86.5% overall yield) as off-white solids. For 27: $^1$H NMR (DMSO-d$_6$, 400 MHz) δ 12.16 (br. s, 1H), 8.95 (s, 1H), 8.70 (s, 1H), 8.48 (s, 1H), 7.62 (dd, 1H, J=3.6, 2.3 Hz), 7.08 (dd, 1H, J=3.5, 1.4 Hz), 4.66 (d, 2H, J=9.4 Hz), 4.28 (d, 2H, J=9.4 Hz), 3.69 (s, 2H), 284 (m, 1H), 1.01 (m, 4H) ppm; C$_{17}$H$_{17}$N$_7$O$_2$S (MW, 383.43), LCMS (EI) m/e 384 (M$^+$+H).

Example 81

2-(3-(4-(7H-Pyrrolo[2,3-d]pyrimidin-4-yl)-1H-pyrazol-1-yl)-1-(cyclopropylsulfonyl)azetidin-3-yl)acetonitrile phosphoric acid salt To a 1 L round bottom flask equipped with a stir bar, an addition funnel, a nitrogen inlet and a condenser was charged 2-(3-(4-(7H-pyrrolo[2,3-d]pyrimidin-4-yl)-1H-pyrazol-1-yl)-1-(cyclopropylsulfonyl)azetidin-3-yl)acetonitrile (27, 11.3 g, 29.5 mmol) and acetonitrile (275 ML) at room temperature. The resulting mixture was warmed to 70° C. before being charged with ethanol (EtOH, 150 mL) in three portions at 70° C. The resulting homogeneous solution was filtered into a clean 1 L round bottom flask equipped with the overhead stirring, an addition funnel, a nitrogen inlet and a condenser. The mixture was then warmed to 67° C. producing a homogeneous solution again. A solution of phosphoric acid (H$_3$PO$_4$, 3.03 g, 30.9 mmol, 1.05 equiv) in ethanol (EtOH, 30 mL) was then charged drop wise to the solution over ten minutes at 67° C. The solution was still homogeneous after the end of the addition of phosphoric acid ethanol solution. The resulting reaction mixture was stirred at 67° C. for 10 minutes before being gradually cooled down to room temperature and stirred at room temperature for 19 h. The solids were collected by filtration and washed with acetonitrile (2×40 mL). The wet cake was partially dried under high vacuum and then transferred to a 75° C. vacuum oven and dried to constant weight to afford 2-(3-(4-(7H-pyrrolo[2,3-d]pyrimidin-4-yl)-1H-pyrazol-1-yl)-1-(cyclopropylsulfonyl)azetidin-3-yl)acetonitrile phosphate (12.0 g, 14.2 g theoretical, 84.5% yield) as white solids. For Phosphate: $^1$H NMR (DMSO-d$_6$, 500 MHz) δ 12.13 (br. s, 1H), 9.20 (br. s, 3H), 8.94 (s, 1H), 8.70 (s, 1H), 8.47 (s, 1H), 7.61 (dd, 1H, J=3.4, 2.3 Hz), 7.07 (dd, 1H, J=3.6, 1.6 Hz), 4.65 (d, 2H, J=9.1 Hz), 4.28 (d, 2H, J=9.7 Hz), 3.68 (s, 2H), 2.82 (m, 1H), 1.01 (m, 4H) ppm; $^{13}$C NMR (DMSO-d$_6$, 125 MHz) δ 152.9, 151.6, 150.0, 140.6, 130.3, 127.7, 122.9, 117.3, 113.8, 100.7, 59.7, 57.1, 27.6, 25.4, 4.9 ppm; C$_{17}$H$_{20}$N$_7$O$_6$PS (MW, 481.42; C$_{17}$H$_{17}$N$_7$O$_2$S for free base, MW, 383.43), LCMS (EI) m/e 384 (M$^+$+H).

Example 82

{1-(Ethylsulfonyl)-3-[3-(7H-pyrrolo[2,3-d]pyrimidin-4-yl)-1H-pyrrol-1-yl]azetidin-3-yl}acetonitrile

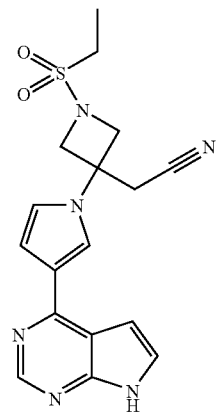

Step 1. 4-(1H-pyrrol-3-yl)-7-{[2-(trimethylsilyl)ethoxy]methyl}-7H-pyrrolo[2,3-d]pyrimidine A mixture of 4-chloro-7-{[2-(trimethylsilyl)ethoxy]methyl}-7H-pyrrolo[2,3-d]pyrimidine (12.9 g, 45.4 mmol) (prepared as in WO 2007/070514, Ex.65) and [1-(triisopropylsilyl)-1H-pyrrol-3-yl]boronic acid (Frontier Scientific) (10.4 g, 38.9 mmol) and sodium carbonate (4.36 g, 41.2 mmol) in 1,2-dimethoxyethane (100 mL) and water (35 mL) was degassed by purging with a stream of nitrogen for 20 minutes. Tetrakis(triphenylphosphine)palladium(0) (2.25 g, 1.94 mmol) was then added and the reaction was heated to reflux for 9 hours. As the coupling reaction proceeded, the TIPS protecting group was also slowly removed. The solvent was removed by rotary evaporation and the product was purified by flash column chromatography, eluting with a gradient from 10-50% ethyl acetate in hexanes to afford the desired product (7 g, 57%).

$^1$H NMR (300 MHz, CDCl$_3$): δ 8.93 (br s, 1H), 8.84 (s, 1H), 7.73-7.69 (m, 1H), 7.33 (d, 1H), 7.04-7.00 (m, 1H), 6.94 (dd, 1H), 6.85 (d, 1H), 5.66 (s, 2H), 3.55 (m, 2H), 0.92 (m, 2H), −0.06 (s, 9H). LCMS (M+H)+: 315.2.

Step 2

A solution of 4-(1H-pyrrol-3-yl)-7-{[2-(trimethylsilyl)ethoxy]methyl}-7H-pyrrolo[2,3-d]pyrimidine (0.100 g, 0.318 mmol) and [1-(ethylsulfonyl)azetidin-3-ylidene]acetonitrile (0.118 g, 0.636 mmol, prepared as in Example 68) in acetonitrile (1 mL) was treated with 1,8-diazabicyclo[5.4.0]undec-7-ene (24 μL, 0.16 mmol). The mixture was stirred for 4 hours. The solvent was evaporated. The residue was partitioned between ethyl acetate and saturated sodium bicarbonate solution, then extracted with two further portions of ethyl acetate. The combined extracts were dried over sodium sulfate, decanted and concentrated. The crude product was stirred with 25% TFA/DCM (8 mL) overnight. The solvents were evaporated. The product was then stirred with ethylenediamine (0.3 mL) in methanol (5 mL). Preparative HPLC-MS (eluting with a gradient of methanol and water containing 0.15% NH$_4$OH) was used to purify the product.

$^1$H NMR (300 MHz, CDCl$_3$): δ 8.59 (s, 1H), 7.54 (dd, 1H), 7.27 (d, 1H), 6.95 (dd, 1H), 6.82 (dd, 1H), 6.74 (d, 1H), 4.49 (d, 2H), 4.15 (d, 2H), 3.24 (s, 2H), 3.02 (q, 2H), 1.33 (t, 3H); LCMS (M+H)+: 371.1.

Example 83

4-{1-[1-(Ethylsulfonyl)-3-(fluoromethyl)azetidin-3-yl]-1H-pyrazol-4-yl}-7H-pyrrolo[2,3-d]pyrimidine trifluoroacetic acid salt

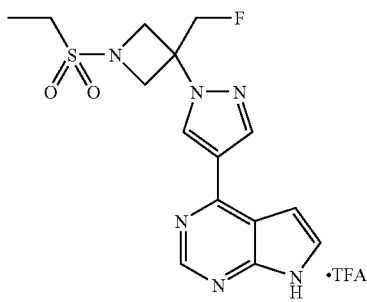

Step 1. tert-butyl 3-[fluoro(phenylsulfonyl)methylene]azetidine-1-carboxylate

To a mixture of fluoromethyl phenyl sulfone (0.50 g, 2.9 mmol) and phosphorochloridic acid, diethyl ester (0.415 mL, 2.87 mmol) in tetrahydrofuran (6 mL, 70 mmol) was added 1.000 M of lithium hexamethyldisilazide in tetrahydrofuran (6.2 mL, 6.2 mmol) dropwise at −78° C. After the mixture was stirred at −78° C. for 1 h, a solution of tert-butyl 3-oxoazetidine-1-carboxylate (0.378 g, 2.21 mmol) in tetrahydrofuran (1.3 mL, 16 mmol) was added. The reaction was allowed to warm to ambient temperature and stirred for 2 h at rt. The reaction was poured into an ice-cold mixture of EtOAc and sat. ammonium chloride. The organic layer was separated and the aq. layer was extracted with EtOAc. The combined organic layers were washed with brine, and dried over sodium sulfate. The solvent was removed under reduced pressure and the resulting residue was purified on silica gel, eluting with 0 to 50% EtOAc in hexane, to give the desired product (560 mg, 77.5%). LCMS calculated for C$_{15}$H$_{18}$FNO$_4$SNa(M+Na)+: m/z=350.1; Found (M+Na) 350.3.

Step 2. tert-butyl 3-[fluoro(phenylsulfonyl)methyl]-3-[4-(7-{[2-(trimethylsilyl)ethoxy]methyl}-7H-pyrrolo[2,3-d]pyrimidin-4-yl)-1H-pyrazol-1-yl]azetidine-1-carboxylate A mixture of 4-(1H-pyrazol-4-yl)-7-{[2-(trimethylsilyl)ethoxy]methyl}-7H-pyrrolo[2,3-d]pyrimidine (0.40 g, 1.3 mmol), tert-butyl 3-[fluoro(phenylsulfonyl)methylene]azetidine-1-carboxylate (0.56 g, 1.7 mmol), and 1,8-diazabicyclo[5.4.0]undec-7-ene (0.182 mL, 1.22 mmol) in acetonitrile (6 mL, 100 mmol) was stirred at rt for 3 h. After evaporation to dryness, the residue was purified on silica gel, eluting with 0 to 100% EtOAc in hexane, to give the desired product (820 mg, 100%). LCMS calculated for C$_{30}$H$_{40}$FN$_6$O$_5$SSi(M+H)+: m/z=643.3; Found: 643.4. $^1$H NMR (CDCl$_3$, 300 MHz) δ 8.92 (1H, s), 8.55 (1H, s), 8.32 (1H, s), 7.87 (2H, m), 7.68 (1H, m), 7.55 (2H, m), 7.47 (1H, d, J=3.6 Hz), 6.84 (1H, d, J=3.6 Hz), 5.77 (1H, d, J=45.6 Hz), 5.74 (2H, s), 4.93 (1H, d, J=10.2 Hz), 4.73~4.58 (3H, m), 3.60 (2H, t, J=8.1 Hz), 1.51 (9H, s), 0.98 (3H, t, J=8.1 Hz), 0.07 (9H, s) ppm. $^{19}$F NMR (CDCl$_3$, 300 MHz) δ −181.84 (1F, d, J=48.6 Hz) ppm.

Step 3. tert-butyl 3-(fluoromethyl)-3-[4-(7-{[2-(trimethylsilyl)ethoxy]methyl}-7H-pyrrolo[2,3-d]pyrimidin-4-yl)-1H-pyrazol-1-yl]azetidine-1-carboxylate To a mixture of tert-butyl 3-[fluoro(phenylsulfonyl)methyl]-3-[4-(7-{[2-(trimethylsilyl)ethoxy]methyl}-7H-pyrrolo[2,3-d]pyrimidin-4-yl)-1H-pyrazol-1-yl]azetidine-1-carboxylate (0.312 g, 0.485 mmol) and disodium hydrogen phosphate (1.38 g, 9.71 mmol) in methanol (7.5 mL, 180 mmol) was added sodium mercury amalgam (2.17 g, 9.71 mmol), under nitrogen, at −20° C. The reaction was stirred at −20 to 0° C. for 1 h, diluted with EtOAc, then quenched with sat. ammonium chloride. The mixture was filtered through Celite and the solid collected was treated with elemental sulfur powder to destroy the mercury residue. The filtrate layers were separated and the organic layers were washed with brine, dried over sodium sulfate and evaporated. The residue was purified on silica gel, eluting with 0 to 80% EtOAc in hexane, to give the desired product (120 mg, 49.2%). LCMS calculated for C$_{24}$H$_{36}$FN$_6$O$_3$Si(M+H)+: m/z=503.3; Found: 503.2.

Step 4. 4-{1-[1-(ethylsulfonyl)-3-(fluoromethyl)azetidin-3-yl]-1H-pyrazol-4-yl}-7-{[2-(trimethylsilyl)ethoxy]methyl}-7H-pyrrolo[2,3-d]pyrimidine tert-Butyl 3-(fluoromethyl)-3-[4-(7-{[2-(trimethylsilyl)ethoxy]methyl}-7H-pyrrolo[2,3-d]pyrimidin-4-yl)-1H-pyrazol-1-yl]azetidine-1-carboxylate (0.120 g, 0.239 mmol) was treated with 4.00 M of hydrogen chloride in 1,4-dioxane (1.0 mL, 4.0 mmol) at rt for 1 h, then evaporated to dryness under reduced pressured. LCMS (M+H) 403.4. To the resultant crude HCl salt in acetonitrile (4 mL, 80 mmol) was added triethylamine (0.0998 ML, 0.716 mmol) followed by ethanesulfonyl chloride (0.0317 mL, 0.334 mmol). The mixture was stirred at rt for 30 min. After quenching with aq. sodium bicarbonate, the mixture was extracted with dichloromethane. The combined organic layers were washed with water, brine and dried over sodium sulfate, evaporated to dry. The residue was used directly in next step. LCMS calculated for $C_{21}H_{32}FN_6O_3SSi(M+H)+$: m/z=495.2; Found: 495.4.

Step 5. 4-{-[1-(ethylsulfonyl)-3-(fluoromethyl)azetidin-3-yl]-1H-pyrazol-4-yl}-7H-pyrrolo[2,3-d]pyrimidine 4-{1-[1-(Ethylsulfonyl)-3-(fluoromethyl)azetidin-3-yl]-1H-pyrazol-4-yl}-7-{[2-(trimethylsilyl)ethoxy]methyl}-7H-pyrrolo[2,3-d]pyrimidine (0.060 g, 0.12 mmol) was treated with 2 mL of TFA at rt for 30 min. The reaction mixture was evaporated to dryness. LCMS (M+H) 395.3. The resulting residue was dissolved in 3 mL of methanol and treated with ethylenediamine (0.0811 mL, 1.21 mmol) at rt for 30 min. The mixture was purified on RP-HPLC (XBridge C18 column, eluting with a gradient of acetone/water containing 0.2% TFA) to give the desired product as TFA salt. LCMS calculated for $C_{15}H_{18}FN_6O_2S(M+H)+$ (free base): m/z=365.1; Found: 365.3. $^1H$ NMR (DMSO-$d_6$, 300 MHz) δ 12.57 (1H, br s), 8.94 (1H, s), 8.81 (1H, s), 8.53 (1H, s), 7.75 (1H, br s), 7.21 (1H, br s), 5.03 (2H, d, J=46.8 Hz), 4.53 (1H, dd, J=9.0 and 2.7 Hz), 4.24 (1H, d, J=9.0 Hz), 3.25 (2H, q, J=7.2 Hz), 1.23 (3H, t, J=7.2 Hz) ppm. $^{19}F$ NMR (DMSO-$d_6$, 300 MHz) δ -74.98 (3F, s), -225.56 (1F, t, J=48.3 Hz) ppm.

Example A

In vitro JAK Kinase Assay

Compounds herein were tested for inhibitory activity of JAK targets according to the following in vitro assay described in Park et al., *Analytical Biochemistry* 1999, 269, 94-104. The catalytic domains of human JAK1 (a.a. 837-1142), Jak2 (a.a. 828-1132) and Jak3 (a.a. 781-1124) with an N-terminal His tag were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). $IC_{50}$s of compounds were measured for each kinase in the reactions that contain the enzyme, ATP and 500 nM peptide in 50 mM Tris (pH 7.8) buffer with 100 mM NaCl, 5 mM DTT, and 0.1 mg/mL (0.01%) BSA. The ATP concentration in the reactions was 90 µM for Jak1, 30 µM for Jak2 and 3 µM for Jak3. Reactions were carried out at room temperature for 1 hr and then stopped with 20 µL 45 mM EDTA, 300 nM SA-APC, 6 nM Eu-Py20 in assay buffer (Perkin Elmer, Boston, Mass.). Binding to the Europium labeled antibody took place for 40 minutes and HTRF signal was measured on a Fusion plate reader (Perkin Elmer, Boston, Mass.). The compounds of Examples 1-60, 82, and 83 were found to have $IC_{50}$ values less than 60 nM for at least one of JAK1, JAK2, and JAK3.

Example B

Cellular Assays

One or more compounds herein were tested for inhibitory activity of JAK targets according to at least one of the following cellular assays.

Cancer cell lines dependent on cytokines and hence JAK/STAT signal transduction, for growth, were plated at 6000 cells per well (96 well plate format) in RPMI 1640, 10% FBS, and 1 nG/mL of appropriate cytokine. Compounds were added to the cells in DMSO/media (final concentration 0.2% DMSO) and incubated for 72 hours at 37° C., 5% $CO_2$. The effect of compound on cell viability was assessed using the CellTiter-Glo Luminescent Cell Viability Assay (Promega) followed by TopCount (Perkin Elmer, Boston, Mass.) quantitation. Potential off-target effects of compounds were measured in parallel using a non-JAK driven cell line with the same assay readout. All experiments were performed in duplicate.

The above cell lines can also be used to examine the effects of compounds on phosphorylation of JAK kinases or potential downstream substrates such as STAT proteins, Akt, Shp2, or Erk. These experiments can be performed following an overnight cytokine starvation, followed by a brief preincubation with compound (2 hours or less) and cytokine stimulation of approximately 1 hour or less. Proteins are then extracted from cells and analyzed by techniques familiar to those schooled in the art including Western blotting or ELISAs using antibodies that can differentiate between phosphorylated and total protein. These experiments can utilize normal or cancer cells to investigate the activity of compounds on tumor cell survival biology or on mediators of inflammatory disease. For example, with regards to the latter, cytokines such as IL-6, IL-12, IL-23, or IFN can be used to stimulate JAK activation resulting in phosphorylation of STAT protein(s) and potentially in transcriptional profiles (assessed by array or qPCR technology) or production and/or secretion of proteins, such as IL-17. The ability of compounds to inhibit these cytokine mediated effects can be measured using techniques common to those schooled in the art.

Compounds herein can also be tested in cellular models designed to evaluate their potency and activity against mutant JAKs, for example, the JAK2V617F mutation found in myeloid proliferative disorders. These experiments often utilize cytokine dependent cells of hematological lineage (e.g. BaF/3) into which the wild-type or mutant JAK kinases are ectopically expressed (James, C., et al. *Nature* 434:1144-1148; Staerk, J., et al. *JBC* 280:41893-41899). Endpoints include the effects of compounds on cell survival, proliferation, and phosphorylated JAK, STAT, Akt, or Erk proteins.

Certain compounds herein have been or can be evaluated for their activity inhibiting T-cell proliferation. Such as assay can be considered a second cytokine (i.e. JAK) driven proliferation assay and also a simplistic assay of immune suppression or inhibition of immune activation. The following is a brief outline of how such experiments can be performed. Peripheral blood mononuclear cells (PBMCs) are prepared from human whole blood samples using Ficoll Hypaque separation method and T-cells (fraction 2000) can be obtained from PBMCs by elutriation. Freshly isolated human T-cells can be maintained in culture medium (RPMI 1640 supplemented with 10% fetal bovine serum, 100 U/ml penicillin, 100 µg/ml streptomycin) at a density of 2×106 cells/ml at 37° C. for up to 2 days. For IL-2 stimulated cell proliferation analysis, T-cells are first treated with Phytohemagglutinin (PHA) at a final concentration of 10 µg/mL for 72 h. After washing once with PBS, 6000 cells/well are plated in 96-well plates and treated with compounds at different concentrations in the culture medium in the presence of 100 U/mL human IL-2 (ProSpec-Tany TechnoGene; Rehovot, Israel). The plates are incubated at 37° C. for 72 h and the proliferation index is assessed using CellTiter-Glo Luminescent reagents following the manufactory suggested protocol (Promega; Madison, Wis.).

Example C

In vivo Anti-tumor Efficacy

Compounds herein can be evaluated in human tumor xenograft models in immune compromised mice. For example, a tumorigenic variant of the INA-6 plasmacytoma cell line can be used to inoculate SCID mice subcutaneously (Burger, R., et al. *Hematol J.* 2:42-53, 2001). Tumor bearing animals can then be randomized into drug or vehicle treatment groups and different doses of compounds can be administered by any number of the usual routes including oral, i.p., or continuous infusion using implantable pumps. Tumor growth is followed over time using calipers. Further, tumor samples can be harvested at any time after the initiation of treatment for analysis as described above (Example B) to evaluate compound effects on JAK activity and downstream signaling pathways. In addition, selectivity of the compound(s) can be assessed using xenograft tumor models that are driven by other know kinases (e.g. Bcr-Abl) such as the K562 tumor model.

Example D

Murine Skin Contact Delayed Hypersensitivity Response Test

Compounds herein can also be tested for their efficacies (of inhibiting JAK targets) in the T-cell driven murine delayed hypersensitivity test model. The murine skin contact delayed-type hypersensitivity (DTH) response is considered to be a valid model of clinical contact dermatitis, and other T-lymphocyte mediated immune disorders of the skin, such as psoriasis (*Immunol Today.* January 1998;19(1):37-44). Murine DTH shares multiple characteristics with psoriasis, including the immune infiltrate, the accompanying increase in inflammatory cytokines, and keratinocyte hyperproliferation. Furthermore, many classes of agents that are efficacious in treating psoriasis in the clinic are also effective inhibitors of the DTH response in mice (Agents Actions. January 1993;38(1-2):116-21).

On Day 0 and 1, Balb/c mice are sensitized with a topical application, to their shaved abdomen with the antigen 2,4, dinitro-fluorobenzene (DNFB). On day 5, ears are measured for thickness using an engineer's micrometer. This measurement is recorded and used as a baseline. Both of the animals' ears are then challenged by a topical application of DNFB in a total of 20 µL (10 µL on the internal pinna and 10 µL on the external pinna) at a concentration of 0.2%. Twenty-four to seventy-two hours after the challenge, ears are measured again. Treatment with the test compounds was given throughout the sensitization and challenge phases (day −1 to day 7) or prior to and throughout the challenge phase (usually afternoon of day 4 to day 7). Treatment of the test compounds (in different concentration) was administered either systemically or topically (topical application of the treatment to the ears). Efficacies of the test compounds are indicated by a reduction in ear swelling comparing to the situation without the treatment. Compounds causing a reduction of 20% or more were considered efficacious. In some experiments, the mice are challenged but not sensitized (negative control).

The inhibitive effect (inhibiting activation of the JAK-STAT pathways) of the test compounds can be confirmed by immunohistochemical analysis. Activation of the JAK-STAT pathway(s) results in the formation and translocation of functional transcription factors. Further, the influx of immune cells and the increased proliferation of keratinocytes should also provide unique expression profile changes in the ear that can be investigated and quantified. Formalin fixed and paraffin embedded ear sections (harvested after the challenge phase in the DTH model) are subjected to immunohistochemical analysis using an antibody that specifically interacts with phosphorylated STAT3 (clone 58E12, Cell Signaling Technologies). The mouse ears are treated with test compounds, vehicle, or dexamethasone (a clinically efficacious treatment for psoriasis), or without any treatment, in the DTH model for comparisons. Test compounds and the dexamethasone can produce similar transcriptional changes both qualitatively and quantitatively, and both the test compounds and dexamethasone can reduce the number of infiltrating cells. Both systemically and topical administration of the test compounds can produce inhibitive effects, i.e., reduction in the number of infiltrating cells and inhibition of the transcriptional changes.

Example E

In vivo Anti-inflammatory Activity

Compounds herein can be evaluated in rodent or non-rodent models designed to replicate a single or complex inflammation response. For instance, rodent models of arthritis can be used to evaluate the therapeutic potential of compounds dosed preventatively or therapeutically. These models include but are not limited to mouse or rat collagen-induced arthritis, rat adjuvant-induced arthritis, and collagen antibody-induced arthritis. Autoimmune diseases including, but not limited to, multiple sclerosis, type I-diabetes mellitus, uveoretinitis, thyroditis, myasthenia gravis, immunoglobulin nephropathies, myocarditis, airway sensitization (asthma), lupus, or colitis may also be used to evaluate the therapeutic potential of compounds herein. These models are well established in the research community and are familiar to those schooled in the art (Current Protocols in Immunology, Vol 3., Coligan, J. E. et al, Wiley Press.; *Methods in Molecular Biology*: Vol. 225, Inflammation Protocols., Winyard, P. G. and Willoughby, D. A., Humana Press, 2003.).

Example F

Animal Models for the Treatment of Dry Eye, Uveitis, and Conjunctivitis

Compounds may be evaluated in one or more preclinical models of dry eye known to those schooled in the art including, but not limited to, the rabbit concanavalin A (ConA) lacrimal gland model, the scopolamine mouse model (subcutaneous or transdermal), the Botulinumn mouse lacrimal gland model, or any of a number of spontaneous rodent autoimmune models that result in ocular gland dysfunction (e.g. NOD-SCID, MRL/lpr, or NZB/NZW) (Barabino et al., Experimental Eye Research 2004, 79, 613-621 and Schrader et al., Developmental Opthalmology, Karger 2008, 41, 298-312, each of which is incorporated herein by reference in its entirety). Endpoints in these models may include histopathology of the ocular glands and eye (cornea, etc.) and possibly the classic Schirmer test or modified versions thereof (Barabino et al.) which measure tear production. Activity may be assessed by dosing via multiple routes of administration (e.g. systemic or topical) which may begin prior to or after measurable disease exists.

Compounds may be evaluated in one or more preclinical models of uveitis known to those schooled in the art. These include, but are not limited to, models of experimental autoimmune uveitis (EAU) and endotoxin induced uveitis (EIU). EAU experiements may be performed in the rabbit, rat, or mouse and may involve passive or activate immunization. For instance, any of a number or retinal antigens may be used to sensitize animals to a relevant immunogen after which animals may be challenged ocuarly with the same antigen. The EIU model is more acute and involves local or systemic administration of lipopolysaccaride at sublethal doses. Endpoints for both the EIU and EAU models may include fundoscopic exam, histopathology amongst others. These models are reviewed by Smith et al. (Immunology and Cell Biology 1998, 76, 497-512, which is incorporated herein by reference in its entirety). Activity is assessed by dosing via multiple routes of administration (e.g. systemic or topical) which may begin prior to or after measurable disease exists. Some models listed above may also develop scleritis/episcleritis, chorioditis, cyclitis, or iritis and are therefore useful in investigating the potential activity of compounds for the therapeutic treatment of these diseases.

Compounds may also be evaluated in one or more preclinical models of conjunctivitis known those schooled in the art. These include, but are not limited to, rodent models utilizing guinea-pig, rat, or mouse. The guinea-pig models include those utilizing active or passive immunization and/or immune challenge protocols with antigens such as ovalbumin or ragweed (reviewed in Groneberg, D. A., et al., Allergy 2003, 58, 1101-1113, which is incorporated herein by reference in its entirety). Rat and mouse models are similar in general design to those in the guinea-pig (also reviewed by Groneberg). Activity may be assessed by dosing via multiple routes of administration (e.g. systemic or topical) which may begin prior to or after measurable disease exists. Endpoints for such studies may include, for example, histological, immunological, biochemical, or molecular analysis of ocular tissues such as the conjunctiva.

Various modifications of the invention, in addition to those described herein, will be apparent to those skilled in the art from the above description. Each reference cited in the present application is incorporated herein by reference in its entirety.

What is claimed is:

1. {1-(Ethylsulfonyl)-3-[4-(7H-pyrrolo[2,3-d]pyrimidin-4-yl)-1H-pyrazol-1-yl]azetidin-3-yl}acetonitrile, or a pharmaceutically acceptable salt thereof.

2. The compound of claim 1 wherein it is {1-(ethylsulfonyl)-3-[4-(7H-pyrrolo[2,3-d]pyrimidin-4-yl)-1H-pyrazol-1-yl]azetidin -3-yl}acetonitrile phosphoric acid salt.

3. A composition comprising a compound of any one of claims 1 or 2 and at least one pharmaceutically acceptable carrier.

* * * * *

UNITED STATES PATENT AND TRADEMARK OFFICE
CERTIFICATE OF CORRECTION

| | |
|---|---|
| PATENT NO. | : 8,158,616 B2 |
| APPLICATION NO. | : 12/401348 |
| DATED | : April 17, 2012 |
| INVENTOR(S) | : James D. Rodgers and Stacey Shepard |

It is certified that error appears in the above-identified patent and that said Letters Patent is hereby corrected as shown below:

In the Specification
In column 49, line 29, please delete "1-y]" and insert --1-yl]--, therefor.

Signed and Sealed this
Twenty-third Day of February, 2016

Michelle K. Lee
*Director of the United States Patent and Trademark Office*

UNITED STATES PATENT AND TRADEMARK OFFICE

(12)            CERTIFICATE EXTENDING PATENT TERM
UNDER 35 U.S.C. 156

| | | | |
|---|---|---|---|
| (68) | PATENT NO. | : | 8,158,616 |
| (45) | ISSUED | : | April 17, 2012 |
| (75) | INVENTOR | : | James D. RODGERS and Stacy SHEPARD |
| (73) | PATENT OWNER | : | Incyte Corporation |
| (95) | PRODUCT | : | OLUMIANT® (baricitinib) |

This is to certify that an application under 35 U.S.C. 156 has been filed in the United States Patent and Trademark Office, requesting extension of the term of U.S. Patent No. 8,158,616 based upon the regulatory review of the product OLUMIANT® (baricitinib) by the Food and Drug Administration. According to United States Patent and Trademark Office records, the original expiration date of the patent as of the date of issuance of this certificate is June 8, 2030. Because it appears that the requirements of the law have been met, this certificate extends the term of the patent for the period of

(94)                               723 days subject to the payment of maintenance fees as provided by law, with all rights pertaining thereto as provided by 35 U.S.C. 156.

I have caused the seal of the United States Patent and Trademark Office to be affixed this 7th day of February 2024.

Kathi Vidal

Katherine K. Vidal
Under Secretary of Commerce for Intellectual Property and Director of the United States Patent and Trademark Office